Figure 1A:
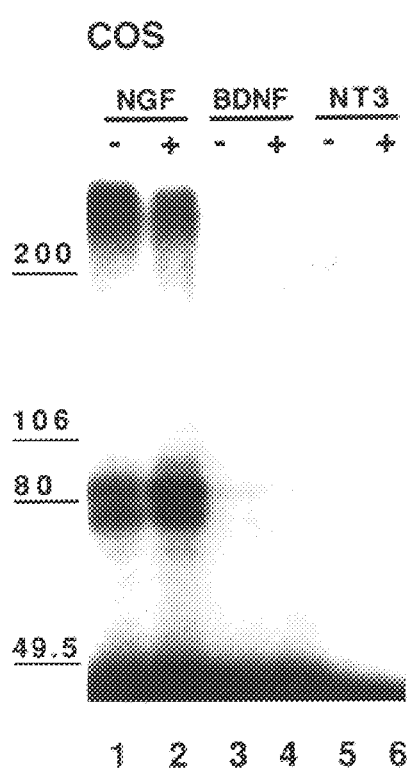

United States Patent [19]
Maisonpierre et al.

[11] Patent Number: 5,843,749
[45] Date of Patent: Dec. 1, 1998

[54] EHK AND ROR TYROSINE KINASES

[75] Inventors: Peter C. Maisonpierre, Croton; Piotr Masiakowski, Pleasant Valley; George D. Yancopoulos, Yorktown Heights, all of N.Y.

[73] Assignee: Regeneron Pharmaceuticals, Inc., Tarrytown, N.Y.

[21] Appl. No.: 469,537

[22] Filed: Jun. 6, 1995

Related U.S. Application Data

[63] Continuation of Ser. No. 406,247, Mar. 17, 1995, abandoned, which is a continuation-in-part of Ser. No. 144,992, Oct. 28, 1993, abandoned, which is a continuation-in-part of Ser. No. 736,559, Jul. 26, 1991, abandoned.

[51] Int. Cl.$^6$ .......................... C12N 15/54; C07K 14/435
[52] U.S. Cl. ...................... 435/194; 536/23.5; 536/23.51
[58] Field of Search ........................... 530/350; 536/23.5, 536/23.51; 435/194

[56] References Cited

U.S. PATENT DOCUMENTS 5,457,048  10/1995  Pasquale et al. ...................... 435/252.3

OTHER PUBLICATIONS

Sajjadi, et al, "Five novel avian Eph–related tyrosine kinases are differentially expressed", *Oncogene* 8, (Jul., 1993), pp. 1807–1813.

*Primary Examiner*—Marianne P. Allen
*Attorney, Agent, or Firm*—Gail M. Kempler; Baker & Botts

[57] ABSTRACT

The present invention provides for novel receptor tyrosine kinases known as Ror-1, Ror-2, Ehk-1 and Ehk-2. The invention also provides for assay systems that may be used to detect and/or measure neurotrophin activity or to identify agents that exhibit neurotrophin-like activity. It is based, at least in part, on the discovery that the trkB proto-oncogene encodes a tyrosine kinase receptor that may serve as a functional binding protein for BDNF and NT-3. The present invention also provides for diagnostic and therapeutic methods based on the interaction between BDNF and/or NT-3 and trkB.

8 Claims, 88 Drawing Sheets

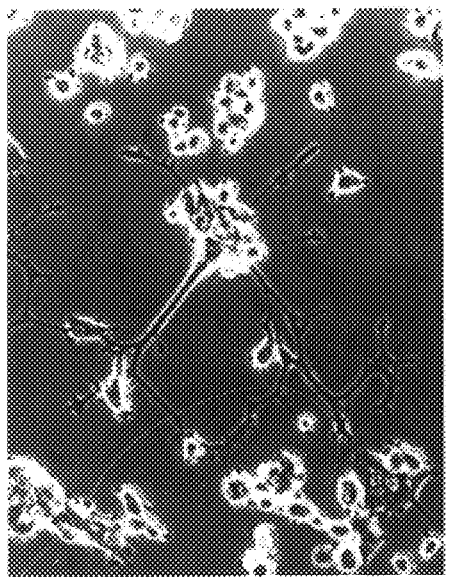 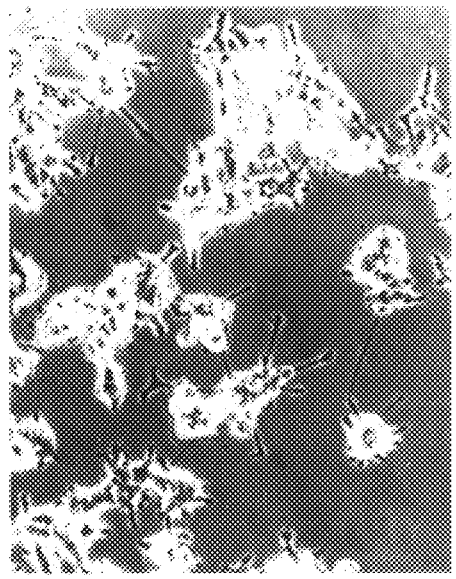
T24-ras + BSA (6500)
FIG.5A
trk B + NGF (ND)
FIG.5B trk B + BSA
(0)

trk B + NT-3
(1200)

trk B + BDNF
(8700)

1) trk-like (RTK-1)

CLVGANLLLVKIGDFGMSRDVYST.DYYRVG..GHTM..LPIRWMPPESIMYRKFTTES

2) CSF1R/PDGFR/kit-like (RTK-6)

VLVTHGKVVKICDFGLARDILSD.SSYVVR..GNAR..LPVKWMAPESLFEGIYTIKS 3) ret-like (RTK-7)

ILVGENYLAKIADFGLSRGQE....VYVKK...TMGRLPVRWMAIESLNYSVYTTNS 4) a. eck-like (alpha) (RTK-8)

ILVNSNLVCKVSDFGLSRVLEDDPEAAYTTTGGK.....IPIRWTAPEAIAYRKFSSAS 5) b. eck-like (beta) (RTK-9)

ILINSNLVCKVSDFGLSRVLEDDPEAAYTTRGGK.....IPIRWTAPEAIAFRKFTSAS

FIG.12B

```
                        20                    40                              60
                         x         x           x              x       x        x
RTK-1   TGC CTA GTT GGA GCC AAC CTT CTA GTG AAG ATT GGA GAT TTT GGC ATG TCC AGG GAC GTC
         C   L   V   G   A   N   L   L   V   K   I   G   D   F   G   M   S   R   D   V
r trkB
        ... t.g ..a ... .ag ... ..g ..g ... ..a ... ..g ..c ..c ..g ... ... c.. ..t ..a
                             E
m trkB
        ... ..g ..g ... .ag ... ..g ..g ... ..a ... ..g ..c ... ..g ... ... c.a ..t ..g
                             E
h trkA
        ..t ... ..g ..c cag gga ..g g.g ..c ... ... ..t ... ... ... ag. ... ..t a..
                         Q   G       V                                              I 80                  100                          120
                         x         x              x          x       x        x
RTK-1   TAC AGT ACT GAT TAC TAC AGG GTG GGA GGA CAC ACC ATG CTC CCC ATC CGC TGG ATG CCA
         Y   S   T   D   Y   Y   R   V   G   G   H   T   M   L   P   I   R   W   M   P
r trkB
        ... ..c ..c ..c ... ... c.. ..t ..t ..c ... ..a ... t.g ... ... ..a ... ... ..t
m trkB
        ... ..c ..c ..c ... ..t c.. ..c ..t ..c ... ..a ... t.g ... ... ..a ... ... ..t
h trkA
        ... ..c ..c ..c ..t ... c.t. ... ... ..c .g. ... ... ..g ... ..t ... ... ...g
                                                  R 140              159
                       x        x       x        x
RTK-1   CCT GAA AGC ATC ATG TAC CGG AAG TTT ACC ACA GAG AGT
         P   E   S   I   M   Y   R   K   F   T   T   E   S
r trkB
        ..a ..g ... ... ... ... a.. ..a ..c ... ..c ... ...
m trkB
        ..a ..g ... ... ... ..t a.. ..a ..c ... ..c ... ..c
h trkA
        ..c ..g ... ... c.. ... ..t ... ..c ... ..c ... ..c
                         L
```

FIG.12C(i)

```
                20                     40                      60
         *       *              *       *              *        *
GTA CTG GTC ACC CAC GGG AAG GTG GTG AAG ATC TGT GAC TTT GGA CTG GCC CGA GAC ATC
 V   L   V   T   H   G   K   V   V   K   I   C   D   F   G   L   A   R   D   I 80                    100                    120
               *        *             *       *              *        *
CTG AGT GAC TCC AGC TAC GTC GTC AGG GGC AAC GCA CGG CTG CCA GTG AAG TGG ATG GCA
 L   S   D   S   S   Y   V   V   R   G   N   A   R   L   P   V   K   W   M   A 140                159
           *       *       *        *
CCT GAG AGC TTG TTT GAA GGG ATC TAT ACA ATC AAG AGT
 P   E   S   L   F   E   G   I   Y   T   I   K   S
```

```
                         20                    40
                 *        *             *       *              *
RTK-6      VLVTHGKVVKICDFGLARDILSDSSYVVRGNARLPVKWMAPESLFEGIYTIKS h kit
           i.l...rit..........kn..n...k.............i.ncv..fe.
h CSF1R
           ..l.n.h.a..g.......mn..n.i.k.............i.dcv..vq.
h PDGFαR
           ..laq..i...........mh..n..sk.stf...........i.dnl..tl.
m CSF1R
           ..l.s.h.a..g.......mn..n...k...-...........i.dcvi.vq.
```

FIG.12C(ii)

```
                20                        40                        60
         x                  x         x              x         x               x
ATT TTA GTT GGC GAA AAC TAC TTA GCC AAA ATA GCA GAT TTT GGA TTG TCA CGA GGT CAA
 I   L   V   G   E   N   Y   L   A   K   I   A   D   F   G   L   S   R   G   Q 80                       100                       120
         x                  x         x              x         x               x
GAA GTG TAT GTG AAA AAG ACA ATG GGA AGG CTT CCA GTG CGC TGG ATG GCA ATT GAG TCT
 E   V   Y   V   K   K   T   M   G   R   L   P   V   R   W   M   A   I   E   S 140       150
         x              x      x
CTG AAC TAT AGT GTC TAT ACA ACC AAC AGT
 L   N   Y   S   V   Y   T   T   N   S
```

```
               20            40
        x         x       x        x        x
RTK-7  ILVGENYLAKIADFGLSRGQEVYVKKTMGRLPVRWMAIESLNYSVYTTNS
                         vye
h ret                     |
       ...a.grkm..s......deds...rsq..i..k......fdhi...q.
```

FIG.12C(iii)

```
              20                    40                    60
              *                     *                     *
h eck  ATC CTC GTC AAC AGC AAC CTG GTC TGC AAG GTG TCT GAC TTT GGC CTG TCC CGC GTG CTG
        I   L   V   N   S   N   L   V   C   K   V   S   D   F   G   L   S   R   V   L
RTK-9
       ... t.a a.. ... ..t ... ..t ..g ... ..a ... ... ... ... ..a ..t ... a.g ... ...
                I
RTK-8
       ... t.g ..g ... ... ... t.. ..a ... ..a ..c ... ..t ..c ... ..c ... ..a ... ...

80                   100                   120
              *                     *                     *
h eck  GAG GAC GAC CCC GAG GCC ACC TAC ACC ACC AGT GGC GGC AAG ATC CCC ATC CGC TGG ACC
        E   D   D   P   E   A   T   Y   T   T   S   G   G   K   I   P   I   R   W   T
RTK-9
       ..a ..t ..t ..t ... ..a g.. ..t ... ..a ..g ..a ... ..a ..t ..a ... a.g ... ..t
RTK-8
       ..a ... ... ..a ..a ..a g.t ..t ..a ..a .c. ..t ..a ..a ..a ..t ..a a.g ... ..a
                                 T 140                   160
                     *                     *
h eck  GCC CCG GAG GCC ATT TCC TAC CGG AAG TTC ACC TCT GCC AGC
        A   P   E   A   I   S   Y   R   K   F   T   S   A   S
RTK-9
       ..t ..a ..a ..a ..g.t .tt ..a ... ..t ... ... ... ..t
                         A   F
RTK-8
       ... ..a ..a ..t ..c g.. ... a.. ..a ... t.. ..a ..g ..t
                         A                 S
```

FIG.12C(iv)

```
                      20              40              60              80
                       *               *               *               *
RTK-1    GPDAMILVDGQPRQAKGELGLSQMLHIASQIASGMVYLASQHFVHRDLATRNCLVGANLLVKIGDFGMSRDVYSTDYYRV r trkB   ....vlmae.n.--p-t..tq......q...a.....................e........................

m trkB   ....vlmae.n.--p-t..tq......q...a.....................e........................

h trkA   ...kl.ag.e-dv.p.p...g.l.av...v.a......gl..............qg.v...........l........

100             120             140             160
                       *               *               *               *
RTK-1    GGHTMLPIRWMPPESIMYRKFTTESDVWSFGVILWEIFTYGKQPWFQLSNTEVIECITQGRVLERPRVCPKEVYDVMLGC r trkB   ....................l..v............y....n..........q...t..q...el....

m trkB   ....................l..v............y....n..........q...t..q...el....

h trkA   ..r.............l..............v............y......a.d......e.....a..p...al.r..

180
                       *       *
RTK-1    WQREPQQRLNIKEIYKILHALGKATPIYLDILG* r trkB   .....ht.k...n.htl.qn.a..s.v......

m trkB   .....ht.k...s.htl.qn.a..s.v......

h trkA   ........hs..dvhar.q..aq.p.v...v..
```

FIG.12D

```
        |---VI-------|-------VII--------|--------VIII--------|------IX-----|
        >>>>>                                                   >>>>
c-Src   YVHRDLRAANILVGENLVCKVADFGLARLIED..NEYTAR..QGAK..FPIKWTAPEAAALYGRFTIKSDVWSFGILLTELTT
c-Yes   YIHRDLRAANILVGENLVCKIADFGLARLIED..NEYTAR..QGAK..FPIKWTAPEAAALYGRFTIKSDVWSFGILQTELVT
HCK     YIHRDLRAANILVSASLVCKIADFGLARVIED..NEYTAR..EGAK..FPIKWTAPEAINFGSFTIKSDVWSFGILLMEIVT
c-Fes   CIHRDLAARNCLVTEKNVLKISDFGMSREEAD..GIYAAC..SGLRQ.VPVKWTAPEALNYGRYSSESDVWSFGILLWETFS
c-Abl   FIHRDLAARNCLVGENHLVKVADFGLSRLMTG..DTYTAH..AGAK..FPIKWTAPESLAYNKFSIKSDVWAFGVLLWEIAT
EGFR    LVHRDLAARNVLVKTPQHVKITDFGLAKLLGAEEKEYHA..EGGK..VPIKWMALESILHRIYTHQSDVWSYGVTVWELMT
Neu     LVHRDLAARNVLVKSPMHVKITDFGLARLLDIDETEYHA..DGGK..VPIKWMALESILRRRFTHQSDVWSYGVTVWELMT
CSF1R   CVHRDVAARNVLLTSGHVAKIGDFGLARDIMND.SNYVVK..GNA...LPNKWMAPESIFDCVITVQSDVWSYGILLWEIFS
PDGFR   CVHRDLAARNVLICEGKLVKICDFGLARDIMRD.SNYISK..GSTY..LPLKWMAPESIFNSLYTTLSDVWSFGILLWEIFT
IR      FVHRDLAARNCMVAHDFTVKIGDFGMTRDIYET.DYYRKG..GKGL..LPVRWMAPESLKDGVFTTSSDMWSFGVVLWEITS
IGF1R   FVHRDLAARNCMVAEDFTVKIGDFGMTRDIYET.DYYRKG..GKGL..LPVRWMSPESLKDGVFTTSSDVWSFGVVLWEIAT
c-Met   FVHRDLAARNCMLDEKFTVKVADFGLARDMYDK.EYYSVHNKTGAK..LPVKWMALESLQTQKFTTKSDVWSFGVVLWELMT
c-Trk   FVHRDLATRNCLVGQGLVVKIGDFGMSRDIYST.DYYRVG..GRTM..LPIRWMPPESILYRKFTTESDVWSFGVVLWEIFT
```

FIG. 12E

FIG.13A(i)

```
Ros     ..........I......................K.............................................................100
(620)   EKLT.RLL..S....E.YEGTAVD.GVGSGE.K.......GST.QEKIE.LK..H.MSKFN.PN.L.QL...LLNE.QYIIL.L.EG...LTY..-KARM.TFY---.L--.LVDLYD>

VSLIAWMT
DILR    ..................................N................................................100          --
(609)   E...IQLAP..Q.S..M.YEGILKSFP.NGVDREC.I..VNE.T.RE.TN.LS..SVMKEFDTY.V.RLL...SR.Q.ALV.M.L..KVE.KSY....R.RSGMRPDDGNVQPP.YGRIYQ>

RS
7less   ..................................I....................--....................................100
(604)   SQLK.L.F..S....E.YEG-QLKTEDSEEPQR..I.S.RKG-ASEFAELLQ..Q.MS.FK..N..RLV.I.FDTESISLIM.H.EA....LSY.-AARAT-STQ.PQ.TAG.SL.EL.A>

MET     ..................................I............................................................100
(544)   VHFNEVI.R.H..C.YHGT-L-.DNDGK..HC....S.NRIT.GFVSQ.LT.GIIMKDFS.PNVLSLL.I.L..S..V-.LP......RN.I.-N—E----TH--..-V-K-DLIG>
```

FIG.13A(ii)

Figure 13A:
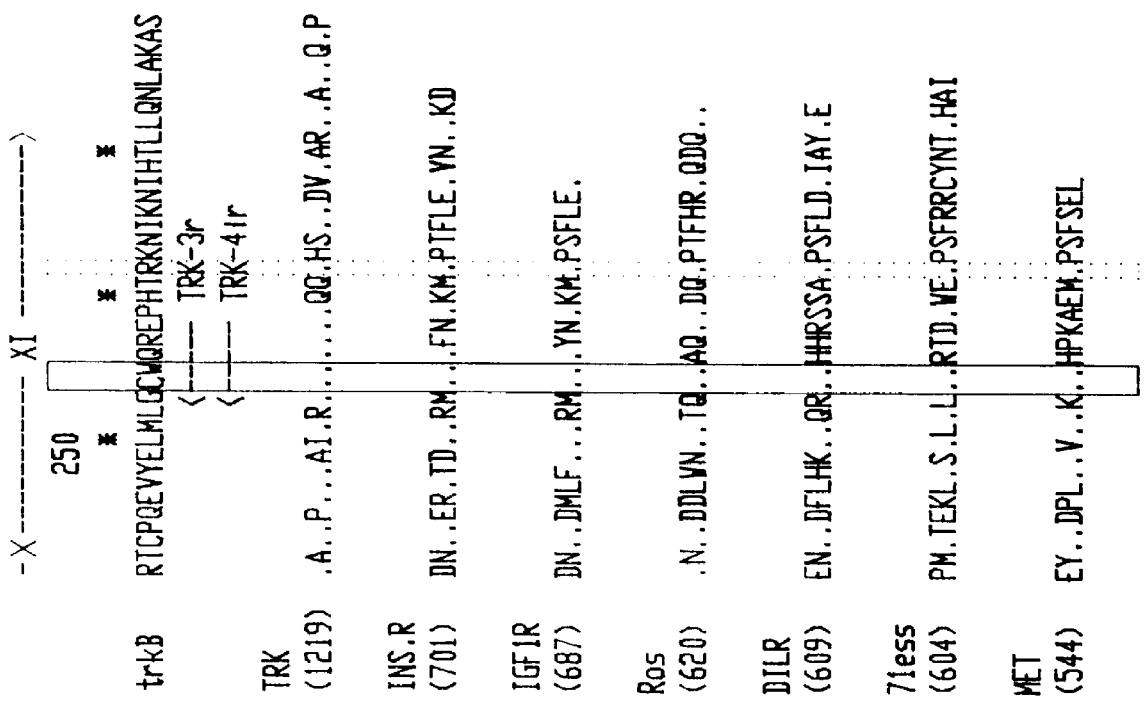

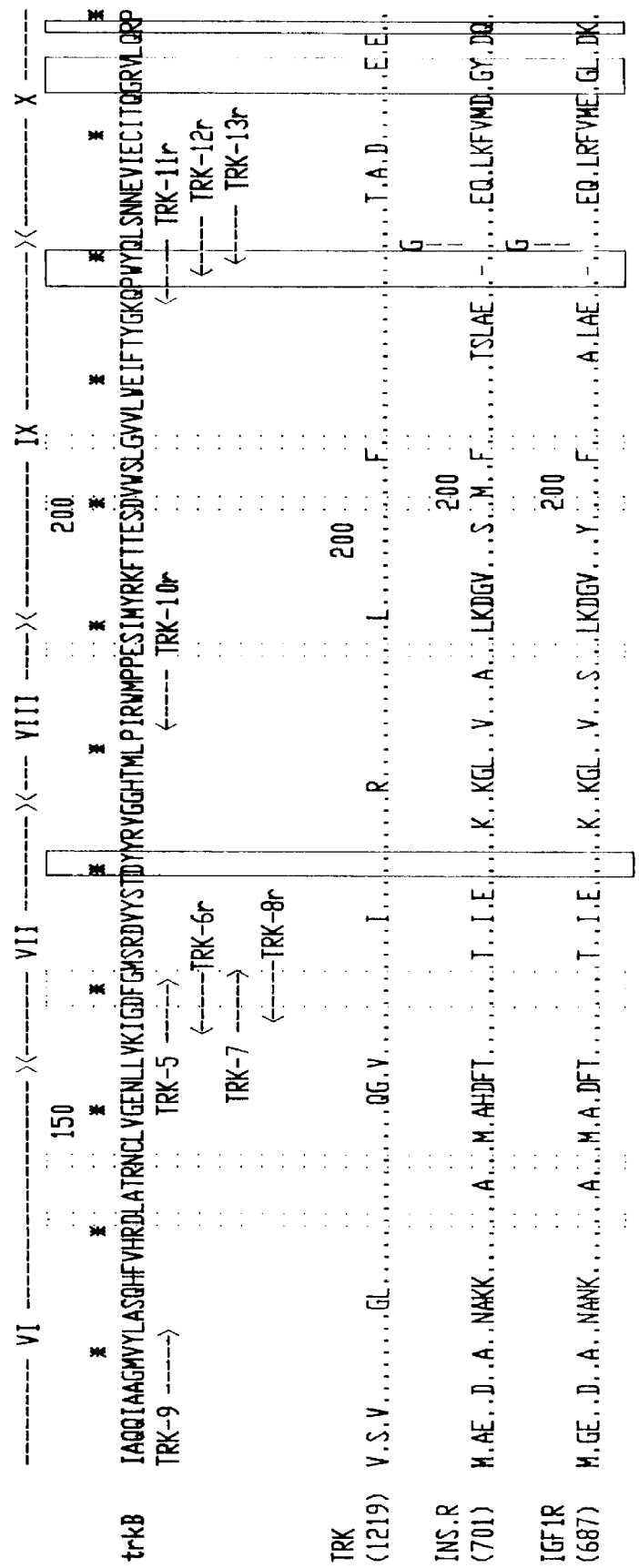
FIG.13A(iii)

```
ROS
(620)   LCVD.SK.C...ERM..I.......A......SSPRI............LA..I.KN....KR.EGL..V....A....L.DGI..Q......F.ILI...L..L..H..YPAH..LD.LNYVQT.GR.EP.

DILR
(609)   V.IE..D..A...AKK..........A....M.ADD..T............T..I.E......K.TKGL..V.....LRDGVYSSA...F..F.....MA.LAA..-.......EQ.LRYVID.G.ME.
                                                                                                      G
                                                                                                      - -

7less
(604)   MCIDV.N.CS..EDM.........C....TDRRRT.............LA..I.KS....KE.EGL..V....S...LVDGL..Q.....AF..LC...L..L..Q..P..AAR.F...LAHYKE.GR...Q.
                                                                     GA                                                    N
                                                                     - -                                                   - -

MET
(544)   FGL.V..KA.K....KK.........A.....MLD.KFT..VA...LA..M.DKE...S.HNK.K...VK..AL..LQTQ....K.....F.....LM..R..R..AP..YPDYNTFDITVYLL....R..IQ.
```

FIG.13A(iv)

Rtk-2

```
TCT AGT CAC TTC TTT GTC CAC AAG GAC CTT GCA GCT CGC AAT ATT TTA ATC GGA GAG CAA CTT CAT GTA AAG
Ser Ser His Phe Phe Val His Lys Asp Leu Ala Ala Arg Asn Ile Leu Ile Gly Glu Gln Leu His Val Lys
                                                                50

ATT TCA GAC TTG GGG CTT TCC AGA GAA ATT TAC TCC GCT GAT TAC TAC AGG GTC CAG AGT AAG TCC TTG CTG
Ile Ser Asp Leu Gly Leu Ser Arg Glu Ile Tyr Ser Ala Asp Tyr Tyr Arg Val Gln Ser Lys Ser Leu Leu
                              100
```

Rtk-3

```
TCC AGC CAC GTG GTT CAC AAG GAC CTG GCC ACC CGC AAT GTG CTA GTG TAC GAC AAG CTG AAC GTG AAG
Ser Ser His Val Val His Lys Asp Leu Ala Thr Arg Asn Val Leu Val Tyr Asp Lys Leu Asn Val Lys
                                                                50

ATC TCA GAC TTG GGC CTC TTC CGA GAG GCC GAT TAC TAC AAG CTG CTG CTG GGG AAC TCG CTG CTG CTG
Ile Ser Asp Leu Gly Leu Phe Arg Glu Ala Asp Tyr Tyr Lys Leu Leu Leu Gly Asn Ser Leu Leu Leu
                              100
```

FIG. 13B

Rtk-4

CTC TCC AGG AAC ATC TAC TCA GCA GAC TAC TAC AAA GCT AAT GAA AAC GAC GCT ATC CCC ATT AGT TGG ATG CCT
Leu Ser Arg Asn Ile Tyr Ser Ala Asp Tyr Tyr Lys Ala Asn Glu Asn Asp Ala Ile Pro Ile Ser Trp Met Pro

Rtk-5

AAG CGC TTT ATT CAC CGT GAC CTG GCT GCC CGC AAT CTG CTG TTG GCT ACC CGC GAC CTG GTC AAA ATC GGT
Lys Arg Phe Ile His Arg Asp Leu Ala Ala Arg Asn Leu Leu Leu Ala Thr Arg Asp Leu Val Lys Ile Gly

GAC TTT GGT
Asp Phe Gly

FIG.13B (i)

```
                          *                *              *              *            50 *            *
human trk         AGMVYLAGLH FVHRDLATRN CLVGQGLVVK IGDEGMSRDI YSTDYYRVGG RTMLPIRWMP
TK subdomains     ----------><---------VI--------><---------VII-------->< ---VIII----

Rtk-2             SSHF ...K...A.. I.I.EQ.H..  .S.L.L.E.  .A......QS KSL.
Rtk-3             SSHH V..K....... V..YDK.N..  .S.L.LF.EV .AA...KLL. NSL.
Rtk-4                                                     L..N. ..A...KANE NDAI
Rtk-5             KR .I.....A.. L.LATRDL.
```

FIG.13C

```
Rtk-2    GGGFFHWSLVCQVWPPSHSKSRYSDEYEEDGFCQPYRGIACARFIGNRTVYMESLHMQGE

Rtk-2    IENQITAAFTMIGTSSHLSDKCSQFAIPSLCHYAFPYCDETSSVVPKPRDLCRDECEILEN

Rtk-2    VLCQTEYIFARSNPMILMRLKLPNCEDLPQPESPEAANCIRIGIPMADPINKNHKCYNST

Rtk-2    GVDYRGTVSVTKSGRQCQPWNSQYPHTHTFTALRFPELNGGHSYCRNPGNQKEAPWCFTL

Rtk-2    DENFKSDLCDIPACDSKDSKEKNKMEILYILVPSVAIPLAIALLFFFICVCRNNQKSSSA h trk
[ 779 ]                                                        ..LS>
```

FIG.13D(i)

```
                                                          200
h IGF-R    .I.AL.-.. VL. IVGG.VIMLY.---FHR.RNNS>
[ 646 ]
                                                          200
h Ins-R    .I-.IGP.IFVFLFSVV.GSIYL.LRKRQPDGPLGPL>
[ 638 ]
                              *           350        *
Rtk-2      PVQRQPKHVRGQNVEMSMLNAYKPKSKAKELPLSAVRFMEELGECAFGKIYKGHLYLPGM
                                                           N
                       *           500              *     —
r trkB     ..DTFVQHIKRHNIVLKR....G.....VFLAEC..CPE>
[ 783 ]
                                                          LA
                                                          —
h trk      .TEGKGSGLQ.HII.-N--PQ.FSDACVHHIKRRDIVLKW....G.....VFEC.NL..EQ>
[ 779 ]

h IGF-R    RLGNGVLYASVNPEYF.AADV.V.--DEW.VAREKITMSR...QGS..MV.E.VAKGVVK>
[ 646 ]

FIG.13D(ii)
```

```
                                                    RD
                                                    --
h Ins-R    YASSN.EYLSASD.-FPC-SV.V.--DEW.VSREKITLLR..QGS..MV.E.NAIIK.E>
[ 638 ]

*           *            400       *
Rtk-2      DHAQLVAIKTLKDYNNPQQWMEFQQEASIMAELHHPNIVCLLGAVTQEQPVCMLFEYINQ r trkB     QDKI...V......-ASDNARKD.HR..E.LTN.Q.EH..KFY.VCVEGD.LI.V...MKH>
[ 783 ]

500
h trk      .K-M...V.A..EASES-ARQD..R..E.LTM.Q.QH..RFF.VC.EGR.LL.V...MRH>
[ 779 ]

R                  300
                 --
h IGF-R    .EPET.....VNEAASMRERI..LN...V.K.FNCHHV.R...V.S.G..TLVIM.LMTR>
[ 646 ]

300
h Ins-R    AETR-..V..VNESASLRERI..LN...V.KGFTCHHV.R...V.SKG..TLVVM.LMAH>
[ 638 ]

FIG.13D(iii)
```

```
Rtk-2            GDLHEFLIMRSPHSDVGCSSDEDGTVKSSLDHGDFLHIAIQIAAGMEYLSSHFFVHKDLA
                                       450                         *
r trkB    600
[ 783 ]   ...NK..RAHG.DA-.--LMA.-.NPPTE.TQSQM....Q......V..A.QH...R...>
h trk                                                  600
[ 779 ]   ...NR..RSHG.DAKLL-AGG..-VAPGP.GL.QL.AV.S.V...V..AGLH...R...>
h IGF-R
[ 646 ]   ...KSY.--..LRPEM---ENNPVLAPP..--SKMIQM.GE..D..A..NANK...R...>
h Ins-R
[ 638 ]   ...KSY.--..LRPE---AENNP.RPPPT.-Q-EMIQM.AE..D..A..NAKK...R...>

Rtk-2            ARNILIGEQLHVKISDLGLSREIYSADYYRVQSKSLLPIRWMPPEAIMYGKFSSDSDIWS
                                       500                         *          700
r trkB
[ 783 ]   T..C.V..N.L...G.F.M..DV..T.....GGHTM.........S...R..TTE..V..>
h trk
[ 779 ]   T..C.V.QG.V...G.F.M..D...T.....GGRTM..............S.L.R..TTE..V..>
```

FIG.13D(iv)

```
h IGF-R    400
[ 646 ]    ...CMVA.DFT...G.F.MT.D..ET....KGG.G...V...S..SLKD.V.TTY..V..> h Ins-R    400
[ 638 ]    ...CMVAHDFT...G.F.MT.D..ET....KGG.G...V...A..SLKD.V.TTS..M..>

*        *              600
                                                                  *
Rtk-2      FGVVLWEIFSFGLQPYYGFSNQEVIEMVRKRQLLPCSEDCPPRMYSLMTECWNEIPSRRP

550                          *
                             *                                    *
r trkB     L..........TY.K..W.QL..N.....CITQGRV.QRPRT..QEV.E..LG..QRE.HT.K>
[ 783 ]

700
h trk              .........TY.K..W.QL..T.A.DCITQGRE.ERPRA...EV.AI.RG..QRE.QQ.H>
[ 779 ]

h IGF-R            .........ATLAE.....Q.L..EQ.LRF.MEGG..DKPDN..DMLFE..RM..QYN.KM..>
[ 646 ]                                                500 h Ins-R                                                500
[ 638 ]            .........T.LAE....Q.L..EQ.LKF.MDGGY.DQPDN..E.VTD..RM..QFN.NM..>
```

FIG.13D(v)

```
Rtk-2              RFKDIHVRLRSWEGLSSHTSSTTPSGGNATTQTTSLSASPVSNLSNPRYPNYMFPSQGIT r trkB  [ 783 ]    NI.N..TL.QN> h trk   [ 779 ]    SI..V.A..QA> h IGF-R [ 646 ]    S.LE.ISSIK> h Ins-R [ 638 ]    T.LE.-.N.LK-DD.>

Rtk-2              PQGQIAGFIGPPIPQNQRFIPINGYPIPPGYAAFPAAHYQPTGPPRVIQHCPPPKSRSPS

Rtk-2              SASGSTSTGHVTSLPSSGSNQEANIPLLPHMSIPNHPGGMGITVFGNKSQKPYKIDSKQA

Rtk-2              SLLGDANIHGHTESMISAEL
```

FIG. 13D(vi)

```
                    *         *         *         *        50         *
AAGGAGGTGGTTCTTCCACTGGAGTCTTGTTGTCAAGTTGGCCCCTCCCACAGCA
 G  G  G  F  F  H  W  S  L  V  C  Q  V  W  P  P  S  H  S>

*         *         *        100         *         *
AGTCCAGATACTCAGATGAGTATGAAGAAGATGGATTCTGTCAGCCATACAGAGGGATTG
 K  S  R  Y  S  D  E  Y  E  E  D  G  F  C  Q  P  Y  R  G  I>

*         *        150         *         *         *
CATGTGCAAGATTATTGGCAACCGTCTATATGGAGTCTTTGCACATGCAAGGGG
 A  C  A  R  F  I  G  N  R  T  V  Y  M  E  S  L  H  M  Q  G>

*         *        200         *         *         *
AAATAGAAAATCAGATCACAGCTGCCTTCACTATGATTGGCACTTCCAGTCACTTATCTG
 E  I  E  N  Q  I  T  A  A  F  T  M  I  G  T  S  S  H  L  S>

*        250         *         *         *        300         *
ATAAGTGTTCTCAGTTCGCCATTCCCTGTGCCACTATGCCTTCCCGTACTGCGATG
 D  K  C  S  Q  F  A  I  P  S  L  C  H  Y  A  F  P  Y  C  D>
```

FIG.14 A

```
AAACTTCATCCGTCCCAAAGCCCCGTGACTTGTGTCGCGATGAATGTGAAATCCTGGAGA
 E  T  S  S  V  P  K  P  R  D  L  C  R  D  E  C  E  I  L  E>

ATGTCCTGTGTCAAACAGAGTACATTTTGCAAGATCAAATCCCATGATTCTGATGAGC
 N  V  L  C  Q  T  E  Y  I  F  A  R  S  N  P  M  I  L  M  R>

TGAAACTGCCAAACTGTGAAGATCTCCCCAGCCAGAGCCCAGAAGCTGCGAACTGTA
 L  K  L  P  N  C  E  D  L  P  Q  P  E  S  P  E  A  A  N  C>

TCCGGATTGGAATTCCCATGGCAGATCCTATAAATAAAAATCACAAGTGTTATAACAGCA
 I  R  I  G  I  P  M  A  D  P  I  N  K  N  H  K  C  Y  N  S>

CAGGTGTGGACTACCGGGGGACCGTCAGTGTGACCAAATCAGGGGCGCCAGTGCCCAGCCAT
 T  G  V  D  Y  R  G  T  V  S  V  T  K  S  G  R  Q  C  Q  P>
```

FIG. 14B

```
GGAATTCCCAGTATCCCCACACACACTTTCACCGCCCTTCGTTCCCAGAGCTGAATG
 W  N  S  Q  Y  P  H  T  H  T  F  T  A  L  R  F  P  P  E  L  N>

GAGGCCATTCCTACTGCCGCAACCCAGGGAATCAAAAGGAAGCTCCCTGGTGCTTCACCT
 G  G  H  S  Y  C  R  N  P  G  N  Q  K  E  A  P  W  C  F  T>

TGGATGAAAACTTTAAGTCTGATCTGTGTGACATCCCAGCTTGCGATTCAAAGGATTCCA
 L  D  E  N  F  K  S  D  L  C  D  I  P  A  C  D  S  K  D  S>

AGGAGAAGAATAAAATGGAAATCCTGTACATACTAGTGCCAAGTGTGGCCATTCCCCTGG
 K  E  K  N  K  M  E  I  L  Y  I  L  V  P  S  V  A  I  P  L>

CCATTGCTTTACTCTTCTTCTTCATTTGCGTCTGTCGGAATAACCAGAAGTCATCGTCGG
 A  I  A  L  L  F  F  F  I  C  V  C  R  N  N  Q  K  S  S  S>
```

FIG.14C

```
CACCAGTCCAGAGGCAACCAAAACAGTCAGAGGTCAAAATGTGGAGATGTCAATGCTGA
 A  P  V  Q  R  Q  P  K  H  V  R  G  Q  N  V  E  M  S  M  L >

ATGCATATAAACCCAAGAGCAAGGCTAAAGAGCTACCTCTTTCTGCTGTACGCTTTATGG
 N  A  Y  K  P  K  S  K  A  K  E  L  P  L  S  A  V  R  F  M >

AAGAATTGGGTGTGAGTGTGCCTTTGGAAAAATCTATAAAGGCCATCTCTATCTCCCAGCA
 E  E  L  G  E  C  A  F  G  K  I  Y  K  G  H  L  Y  L  P  G >

TGGACCATGCTCAGCTGGTTGCTATCAAGACCTTGAAAGACTATAACAACCCCCAGCAAT
 M  D  H  A  Q  L  V  A  I  K  T  L  K  D  Y  N  N  P  Q  Q >

GGATGGAATTTCAACAAGAAGCCTCCCTAATGGCAGAACTGCACCACCCCAATATTGTCT
 W  M  E  F  Q  Q  E  A  S  L  M  A  E  L  H  H  P  N  I  V >
```

FIG. 14D

```
GCCTTCTAGGTGCCGTCACTCAGGAACAACCTGTGTGCATGCTTTTTGAGTATATTAATC
 C  L  L  G  A  V  T  Q  E  Q  P  V  C  M  L  F  E  Y  I  N>

AGGGGGATCTCCATGAGTTCCTCATCATGAGATCCCCACACTCTGATGTTGGCTGCAGCA
 Q  G  D  L  H  E  F  L  I  M  R  S  P  H  S  D  V  G  C  S>

GTGATGAAGATGGGACTGTGAAATCCAGCTCACTGGACCACGGAGATTTCTGCACATTGCAA
 S  D  E  D  G  T  V  K  S  S  L  D  H  G  D  F  L  H  I  A>

TTCAGATTGCAGCTGGCATGGAATACCTGTCTAGTCACTTCTTTGTCCACAAGGACCTTG
 I  Q  I  A  A  G  M  E  Y  L  S  S  H  F  F  V  H  K  D  L>

CAGCTCGCAATATTTTAATCGGAGAGCAACTTCATGTAAAGATTTCAGACTTGGGCTTT
 A  A  R  N  I  L  I  G  E  Q  L  H  V  K  I  S  D  L  G  L>
```

FIG.14E

```
                *              1550            *
CCAGAGAAATTACTCCGCTGATTACTACAGGGTCCAGAGTAAGTCCTTGCTGCCCATTC
 S  R  E  I  Y  S  A  D  Y  Y  R  V  Q  S  K  S  L  L  P  I>

*                *            1600            *
GCTGGATGCCCCCTGAAGCCATCATGTATGGCAAATTCTCTTCTGATTCAGATATCTGT
 R  W  M  P  P  E  A  I  M  Y  G  K  F  S  S  D  D  I  W>

*              1650            *
CCTTTGGGTGTGTCTCTTGTGGGAGATTTTCAGTTTTTGGACTCCAGCCATATTATGGATTCA
 S  F  G  V  V  L  W  E  I  F  S  F  G  L  Q  P  Y  Y  G  F>

*                *            1700            *
GTAACCAGGAAGTGATTGAGATGGTGAGAAAACGGCAGCTCTTACCATGCTCTGAAGACT
 S  N  Q  E  V  I  E  M  V  R  K  R  Q  L  L  P  C  S  E  D>

*              1750            *         1800    *
GCCCCACCCAGAATGTACAGCCTCATGACAGAGTGCTGGAATGAGATTCCTTCTAGGAGAC
 C  P  P  R  M  Y  S  L  M  T  E  C  W  N  E  I  P  S  R  R>
```

FIG.14F

```
                                                     *
CAAGAGATTAAAGATATTCACGTCCGGCTTCGGTCCTGGAGGACTCTCAAGTCACACAA
 P   R   F   K   D   I   H   V   R   L   R   S   W   E   G   L   S   S   H   T >

*
GCTCTACTACTCCCTTCAGGGGGAAATGCCACCACAGACAACCTCCCTCAGTGCCAGCC
 S   S   T   T   P   S   G   G   N   A   T   T   Q   T   T   S   L   S   A   S >

*
CAGTGAGTAATCTCAGTAACCCCAGAGATATCCTAATTACATGTTCCCGAGCCAGGGTATTA
 P   V   S   N   L   S   N   P   R   Y   P   N   Y   M   F   P   S   Q   G   I >

*
CACCACAGGGCCAGATTGCTGGTTTCATTGGCCCGCCAATACCTCAGAACCAGCGATTCA
 T   P   Q   G   Q   I   A   G   F   I   G   P   P   I   P   Q   N   Q   R   F >

*                   2100
TTCCCATCAATGGATACCCAATACCTCCTGGATATGCCAGCGTTTCCAGCTGCCCACTACC
 I   P   I   N   G   Y   P   I   P   P   G   Y   A   A   F   P   A   A   H   Y >
```

FIG.14G

```
AGCCACAGGTCCTCCCAGAGTGATTCAGCACTGCCCACCTCCCAAGAGTCGGTCCCAA
 Q  P  T  G  P  P  P  R  V  I  Q  H  C  P  P  P  K  S  R  S  P>

GCAGTGCCAGTGGGTCGACTAGCACTGGCCATGTGACTAGCTTGCCCTCATCAGGATCCA
 S  S  A  S  G  S  T  S  T  G  H  V  T  S  L  P  S  S  G  S>

ATCAGGAAGCAAATATTCCTTACTACCACATGTCAATTCCAAATCATCCTGGTGGAA
 N  Q  E  A  N  I  P  L  L  P  H  M  S  I  P  N  H  P  G  G>

TGGGTATCACCGTTTTTGGCAACAAATCTCAAAAACCTACAAAATTGACTCAAAGCAAG
 M  G  I  T  V  F  G  N  K  S  Q  K  P  Y  K  I  D  S  K  Q>

CATCTTTACTAGGAGACGCCAATATTCATGGACACACCGAATCTATGATTTCTGCAGAAC
 A  S  L  L  G  D  A  N  I  H  G  H  T  E  S  M  I  S  A  E>

FIG.14H
```

```
TGTAAAATGCACAACTTTTGTAAATGTGGTATACAGGACAAACTAGACGGGCCCGTAGAAAA
L>
GATTTATATTCAAATGTTTTATTAAAGTAAGGTTCTCATTTAGCAGACATCGCAACAAG

TACCTTCTGTGAAGTTCACTGTGTCTTACCAAGCAGGACACAGACACTCGGCCAGAAAAAA

GAAAAAAAAAAAAA
```

FIG. 14 I

```
TCGCCGCACTCGGACGTGGGAGCACCGATGATGACCGGTGAAGTCCGCCCTGGAG
 S  P  H  S  D  V  G  S  T  D  D  D  R  T  V  K  S  A  L  E>

CCCCCGACTTCGTGCACCTTGTGGCACAGATCGCGGGGATGGAGTACCTATCCAGC
 P  P  D  F  V  H  L  V  A  Q  I  A  A  G  M  E  Y  L  S  S>

CACCACGTGGTTCACAAGGACCTGGCCACCCGCAATGTGCTAGTGTACGACAAGCTGAAC
 H  H  V  V  H  K  D  L  A  T  R  N  V  L  V  Y  D  K  L  N>

GTGAAGATCTCAGACTTGGGCCTCTTCCGAGAGGTGTATGCCGCCGATTACTACAAGCTG
 V  K  I  S  D  L  G  L  F  R  E  V  Y  A  A  D  Y  Y  K  L>
```

FIG.15A

```
         250                          300
          *     *     *     *     *    *
CTGGGGAACTCGCTGCTGCCTATCCGCTGGATGGCCCCAGAGGCCATCATGTACGGCAAG
 L  G  N  S  L  L  P  I  R  W  M  A  P  E  A  I  M  Y  G  K >

350
          *     *      *    *     *     *
TTCTCCATCGACTTCAGAGACATCTGGTCCTACGGTGTCCTGTGGGAGGTCTTCAGCTAC
 F  S  I  D  S  D  I  W  S  Y  G  V  V  L  W  E  V  F  S  Y >

400
          *     *     *        *    *     *
GGCCTGCAGCCCTACTGCGGGGTATTCCAACCAGGATGTGGTGGAGATGATCCGGAACCGG
 G  L  Q  P  Y  C  G  Y  S  N  Q  D  V  V  E  M  I  R  N  R >

450
          *     *     *     *          *    *
CAGGTGCTGCCTTGCCCCGATGACTGTCCCGCTGTATGCCCTCATGATCGAGTGC
 Q  V  L  P  C  P  D  D  C  P  A  W  V  Y  A  L  M  I  E  C >
```

FIG.15B

```
                500                              *                              600
     *           *                *               *               *               *
TGGAACGAGTTCCCCAGCCGCTTCAAGGACATCCACAGCCGGCTCCGAGCC
 W  N  E  F  P  S  R  R  P  R  F  K  D  I  H  S  R  L  R  A>
                550                              *               *
     *           *                *               *               *
TGGGGCAACCTTTCCAACTACAACAGCTCGGCGCAGACCTCGGGGCCAGCAACACCACG
 W  G  N  L  S  N  Y  N  S  S  A  Q  T  S  G  A  S  N  T  T>
                                                                650
     *           *                *               *               *
CAGACCAGCTCCCTGAGCACCAGCCCAGTGAGCAATGTGAGCAACGCCCGTACGTGGGG
 Q  T  S  S  L  S  T  S  P  V  S  N  V  S  N  A  R  Y  V  G>
                                                 700
     *           *                *               *               *
CCCAAGCAGTTGGCCCCGCCCTTCCCACAGCCCAGTTCATCCCCATGAAGGGCCAGATC
 P  K  Q  L  A  P  P  F  P  Q  P  Q  F  I  P  M  K  G  Q  I>
                                                 750
     *           *                *               *
AGACCCATGGTGCCGGCCGCAGCTCTACATCCC
 R  P  M  V  P  A  P  Q  L  Y  I>

FIG.15C
```

```
Rtk-3        SPHSDVGSTDDDRTVKSALEPPDFVHLVAQIAAGMEYLSSHHVVHKDLATRNVLVYDKLN
                      *           *         *       *   *              *
                                            50                          *

Rtk-2       ..........S.E.G.....S.DHG..L.IAI...............FF......A..I.IGEQ.H>
[ 891 ]        C
                |
                |
r trkB                                  TE.TQSQML.IAQ......V..A.Q.F..R.......C..GEN.L>
[ 525 ]

h trk       G.DAKLLAGGE.-VAPGP.GLGQLLAVAS.V....V..AGL.F..R.......C..GQG.V>
[ 516 ]                                              600 h IGF-R             ENNP.LAPPSLSKMIQMAGE..D..A..NANKF..R....A..CM..AEDFT>
[ 466 ]                                                                400 h Ins-R     PEAENNPGRPPPTLQEMIQMA.E..D..A..NAKKF..R...A..CM..AHDFT>
[ 457 ]                                                          400
```

FIG.16A

```
              *         *         *         *         *         *
       VKISDLGLFREVYAADYYKLLGNSLLPIRWMAPEAIMYGKFSIDSDIWSYGVVLWEVFSY
Rtk-3

Rtk-2  .........S...I.S....RVQSK.........P.............S......F......I..F>
[891]         500                             100                 700 r trkB ...G.F.MS.D..ST...RVG.HTM.........P...S....R..TTE..V...L......I.T.>
[525]

h trk  ...G.F.MS.DI.ST...RVG.RTM.........P...S.L.R..TTE..V...F......I.T.>
[516]

h IGF-R ...G.F.MT.DI.ET...RKG.KG...V......S...SLKD.V.TTY..V...F......IATL>
[466]

h Ins-R ...G.F.MT.DI.ET...RKG.KG...V..........SLKD.V.TTS..M...F......IT.L>
[457]
```

FIG. 16B

```
Rtk-3           GLQPYCGYSNQDVVEMIRNRQVLPCDDCPAWVYALMIECWNEFPSRRPRFKDIHSRLRA
                                  *            *                  *             *

Rtk-2      [ 891 ]   .....Y.F...E.I..V.K..L...SE...PRM.S..T......I...........V....S> r trkB     [ 525 ]   .K..WYQL..NE.I.C.TQGR..QR.RT..QE..E..LG..QRE.HT.KNI.N...TL.Q> h trk      [ 516 ]   .K..WYQL..TEAIDC.TQGRE.ER.RA..PE....I.RG..QRE.QQ.HSI..V.A..Q.> h IGF-R    [ 466 ]   AE...Q.L..EQ.LRFVMEGGL.DK..N..DMLFE..RM..QYN.KM..S..LE.I.SIKE>
                                                                              N
                                                                              ─
                                                                              ─ h Ins-R    [ 457 ]   AE...Q.L..EQ.LKFVMDGGY.DQ..N..ER.TD..RM..-Q..NM..T.LE.VNL.K>
```

FIG.16C

```
                                   200
                   *    *    *      *      *      *      *                    *
Rtk-3              WGNLSNYNSSAQTSGASNTTQTSSLSTSPVSNVSNARYVGPKQLAPPFPQPQFIPMKGQI
Rtk-2              .EG..SHT..TTP..GNA....T...A.....L..P..PN-YMFPSQGIT..-GQIA.F.>
[ 891 ]
                                        F
                                        |
h IGF-R            -EMEPGFREVSYY.EENKLPEPEE.DLE.-E.MESVP-LD.SASSSSL.L.D--RHS.HK>
[ 466 ]

250
                        *
Rtk-3              RPMVPAPQLYI
Rtk-2              G.PI.QN.RF.>
[ 891 ]
h IGF-R            AENG.G.GVLV>
[ 466 ]
```

FIG.16D

FIG. 20A

```
470 —AMKYIQV- MNEIVTLNYL EPRTDYELCV QLVRPGEGGE GHPCPVRRFT TASIGLPPPR GLSLLPKSQT A-LNLTWQ-- -PIFTSSEDE FYVEVERWSQ    rTIE-2
489 MIT.SA.V.D PS.N...MN. K.R.G.NVR. ..S........ .AW..STLM. .DCPEPLLQ. WVESMNVEGP DR.RVS.SLP SVP-L.G.G .LLRL--DG    rTIE-1
489 TMD.ST.V.D PS.N...MN. R.K.G.SVR. ..S........ .AW..PTLM. .DCPEPLLQ. WLEGMHVEGT DR.RVS.SLP LVPGPLVG.G .LLRL--DG    hTIE-1
                                                            <--------------------------------------------FNIII 2

563 -QTRSDQQNI KVPGNLTSYL LNNLLPREQY SVRARVNTKA QQEWSEELRA WTLDDDSDILP PQPENIKITN ITDYTALVSW TIVDGYSISS IIIRYKVQCK   rTIE-2
585 ARGQERRE.. SS.QAR.A-. .TG.T.GTH. QLDV.LYHCT LLGPASPSAH VH.PL.G--. .A.RHLRAQA LS.SEIRLM. QHPEAPPG   P.SK.I.EI.    rTIE-1
587 TRGQERRE.V SS.QAR.A-. .TG.T.GTH. QLDVQLYHCT LLGPASPPAH VL.PP.G--. .A.RHLHAQA LS.SEIQLT. KHPEALPC   P.SK.V.EV.    hTIE-1
                                                                                                          FNIII 3

662 NEDQHIDVKI KNATIIQYQL KGLEPETTYH VDIFAENNIG SSNPAFSQ— EIRTLPAP-- --------- KDLGGGKMLL IAILGSAGMT CITVLLAFLI    rTIE-2
680 VAGGSC.PQW MDVDKPEETS TTVRGLNAST RYL.RVRASV QGLGDW.NTV .ET.GNGLQ SASPVQESRV AED.LDQQ.V L.VV..VSA. .L.I.A.L.A    rTIE-1
682 VAGGAG.PLW IDVDRPEETS TIIRGLNAST RYL.RMRASI QGLGDW.NTV .ES.GNGLQ AEGPVQESRA AEE.LDQQ.L L.VV..VSA. .L.I.A.L.T    hTIE-1
                                                          <------>                                           TM
                                                          FNIII 3

748 MLQLKRANVQ RRMAQAFQNV R-EEPAVQFN SGTLALNRKA KNNPDPTIYP VLDWNDIKFQ DVIGEGNFGQ VLKARIKKDG LRMDAAIKRM KEYASKDDHR   rTIE-2
  1                                                                                                              mTEK
780 LVCIR.SCLH ..HTFTY.SG SG.TIL.S.. ....T.T.RP .PQ.E.LS.. .E.E..T.E .L..... ......... .IR.M..... .K.N.....ML   ......EN...   rTIE-1
782 LVCIR.SCLH ..RTFTY.SG SG.TIL.S.. ....T.T.RP .LQ.E.LS.. .E.E..T.E .L..... ......... .IR.M..... .K.N.....ML   ......EN...   hTIE-1
     TM >                                                                                                 KINASE

847 DFAGELEVLC KLGHHPNIIN LLGACEHRGY LYLAIEYAPH GNLLDFLRKS RVLETDPAFA IANSTASTLS SQQLLHFAAD VARGMDYLSQ KQFIHRDLAA   rTIE-2
 45 ........  ..........  .......... ..........  .........  .......... .......... .......... .......... ..........   mTEK
880 ........  ..........  .......... .........Y ........   .......... REHG...... R..R.R.S.. A.N..Q..E. ..........   rTIE-1
882 ........  ...KN....  .......... .........Y ........   .......... REHG...... R..R.R.S.. A.N..Q..E. ..........   hTIE-1
    KINASE --------------------------------<--- INSERT -->X-------------------------------------------------- KINASE
```

FIG. 20B

```
     947 RNILVGENYI AKIADFGLSR GQEVYVKKTM GRLPVRMMAI ESLNYSVYTT NSDVWSYGVL LWEIVSLGGT PYCGMTCAEL YEKLPQGYRL EKPLNCDDEV  rTIE-2
     145 ................................................................................................... mTEK
     980 .V.....LA.S..........E........................................F..................................M..Q.R..  rTIE-1
     982 .V.....LA.S..........E........................................F................................A.M..Q.R..  hTIE-1
         .KINASE---------------------------------------------------------------------------------------------KINASE

1047 YDLMRQCWRE KPYERPSFAQ ILVSLNRMLE ERKTYVNTTL YEKFTYAGID CSAEEAA*  1103  rTIE-2
     245 ..............................................*                  301  mTEK
    1080 .E.......DR......P.......ALQ.G......A..A...MS..F.N.......AT....* 1135  rTIE-1
    1082 .E.......DR......P.......ALQ.G......A..A...MS..F.N.......AT....* 1137  hTIE-1
         .KINASE---------------->

FIG. 20C
```

SEQ ID NO. 100 and 101

```
GACCTCGTTCTGGGGTTTCT GAGACACAAGACACAGGAAA GTTCTGGATGCCCAGNCTAC CCTTGCAATCTGCTGTGCCT CCTCTGATCTGGGCTCTGCA GAGCCCACTTGGGTCCAAA GAGGAACTTGGGTCCAAGA    140

ACTGCACCTTCACTACCCGC CGGGATGTCCCTACCCACCC CCAGGAACCTCCTAGAGCA CCCTCCCCGTCCACAATCC CCCTCCCCCAAACTACAGCCT GAGCTCGGCTCTTGCCGCGC GCTCTCCTGGGCCCAAGTGA    280

ATAGTCCTAGCTCGACCGCG ACACGGTGGATACAATT CCCCTCGCCTCCAGCCCCA GGAGCTCTCCGGCGGCCCAG GCAGCATCGTCCCTCAAGC AGCCTGGACCCTCGTGCCCT    420

GCTCACGGGGCCTCGCCGG CGGGCCCCGGACTTCCC CTGCGGACCGGGTGGACGAG GAAGAGGAGGAGGAAGA AGAGGGCTTGGTTCAGGACC CCCACCCCACTAGGAACACC TGGCTTCCGTCGCCCA    560

CTTCTTTTTAAGGAGGAGAA GAGAACCAGCCAGAGCC ATG GGG GGC TGC GAA GTC CGG GAA TTT CTT TTG CAA TTT GGT TTC TTC CTG ACA GCT TGG ACC GGC GAC TGC    678
                                               M   G   G   C   E   V   R   E   F   L   L   Q   F   G   F   F   L   T   A   W   T   G   D   C     27
                                                                                                                                        •

AGT CAC GTC TCC AAC CAA GTT GTG CTG CTT GAT ACA TCT ACA GTG ATG GGA GAA CTA GGA GAA TGG AAA ACA TAT CCA CTG AAT GGG TGG GAT GCC ATT ACT GAA ATG GAT GAA   789
 S   H   V   S   N   Q   V   V   L   L   D   T   S   T   V   M   G   E   L   G   E   W   K   T   Y   P   L   N   G   W   D   A   I   T   E   M   D   E    64

CAC AAC AGG CCC ATA TAC CAG GTA TGC AAT GTC ATG GAA CCA AAC CAG AAC TGG CTT CGT ACT GCT CTT GAT GCT GCT CAG AAA ATC TAT GTG    900
 H   N   R   P   I   Y   Q   V   C   N   V   M   E   P   N   Q   N   W   L   R   T   A   L   D   A   A   Q   K   I   Y   V   101

GAA ATG AAG TTC ACA GGT AGA GAT TGT AAC AGC ATC CCA TGG GTC TTG GGA ACC AGT TTT ACT CAG GAC ATG GAT TTG GGT GAT CCT AAC ACT GAA GTT CCT GAG GTG    1011
 E   M   K   F   T   L   R   D   C   N   S   I   P   W   V   L   G   T   C   K   E   T   F   T   Q   D   M   D   L   G   D   P   N   T   E   V   R   E   V   138
                                •                                •

TTC AAC CCA AGC CAA AGG AAA GGA TTC TTT CAA GAT ATT GCT TTT CAA GAT ATT GGA GCA TGC ATT GCT CTG GTC TGA GTC CGT GTG TTC TAC AAA AAA TGC CCC TTC ACT GTG CGG AAC    1122
 F   N   P   S   Q   R   K   G   F   F   Q   D   I   A   F   Q   D   I   G   A   C   I   A   L   V   •   S   V   R   V   F   Y   K   K   C   P   F   T   V   R   N   175
                                                                                •

GGG CCA ATA GAA AGG AAA GGA TTC TTT CAA GAT ATT GCT TTT CAA GAT ATT GGA GCA TGC ATT GCT CTG GTC TGA GTC CGT GTG TTC TAC AAA AAA TGC CCC TTC ACT GTG CGG AAC    1233
 G   P   I   E   R   K   G   F   F   Q   D   I   A   F   Q   D   I   G   A   C   I   A   L   V   •   S   V   R   V   F   Y   K   K   C   P   F   T   V   R   N   212

TTG GCT ATG TTT CCG GAT ACC ATC CCA AGG GTT GAC TTC TCC TCT GTT GAC GTC CGG TCA TGC GTC AAG AGT TCT GAG GAG CCA GAT ACT CCT AAA CTC TAC TGT    1344
 L   A   M   F   P   D   T   I   P   R   V   D   S   S   S   L   V   E   V   R   G   S   C   V   K   S   S   E   E   R   D   T   P   K   L   Y   C   249
                                                                                                                        •
```

FIG. 21A

FIG. 21B

```
GAA TTT GAA AAA GAG ATT GAC CCT TCA AGA ATT CCC ATT GAG AGA GTC ATT GGA GCA GGT GAA TTT GGA GAA GTC TGC AGT GGG CGT TTA AAG ACA CCA GGG AAA AGG GGA  2565
 E   F   E   K   E   I   D   P   S   R   I   P   I   E   R   V   I   G   A   G   E   F   G   E   V   C   S   G   R   L   K   T   P   G   K   R   E    656

ATC CCA GTT GCC ATT AAA ACC TTG AAA GGT GGC CAT ATG GAC AGA GAT TTT CTA AGA GAA GCT ATC ATG GGT CAG TTT GAC CAC CCA AAC ATC CGC  2676
 I   P   V   A   I   K   T   L   K   G   G   H   M   D   R   D   F   L   R   E   A   I   M   G   Q   F   D   H   P   N   I   R    693

CTA GAA GGT GTT GTT ACT AAA AGA TCC TTC CCA GCC AAT GGG GTG GAA GCC TTC TGC CCC AGC TTC CTA AAT GCC ATC CAA GCA CCA CAT CCA GTC  2787
 L   E   G   V   V   T   K   R   S   F   P   A   N   G   V   E   A   F   C   P   S   F   L   N   A   I   Q   A   P   H   P   V    730

ACT GCA GGA TCT CTC CCC CCC AGG ATC CCT GCA GCC CGG CCA ATA ATC GTA GAG TAT ATG GAG AAT GGA TCT CTA GAC TCC TTT TTG CGG AAG CAC GAT GGC  2898
 T   A   G   S   L   P   P   R   I   P   A   A   R   P   I   I   V   E   Y   M   E   N   G   S   L   D   S   F   L   R   K   H   D   G    767

CAC TTC ACC GTC ATC CAG TTG GTC GGG ATG CTT CGG GGC ATT GCA TCA GGC ATG AAG TAT CTT TCC GAC ATG GGA TAC GTT CAT CGA GAC CTA GCT AGG AAC ATC TTG  3009
 H   F   T   V   I   Q   L   V   G   M   L   R   G   I   A   S   G   M   K   Y   L   S   D   M   G   Y   V   H   R   D   L   A   A   R   N   I   L    804

GTG AAC AGC AAC TTG GTA TGC AAA GTC TGT TCT GAT TTC GGC CTC TCA AGG GTC CTG GAA GAC GAT CCT GAA GCA GCT TAT ACA ACT TTT GGG AAA ATA CCT ATA AGC TGG  3120
 V   N   S   N   L   V   C   K   V   C   S   D   F   G   L   S   R   V   L   E   D   D   P   E   A   A   Y   T   T   T   F   G   G   K   I   P   I   R   W    841

ACA GCC CCA GAA GCT ATC GCC TAC AGG AAA TTC TCC TCA GCC AGT GAT GTC TGG AGC TAC GGC ATG CTC CTG CAC CAG CTC ATG CTC CAC ACG CTG GTG GAG AGG CCA TAC TGG GAA  3231
 T   A   P   E   A   I   A   Y   R   K   F   S   S   A   S   D   V   W   S   Y   G   M   L   L   H   Q   L   M   L   H   T   L   V   E   R   P   Y   W   E    878

ATG TCC AAC CAG CAG GAT GTT ATT TTA TCC ATT GAA GAA GGT TAC CGA CTT CCT GCT CCA CCG AGC CTT CAC ACG CTG ATT CGC AAG CCC TTG CAC CAG CTC TGC TGG CAG AAG GAG  3342
 M   S   N   Q   Q   D   V   I   L   S   I   E   E   G   Y   R   L   P   A   P   P   S   L   H   Q   L   I   R   K   P   L   H   C   W   Q   K   E    915

AGA AAC CAC AGG CCA AAA TTC ACT GAC ATC GTC AGC TTC CTG GAC AAA CTG CGC GAG GAC ATC CTC GTG TAAGATGCATAATGT  3456
 R   N   H   R   P   K   F   T   D   I   V   S   F   L   D   K   L   R   E   D   I   L   V   *                                  948

TGGTACTTTCTCCCCG ACAGTCACAATCGTTCAGGC TGCAGGCAAGAGGAACAGAT AGGGGGAACGACGACTTGCCTT AGTAGNTGTCCAATTATCAA CCCTCTATAACTCTTATCGG GTTCATTAGCTTCATCAGATT  3592

FIG.21C
```

SEQ ID NO. 102 and 103

```
CGAAAACATCATCTAGATT TAAGATGACTCGTCTCTCTTT AATCTCGTCCGTATCAGCAC TGAAGACTGAAAGGAACCT TCACCACCACTCCAACCCTG GTGGCACTTAAAAAAAAAA ATAACAGTTCTAAAAAAGAA    140

AGGGGGACCAAAAAACAGAA AAAGAAAGTCTTAAGAGCC CCTCTGAGAGACCCTTGACTC AGCCCACCCAGACGACCGTACT AGCCATCCCGAACTTCTAATT CATCTTATCCAACTGAAAGC                        280

GAGGGCGGCACAAGCCAGAA GCAAACTTCGCGGTCTCTG CGGATCTGTGATTCCCACAT TGAGAGGGGTCGAGAGCCAG CCGGCACAGACGACCCCACCAG GAGGAGGACTTCCGCGCCTC TCTCGCCCCCTTCCACCAGC    420

CTGAACCTTAGACTGAACCA CCCGGACGACTTAAGAGCAGA AGAGGGTAGTAGAAAA ATG CGG GGC TCC GGC CCC CGT GCG GGA CCG AGA CGG CAG CGG ACC CAG GGC CGG GGC GGC GAC           541
                                                          *   *   M   R   G   S   G   P   R   G   A   G   R   R   R   T   Q   G   R   G   G   G   D      22

ACC CCC CGC GTC CCT GCC TCT CTG GCA GGC TGC TAT TCC GCA GCT CTA AAG GGG CCC CTC TGG ACG TGC CTT CTC CTG TGT GCG CTG ACC CTT TTG GCC AGC CCC                652
 T   P   R   V   P   A   S   L   A   G   C   Y   S   A   A   L   K   G   P   L   W   T   C   L   L   L   C   A   A   L   R   T   L   L   A   S   P        59

AGT AAC GAA GTG AAT TTA TTG GAT TCG CGC ACT GTC CTG GGA GAC CTT GGA TGG ATT GCT TTT CCA AAG AAT GGG TGG GAA GAG ATT GGT GAA GTT GAT GAA AAC TAT GCC         763
 S   N   E   V   N   L   L   D   S   R   T   V   L   G   D   L   G   W   I   A   F   P   K   N   G   W   E   E   I   G   E   V   D   E   N   Y   A        96

CCC ATC CAC ACC TAT CAA GTC TGC AAA GTT ATG GAA CAG AAT CAA AAT TGG CTG TTG ACC AGT TGG ATC TCT AAC GAA GGT GCT TCC AGA ATT TTT ATT GAA CTC AAG              874
 P   I   H   T   Y   Q   V   C   K   V   M   E   Q   N   Q   N   W   L   L   T   S   W   I   S   N   E   G   A   S   R   I   F   I   E   L   K           133

TTT ACT CTG AGG GAT TGC AAC AGC CTT CCT GGA GGA CTG GGG ACT TGC GGG CTG GGT CTC AAG GAG AAG GAG ACC TTT AAC ATG TAT TAT TTT GAG AAT GGG AGA AAT ATC AAA GAC  985
 F   T   L   R   D   C   N   S   L   P   G   G   L   G   T   C   G   L   G   L   K   E   T   F   N   M   Y   Y   F   E   S   D   D   E   N   G   R   N   I   K   E  170

AAC CAG TAC ATC AAG ATC GAT ACC ATT GCT GCT GAT GAG AGC TTC ACC GAA CTT GAC CTT GGT GAT CGT GTC ATG AAG CTG AAT ACG GAG GTC AGA GAT GTA GGA CCT CTG         1096
 N   Q   Y   I   K   I   D   T   I   A   A   D   E   S   F   T   E   L   D   L   G   D   R   V   M   K   L   N   T   E   V   R   D   V   G   P   L        207

AGC AAA AAG GGA TAC ATC ACT GCT TTC TTC CAA GAT GTC GCT GCT ATC GCT CTG GTT TCT GTC GTC TAC TAT AAA AAA TGT CCT TCT GTA GTT AGA CAT TTG GCT GTT              1207
 S   K   K   G   Y   I   T   A   F   F   Q   D   V   A   A   I   A   L   V   S   V   V   Y   Y   K   K   C   P   S   V   V   R   H   L   A   V           244

TTC CCT GAC ACG ATC ACT GGA GCA GAC TCT TCC CAG CTG CTA GAG GTG TCC GGC TCC TGC GTC AAC CAT CTG ACA GAC GAT CCT CCC AAA ATG CAT TGC AGT GCT GAA              1318
 F   P   D   T   I   T   G   A   D   S   S   Q   L   L   E   V   S   G   S   C   V   N   H   S   V   T   D   D   P   P   K   M   H   C   S   A   E        281
```

```
CAA TAA ATG CTG GAT TGC TGG CAG AAA GAT CGC AAC AGC AGG CCC AAG TTT GAT GAC ATA GTC AAC ATG CTG GAT AAC CTG ATA CGA AAC CCA AGT AGT TTG AAG ACA CTG      3316
 Q   *   M   L   D   C   W   Q   K   D   R   N   S   R   P   K   F   D   D   I   V   N   M   L   D   K   L   I   R   N   P   S   S   L   K   T   L      947

GTC AAC GCC TCA AGC AGG GTA TCT ACT TTC TTG GCA GAA CAT GGA TCT TTG GGC TCT GGG GCC TAC AGA TCA GTA GGT GAA TGG CTA GAA GCA ACC AAA ATG GGC CGG TAC      3427
 V   N   A   S   S   R   V   S   T   L   L   A   E   H   G   S   L   G   S   G   A   Y   R   S   V   G   E   W   L   E   A   T   K   M   G   R   Y      984

ACA GAG ATT TTC ATG GAA AAT GGA TAC AGT TCA ATG GAC GCT GTG GCT CAG GTG ACC TTG GAG TGA GTAGTTT TTCTGATAATTTTTACATAG CTGTTGGGCCAAGAAAAGTA                 3540
 T   E   I   F   M   E   N   G   Y   S   S   M   D   A   V   A   Q   V   T   L   E   *                                                                  1004

TATTCAGACAACACAGTGAA TGCAATCAAGGGAAAACAGT TTACCTGTGTCCATATGTGT CAGTTCCAAAGAAGCCCTCA TCTTTTTTTAGCCTGTGCTG TTAACAGCTGCATGGTTCCT GCTTCTTGTGTCCAGAATCT       3680

TTGCTATTTGTTCACAAAC AGCACTTGAGAGTTTGGATA ATTGGATTACAACCCTTGGC AAAGTACTGGTACTTTGTGT TGTGAAAAAAAGACATTTC CTTGAGTTTTATACTGGTA CTTATGTTACATGAATGTAA         3820

ATATAAAACAAAACAAGCTG TAAGCACGAATTGGTGTGGTT AGTCTTGTGTAACAAAAACA TAAAAAGATTAAAAAAAAAA AAAAAA                                                             3906
```

FIG. 22D

Ehk-1    Ehk-2

Human ROR1

Sequence Range: 1 to 3358

```
         10         20         30         40         50         60
         *          *          *          *          *          *
GAGCTGGAGC AGCCGCCACC GCCGCCGCCG AGGGAGCCCC GGGACGGCAG CCCCTGGGCG 70         80         90        100        110        120
         *          *          *          *          *          *
CAGGGTGCGC TGTTCTCGGA GTCCGACCCA GGGCGACTCA CGCCCACTGG TGCGACCCGG 130        140        150        160        170        180
         *          *          *          *          *          *
ACAGCCTGGG ACTGACCCGC CGGCCCAGGC GAGGCTGCAG CCAGAGGGCT GGGAAGGGAT 190        200        210        220        230        240
         *          *          *          *          *          *
CGCGCTCGCG GCATCCAGAG GCGGCCAGGC GGAGGCGAGG GAGCAGGTTA GAGGGACAAA 250        260        270        280        290        300
         *          *          *          *          *          *
GAGCTTTGCA GACGTCCCCG GCGTCCTGCG AGCGCCAGCG GCCGGGACGA GGCGGCCGGG 310        320        330        340        350        360
         *          *          *          *          *          *
AGCCCGGGAA GAGCCCGTGG ATGTTCTGCG CGCGGCCTGG GAGCCGCCGC CGCCGCCGCC 370        380        390        400        410
         *          *          *          *          *
TCAGCGAGAG GAGGA ATG CAC CGG CCG CGC CGC CGC GGG ACG CGC CCG CCG
               M   H   R   P   R   R   R   G   T   R   P   P>

420        430        440        450
               *          *          *          *
CTC CTG GCG CTG CTG GCC GCG CTG CTG CTG GCC GCA CGC GGG GCT GCT
 L   L   A   L   L   A   A   L   L   L   A   A   R   G   A   A>

460        470        480        490        500
 *          *          *          *          *
GCC CAA GAA ACA GAG CTG TCA GTC AGT GCT GAA TTA GTG CCT ACC TCA
 A   Q   E   T   E   L   S   V   S   A   E   L   V   P   T   S>

510        520        530        540        550
 *          *          *          *          *
TCA TGG AAC ATC TCA AGT GAA CTC AAC AAA GAT TCT TAC CTG ACC CTT
 S   W   N   I   S   S   E   L   N   K   D   S   Y   L   T   L>

560        570        580        590        600
 *          *          *          *          *
GAT GAA CCA ATG AAT AAC ATC ACC ACG TCT CTG GGC CAG ACA GCA GAA
 D   E   P   M   N   N   I   T   T   S   L   G   Q   T   A   E>
```

FIG.26A

```
      610         620         630         640         650
       *     *     *     *     *     *     *     *     *     *
CTG CAC TGC AAA GTC TCT GGG AAT CCA CCT CCC ACC ATC CGC TGG TTC
 L   H   C   K   V   S   G   N   P   P   P   T   I   R   W   F>

660         670         680         690
       *     *     *     *     *     *     *     *     *
AAA AAT GAT GCT CCT GTG GTC CAG GAG CCC CGG AGG CTC TCC TTT CGG
 K   N   D   A   P   V   V   Q   E   P   R   R   L   S   F   R>

700         710         720         730         740
  *     *     *     *     *     *     *     *     *     *
TCC ACC ATC TAT GGC TCT CGG CTG CGG ATT AGA AAC CTC GAC ACC ACA
 S   T   I   Y   G   S   R   L   R   I   R   N   L   D   T   T>

750         760         770         780         790
  *     *     *     *     *     *     *     *     *     *
GAC ACA GGC TAC TTC CAG TGC GTG GCA ACA AAC GGC AAG GAG GTG GTT
 D   T   G   Y   F   Q   C   V   A   T   N   G   K   E   V   V>

800         810         820         830         840
       *     *     *     *     *     *     *     *     *
TCT TCC ACT GGA GTC TTG TTT GTC AAG TTT GGC CCC CCT CCC ACT GCA
 S   S   T   G   V   L   F   V   K   F   G   P   P   P   T   A>

850         860         870         880         890
       *     *     *     *     *     *     *     *     *     *
AGT CCA GGA TAC TCA GAT GAG TAT GAA GAA GAT GGA TTC TGT CAG CCA
 S   P   G   Y   S   D   E   Y   E   E   D   G   F   C   Q   P>

900         910         920         930
       *     *     *     *     *     *     *     *     *
TAC AGA GGG ATT GCA TGT GCA AGA TTT ATT GGC AAC CGC ACC GTC TAT
 Y   R   G   I   A   C   A   R   F   I   G   N   R   T   V   Y>

940         950         960         970         980
  *     *     *     *     *     *     *     *     *     *
ATG CAG TCT TTG CAC ATG CAA GGG GAA ATA GAA AAT CAG ATC ACA GCT
 M   Q   S   L   H   M   Q   G   E   I   E   N   Q   I   T   A>

990         1000        1010        1020        1030
  *     *     *     *     *     *     *     *     *     *
GCC TTC ACT ATG ATT GGC ACT TCC AGT CAC TTA TCT GAT AAG TGT TCT
 A   F   T   M   I   G   T   S   S   H   L   S   D   K   C   S>

1040        1050        1060        1070        1080
  *     *     *     *     *     *     *     *     *
CAG TTC GCC ATT CCT TCC CTG TGC CAC TAT GCC TTC CCG TAC TGC GAT
 Q   F   A   I   P   S   L   C   H   Y   A   F   P   Y   C   D>

1090        1100        1110        1120        1130
  *     *     *     *     *     *     *     *     *     *
GAA ACT TCA TCC GTC CCA AAG CCC CGT GAC TTG TGT CGC GAT GAA TGT
 E   T   S   S   V   P   K   P   R   D   L   C   R   D   E   C>
```

FIG.26B

```
            1140          1150          1160          1170
        *     *     *     *     *     *     *     *     *
        GAA ATC CTG GAG AAT GTC CTG TGT CAA ACA GAG TAC ATT TTT GCA AGA
         E   I   L   E   N   V   L   C   Q   T   E   Y   I   F   A   R>

1180          1190          1200          1210          1220
  *     *     *     *     *     *     *     *     *     *
  TCA AAT CCC ATG ATT CTG ATG AGG CTG AAA CTG CCA AAC TGT GAA GAT
   S   N   P   M   I   L   M   R   L   K   L   P   N   C   E   D>

1230          1240          1250          1260          1270
  *     *     *     *     *     *     *     *     *     *
  CTC CCC CAG CCA GAG AGC CCA GAA GCT GCG AAC TGT ATC CGG ATT GGA
   L   P   Q   P   E   S   P   E   A   A   N   C   I   R   I   G>

1280          1290          1300          1310          1320
            *     *     *     *     *     *     *     *     *
        ATT CCC ATG GCA GAT CCT ATA AAT AAA AAT CAC AAG TGT TAT AAC AGC
         I   P   M   A   D   P   I   N   K   N   H   K   C   Y   N   S>

1330          1340          1350          1360          1370
                *     *     *     *     *     *     *     *     *     *
            ACA GGT GTG GAC TAC CGG GGG ACC GTC AGT GTG ACC AAA TCA GGG CGC
             T   G   V   D   Y   R   G   T   V   S   V   T   K   S   G   R>

1380          1390          1400          1410
                    *     *     *     *     *     *     *     *
                CAG TGC CAG CCA TGG AAT TCC CAG TAT CCC CAC ACA CAC ACT TTC ACC
                 Q   C   Q   P   W   N   S   Q   Y   P   H   T   H   T   F   T>

1420          1430          1440          1450          1460
  *     *     *     *     *     *     *     *     *     *
  GCC CTT CGT TTC CCA GAG CTG AAT GGA GGC CAT TCC TAC TGC CGC AAC
   A   L   R   F   P   E   L   N   G   G   H   S   Y   C   R   N>

1470          1480          1490          1500          1510
  *     *     *     *     *     *     *     *     *     *
  CCA GGG AAT CAA AAG GAA GCT CCC TGG TGC TTC ACC TTG GAT GAA AAC
   P   G   N   Q   K   E   A   P   W   C   F   T   L   D   E   N>

1520          1530          1540          1550          1560
  *     *     *     *     *     *     *     *     *
  TTT AAG TCT GAT CTG TGT GAC ATC CCA GCT TGC GAT TCA AAG GAT TCC
   F   K   S   D   L   C   D   I   P   A   C   D   S   K   D   S>

1570          1580          1590          1600          1610
            *     *     *     *     *     *     *     *     *     *
        AAG GAG AAG AAT AAA ATG GAA ATC CTG TAC ATA CTA GTG CCA AGT GTG
         K   E   K   N   K   M   E   I   L   Y   I   L   V   P   S   V>

1620          1630          1640          1650
                *     *     *     *     *     *     *     *
            GCC ATT CCC CTG GCC ATT GCT TTA CTC TTC TTC TTC ATT TGC GTC TGT
             A   I   P   L   A   I   A   L   L   F   F   F   I   C   V   C>
```

FIG.26C

```
     1660          1670          1680          1690          1700
   *    *    *    *    *    *    *    *    *    *    *
  CGG  AAT  AAC  CAG  AAG  TCA  TCG  TCG  GCA  CCA  GTC  CAG  AGG  CAA  CCA  AAA
   R    N    N    Q    K    S    S    S    A    P    V    Q    R    Q    P    K>

1710          1720          1730          1740          1750
   *    *    *    *    *    *    *    *    *    *    *
  CAC  GTC  AGA  GGT  CAA  AAT  GTG  GAG  ATG  TCA  ATG  CTG  AAT  GCA  TAT  AAA
   H    V    R    G    Q    N    V    E    M    S    M    L    N    A    Y    K>

1760          1770          1780          1790          1800
   *    *    *    *    *    *    *    *    *    *
  CCC  AAG  AGC  AAG  GCT  AAA  GAG  CTA  CCT  CTT  TCT  GCT  GTA  CGC  TTT  ATG
   P    K    S    K    A    K    E    L    P    L    S    A    V    R    F    M>

1810          1820          1830          1840          1850
   *    *    *    *    *    *    *    *    *    *    *
  GAA  GAA  TTG  GGT  GAG  TGT  GCC  TTT  GGA  AAA  ATC  TAT  AAA  GGC  CAT  CTC
   E    E    L    G    E    C    A    F    G    K    I    Y    K    G    H    L>

1860          1870          1880          1890
   *    *    *    *    *    *    *    *    *
  TAT  CTC  CCA  GGC  ATG  GAC  CAT  GCT  CAG  CTG  GTT  GCT  ATC  AAG  ACC  TTG
   Y    L    P    G    M    D    H    A    Q    L    V    A    I    K    T    L>

1900          1910          1920          1930          1940
   *    *    *    *    *    *    *    *    *    *    *
  AAA  GAC  TAT  AAC  AAC  CCC  CAG  CAA  TGG  ATG  GAA  TTT  CAA  CAA  GAA  GCC
   K    D    Y    N    N    P    Q    Q    W    M    E    F    Q    Q    E    A>

1950          1960          1970          1980          1990
   *    *    *    *    *    *    *    *    *    *
  TCC  CCA  ATG  GCA  GAA  CTG  CAC  CAC  CCC  AAT  ATT  GTC  TGC  CTT  CTA  GGT
   S    P    M    A    E    L    H    H    P    N    I    V    C    L    L    G>

2000          2010          2020          2030          2040
   *    *    *    *    *    *    *    *    *    *
  GCC  GTC  ACT  CAG  GAA  CAA  CCT  GTG  TGC  ATG  CTT  TTT  GAG  TAT  ATT  AAT
   A    V    T    Q    E    Q    P    V    C    M    L    F    E    Y    I    N>

2050          2060          2070          2080          2090
   *    *    *    *    *    *    *    *    *    *
  CAG  GGG  GAT  CTC  CAT  GAG  TTC  CTC  ATC  ATG  AGA  TCC  CCA  CAC  TCT  GAT
   Q    G    D    L    H    E    F    L    I    M    R    S    P    H    S    D>

2100          2110          2120          2130
        *    *    *    *    *    *    *    *    *
  GTT  GGC  TGC  AGC  AGT  GAT  GAA  GAT  GGG  ACT  GTG  AAA  TCC  AGC  CTG  GAC
   V    G    C    S    S    D    E    D    G    T    V    K    S    S    L    D>

2140          2150          2160          2170          2180
   *    *    *    *    *    *    *    *    *    *    *
  CAC  GGA  GAT  TTT  CTG  CAC  ATT  GCA  ATT  CAG  ATT  GCA  GCT  GGC  ATG  GAA
   H    G    D    F    L    H    I    A    I    Q    I    A    A    G    M    E>
```

FIG.26D

```
      2190            2200           2210           2220           2230
       *        *      *       *      *       *      *       *      *       *
      TAC      CTG    TCT     AGT    CAC     TTC    TTT     GTC    CAC     AAG    GAC    CTT    GCA    GCT    CGC    AAT
       Y        L      S       S      H       F      F       V      H       K      D      L      A      A      R      N>

2240           2250           2260           2270           2280
       *        *      *       *      *       *      *       *      *       *
      ATT      TTA    ATC     GGA    GAG     CAA    CTT     CAT    GTA     AAG    ATT    TCA    GAC    TTG    GGG    CTT
       I        L      I       G      E       Q      L       H      V       K      I      S      D      L      G      L>

2290           2300           2310           2320           2330
       *        *      *       *      *       *      *       *      *       *
      TCC      AGA    GAA     ATT    TAC     TCC    GCT     GAT    TAC     TAC    AGG    GTC    CAG    AGT    AAG    TCC
       S        R      E       I      Y       S      A       D      Y       Y      R      V      Q      S      K      S>

2340           2350           2360           2370
       *        *      *       *      *       *      *       *      *
      TTG      CTG    CCC     ATT    CGC     TGG    ATG     CCC    CCT     GAA    GCC    ATC    ATG    TAT    GGC    AAA
       L        L      P       I      R       W      M       P      P       E      A      I      M      Y      G      K>

2380           2390           2400           2410           2420
       *        *      *       *      *       *      *       *      *       *
      TTC      TCT    TCT     GAT    TCA     GAT    ATC     TGG    TCC     TTT    GGG    GTT    GTC    TTG    TGG    GAG
       F        S      S       D      S       D      I       W      S       F      G      V      V      L      W      E>

2430           2440           2450           2460           2470
       *        *      *       *      *       *      *       *      *       *
      ATT      TTC    AGT     TTT    GGA     CTC    CAG     CCA    TAT     TAT    GGA    TTC    AGT    AAC    CAG    GAA
       I        F      S       F      G       L      Q       P      Y       Y      G      F      S      N      Q      E>

2480           2490           2500           2510           2520
       *        *      *       *      *       *      *       *      *       *
      GTG      ATT    GAG     ATG    GTG     AGA    AAA     CGG    CAG     CTC    TTA    CCA    TGC    TCT    GAA    GAC
       V        I      E       M      V       R      K       R      Q       L      L      P      C      S      E      D>

2530           2540           2550           2560           2570
       *        *      *       *      *       *      *       *      *       *
      TGC      CCA    CCC     AGA    ATG     TAC    AGC     CTC    ATG     ACA    GAG    TGC    TGG    AAT    GAG    ATT
       C        P      P       R      M       Y      S       L      M       T      E      C      W      N      E      I>

2580           2590           2600           2610
       *        *      *       *      *       *      *       *      *
      CCT      TCT    AGG     AGA    CCA     AGA    TTT     AAA    GAT     ATT    CAC    GTC    CGG    CTT    CGG    TCC
       P        S      R       R      P       R      F       K      D       I      H      V      R      L      R      S>

2620           2630           2640           2650           2660
       *        *      *       *      *       *      *       *      *       *
      TGG      GAG    GGA     CTC    TCA     AGT    CAC     ACA    AGC     TCT    ACT    ACT    CCT    TCA    GGG    GGA
       W        E      G       L      S       S      H       T      S       S      T      T      P      S      G      G>

2670           2680           2690           2700           2710
       *        *      *       *      *       *      *       *      *       *
      AAT      GCC    ACC     ACA    CAG     ACA    ACC     TCC    CTC     AGT    GCC    AGC    CCA    GTG    AGT    AAT
       N        A      T       T      Q       T      T       S      L       S      A      S      P      V      S      N>
```

FIG.26E

```
       2720         2730         2740         2750         2760
         *     *       *     *      *     *      *     *      *     *
CTC AGT AAC CCC AGA TAT CCT AAT TAC ATG TTC CCG AGC CAG GGT ATT
 L   S   N   P   R   Y   P   N   Y   M   F   P   S   Q   G   I>

2770         2780         2790         2800         2810
         *     *      *     *      *     *      *     *      *     *
ACA CCA CAG GGC CAG ATT GCT GGT TTC ATT GGC CCG CCA ATA CCT CAG
 T   P   Q   G   Q   I   A   G   F   I   G   P   P   I   P   Q>

2820         2830         2840         2850
         *     *      *     *      *     *      *     *      *
AAC CAG CGA TTC ATT CCC ATC AAT GGA TAC CCA ATA CCT CCT GGA TAT
 N   Q   R   I   I   P   I   N   G   Y   P   I   P   P   G   Y>

2860         2870         2880         2890         2900
   *     *      *     *      *     *      *     *      *     *
GCA GCG TTT CCA GCT GCC CAC TAC CAG CCA ACA GGT CCT CCC AGA GTG
 A   A   F   P   A   A   H   Y   Q   P   T   G   P   P   R   V>

2910         2920         2930         2940         2950
   *     *      *     *      *     *      *     *      *     *
ATT CAG CAC TGC CCA CCT CCC AAG AGT CGG TCC CCA AGC AGT GCC AGT
 I   Q   H   C   P   P   P   K   S   R   S   P   S   S   A   S>

2960         2970         2980         2990         3000
         *     *      *     *      *     *      *     *      *     *
GGG TCG ACT AGC ACT GGC CAT GTG ACT AGC TTG CCC TCA TCA GGA TCC
 G   S   T   S   T   G   H   V   T   S   L   P   S   S   G   S>

3010         3020         3030         3040         3050
         *     *      *     *      *     *      *     *      *     *
AAT CAG GAA GCA AAT ATT CCT TTA CTA CCA CAC ATG TCA ATT CCA AAT
 N   Q   E   A   N   I   P   L   L   P   H   M   S   I   P   N>

3060         3070         3080         3090
         *     *      *     *      *     *      *     *      *
CAT CCT GGT GGA ATG GGT ATC ACC GTT TTT GGC AAC AAA TCT CAA AAA
 H   P   G   G   M   G   I   T   V   F   G   N   K   S   Q   K>

3100         3110         3120         3130         3140
   *     *      *     *      *     *      *     *      *     *
CCC TAC AAA ATT GAC TCA AAG CAA GCA TCT TTA CTA GGA GAC GCC AAT
 P   Y   K   I   D   S   K   Q   A   S   L   L   G   D   A   N>

3150         3160         3170         3180         3190
   *     *      *     *      *     *      *     *      *
ATT CAT GGA CAC ACC GAA TCT ATG ATT TCT GCA GAA CTG TAA A
 I   H   G   H   T   F   S   M   I   S   A   E   L   *>

3200         3210         3220         3230         3240         3250
         *     *      *     *      *     *      *     *      *     *      *     *
AIGCACAACT TTTGTAAATG TGGTATACAG GACAAACTAG ACGGCCGTAG AAAAGATTTA 3260         3270         3280         3290         3300         3310
         *     *      *     *      *     *      *     *      *     *      *     *
TATTCAAATC TTTTTATTAA AGTAAGGTTC TCATTTAGCA GACATCGCAA CAAGTACCTT
```

FIG.26F

```
       3320       3330       3340       3350
   *    *     *    *     *    *     *    *     *
CTGTGAAGTT TCACTGTGTC TTACCAAGCA GGACAGACAC TCGGCCAG
```

FIG.26G

HUMAN ROR2

Sequence Range: 1 to 4092

```
             10          20          30          40          50          60
          *    *       *    *      *    *      *    *       *    *      *    *
      AGCCAGCCCT TGCCGTGGCC GGAGCCGAGC GGCGCATCCG GGCCGGAGAA GAGGACGACG 70          80          90         100         110         120
          *    *       *    *      *    *      *    *       *    *      *    *
      ACGAGGTCCT CGAAGTGGAC CCGTTTGCGA AGCGCCAGGG AGAAGGAGGA GCGGACGCAT 130         140         150         160         170         180
         *    *       *    *      *    *      *    *       *    *      *    *
      CGTAGAAAGG GGTGGTGGCG CCCGACCCCG CGCCCCGGCC CGAAGCTCTG AGGGCTTCCC 190         200         210         220         230
         *    *       *    *      *    *      *    *       *    *
      GGCCCCCACT GCCTGCGGC ATG GCC CGG GGC TCG GCG CTC CCG CGG CGG CCG
                              M   A   R   G   S   A   L   P   R   R   P>

240         250         260         270         280
          *    *      *    *      *    *      *    *      *    *       *
      CTG CTG TGC ATC CCG GCC GTC TGG GCG GCC GCC GCG CTT CTG CTC TCA
       L   L   C   I   P   A   V   W   A   A   A   A   L   L   L   S>

290         300         310         320
            *    *      *    *      *    *      *    *      *
      GTG TCC CGG ACT TCA GGT GAA GTG GAG GTT CTG GAT CCG AAC GAC CCT
       V   S   R   T   S   G   E   V   E   V   L   D   P   N   D   P>

330        340         350         360         370
        *      *    *      *    *      *    *      *    *      *
      TTA GCA CCC CTT GAT GGG CAG GAC GGC CCG ATT CCA ACT CTG AAA GGT
       L   G   P   L   D   G   Q   D   G   P   I   P   T   L   K   G>

380         390         400         410         420
           *      *    *      *    *      *    *      *    *      *
      TAC TTT CTG AAT TTT CTG GAG CCA GTA AAC AAT ATC ACC ATT GTC CAA
       Y   F   L   N   F   L   E   P   V   N   N   I   T   I   V   Q>

430         440         450         460         470
        *    *      *    *      *    *      *    *      *    *      *
      GGC CAG ACG GCA ATT CTG CAC TGC AAG GTG GCA GGA AAC CCA CCC CCT
       G   Q   T   A   I   L   H   C   K   V   A   G   N   P   P   P>
            480         490         500         510         520
          *    *      *    *      *    *     ,*    *      *    *      *
      AAC GTG CGG TGG CTA AAG AAT GAT GCC CCG GTG GTG CAG GAG CCG CGG
       N   V   R   W   L   K   N   D   A   P   V   V   Q   E   P   R>

530         540         550         560
            *    *      *    *      *    *      *    *      *
      CGG ATC ATC ATC CGG AAG ACA GAA TAT GGT TCA CGA CTG CGA ATC CAG
       R   I   I   I   R   K   T   E   Y   G   S   R   L   R   I   Q>
```

FIG.27A

```
 570         580         590         600         610
  *     *    *     *    *     *     *     *    *     *
GAC CTG GAC ACG ACA GAC ACT GGC TAC TAC CAG TGC GTG GCC ACC AAC
 D   L   D   T   T   D   T   G   Y   Y   Q   C   V   A   T   N>

620         630         640         650         660
  *     *    *     *    *     *     *     *    *     *
GGG ATG AAG ACC ATT ACC GCC ACT GGC GTC CTG TTT GTG CGG CTG GGT
 G   M   K   T   I   T   A   T   G   V   L   F   V   R   L   G>

670         680         690         700         710
  *    *    *     *    *     *    *     *    *     *
CCA ACG CAC AGC CCA AAT CAT AAC TTT CAG GAT GAT TAC CAC GAG GAT
 P   T   H   S   P   N   H   N   F   Q   D   D   Y   H   E   D>

720         730         740         750         760
  *    *    *     *    *     *    *     *    *     *
GGG TTC TGC CAG CCT TAC CGG GGA ATT GCC TGT GCA CGC TTC ATT GGC
 G   F   C   Q   P   Y   R   G   I   A   C   A   R   F   I   G>

770         780         790         800
  *    *    *     *    *     *    *     *    *
AAC CGG ACC ATT TAT GTG GAC TCG CTT CAG ATG CAG GGG GAG ATT GAA
 N   R   T   I   Y   V   D   S   L   Q   M   Q   G   E   I   E>

810         820         830         840         850
  *    *     *    *    *     *    *     *     *    *
AAC CGA ATC ACA GCG GCC TTC ACC ATG ATC GGC ACG TCT ACG CAC CTG
 N   R   I   T   A   A   F   T   M   I   G   T   S   T   H   L>

860         870         880         890         900
  *    *     *    *    *     *    *     *     *
TCG GAC CAG TGC TCA CAG TTC GCC ATC CCA TCC TTC TGC CAC TTC GTG
 S   D   Q   C   S   Q   F   A   I   P   S   F   C   H   F   V>

910         920         930         940         950
  *    *    *     *    *     *    *     *    *     *
TTT CCT CTG TGC GAC GCG CGC TCC CGG GCA CCC AAG CCG CGT GAG CTG
 F   P   L   C   D   A   R   S   R   A   P   K   P   R   E   L>

960         970         980         990        1000
  *    *    *     *    *     *    *     *    *     *
TGC CGC GAC GAG TGC GAG GTG CTG GAG AGC GAC CTG TGC CGC CAG GAG
 C   R   D   E   C   E   V   L   E   S   D   L   C   R   Q   E>

1010        1020        1030        1040
  *        *    *     *    *     *    *     *    *
TAC ACC ATC GCC CGC TCC AAC CCG CTC ATC CTC ATG CGG CTT CAG CTG
 Y   T   I   A   R   S   N   P   L   I   L   M   R   L   Q   L>

1050        1060        1070        1080        1090
  *    *     *    *    *     *    *     *    *     *
CCC AAG TGT GAG GCG CTG CCC ATG CCT GAG AGC CCC GAC GCT GCC AAC
 P   K   C   E   A   L   P   M   P   E   S   P   D   A   A   N>
```

FIG. 27B

```
      1100          1110         1120          1130         1140
        *             *            *             *            *
TGC ATG CGC ATT GGC ATC CCA GCC GAG AGG CTG GGC CGC TAC CAT CAG
 C   M   R   I   G   I   P   A   E   R   L   G   R   Y   H   Q>

1150         1160          1170         1180          1190
  *      *     *      *      *      *     *      *     *      *
TGC TAT AAC GGC TCA GGC ATG GAT TAC AGA GGA ACG GCA AGC ACC ACC
 C   Y   N   G   S   G   M   D   Y   R   G   T   A   S   T   T>

1200          1210         1220          1230         1240
   *      *      *      *     *      *      *      *     *      *
AAG TCA GGC CAC CAG TGC CAG CCG TGG GCC CTG CAG CAC CCC CAC AGC
 K   S   G   H   Q   C   Q   P   W   A   L   Q   H   P   H   S>

1250         1260          1270         1280
    *      *      *     *      *      *     *      *      *
CAC CAC CTG TCC AGC ACA GAC TTC CCT GAG CTT GGA GGG GGG CAC GCC
 H   H   L   S   S   T   D   F   P   E   L   G   G   G   H   A>

1290         1300          1310         1320          1330
  *     *      *      *     *      *      *      *     *      *
TAC TGC CGG AAC CCC GGA GGC CAG ATG GAG GGC CCC TGG TGC TTT ACG
 Y   C   R   N   P   G   G   Q   M   E   G   P   W   C   F   T>

1340         1350          1360         1370          1380
    *     *      *     *      *      *      *     *      *
CAG AAT AAA AAC GTA CGC ATG GAA CTG TGT GAC GTA CCC TCG TGT AGT
 Q   N   K   N   V   R   M   E   L   C   D   V   P   S   C   S>

1390          1400         1410          1420          1430
  *      *     *      *     *      *      *      *     *      *
CCC CGA GAC AGC AGC AAG ATG GGG ATT CTG TAC ATC TTG GTC CCC AGC
 P   R   D   S   S   K   M   G   I   L   Y   I   L   V   P   S>

1440          1450         1460          1470          1480
    *      *      *      *     *      *      *      *     *      *
ATC CCA ATT CCA CTG GTC ATC GCT TGC CTT TTC TTC TTG GTT TGC ATG
 I   A   I   P   L   V   I   A   C   L   F   F   L   V   C   M>

1490         1500          1510          1520
    *      *      *      *     *      *      *      *     *
TGC CGG AAT AAG CAG AAG GCA TCT GCG TCC ACA CCG CAG CGG CGA CAG
 C   R   N   K   Q   K   A   S   A   S   T   P   Q   R   R   Q>

1530         1540          1550          1560          1570
  *     *      *      *     *      *      *      *     *      *
CTG ATG GCC TCG CCC AGC CAA GAC ATG GAA ATG CCC CTC ATT AAC CAG
 L   M   A   S   P   S   Q   D   M   E   M   P   L   I   N   Q>

1580         1590          1600          1610          1620
    *     *      *      *     *      *      *      *     *      *
CAC AAA CAG GCC AAA CTC AAA GAG ATC AGC CTG TCT GCG GTG AGG TTC
 H   K   Q   A   K   L   K   E   I   S   L   S   A   V   R   F>
```

FIG.27C

```
       1630         1640         1650         1660         1670
   *     *     *     *     *     *     *     *     *     *
 ATG GAG GAG CTG GGA GAG GAC CGG TTT GGG AAA GTC TAC AAA GGT CAC
  M   E   E   L   G   E   D   R   F   G   K   V   Y   K   G   H>

1680         1690         1700         1710         1720
      *     *     *     *     *     *     *     *     *     *
 CTG TTC GGC CCT GCC CCG GGG GAG CAG ACC CAG GCT GTG GCC ATC AAA
  L   F   G   P   A   P   G   E   Q   T   Q   A   V   A   I   K>

1730         1740         1750         1760
        *     *     *     *     *     *     *     *     *
 ACG CTG AAG GAC AAA GCG GAG GGG CCC CTG CGG GAG GAG TTC CGG CAT
  T   L   K   D   K   A   E   G   P   L   R   E   E   F   R   H>

1770         1780         1790         1800         1810
   *     *     *     *     *     *     *     *     *     *
 GAG GCT ATG CTG CGA GCA CGG CTG CAA CAC CCC AAC GTC GTC TGC CTG
  E   A   M   L   R   A   R   L   Q   H   P   N   V   V   C   L>

1820         1830         1840         1850         1860
   *     *     *     *     *     *     *     *     *     *
 CTG GGC GTG GTG ACC AAG GAC CAG CCC CTG AGC ATG ATC TTC AGC TAC
  L   G   V   V   T   K   D   Q   P   L   S   M   I   F   S   Y>

1870         1880         1890         1900         1910
     *     *     *     *     *     *     *     *     *     *
 TGT TCG CAC GGC GAC CTC CAC GAA TTC CTG GTC ATG CGC TCG CCG CAC
  C   S   H   G   D   L   H   E   F   L   V   M   R   S   P   H>

1920         1930         1940         1950         1960
     *     *     *     *     *     *     *     *     *     *
 TCG GAC GTG GGC AGC ACC GAT GAT GAC CGC ACG GTG AAG TCC GCC CTG
  S   D   V   G   S   T   D   D   D   R   T   V   K   S   A   L>

1970         1980         1990         2000
      *     *     *     *     *     *     *     *     *
 GAG CCC CCC GAC TTC GTG CAC CTT GTG GCA CAG ATC GCG GCG GGG ATG
  E   P   P   D   F   V   H   L   V   A   Q   I   A   A   G   M>

2010         2020         2030         2040         2050
    *     *     *     *     *     *     *     *     *     *
 GAG TAC CTA TCC AGC CAC CAC GTG GTT CAC AAG GAC CTG GCC ACC CGC
  E   Y   L   S   S   H   H   V   V   H   K   D   L   A   T   R>

2060         2070         2080         2090         2100
      *     *     *     *     *     *     *     *     *     *
 AAT GTG CTA GTG TAC GAC AAG CTG AAC GTG AAG ATC TCA GAC TTG GGC
  N   V   L   V   Y   D   K   L   N   V   K   I   S   D   L   G>

2110         2120         2130         2140         2150
   *     *     *     *     *     *     *     *     *     *
 CTC TTC CGA GAG GTG TAT GCC GCC GAT TAC TAC AAG CTG CTG GGG AAC
  L   F   R   E   V   Y   A   A   D   Y   Y   K   L   L   G   N>
```

FIG.27D

```
         2160        2170        2180        2190        2200
    *     *     *     *     *     *     *     *     *     *
   TCG   CTG   CTG   CCT   ATC   CGC   TGG   ATG   GCC   CCA   GAG   GCC   ATC   ATG   TAC   GGC
    S     L     L     P     I     R     W     M     A     P     E     A     I     M     Y     G>

2210        2220        2230        2240
    *     *     *     *     *     *     *     *     *
   AAG   TTC   TCC   ATC   GAC   TCA   GAC   ATC   TGG   TCC   TAC   GGT   GTG   GTC   CTG   TGG
    K     F     S     I     D     S     D     I     W     S     Y     G     V     V     L     W>

2250        2260        2270        2280        2290
    *     *     *     *     *     *     *     *     *     *
   GAG   GTC   TTC   AGC   TAC   GGC   CTG   CAG   CCC   TAC   TGC   GGG   TAC   TCC   AAC   CAG
    E     V     F     S     Y     G     L     Q     P     Y     C     G     Y     S     N     Q>

2300        2310        2320        2330        2340
    *     *     *     *     *     *     *     *     *
   GAT   GTG   GTG   GAG   ATG   ATC   CGG   AAC   CGG   CAG   GTG   CTG   CCT   TGC   CCC   GAT
    D     V     V     E     M     I     R     N     R     Q     V     L     P     C     P     D>

2350        2360        2370        2380        2390
    *     *     *     *     *     *     *     *     *     *
   GAC   TGT   CCC   GCC   TGG   GTG   TAT   GCC   CTC   ATG   ATC   GAG   TGC   TGG   AAC   GAG
    D     C     P     A     W     V     Y     A     L     M     I     E     C     W     N     E>

2400        2410        2420        2430        2440
    *     *     *     *     *     *     *     *     *     *
   TTC   CCC   AGC   CGG   CGG   CCC   CGC   TTC   AAG   GAC   ATC   CAC   AGC   CGG   CTC   CGA
    F     P     S     R     R     P     R     F     K     D     I     H     S     R     L     R>

2450        2460        2470        2480
    *     *     *     *     *     *     *     *     *
   GCC   TGG   GGC   AAC   CTT   TCC   AAC   TAC   AAC   AGC   TCG   GCG   CAG   ACC   TCG   GGG
    A     W     G     N     L     S     N     Y     N     S     S     A     Q     T     S     G>

2490        2500        2510        2520        2530
    *     *     *     *     *     *     *     *     *     *
   GCC   TGG   AAC   ACC   ACG   CAG   ACC   AGC   TCC   CTG   AGC   ACC   AGC   CCA   GTG   AGC
    A     S     N     T     T     Q     T     S     S     L     S     T     S     P     V     S>

2540        2550        2560        2570        2580
    *     *     *     *     *     *     *     *     *
   AAT   GTG   AGC   AAC   GCC   CGC   TAC   GTG   GGG   CCC   AAG   CAG   AAG   GCC   CCG   CCC
    N     V     S     N     A     R     Y     V     G     P     K     Q     K     A     P     P>

2590        2600        2610        2620        2630
    *     *     *     *     *     *     *     *     *     *
   TTC   CCA   CAG   CCC   CAG   TTC   ATC   CCC   ATG   AAG   GGC   CAG   ATC   AGA   CCC   ATG
    F     P     Q     P     Q     F     I     P     M     K     G     Q     I     R     P     M>

2640        2650        2660        2670        2680
    *     *     *     *     *     *     *     *     *     *
   GTG   CCC   CCG   CCG   CAG   CTC   TAC   GTC   CCC   GTC   AAC   GGC   TAC   CAG   CCG   GTG
    V     P     P     P     Q     L     Y     V     P     V     N     G     Y     Q     P     V>
```

FIG.27E

```
         2690          2700         2710          2720
        *    *    *    *    *    *    *    *    *    *
CCG GCC TAT GGG GCC TAC CTG CCC AAC TTC TAC CCG GTG CAG ATC CCA
 P   A   Y   G   A   Y   L   P   N   F   Y   P   V   Q   I   P>

2730          2740         2750          2760         2770
  *    *    *    *    *    *    *    *    *    *    *
ATG CAG ATG GCC CCG CAG CAG GTG CCT CCT CAG ATG GTC CCC AAG CCC
 M   Q   M   A   P   Q   Q   V   P   P   Q   M   V   P   K   P>

2780         2790         2800          2810         2820
   *    *    *    *    *    *    *    *    *    *
AGC TCA CAC CAC AGT GGC AGT GGC TCC ACC AGC ACA GGC TAC GTC ACC
 S   S   H   H   S   G   S   G   S   T   S   T   G   Y   V   T>

2830         2840         2850          2860         2870
  *    *    *    *    *    *    *    *    *    *
ACG GCC CCC TCC AAC ACA TCC ATG GCA GAC AGG GCA GCC CTG CTC TCA
 T   A   P   S   N   T   S   M   A   D   R   A   A   L   L   S>

2880         2890          2900         2910         2920
        *    *    *    *    *    *    *    *    *    *
GAG GGC GCT GAT GAC ACA CAG AAC GCC CCA GAA GAT GGG GCC CAG AGC
 E   G   A   D   D   T   Q   N   A   P   E   D   G   A   Q   S>

2930         2940         2950          2960
        *    *    *    *    *    *    *    *    *
ACC GTG CAG GAA GCA GAG GAG GAG GAG GAA GGC TCT GTC CCA GAG ACT
 T   V   Q   E   A   E   E   E   E   E   G   S   V   P   E   T>

2970         2980          2990         3000         3010
  *    *    *    *    *    *    *    *    *    *    *
GAG CTG CTG GGG GAC TGT GAC ACT CTG CAG GTG GAC GAG GCC CAA GTC
 E   L   L   G   D   C   D   T   L   Q   V   D   E   A   Q   V>

3020         3030         3040          3050         3060         3070
   *    *    *    *    *    *    *    *    *    *    *    *
CAG CTG GAA GCT TGA GTGGCACCA GGGCCCGGGG TTCGGGGATA GAAGCCCCGC
 Q   L   E   A   *>

3080         3090         3100          3110         3120         3130
        *    *    *    *    *    *    *    *    *    *    *    *
CGAGACCCCA CAGGGACCTC AGTCACCTTT GAGAAGACAC CATACTCAGC AATCACAAGA 3140         3150         3160         3170         3180         3190
   *    *    *    *    *    *    *    *    *    *    *    *
GCCCGCCGGC CAGTGGGCTT GTTTGCAGAC TGGGTGAGGT GGAGCCCTGC TCCTCTCTGT 3200         3210         3220         3230         3240         3250
   *    *    *    *    *    *    *    *    *    *    *    *
CCTCTGACAC AGAGAGCTGC CCTGCCTAGG AGCACCCAAG CCAGGCAGGG GGTCTGGCAG 3260         3270         3280         3290         3300         3310
   *    *    *    *    *    *    *    *    *    *    *    *
CACGCCGTCC TGGGGAGCAG GACACATGGT CATCCCCAGG GCTGTATACA TTGATTCTGG
```

FIG.27F

```
        3320       3330       3340       3350       3360       3370
      *    *     *    *     *    *     *    *     *    *     *    *
   TGGTAGACTG GTAGTGAGCA GCAAATGCCT TTCAAGAAAA TAGGTGGCAG CTTCACTCCA 3380       3390       3400       3410       3420       3430
      *    *     *    *     *    *     *    *     *    *     *    *
   TGTCATATAT GGAGTGAATA TTTCAAAACG TTGGGAATAA GGGCCTGCAA AAGGCAGCGA 3440       3450       3460       3470       3480       3490
      *    *     *    *     *    *     *    *     *    *     *    *
   GGAGGCACCT CGGGTCTTGA GGTTCCTGAC AACCGATCTG GTCTGTTGGT TTGAGGATGA 3500       3510       3520       3530       3540       3550
      *    *     *    *     *    *     *    *     *    *     *    *
   AGGGGCTCCA TTTCTGCTGC CTCCCTGCTG AGAATATTCT CCCTTTAGCA GCCAAAGATT 3560       3570       3580       3590       3600       3610
      *    *     *    *     *    *     *    *     *    *     *    *
   CGCTGGAACG GAGGCTGCCC TCTGCTGCCT GTTGGGGTCG GAAGACAAGG GGCTTCTGAA 3620       3630       3640       3650       3660       3670
      *    *     *    *     *    *     *    *     *    *     *    *
   ATGGGAGTTC CTGAGATACA ACAAAATGTG TGCCTTCAAA GAAACTGACA GCTTTGTATT 3680       3690       3700       3710       3720       3730
      *    *     *    *     *    *     *    *     *    *     *    *
   TGGTGAAATG GTTTTAATTA TACTCCATGT GTATTTTGCC CACTTTTTTT GGGAATTCAA 3740       3750       3760       3770       3780       3790
      *    *     *    *     *    *     *    *     *    *     *    *
   GGGAAAGTGT TTCTTGGGTT TGGAATGTTC AGAGGAAGCA GTATTGTACA GAACACGGTA 3800       3810       3820       3830       3840       3850
      *    *     *    *     *    *     *    *     *    *     *    *
   TTGTTATTTT TGTTAAGAAT CATGTACAGA GCTTAAATGT AATTTATATG TTTTTAATAT 3860       3870       3880       3890       3900       3910
      *    *     *    *     *    *     *    *     *    *     *    *
   GCCATTTTCA TTGAAGTATT TTGGTCTTAA GATGACTTTA GTAATTTAAC TGTTTATGTT 3920       3930       3940       3950       3960       3970
      *    *     *    *     *    *     *    *     *    *     *    *
   ACCCACGTTG GGATCCAGTT GGTCTTGGTT TGCTTCTCTC TGTACCACGT GCACATGAGG 3980       3990       4000       4010       4020       4030
      *    *     *    *     *    *     *    *     *    *     *    *
   TCCATTCATT TTACAGCCCC TGTTACACAC AGACCCACAG GCAGCCGTCT GTGCCCGCAC 4040       4050       4060       4070       4080       4090
      *    *     *    *     *    *     *    *     *    *     *    *
   ACATTGTTGG TCCTATTTGT AAATCCCACA CCCGGTGTAT CCAATAAAGT GAAACCAACC
   CC
```

FIG.27G

SEQUENCE LISTING ( 1 ) GENERAL INFORMATION:

( i i i ) NUMBER OF SEQUENCES: 107

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: modified_base
        ( B ) LOCATION: 14
        ( D ) OTHER INFORMATION: /mod_base=OTHER
            / label= Y
            / note= "Y = T or C"

( i x ) FEATURE:
        ( A ) NAME/KEY: modified_base
        ( B ) LOCATION: 15
        ( D ) OTHER INFORMATION: /mod_base=OTHER
            / label= Y
            / note= "Y = T or C"

( i x ) FEATURE:
        ( A ) NAME/KEY: modified_base
        ( B ) LOCATION: 17
        ( D ) OTHER INFORMATION: /mod_base=OTHER
            / label= N
            / note= "N = G,A,C or T"

( i x ) FEATURE:
        ( A ) NAME/KEY: modified_base
        ( B ) LOCATION: 20
        ( D ) OTHER INFORMATION: /mod_base=OTHER
            / label= N
            / note= "N = G,A,C or T"

( i x ) FEATURE:
        ( A ) NAME/KEY: modified_base
        ( B ) LOCATION: 23
        ( D ) OTHER INFORMATION: /mod_base=OTHER
            / label= N
            / note= "N = G,A,C, or T"

( i x ) FEATURE:
        ( A ) NAME/KEY: modified_base
        ( B ) LOCATION: 24
        ( D ) OTHER INFORMATION: /mod_base=OTHER
            / label= M
            / note= "M = A or C"

( i x ) FEATURE:
    ( A ) NAME/KEY: modified_base
    ( B ) LOCATION: 26
    ( D ) OTHER INFORMATION: /mod_base=OTHER
       / label= N
       / note= "N = G,A,C or T"

( x i ) SEQUENCE DESCRIPTION: SEQ ID NO:1:

TCTTGACTCG AGAYYTNGCN GCNMGNAA                                                                  2 8

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: modified_base
        ( B ) LOCATION: 14
        ( D ) OTHER INFORMATION: /mod_base=OTHER
           / label= Y
           / note= "Y = C or T"

( i x ) FEATURE:
        ( A ) NAME/KEY: modified_base
        ( B ) LOCATION: 15
        ( D ) OTHER INFORMATION: /mod_base=OTHER
           / label= Y
           / note= "Y = C or T"

( i x ) FEATURE:
        ( A ) NAME/KEY: modified_base
        ( B ) LOCATION: 17
        ( D ) OTHER INFORMATION: /mod_base=OTHER
           / label= N
           / note= "N = G,A,C or T"

( i x ) FEATURE:
        ( A ) NAME/KEY: modified_base
        ( B ) LOCATION: 20
        ( D ) OTHER INFORMATION: /mod_base=OTHER
           / label= N
           / note= "N = G,A,C or T"

( i x ) FEATURE:
        ( A ) NAME/KEY: modified_base
        ( B ) LOCATION: 23
        ( D ) OTHER INFORMATION: /mod_base=OTHER
           / label= N
           / note= "N = G,A,C or T"

( i x ) FEATURE:
        ( A ) NAME/KEY: modified_base
        ( B ) LOCATION: 24
        ( D ) OTHER INFORMATION: /mod_base=OTHER
           / label= M
           / note= "M = A or C"

( i x ) FEATURE:
        ( A ) NAME/KEY: modified_base
        ( B ) LOCATION: 26
        ( D ) OTHER INFORMATION: /mod_base=OTHER
           / label= N
           / note= "N = G,A,C or T"

( x i ) SEQUENCE DESCRIPTION: SEQ ID NO:2:

TCTTGACTCG AGAYYTNGCN ACNMGNAA                                                                  2 8

( 2 ) INFORMATION FOR SEQ ID NO:3:

( i ) SEQUENCE CHARACTERISTICS:
        ( A ) LENGTH: 29 base pairs (B) TYPE: nucleic acid
(C) STRANDEDNESS: single
(D) TOPOLOGY: unknown (i i) MOLECULE TYPE: cDNA (i x) FEATURE:
(A) NAME/KEY: modified_base
(B) LOCATION: 3
(D) OTHER INFORMATION: /mod_base=OTHER
/ label= R
/ note= "R = A or G"

(i x) FEATURE:
(A) NAME/KEY: modified_base
(B) LOCATION: 6
(D) OTHER INFORMATION: /mod_base=OTHER
/ label= N
/ note= "N = G,A,C or T"

(i x) FEATURE:
(A) NAME/KEY: modified_base
(B) LOCATION: 10
(D) OTHER INFORMATION: /mod_base=OTHER
/ label= W
/ note= "W = A or T"

(i x) FEATURE:
(A) NAME/KEY: modified_base
(B) LOCATION: 11
(D) OTHER INFORMATION: /mod_base=OTHER
/ label= S
/ note= "S = G or C"

(i x) FEATURE:
(A) NAME/KEY: modified_base
(B) LOCATION: 12
(D) OTHER INFORMATION: /mod_base=OTHER
/ label= N
/ note= "N = G,A,C or T"

(i x) FEATURE:
(A) NAME/KEY: modified_base
(B) LOCATION: 15
(D) OTHER INFORMATION: /mod_base=OTHER
/ label= R
/ note= "R = A or G"

(x i) SEQUENCE DESCRIPTION: SEQ ID NO:3:

CTRCANACCW SNATRCCCTC GAGCTTAAG 29

(2) INFORMATION FOR SEQ ID NO:4:

(i) SEQUENCE CHARACTERISTICS:
(A) LENGTH: 29 base pairs
(B) TYPE: nucleic acid
(C) STRANDEDNESS: single
(D) TOPOLOGY: unknown (i i) MOLECULE TYPE: cDNA (i x) FEATURE:
(A) NAME/KEY: modified_base
(B) LOCATION: 3
(D) OTHER INFORMATION: /mod_base=OTHER
/ label= R
/ note= "R = A or G"

(i x) FEATURE:
(A) NAME/KEY: modified_base
(B) LOCATION: 6
(D) OTHER INFORMATION: /mod_base=OTHER
/ label= N
/ note= "N = G,A,C, or T"

(i x) FEATURE:
(A) NAME/KEY: modified_base
(B) LOCATION: 10

(D) OTHER INFORMATION: /mod_base=OTHER
/ label= W
/ note= "W = A or T"

(ix) FEATURE:
(A) NAME/KEY: modified_base
(B) LOCATION: 11
(D) OTHER INFORMATION: /mod_base=OTHER
/ label= S
/ note= "S = G or C"

(ix) FEATURE:
(A) NAME/KEY: modified_base
(B) LOCATION: 12
(D) OTHER INFORMATION: /mod_base=OTHER
/ label= N
/ note= "N = G,A,C or T"

(ix) FEATURE:
(A) NAME/KEY: modified_base
(B) LOCATION: 15
(D) OTHER INFORMATION: /mod_base=OTHER
/ label= R
/ note= "R = A or G"

(xi) SEQUENCE DESCRIPTION: SEQ ID NO:4:

CTRCANACCW SNAARCCCTC GAGCTTAAG  29

(2) INFORMATION FOR SEQ ID NO:5:

(i) SEQUENCE CHARACTERISTICS:
(A) LENGTH: 29 base pairs
(B) TYPE: nucleic acid
(C) STRANDEDNESS: single
(D) TOPOLOGY: unknown (ii) MOLECULE TYPE: cDNA (ix) FEATURE:
(A) NAME/KEY: modified_base
(B) LOCATION: 3
(D) OTHER INFORMATION: /mod_base=OTHER
/ label= R
/ note= "R = A or G"

(ix) FEATURE:
(A) NAME/KEY: modified_base
(B) LOCATION: 6
(D) OTHER INFORMATION: /mod_base=OTHER
/ label= N
/ note= "N = G,A,C or T"

(ix) FEATURE:
(A) NAME/KEY: modified_base
(B) LOCATION: 10
(D) OTHER INFORMATION: /mod_base=OTHER
/ label= W
/ note= "W = A or T"

(ix) FEATURE:
(A) NAME/KEY: modified_base
(B) LOCATION: 11
(D) OTHER INFORMATION: /mod_base=OTHER
/ label= S
/ note= "S = G or C"

(ix) FEATURE:
(A) NAME/KEY: modified_base
(B) LOCATION: 12
(D) OTHER INFORMATION: /mod_base=OTHER
/ label= N
/ note= "N = G,A,C or T"

(ix) FEATURE:
(A) NAME/KEY: modified_base
(B) LOCATION: 13
(D) OTHER INFORMATION: /mod_base=OTHER
/ label= R / note= "R = A or G"

( i x ) FEATURE:
    ( A ) NAME/KEY: modified_base
    ( B ) LOCATION: 15
    ( D ) OTHER INFORMATION: /mod_base=OTHER
        / label= N
        / note= "N = G,A,C or T"

( x i ) SEQUENCE DESCRIPTION: SEQ ID NO:5:

CTRCANACCW SNRANCCCTC GAGCTTAAG 29

( 2 ) INFORMATION FOR SEQ ID NO:6:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:6:

Cys Leu Val Gly Ala Asn Leu Leu Val Lys Ile Gly Asp Phe Gly Met
1               5                   10                  15

Ser Arg Asp Val Tyr Ser Thr Asp Tyr Tyr Arg Val Gly Gly His Thr
                20                  25                  30

Met Leu Pro Ile Arg Trp Met Pro Pro Glu Ser Ile Met Tyr Arg Lys
            35                  40                  45

Phe Thr Thr Glu Ser
            50

( 2 ) INFORMATION FOR SEQ ID NO:7:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:7:

Val Leu Val Thr His Gly Lys Val Val Lys Ile Cys Asp Phe Gly Leu
1               5                   10                  15

Ala Arg Asp Ile Leu Ser Asp Ser Ser Tyr Val Val Arg Gly Asn Ala
                20                  25                  30

Arg Leu Pro Val Lys Trp Met Ala Pro Glu Ser Leu Phe Glu Gly Ile
            35                  40                  45

Tyr Thr Ile Lys Ser
            50

( 2 ) INFORMATION FOR SEQ ID NO:8:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:8:

Ile Leu Val Gly Glu Asn Tyr Leu Ala Lys Ile Ala Asp Phe Gly Leu
1               5                   10                  15

Ser Arg Gly Gln Glu Val Tyr Val Lys Lys Thr Met Gly Arg Leu Pro

|   |   |   | 20 |   |   |   | 25 |   |   |   | 30 |   |   |
|---|---|---|---|---|---|---|---|---|---|---|---|---|---|
| Val | Arg | Trp | Met | Ala | Ile | Glu | Ser | Leu | Asn | Tyr | Ser | Val | Tyr | Thr | Thr |
|   |   | 35 |   |   |   |   | 40 |   |   |   |   | 45 |   |   |

Asn Ser
 50

( 2 ) INFORMATION FOR SEQ ID NO:9:

( i ) SEQUENCE CHARACTERISTICS:
     ( A ) LENGTH: 54 amino acids
     ( B ) TYPE: amino acid
     ( C ) STRANDEDNESS: single
     ( D ) TOPOLOGY: unknown ( i i ) MOLECULE TYPE: peptide ( x i ) SEQUENCE DESCRIPTION: SEQ ID NO:9:

Ile Leu Val Asn Ser Asn Leu Val Cys Lys Val Ser Asp Phe Gly Leu
 1               5                  10                  15

Ser Arg Val Leu Glu Asp Asp Pro Glu Ala Ala Tyr Thr Thr Thr Gly
              20                  25                  30

Gly Lys Ile Pro Ile Arg Trp Thr Ala Pro Glu Ala Ile Ala Tyr Arg
              35                  40                  45

Lys Phe Ser Ser Ala Ser
              50

( 2 ) INFORMATION FOR SEQ ID NO:10:

( i ) SEQUENCE CHARACTERISTICS:
     ( A ) LENGTH: 54 amino acids
     ( B ) TYPE: amino acid
     ( C ) STRANDEDNESS: single
     ( D ) TOPOLOGY: unknown ( i i ) MOLECULE TYPE: peptide ( x i ) SEQUENCE DESCRIPTION: SEQ ID NO:10:

Ile Leu Ile Asn Ser Asn Leu Val Cys Lys Val Ser Asp Phe Gly Leu
 1               5                  10                  15

Ser Arg Val Leu Glu Asp Asp Pro Glu Ala Ala Tyr Thr Thr Arg Gly
              20                  25                  30

Gly Lys Ile Pro Ile Arg Trp Thr Ala Pro Glu Ala Ile Ala Phe Arg
              35                  40                  45

Lys Phe Thr Ser Ala Ser
              50

( 2 ) INFORMATION FOR SEQ ID NO:11:

( i ) SEQUENCE CHARACTERISTICS:
     ( A ) LENGTH: 159 base pairs
     ( B ) TYPE: nucleic acid
     ( C ) STRANDEDNESS: double
     ( D ) TOPOLOGY: unknown ( i i ) MOLECULE TYPE: cDNA ( i x ) FEATURE:
     ( A ) NAME/KEY: CDS
     ( B ) LOCATION: 1..159

( x i ) SEQUENCE DESCRIPTION: SEQ ID NO:11:

```
TGC CTA GTT GGA GCC AAC CTT CTA GTG AAG ATT GGA GAT TTT GGC ATG      48
Cys Leu Val Gly Ala Asn Leu Leu Val Lys Ile Gly Asp Phe Gly Met
 1               5                  10                  15

TCC AGG GAC GTC TAC AGT ACT GAT TAC TAC AGG GTG GGA GGA CAC ACC      96
```

| Ser | Arg | Asp | Val | Tyr | Ser | Thr | Asp | Tyr | Tyr | Arg | Val | Gly | Gly | His | Thr |     |
|-----|-----|-----|-----|-----|-----|-----|-----|-----|-----|-----|-----|-----|-----|-----|-----|-----|
|     |     |     | 20  |     |     |     |     | 25  |     |     |     |     | 30  |     |     |     |

| ATG | CTC | CCC | ATC | CGC | TGG | ATG | CCA | CCT | GAA | AGC | ATC | ATG | TAC | CGG | AAG | 144 |
|-----|-----|-----|-----|-----|-----|-----|-----|-----|-----|-----|-----|-----|-----|-----|-----|-----|
| Met | Leu | Pro | Ile | Arg | Trp | Met | Pro | Pro | Glu | Ser | Ile | Met | Tyr | Arg | Lys |     |
|     |     |     | 35  |     |     |     |     | 40  |     |     |     |     | 45  |     |     |     |

| TTT | ACC | ACA | GAG | AGT | 159 |
|-----|-----|-----|-----|-----|-----|
| Phe | Thr | Thr | Glu | Ser |     |
|     | 50  |     |     |     |     |

( 2 ) INFORMATION FOR SEQ ID NO:12:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Cys | Leu | Val | Gly | Ala | Asn | Leu | Leu | Val | Lys | Ile | Gly | Asp | Phe | Gly | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Arg | Asp | Val | Tyr | Ser | Thr | Asp | Tyr | Tyr | Arg | Val | Gly | Gly | His | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Met | Leu | Pro | Ile | Arg | Trp | Met | Pro | Pro | Glu | Ser | Ile | Met | Tyr | Arg | Lys |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Phe | Thr | Thr | Glu | Ser |
|-----|-----|-----|-----|-----|
|     | 50  |     |     |     |

( 2 ) INFORMATION FOR SEQ ID NO:13:

( i ) SEQUENCE CHARACTERISTICS:
        ( A ) LENGTH: 159 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..159

( x i ) SEQUENCE DESCRIPTION: SEQ ID NO:13:

| TGC | TTG | GTA | GGA | GAG | AAC | CTG | CTG | GTG | AAA | ATT | GGG | GAC | TTC | GGG | ATG | 48  |
|-----|-----|-----|-----|-----|-----|-----|-----|-----|-----|-----|-----|-----|-----|-----|-----|-----|
| Cys | Leu | Val | Gly | Glu | Asn | Leu | Leu | Val | Lys | Ile | Gly | Asp | Phe | Gly | Met |     |
| 1   |     |     |     | 5   |     |     |     |     | 10  |     |     |     |     | 15  |     |     |

| TCC | CGG | GAT | GTA | TAC | AGC | ACC | GAC | TAC | TAC | CGG | GTT | GGT | GGC | CAC | ACA | 96  |
|-----|-----|-----|-----|-----|-----|-----|-----|-----|-----|-----|-----|-----|-----|-----|-----|-----|
| Ser | Arg | Asp | Val | Tyr | Ser | Thr | Asp | Tyr | Tyr | Arg | Val | Gly | Gly | His | Thr |     |
|     |     |     | 20  |     |     |     |     | 25  |     |     |     |     | 30  |     |     |     |

| ATG | TTG | CCC | ATC | CGA | TGG | ATG | CCT | CCA | GAG | AGC | ATC | ATG | TAC | AGG | AAA | 144 |
|-----|-----|-----|-----|-----|-----|-----|-----|-----|-----|-----|-----|-----|-----|-----|-----|-----|
| Met | Leu | Pro | Ile | Arg | Trp | Met | Pro | Pro | Glu | Ser | Ile | Met | Tyr | Arg | Lys |     |
|     |     |     | 35  |     |     |     |     | 40  |     |     |     |     | 45  |     |     |     |

| TTC | ACC | ACC | GAG | AGT | 159 |
|-----|-----|-----|-----|-----|-----|
| Phe | Thr | Thr | Glu | Ser |     |
|     | 50  |     |     |     |     |

( 2 ) INFORMATION FOR SEQ ID NO:14:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Cys | Leu | Val | Gly | Glu | Asn | Leu | Leu | Val | Lys | Ile | Gly | Asp | Phe | Gly | Met |
| 1 | | | | 5 | | | | | 10 | | | | | | 15 |

| Ser | Arg | Asp | Val | Tyr | Ser | Thr | Asp | Tyr | Tyr | Arg | Val | Gly | Gly | His | Thr |
| | | | 20 | | | | | 25 | | | | | 30 | | |

| Met | Leu | Pro | Ile | Arg | Trp | Met | Pro | Pro | Glu | Ser | Ile | Met | Tyr | Arg | Lys |
| | | 35 | | | | | 40 | | | | | 45 | | | |

| Phe | Thr | Thr | Glu | Ser |
| | | | | 50 |

(2) INFORMATION FOR SEQ ID NO:15:

(i) SEQUENCE CHARACTERISTICS:
        (A) LENGTH: 159 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..159

(xi) SEQUENCE DESCRIPTION: SEQ ID NO:15:

| TGC | CTG | GTG | GGA | GAG | AAC | CTG | CTG | GTG | AAA | ATT | GGG | GAC | TTT | GGG | ATG | 48 |
| Cys | Leu | Val | Gly | Glu | Asn | Leu | Leu | Val | Lys | Ile | Gly | Asp | Phe | Gly | Met | |
| 1 | | | | 5 | | | | | 10 | | | | | | 15 | |

| TCC | CGA | GAT | GTG | TAC | AGC | ACC | GAC | TAC | TAT | CGG | GTC | GGT | GGC | CAC | ACA | 96 |
| Ser | Arg | Asp | Val | Tyr | Ser | Thr | Asp | Tyr | Tyr | Arg | Val | Gly | Gly | His | Thr | |
| | | | 20 | | | | | 25 | | | | | 30 | | | |

| ATG | TTG | CCC | ATC | CGA | TGG | ATG | CCT | CCA | GAG | AGC | ATC | ATG | TAT | AGG | AAA | 144 |
| Met | Leu | Pro | Ile | Arg | Trp | Met | Pro | Pro | Glu | Ser | Ile | Met | Tyr | Arg | Lys | |
| | | 35 | | | | | 40 | | | | | 45 | | | | |

| TTC | ACC | ACC | GAG | AGC | | | | | | | | | | | | 159 |
| Phe | Thr | Thr | Glu | Ser | | | | | | | | | | | | |
| 50 | | | | | | | | | | | | | | | | |

(2) INFORMATION FOR SEQ ID NO:16:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:16:

| Cys | Leu | Val | Gly | Glu | Asn | Leu | Leu | Val | Lys | Ile | Gly | Asp | Phe | Gly | Met |
| 1 | | | | 5 | | | | | 10 | | | | | | 15 |

| Ser | Arg | Asp | Val | Tyr | Ser | Thr | Asp | Tyr | Tyr | Arg | Val | Gly | Gly | His | Thr |
| | | | 20 | | | | | 25 | | | | | 30 | | | |

| Met | Leu | Pro | Ile | Arg | Trp | Met | Pro | Pro | Glu | Ser | Ile | Met | Tyr | Arg | Lys |
| | | 35 | | | | | 40 | | | | | 45 | | | |

| Phe | Thr | Thr | Glu | Ser |
| | | | | 50 |

(2) INFORMATION FOR SEQ ID NO:17:

(i) SEQUENCE CHARACTERISTICS:
        (A) LENGTH: 159 base pairs
        (B) TYPE: nucleic acid
        (C) STRANDEDNESS: double
        (D) TOPOLOGY: unknown (ii) MOLECULE TYPE: cDNA ( i x ) FEATURE:
    ( A ) NAME/KEY: CDS
    ( B ) LOCATION: 1..159

( x i ) SEQUENCE DESCRIPTION: SEQ ID NO:17:

| TGT | CTA | GTG | GGC | CAG | GGA | CTG | GTG | GTC | AAG | ATT | GGT | GAT | TTT | GGC | ATG | 48 |
|---|---|---|---|---|---|---|---|---|---|---|---|---|---|---|---|---|
| Cys | Leu | Val | Gly | Gln | Gly | Leu | Val | Val | Lys | Ile | Gly | Asp | Phe | Gly | Met | |
| 1 | | | | 5 | | | | | 10 | | | | | 15 | | |

| AGC | AGG | GAT | ATC | TAC | AGC | ACC | GAC | TAT | TAC | CGT | GTG | GGA | GGC | CGC | ACC | 96 |
|---|---|---|---|---|---|---|---|---|---|---|---|---|---|---|---|---|
| Ser | Arg | Asp | Ile | Tyr | Ser | Thr | Asp | Tyr | Tyr | Arg | Val | Gly | Gly | Arg | Thr | |
| | | | 20 | | | | | | 25 | | | | | 30 | | |

| ATG | CTG | CCC | ATT | CGC | TGG | ATG | CCG | CCC | GAG | AGC | ATC | CTG | TAC | CGT | AAG | 144 |
|---|---|---|---|---|---|---|---|---|---|---|---|---|---|---|---|---|
| Met | Leu | Pro | Ile | Arg | Trp | Met | Pro | Pro | Glu | Ser | Ile | Leu | Tyr | Arg | Lys | |
| | | | | 35 | | | | | 40 | | | | | 45 | | |

| TTC | ACC | ACC | GAG | AGC | | | | | | | | | | | | 159 |
|---|---|---|---|---|---|---|---|---|---|---|---|---|---|---|---|---|
| Phe | Thr | Thr | Glu | Ser | | | | | | | | | | | | |
| | | | | 50 | | | | | | | | | | | | |

( 2 ) INFORMATION FOR SEQ ID NO:18:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Cys | Leu | Val | Gly | Gln | Gly | Leu | Val | Val | Lys | Ile | Gly | Asp | Phe | Gly | Met |
|---|---|---|---|---|---|---|---|---|---|---|---|---|---|---|---|
| 5 | | | | 10 | | | | | 15 | | | | | 15 | |
| 1 | | | | 5 | | | | | 10 | | | | | 15 | |

| Ser | Arg | Asp | Ile | Tyr | Ser | Thr | Asp | Tyr | Tyr | Arg | Val | Gly | Gly | Arg | Thr |
|---|---|---|---|---|---|---|---|---|---|---|---|---|---|---|---|
| | | | 20 | | | | | | 25 | | | | | 30 | |

| Met | Leu | Pro | Ile | Arg | Trp | Met | Pro | Pro | Glu | Ser | Ile | Leu | Tyr | Arg | Lys |
|---|---|---|---|---|---|---|---|---|---|---|---|---|---|---|---|
| | | | | 35 | | | | | 40 | | | | | 45 | |

| Phe | Thr | Thr | Glu | Ser |
|---|---|---|---|---|
| | | | | 50 |

( 2 ) INFORMATION FOR SEQ ID NO:19:

( i ) SEQUENCE CHARACTERISTICS:
        ( A ) LENGTH: 159 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..159

( x i ) SEQUENCE DESCRIPTION: SEQ ID NO:19:

| GTA | CTG | GTC | ACC | CAC | GGG | AAG | GTG | GTG | AAG | ATC | TGT | GAC | TTT | GGA | CTG | 48 |
|---|---|---|---|---|---|---|---|---|---|---|---|---|---|---|---|---|
| Val | Leu | Val | Thr | His | Gly | Lys | Val | Val | Lys | Ile | Cys | Asp | Phe | Gly | Leu | |
| 1 | | | | 5 | | | | | 10 | | | | | 15 | | |

| GCC | CGA | GAC | ATC | CTG | AGT | GAC | TCC | AGC | TAC | GTC | GTC | AGG | GGC | AAC | GCA | 96 |
|---|---|---|---|---|---|---|---|---|---|---|---|---|---|---|---|---|
| Ala | Arg | Asp | Ile | Leu | Ser | Asp | Ser | Ser | Tyr | Val | Val | Arg | Gly | Asn | Ala | |
| | | | 20 | | | | | | 25 | | | | | 30 | | |

| CGG | CTG | CCA | GTG | AAG | TGG | ATG | GCA | CCT | GAG | AGC | TTG | TTT | GAA | GGG | ATC | 144 |
|---|---|---|---|---|---|---|---|---|---|---|---|---|---|---|---|---|
| Arg | Leu | Pro | Val | Lys | Trp | Met | Ala | Pro | Glu | Ser | Leu | Phe | Glu | Gly | Ile | |
| | | | | 35 | | | | | 40 | | | | | 45 | | |

| TAT | ACA | ATC | AAG | AGT | | | | | | | | | | | | 159 |
|---|---|---|---|---|---|---|---|---|---|---|---|---|---|---|---|---|
| Tyr | Thr | Ile | Lys | Ser | | | | | | | | | | | | |
| | | | | 50 | | | | | | | | | | | | |

( 2 ) INFORMATION FOR SEQ ID NO:20:

( i ) SEQUENCE CHARACTERISTICS:
       ( A ) LENGTH: 53 amino acids
       ( B ) TYPE: amino acid
       ( D ) TOPOLOGY: linear ( i i ) MOLECULE TYPE: protein ( x i ) SEQUENCE DESCRIPTION: SEQ ID NO:20:

```
Val Leu Val Thr His Gly Lys Val Val Lys Ile Cys Asp Phe Gly Leu
 1               5                  10                  15
Ala Arg Asp Ile Leu Ser Asp Ser Ser Tyr Val Val Arg Gly Asn Ala
             20                  25                  30
Arg Leu Pro Val Lys Trp Met Ala Pro Glu Ser Leu Phe Glu Gly Ile
         35                  40                  45
Tyr Thr Ile Lys Ser
         50
```

( 2 ) INFORMATION FOR SEQ ID NO:21:

( i ) SEQUENCE CHARACTERISTICS:
       ( A ) LENGTH: 53 amino acids
       ( B ) TYPE: amino acid
       ( C ) STRANDEDNESS: single
       ( D ) TOPOLOGY: unknown ( i i ) MOLECULE TYPE: peptide ( x i ) SEQUENCE DESCRIPTION: SEQ ID NO:21:

```
Ile Leu Leu Thr His Gly Arg Ile Thr Lys Ile Cys Asp Phe Gly Leu
 1               5                  10                  15
Ala Arg Asp Ile Lys Asn Asp Ser Asn Tyr Val Val Lys Gly Asn Ala
             20                  25                  30
Arg Leu Pro Val Lys Trp Met Ala Pro Glu Ser Ile Phe Asn Cys Val
         35                  40                  45
Tyr Thr Phe Glu Ser
         50
```

( 2 ) INFORMATION FOR SEQ ID NO:22:

( i ) SEQUENCE CHARACTERISTICS:
       ( A ) LENGTH: 53 amino acids
       ( B ) TYPE: amino acid
       ( C ) STRANDEDNESS: single
       ( D ) TOPOLOGY: unknown ( i i ) MOLECULE TYPE: peptide ( x i ) SEQUENCE DESCRIPTION: SEQ ID NO:22:

```
Val Leu Leu Thr Asn Gly His Val Ala Lys Ile Gly Asp Phe Gly Leu
 1               5                  10                  15
Ala Arg Asp Ile Met Asn Asp Ser Asn Tyr Ile Val Lys Gly Asn Ala
             20                  25                  30
Arg Leu Pro Val Lys Trp Met Ala Pro Glu Ser Ile Phe Asp Cys Val
         35                  40                  45
Tyr Thr Val Gln Ser
         50
```

( 2 ) INFORMATION FOR SEQ ID NO:23:

( i ) SEQUENCE CHARACTERISTICS:
       ( A ) LENGTH: 53 amino acids
       ( B ) TYPE: amino acid ( C ) STRANDEDNESS: single
( D ) TOPOLOGY: unknown ( i i ) MOLECULE TYPE: peptide ( x i ) SEQUENCE DESCRIPTION: SEQ ID NO:23:

Val Leu Leu Ala Gln Gly Lys Ile Val Lys Ile Cys Asp Phe Gly Leu
1               5                   10                  15

Ala Arg Asp Ile Met His Asp Ser Asn Tyr Val Ser Lys Gly Ser Thr
            20                  25                  30

Phe Leu Pro Val Lys Trp Met Ala Pro Glu Ser Ile Phe Asp Asn Leu
        35                  40                  45

Tyr Thr Thr Leu Ser
        50

( 2 ) INFORMATION FOR SEQ ID NO:24:

( i ) SEQUENCE CHARACTERISTICS:
( A ) LENGTH: 53 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:24:

Val Leu Leu Thr Ser Gly His Val Ala Lys Ile Gly Asp Phe Gly Leu
1               5                   10                  15

Ala Arg Asp Ile Met Asn Asp Ser Asn Tyr Val Val Lys Gly Asn Ala
            20                  25                  30

Xaa Leu Pro Val Lys Trp Met Ala Pro Glu Ser Ile Phe Asp Cys Val
        35                  40                  45

Ile Thr Val Gln Ser
        50

( 2 ) INFORMATION FOR SEQ ID NO:25:

( i ) SEQUENCE CHARACTERISTICS:
( A ) LENGTH: 150 base pairs
( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 1..150

( x i ) SEQUENCE DESCRIPTION: SEQ ID NO:25:

ATT TTA GTT GGC GAA AAC TAC TTA GCC AAA ATA GCA GAT TTT GGA TTG        48
Ile Leu Val Gly Glu Asn Tyr Leu Ala Lys Ile Ala Asp Phe Gly Leu
1               5                   10                  15

TCA CGA GGT CAA GAA GTG TAT GTG AAA AAG ACA ATG GGA AGG CTT CCA        96
Ser Arg Gly Gln Glu Val Tyr Val Lys Lys Thr Met Gly Arg Leu Pro
            20                  25                  30

GTG CGC TGG ATG GCA ATT GAG TCT CTG AAC TAT AGT GTC TAT ACA ACC       144
Val Arg Trp Met Ala Ile Glu Ser Leu Asn Tyr Ser Val Tyr Thr Thr
        35                  40                  45

AAC AGT                                                                150
Asn Ser
    50

( 2 ) INFORMATION FOR SEQ ID NO:26:

(i) SEQUENCE CHARACTERISTICS:
  (A) LENGTH: 50 amino acids
  (B) TYPE: amino acid
  (D) TOPOLOGY: linear (ii) MOLECULE TYPE: protein (xi) SEQUENCE DESCRIPTION: SEQ ID NO:26:

```
Ile Leu Val Gly Glu Asn Tyr Leu Ala Lys Ile Ala Asp Phe Gly Leu
 1               5                  10                  15

Ser Arg Gly Gln Glu Val Tyr Val Lys Lys Thr Met Gly Arg Leu Pro
                20                  25                  30

Val Arg Trp Met Ala Ile Glu Ser Leu Asn Tyr Ser Val Tyr Thr Thr
                35                  40                  45

Asn Ser
 50
```

(2) INFORMATION FOR SEQ ID NO:27:

(i) SEQUENCE CHARACTERISTICS:
    (A) LENGTH: 53 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:27:

```
Ile Leu Val Ala Glu Gly Arg Lys Met Lys Ile Ser Asp Phe Gly Leu
 1               5                  10                  15

Ser Arg Asp Val Tyr Glu Glu Asp Ser Tyr Val Lys Arg Ser Gln Gly
                20                  25                  30

Arg Ile Pro Val Lys Trp Met Ala Ile Glu Ser Leu Phe Asp His Ile
                35                  40                  45

Tyr Thr Thr Gln Ser
                50
```

(2) INFORMATION FOR SEQ ID NO:28:

(i) SEQUENCE CHARACTERISTICS:
    (A) LENGTH: 162 base pairs
    (B) TYPE: nucleic acid
    (C) STRANDEDNESS: double
    (D) TOPOLOGY: unknown (ii) MOLECULE TYPE: cDNA (ix) FEATURE:
    (A) NAME/KEY: CDS
    (B) LOCATION: 1..162

(xi) SEQUENCE DESCRIPTION: SEQ ID NO:28:

```
ATC CTC GTC AAC AGC AAC CTG GTC TGC AAG GTG TCT GAC TTT GGC CTG       48
Ile Leu Val Asn Ser Asn Leu Val Cys Lys Val Ser Asp Phe Gly Leu
 1               5                  10                  15

TCC CGC GTG CTG GAG GAC GAC CCC GAG GCC ACC TAC ACC ACC AGT GGC       96
Ser Arg Val Leu Glu Asp Asp Pro Glu Ala Thr Tyr Thr Thr Ser Gly
                20                  25                  30

GGC AAG ATC CCC ATC CGC TGG ACC GCC CCG GAG GCC ATT TCC TAC CGG      144
Gly Lys Ile Pro Ile Arg Trp Thr Ala Pro Glu Ala Ile Ser Tyr Arg
                35                  40                  45

AAG TTC ACC TCT GCC AGC                                              162
Lys Phe Thr Ser Ala Ser
 50
```

( 2 ) INFORMATION FOR SEQ ID NO:29:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Ile  Leu  Val  Asn  Ser  Asn  Leu  Val  Cys  Lys  Val  Ser  Asp  Phe  Gly  Leu
 1              5                        10                       15

Ser  Arg  Val  Leu  Glu  Asp  Asp  Pro  Glu  Ala  Thr  Tyr  Thr  Thr  Ser  Gly
          20                       25                       30

Gly  Lys  Ile  Pro  Ile  Arg  Trp  Thr  Ala  Pro  Glu  Ala  Ile  Ser  Tyr  Arg
          35                  40                       45

Lys  Phe  Thr  Ser  Ala  Ser
          50
```

( 2 ) INFORMATION FOR SEQ ID NO:30:

( i ) SEQUENCE CHARACTERISTICS:
        ( A ) LENGTH: 162 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..162

( x i ) SEQUENCE DESCRIPTION: SEQ ID NO:30:

```
ATC  TTA  ATC  AAC  AGT  AAC  CTT  GTG  TGC  AAA  GTG  TCT  GAC  TTT  GGA  CTT      48
Ile  Leu  Ile  Asn  Ser  Asn  Leu  Val  Cys  Lys  Val  Ser  Asp  Phe  Gly  Leu
 1              5                        10                       15

TCC  AGG  GTG  CTG  GAA  GAT  GAT  CCT  GAG  GCA  GCC  TAT  ACC  ACA  AGG  GGA      96
Ser  Arg  Val  Leu  Glu  Asp  Asp  Pro  Glu  Ala  Ala  Tyr  Thr  Thr  Arg  Gly
          20                       25                       30

GGC  AAA  ATT  CCA  ATC  AGG  TGG  ACT  GCT  CCA  GAA  GCA  ATA  GCT  TTT  CGA     144
Gly  Lys  Ile  Pro  Ile  Arg  Trp  Thr  Ala  Pro  Glu  Ala  Ile  Ala  Phe  Arg
          35                  40                       45

AAG  TTT  ACC  TCT  GCC  AGT                                                       162
Lys  Phe  Thr  Ser  Ala  Ser
          50
```

( 2 ) INFORMATION FOR SEQ ID NO:31:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Ile  Leu  Ile  Asn  Ser  Asn  Leu  Val  Cys  Lys  Val  Ser  Asp  Phe  Gly  Leu
 1              5                        10                       15

Ser  Arg  Val  Leu  Glu  Asp  Asp  Pro  Glu  Ala  Ala  Tyr  Thr  Thr  Arg  Gly
          20                       25                       30

Gly  Lys  Ile  Pro  Ile  Arg  Trp  Thr  Ala  Pro  Glu  Ala  Ile  Ala  Phe  Arg
          35                  40                       45

Lys  Phe  Thr  Ser  Ala  Ser
          50
```

( 2 ) INFORMATION FOR SEQ ID NO:32:

( i ) SEQUENCE CHARACTERISTICS:
        ( A ) LENGTH: 162 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..162

( x i ) SEQUENCE DESCRIPTION: SEQ ID NO:32:

```
ATC  TTG  GTG  AAC  AGC  AAC  TTG  GTA  TGC  AAA  GTC  TCT  GAT  TTC  GGC  CTC        48
Ile  Leu  Val  Asn  Ser  Asn  Leu  Val  Cys  Lys  Val  Ser  Asp  Phe  Gly  Leu
 1                    5                        10                       15

TCC  CGA  GTG  CTG  GAA  GAC  GAC  CCA  GAA  GCA  GCT  TAT  ACA  ACA  ACT  GGT        96
Ser  Arg  Val  Leu  Glu  Asp  Asp  Pro  Glu  Ala  Ala  Tyr  Thr  Thr  Thr  Gly
               20                       25                       30

GGA  AAA  ATA  CCT  ATA  AGG  TGG  ACA  GCC  CCA  GAA  GCT  ATC  GCC  TAC  AGG       144
Gly  Lys  Ile  Pro  Ile  Arg  Trp  Thr  Ala  Pro  Glu  Ala  Ile  Ala  Tyr  Arg
          35                       40                       45

AAA  TTC  TCC  TCA  GCG  AGT                                                         162
Lys  Phe  Ser  Ser  Ala  Ser
 50
```

( 2 ) INFORMATION FOR SEQ ID NO:33:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Ile  Leu  Val  Asn  Ser  Asn  Leu  Val  Cys  Lys  Val  Ser  Asp  Phe  Gly  Leu
 1                    5                        10                       15

Ser  Arg  Val  Leu  Glu  Asp  Asp  Pro  Glu  Ala  Ala  Tyr  Thr  Thr  Thr  Gly
               20                       25                       30

Gly  Lys  Ile  Pro  Ile  Arg  Trp  Thr  Ala  Pro  Glu  Ala  Ile  Ala  Tyr  Arg
          35                       40                       45

Lys  Phe  Ser  Ser  Ala  Ser
 50
```

( 2 ) INFORMATION FOR SEQ ID NO:34:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:34:

```
Gly  Pro  Asp  Ala  Met  Ile  Leu  Val  Asp  Gly  Gln  Pro  Arg  Gln  Ala  Lys
 1                    5                        10                       15

Gly  Glu  Leu  Gly  Leu  Ser  Gln  Met  Leu  His  Ile  Ala  Ser  Gln  Ile  Ala
               20                       25                       30

Ser  Gly  Met  Val  Tyr  Leu  Ala  Ser  Gln  His  Phe  Val  His  Arg  Asp  Leu
          35                       40                       45

Ala  Thr  Arg  Asn  Cys  Leu  Val  Gly  Ala  Asn  Leu  Leu  Val  Lys  Ile  Gly
```

|   |   |   |   |   | 50 |   |   |   |   | 55 |   |   |   |   | 60 |   |   |   |   |
|---|---|---|---|---|---|---|---|---|---|---|---|---|---|---|---|---|---|---|---|

Asp Phe Gly Met Ser Arg Asp Val Tyr Ser Thr Asp Tyr Tyr Arg Val
65                  70                   75                    80

Gly Gly His Thr Met Leu Pro Ile Arg Trp Met Pro Pro Glu Ser Ile
              85                   90                   95

Met Tyr Arg Lys Phe Thr Thr Glu Ser Asp Val Trp Ser Phe Gly Val
             100                 105                 110

Ile Leu Trp Glu Ile Phe Thr Tyr Gly Lys Gln Pro Trp Phe Gln Leu
             115                 120                 125

Ser Asn Thr Glu Val Ile Glu Cys Ile Thr Gln Gly Arg Val Leu Glu
         130                 135                 140

Arg Pro Arg Val Cys Pro Lys Glu Val Tyr Asp Val Met Leu Gly Cys
145                 150                 155                 160

Trp Gln Arg Glu Pro Gln Gln Arg Leu Asn Ile Lys Glu Ile Tyr Lys
                165                 170                 175

Ile Leu His Ala Leu Gly Lys Ala Thr Pro Ile Tyr Leu Asp Ile Leu
             180                 185                 190

Gly ( 2 ) INFORMATION FOR SEQ ID NO:35:

( i ) SEQUENCE CHARACTERISTICS:
      ( A ) LENGTH: 190 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:35:

Gly Pro Asp Ala Val Leu Met Ala Glu Gly Asn Pro Pro Thr Glu Leu
1               5                   10                  15

Thr Gln Ser Gln Met Leu His Ile Ala Gln Gln Ile Ala Ala Gly Met
             20                  25                  30

Val Tyr Leu Ala Ser Gln His Phe Val His Arg Asp Leu Ala Thr Arg
         35                  40                  45

Asn Cys Leu Val Gly Glu Asn Leu Leu Val Lys Ile Gly Asp Phe Gly
     50                  55                  60

Met Ser Arg Asp Val Tyr Ser Thr Asp Tyr Tyr Arg Val Gly Gly His
65                  70                  75                  80

Thr Met Leu Pro Ile Arg Trp Met Pro Pro Glu Ser Ile Met Tyr Arg
                 85                  90                  95

Lys Phe Thr Thr Glu Ser Asp Val Trp Ser Leu Gly Val Val Leu Trp
             100                 105                 110

Glu Ile Phe Thr Tyr Gly Lys Gln Pro Trp Tyr Gln Leu Ser Asn Asn
             115                 120                 125

Glu Val Ile Glu Cys Ile Thr Gln Gly Arg Val Leu Gln Arg Pro Arg
         130                 135                 140

Thr Cys Pro Gln Glu Val Tyr Glu Leu Met Leu Gly Cys Trp Gln Arg
145                 150                 155                 160

Glu Pro His Thr Arg Lys Asn Ile Lys Asn Ile His Thr Leu Leu Gln
                165                 170                 175

Asn Leu Ala Lys Ala Ser Pro Val Tyr Leu Asp Ile Leu Gly
             180                 185                 190

( 2 ) INFORMATION FOR SEQ ID NO:36:

( i ) SEQUENCE CHARACTERISTICS:
  ( A ) LENGTH: 190 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:36:

```
Gly Pro Asp Ala Val Leu Met Ala Glu Gly Asn Pro Pro Thr Glu Leu
1               5                   10                  15

Thr Gln Ser Gln Met Leu His Ile Ala Gln Gln Ile Ala Ala Gly Met
            20                  25                  30

Val Tyr Leu Ala Ser Gln His Phe Val His Arg Asp Leu Ala Thr Arg
        35                  40                  45

Asn Cys Leu Val Gly Glu Asn Leu Leu Val Lys Ile Gly Asp Phe Gly
    50                  55                  60

Met Ser Arg Asp Val Tyr Ser Thr Asp Tyr Tyr Arg Val Gly Gly His
65                  70                  75                  80

Thr Met Leu Pro Ile Arg Trp Met Pro Pro Glu Ser Ile Met Tyr Arg
                85                  90                  95

Lys Phe Thr Thr Glu Ser Asp Val Trp Ser Leu Gly Val Val Leu Trp
            100                 105                 110

Glu Ile Phe Thr Tyr Gly Lys Gln Pro Trp Tyr Gln Leu Ser Asn Asn
        115                 120                 125

Glu Val Ile Glu Cys Ile Thr Gln Gly Arg Val Leu Gln Arg Pro Arg
    130                 135                 140

Thr Cys Pro Gln Glu Val Tyr Glu Leu Met Leu Gly Cys Trp Gln Arg
145                 150                 155                 160

Glu Pro His Thr Arg Lys Asn Ile Lys Ser Ile His Thr Leu Leu Gln
                165                 170                 175

Asn Leu Ala Lys Ala Ser Pro Val Tyr Leu Asp Ile Leu Gly
            180                 185                 190
```

( 2 ) INFORMATION FOR SEQ ID NO:37:

( i ) SEQUENCE CHARACTERISTICS:
    ( A ) LENGTH: 192 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:37:

```
Gly Pro Asp Ala Lys Leu Leu Ala Gly Gly Glu Asp Val Ala Pro Gly
1               5                   10                  15

Pro Leu Gly Leu Gly Gln Leu Leu Ala Val Ala Ser Gln Val Ala Ala
            20                  25                  30

Gly Met Val Tyr Leu Ala Gly Leu His Phe Val His Arg Asp Leu Ala
        35                  40                  45

Thr Arg Asn Cys Leu Val Gly Gln Gly Leu Val Val Lys Ile Gly Asp
    50                  55                  60

Phe Gly Met Ser Arg Asp Ile Tyr Ser Thr Asp Tyr Tyr Arg Val Gly
65                  70                  75                  80

Gly Arg Thr Met Leu Pro Ile Arg Trp Met Pro Pro Glu Ser Ile Leu
                85                  90                  95

Tyr Arg Lys Phe Thr Thr Glu Ser Asp Val Trp Ser Phe Gly Val Val
            100                 105                 110
```

|  |  |  |  |  |  |  |  |  |  |  |  |  |  |  |
|---|---|---|---|---|---|---|---|---|---|---|---|---|---|---|
| Leu | Trp | Glu<br>115 | Ile | Phe | Thr | Tyr | Gly | Lys<br>120 | Gln | Pro | Trp | Tyr<br>125 | Gln | Leu | Ser |
| Asn | Thr<br>130 | Glu | Ala | Ile | Asp | Cys<br>135 | Ile | Thr | Gln | Gly | Arg<br>140 | Glu | Leu | Glu | Arg |
| Pro<br>145 | Arg | Ala | Cys | Pro | Pro<br>150 | Glu | Val | Tyr | Ala | Ile<br>155 | Met | Arg | Gly | Cys | Trp<br>160 |
| Gln | Arg | Glu | Pro | Gln<br>165 | Gln | Arg | His | Ser | Ile<br>170 | Lys | Asp | Val | His<br>175 | Ala | Arg |
| Leu | Gln | Ala | Leu | Ala<br>180 | Gln | Ala | Pro | Pro<br>185 | Val | Tyr | Leu | Asp | Val<br>190 | Leu | Gly |

( 2 ) INFORMATION FOR SEQ ID NO:38:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:38:

|  |  |  |  |  |  |  |  |  |  |  |  |  |  |  |
|---|---|---|---|---|---|---|---|---|---|---|---|---|---|---|
| Tyr<br>1 | Val | His | Arg | Asp<br>5 | Leu | Arg | Ala | Ala | Asn<br>10 | Ile | Leu | Val | Gly | Glu<br>15 | Asn |
| Leu | Val | Cys | Lys<br>20 | Val | Ala | Asp | Phe | Gly<br>25 | Leu | Ala | Arg | Leu | Ile<br>30 | Glu | Asp |
| Asn | Glu | Tyr<br>35 | Thr | Ala | Arg | Gln | Gly<br>40 | Ala | Lys | Phe | Pro | Ile<br>45 | Lys | Trp | Thr |
| Ala | Pro<br>50 | Glu | Ala | Ala | Leu | Tyr<br>55 | Gly | Arg | Phe | Thr | Ile<br>60 | Lys | Ser | Asp | Val |
| Trp<br>65 | Ser | Phe | Gly | Ile | Leu<br>70 | Leu | Thr | Glu | Leu | Thr<br>75 | Thr |  |  |  |  |

( 2 ) INFORMATION FOR SEQ ID NO:39:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:39:

|  |  |  |  |  |  |  |  |  |  |  |  |  |  |  |
|---|---|---|---|---|---|---|---|---|---|---|---|---|---|---|
| Tyr<br>1 | Ile | His | Arg | Asp<br>5 | Leu | Arg | Ala | Ala | Asn<br>10 | Ile | Leu | Val | Gly | Glu<br>15 | Asn |
| Leu | Val | Cys | Lys<br>20 | Ile | Ala | Asp | Phe | Gly<br>25 | Leu | Ala | Arg | Leu | Ile<br>30 | Glu | Asp |
| Asn | Glu | Tyr<br>35 | Thr | Ala | Arg | Gln | Gly<br>40 | Ala | Lys | Phe | Pro | Ile<br>45 | Lys | Trp | Thr |
| Ala | Pro<br>50 | Glu | Ala | Ala | Leu | Tyr<br>55 | Gly | Arg | Phe | Thr | Ile<br>60 | Lys | Ser | Asp | Val |
| Trp<br>65 | Ser | Phe | Gly | Ile | Leu<br>70 | Gln | Thr | Glu | Leu | Val<br>75 | Thr |  |  |  |  |

( 2 ) INFORMATION FOR SEQ ID NO:40:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: unknown (i i) MOLECULE TYPE: peptide (x i) SEQUENCE DESCRIPTION: SEQ ID NO:40:

| Tyr | Ile | His | Arg | Asp | Leu | Arg | Ala | Ala | Asn | Ile | Leu | Val | Ser | Ala | Ser |
|---|---|---|---|---|---|---|---|---|---|---|---|---|---|---|---|
| 1 | | | | 5 | | | | | 10 | | | | | 15 | |
| Leu | Val | Cys | Lys | Ile | Ala | Asp | Phe | Gly | Leu | Ala | Arg | Val | Ile | Glu | Asp |
| | | | 20 | | | | | 25 | | | | | 30 | | |
| Asn | Glu | Tyr | Thr | Ala | Arg | Glu | Gly | Ala | Lys | Phe | Pro | Ile | Lys | Trp | Thr |
| | | | 35 | | | | | 40 | | | | | 45 | | |
| Ala | Pro | Glu | Ala | Ile | Asn | Phe | Gly | Ser | Phe | Thr | Ile | Lys | Ser | Asp | Val |
| | | 50 | | | | 55 | | | | | 60 | | | | |
| Trp | Ser | Phe | Gly | Ile | Leu | Leu | Met | Glu | Ile | Val | Thr | | | | |
| 65 | | | | | 70 | | | | | 75 | | | | | |

(2) INFORMATION FOR SEQ ID NO:41:

(i) SEQUENCE CHARACTERISTICS:
        (A) LENGTH: 77 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:41:

| Cys | Ile | His | Arg | Asp | Leu | Ala | Ala | Arg | Asn | Cys | Leu | Val | Thr | Glu | Lys |
|---|---|---|---|---|---|---|---|---|---|---|---|---|---|---|---|
| 1 | | | | 5 | | | | | 10 | | | | | 15 | |
| Asn | Val | Leu | Lys | Ile | Ser | Asp | Phe | Gly | Met | Ser | Arg | Glu | Glu | Ala | Asp |
| | | | 20 | | | | | 25 | | | | | 30 | | |
| Gly | Ile | Tyr | Ala | Ala | Cys | Ser | Gly | Leu | Arg | Gln | Val | Pro | Val | Lys | Trp |
| | | | 35 | | | | | 40 | | | | | 45 | | |
| Thr | Ala | Pro | Glu | Ala | Leu | Asn | Tyr | Gly | Arg | Tyr | Ser | Ser | Glu | Ser | Asp |
| | | 50 | | | | 55 | | | | | 60 | | | | |
| Val | Trp | Ser | Phe | Gly | Ile | Leu | Leu | Trp | Glu | Thr | Phe | Ser | | | |
| 65 | | | | | 70 | | | | | 75 | | | | | |

(2) INFORMATION FOR SEQ ID NO:42:

(i) SEQUENCE CHARACTERISTICS:
        (A) LENGTH: 76 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:42:

| Phe | Ile | His | Arg | Asp | Leu | Ala | Ala | Arg | Asn | Cys | Leu | Val | Gly | Glu | Asn |
|---|---|---|---|---|---|---|---|---|---|---|---|---|---|---|---|
| 1 | | | | 5 | | | | | 10 | | | | | 15 | |
| His | Leu | Val | Lys | Val | Ala | Asp | Phe | Gly | Leu | Ser | Arg | Leu | Met | Thr | Gly |
| | | | 20 | | | | | 25 | | | | | 30 | | |
| Asp | Thr | Tyr | Thr | Ala | His | Ala | Gly | Ala | Lys | Phe | Pro | Ile | Lys | Trp | Thr |
| | | | 35 | | | | | 40 | | | | | 45 | | |
| Ala | Pro | Glu | Ser | Leu | Ala | Tyr | Asn | Lys | Phe | Ser | Ile | Lys | Ser | Asp | Val |
| | | 50 | | | | 55 | | | | | 60 | | | | |
| Trp | Ala | Phe | Gly | Val | Leu | Leu | Trp | Glu | Ile | Ala | Thr | | | | |
| 65 | | | | | 70 | | | | | 75 | | | | | |

(2) INFORMATION FOR SEQ ID NO:43:

(i) SEQUENCE CHARACTERISTICS:
        (A) LENGTH: 77 amino acids (B) TYPE: amino acid
(C) STRANDEDNESS: single
(D) TOPOLOGY: unknown (i i) MOLECULE TYPE: peptide (x i) SEQUENCE DESCRIPTION: SEQ ID NO:43:

| Leu | Val | His | Arg | Asp | Leu | Ala | Ala | Arg | Asn | Val | Leu | Val | Lys | Thr | Pro |
|---|---|---|---|---|---|---|---|---|---|---|---|---|---|---|---|
| 1 | | | | 5 | | | | | 10 | | | | | 15 | |
| Gln | His | Val | Lys | Ile | Thr | Asp | Phe | Gly | Leu | Ala | Lys | Leu | Leu | Gly | Ala |
| | | | 20 | | | | | 25 | | | | | 30 | | |
| Glu | Glu | Lys | Glu | Tyr | His | Ala | Glu | Gly | Gly | Lys | Val | Pro | Ile | Lys | Trp |
| | | 35 | | | | | 40 | | | | | 45 | | | |
| Met | Ala | Leu | Glu | Ser | Ile | Leu | His | Arg | Ile | Tyr | Thr | His | Gln | Ser | Asp |
| | | 50 | | | | 55 | | | | | 60 | | | | |
| Val | Trp | Ser | Tyr | Gly | Val | Thr | Val | Trp | Glu | Leu | Met | Thr | | | |
| 65 | | | | | 70 | | | | | 75 | | | | | |

(2) INFORMATION FOR SEQ ID NO:44:

(i) SEQUENCE CHARACTERISTICS:
(A) LENGTH: 77 amino acids
(B) TYPE: amino acid
(C) STRANDEDNESS: single
(D) TOPOLOGY: unknown (i i) MOLECULE TYPE: peptide (x i) SEQUENCE DESCRIPTION: SEQ ID NO:44:

| Leu | Val | His | Arg | Asp | Leu | Ala | Ala | Arg | Asn | Val | Leu | Val | Lys | Ser | Pro |
|---|---|---|---|---|---|---|---|---|---|---|---|---|---|---|---|
| 1 | | | | 5 | | | | | 10 | | | | | 15 | |
| Met | His | Val | Lys | Ile | Thr | Asp | Phe | Gly | Leu | Ala | Arg | Leu | Leu | Asp | Ile |
| | | | 20 | | | | | 25 | | | | | 30 | | |
| Asp | Glu | Thr | Glu | Tyr | His | Ala | Asp | Gly | Gly | Lys | Val | Pro | Ile | Lys | Trp |
| | | 35 | | | | | 40 | | | | | 45 | | | |
| Met | Ala | Leu | Glu | Ser | Ile | Leu | Arg | Arg | Arg | Phe | Thr | His | Gln | Ser | Asp |
| | | 50 | | | | 55 | | | | | 60 | | | | |
| Val | Trp | Ser | Tyr | Gly | Val | Thr | Val | Trp | Glu | Leu | Met | Thr | | | |
| 65 | | | | | 70 | | | | | 75 | | | | | |

(2) INFORMATION FOR SEQ ID NO:45:

(i) SEQUENCE CHARACTERISTICS:
(A) LENGTH: 76 amino acids
(B) TYPE: amino acid
(C) STRANDEDNESS: single
(D) TOPOLOGY: unknown (i i) MOLECULE TYPE: peptide (x i) SEQUENCE DESCRIPTION: SEQ ID NO:45:

| Cys | Val | His | Arg | Asp | Val | Ala | Ala | Arg | Asn | Val | Leu | Leu | Thr | Ser | Gly |
|---|---|---|---|---|---|---|---|---|---|---|---|---|---|---|---|
| 1 | | | | 5 | | | | | 10 | | | | | 15 | |
| His | Val | Ala | Lys | Ile | Gly | Asp | Phe | Gly | Leu | Ala | Arg | Asp | Ile | Met | Asn |
| | | | 20 | | | | | 25 | | | | | 30 | | |
| Asp | Ser | Asn | Tyr | Val | Val | Lys | Gly | Asn | Ala | Leu | Pro | Asn | Lys | Trp | Met |
| | | 35 | | | | | 40 | | | | | 45 | | | |
| Ala | Pro | Glu | Ser | Ile | Phe | Asp | Cys | Val | Ile | Thr | Val | Gln | Ser | Asp | Val |
| | | 50 | | | | 55 | | | | | 60 | | | | |
| Trp | Ser | Tyr | Gly | Ile | Leu | Leu | Trp | Glu | Ile | Phe | Ser | | | | |
| 65 | | | | | 70 | | | | | 75 | | | | | |

( 2 ) INFORMATION FOR SEQ ID NO:46:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:46:

```
Cys Val His Arg Asp Leu Ala Ala Arg Asn Val Leu Ile Cys Glu Gly
  1               5                  10                  15
Lys Leu Val Lys Ile Cys Asp Phe Gly Leu Ala Arg Asp Ile Met Arg
             20                  25                  30
Asp Ser Asn Tyr Ile Ser Lys Gly Ser Thr Tyr Leu Pro Leu Lys Trp
         35                  40                  45
Met Ala Pro Glu Ser Ile Phe Asn Ser Leu Tyr Thr Thr Leu Ser Asp
     50                  55                  60
Val Trp Ser Phe Gly Ile Leu Leu Trp Glu Ile Phe Thr
 65                  70                  75
```

( 2 ) INFORMATION FOR SEQ ID NO:47:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:47:

```
Phe Val His Arg Asp Leu Ala Ala Arg Asn Cys Met Val Ala His Asp
  1               5                  10                  15
Phe Thr Val Lys Ile Gly Asp Phe Gly Met Thr Arg Asp Ile Tyr Glu
             20                  25                  30
Thr Asp Tyr Tyr Arg Lys Gly Gly Lys Gly Leu Leu Pro Val Arg Trp
         35                  40                  45
Met Ala Pro Glu Ser Leu Lys Asp Gly Val Phe Thr Thr Ser Ser Asp
     50                  55                  60
Met Trp Ser Phe Gly Val Val Leu Trp Glu Ile Thr Ser
 65                  70                  75
```

( 2 ) INFORMATION FOR SEQ ID NO:48:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:48:

```
Phe Val His Arg Asp Leu Ala Ala Arg Asn Cys Met Val Ala Glu Asp
  1               5                  10                  15
Phe Thr Val Lys Ile Gly Asp Phe Gly Met Thr Arg Asp Ile Tyr Glu
             20                  25                  30
Thr Asp Tyr Tyr Arg Lys Gly Gly Lys Gly Leu Leu Pro Val Arg Trp
         35                  40                  45
Met Ser Pro Glu Ser Leu Lys Asp Gly Val Phe Thr Thr Ser Ser Asp
     50                  55                  60
```

```
        Val  Trp  Ser  Phe  Gly  Val  Val  Leu  Trp  Glu  Ile  Ala  Thr
        65                  70                  75
```

(2) INFORMATION FOR SEQ ID NO:49:

(i) SEQUENCE CHARACTERISTICS:
        (A) LENGTH: 79 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:49:

```
        Phe  Val  His  Arg  Asp  Leu  Ala  Ala  Arg  Asn  Cys  Met  Leu  Asp  Glu  Lys
        1                   5                   10                  15

Phe  Thr  Val  Lys  Val  Ala  Asp  Phe  Gly  Leu  Ala  Arg  Asp  Met  Tyr  Asp
                            20                  25                  30

Lys  Glu  Tyr  Tyr  Ser  Val  His  Asn  Lys  Thr  Gly  Ala  Lys  Leu  Pro  Val
                       35                  40                  45

Lys  Trp  Met  Ala  Leu  Glu  Ser  Leu  Gln  Thr  Gln  Lys  Phe  Thr  Thr  Lys
                  50                  55                  60

Ser  Asp  Val  Trp  Ser  Phe  Gly  Val  Val  Leu  Trp  Glu  Leu  Met  Thr
        65                  70                  75
```

(2) INFORMATION FOR SEQ ID NO:50:

(i) SEQUENCE CHARACTERISTICS:
        (A) LENGTH: 77 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:50:

```
        Phe  Val  His  Arg  Asp  Leu  Ala  Thr  Arg  Asn  Cys  Leu  Val  Gly  Gln  Gly
        1                   5                   10                  15

Leu  Val  Val  Lys  Ile  Gly  Asp  Phe  Gly  Met  Ser  Arg  Asp  Ile  Tyr  Ser
                            20                  25                  30

Thr  Asp  Tyr  Tyr  Arg  Val  Gly  Gly  Arg  Thr  Met  Leu  Pro  Ile  Arg  Trp
                       35                  40                  45

Met  Pro  Pro  Glu  Ser  Ile  Leu  Tyr  Arg  Lys  Phe  Thr  Thr  Glu  Ser  Asp
                  50                  55                  60

Val  Trp  Ser  Phe  Gly  Val  Val  Leu  Trp  Glu  Ile  Phe  Thr
        65                  70                  75
```

(2) INFORMATION FOR SEQ ID NO:51:

(i) SEQUENCE CHARACTERISTICS:
        (A) LENGTH: 279 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:51:

```
        His  Asn  Ile  Val  Leu  Lys  Arg  Glu  Leu  Gly  Glu  Gly  Ala  Phe  Gly  Lys
        1                   5                   10                  15

Val  Phe  Leu  Ala  Glu  Cys  Tyr  Asn  Leu  Cys  Pro  Glu  Gln  Asp  Lys  Ile
                            20                  25                  30

Leu  Val  Ala  Val  Lys  Thr  Leu  Lys  Asp  Ala  Ser  Asp  Asn  Ala  Arg  Lys
                       35                  40                  45
```

| | | | | | | | | | | | | | | |
|---|---|---|---|---|---|---|---|---|---|---|---|---|---|---|
|Asp|Phe|His|Arg|Glu|Ala|Glu|Leu|Leu|Thr|Asn|Leu|Gln|His|Glu|His|
| |50| | | |55| | | | |60| | | | |
|Ile|Val|Lys|Phe|Tyr|Gly|Val|Cys|Val|Glu|Gly|Asp|Pro|Leu|Ile|Met|
|65| | | |70| | | |75| | | | | |80|
|Val|Phe|Glu|Tyr|Met|Lys|His|Gly|Asp|Leu|Asn|Lys|Phe|Leu|Arg|Ala|
| | | | |85| | | |90| | | |95| | |
|His|Gly|Pro|Asp|Ala|Val|Leu|Met|Ala|Glu|Gly|Asn|Pro|Pro|Thr|Glu|
| | | |100| | | |105| | | |110| | | |
|Leu|Thr|Gln|Ser|Gln|Met|Leu|His|Ile|Ala|Gln|Gln|Ile|Ala|Ala|Gly|
| | |115| | | |120| | | |125| | | | |
|Met|Val|Tyr|Leu|Ala|Ser|Gln|His|Phe|Val|His|Arg|Asp|Leu|Ala|Thr|
| |130| | | |135| | | |140| | | | | |
|Arg|Asn|Cys|Leu|Val|Gly|Glu|Asn|Leu|Leu|Val|Lys|Ile|Gly|Asp|Phe|
|145| | | |150| | | |155| | | | | |160|
|Gly|Met|Ser|Arg|Asp|Val|Tyr|Ser|Thr|Asp|Tyr|Tyr|Arg|Val|Gly|Gly|
| | | |165| | | |170| | | |175| | | |
|His|Thr|Met|Leu|Pro|Ile|Arg|Trp|Met|Pro|Glu|Ser|Ile|Met|Tyr|
| | | |180| | | |185| | | |190| | | |
|Arg|Lys|Phe|Thr|Thr|Glu|Ser|Asp|Val|Trp|Ser|Leu|Gly|Val|Val|Leu|
| | |195| | | |200| | | |205| | | | |
|Trp|Glu|Ile|Phe|Thr|Tyr|Gly|Lys|Gln|Pro|Trp|Tyr|Gln|Leu|Ser|Asn|
| |210| | | |215| | | |220| | | | | |
|Asn|Glu|Val|Ile|Glu|Cys|Ile|Thr|Gln|Gly|Arg|Val|Leu|Gln|Arg|Pro|
|225| | | |230| | | |235| | | | | |240|
|Arg|Thr|Cys|Pro|Gln|Glu|Val|Tyr|Glu|Leu|Met|Leu|Gly|Cys|Trp|Gln|
| | | |245| | | |250| | | |255| | | |
|Arg|Glu|Pro|His|Thr|Arg|Lys|Asn|Ile|Lys|Asn|Ile|His|Thr|Leu|Leu|
| | |260| | | |265| | | |270| | | | |
|Gln|Asn|Leu|Ala|Lys|Ala|Ser|
| | |275| | | | |

( 2 ) INFORMATION FOR SEQ ID NO:52:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:52:

| | | | | | | | | | | | | | | |
|---|---|---|---|---|---|---|---|---|---|---|---|---|---|---|
|Arg|Asp|Ile|Val|Leu|Lys|Trp|Glu|Leu|Gly|Glu|Gly|Ala|Phe|Gly|Lys|
|1| | | |5| | | |10| | | |15| | |
|Val|Phe|Leu|Ala|Glu|Cys|His|Asn|Leu|Leu|Pro|Glu|Gln|Asp|Lys|Met|
| | | |20| | | |25| | | |30| | | |
|Leu|Val|Ala|Val|Lys|Ala|Leu|Lys|Glu|Ala|Ser|Glu|Ser|Ala|Arg|Gln|
| | |35| | | |40| | | |45| | | | |
|Asp|Phe|Gln|Arg|Glu|Ala|Glu|Leu|Leu|Thr|Met|Leu|Gln|His|Gln|His|
| |50| | | |55| | | | |60| | | | |
|Ile|Val|Arg|Phe|Phe|Gly|Val|Cys|Thr|Glu|Gly|Arg|Pro|Leu|Leu|Met|
|65| | | |70| | | |75| | | | | |80|
|Val|Phe|Glu|Tyr|Met|Arg|His|Gly|Asp|Leu|Asn|Arg|Phe|Leu|Arg|Ser|
| | | | |85| | | |90| | | |95| | |
|His|Gly|Pro|Asp|Ala|Lys|Leu|Leu|Gly|Gly|Ala|Glu|Asp|Val|Ala|Pro|
| | | |100| | | |105| | | |110| | | |

| | | | | | | | | | | | | | | |
|---|---|---|---|---|---|---|---|---|---|---|---|---|---|---|
|Gly|Pro|Leu<br>115|Gly|Leu|Gly|Gln|Leu<br>120|Leu|Ala|Val|Ala|Ser<br>125|Gln|Val|Ala|
|Ala|Gly<br>130|Met|Val|Tyr|Leu<br>135|Ala|Gly|Leu|His|Phe|Val<br>140|His|Arg|Asp|Leu|
|Ala<br>145|Thr|Arg|Asn|Cys|Leu<br>150|Val|Gly|Gln|Gly|Leu<br>155|Val|Val|Lys|Ile|Gly<br>160|
|Asp|Phe|Gly|Met|Ser<br>165|Arg|Asp|Ile|Tyr|Ser<br>170|Thr|Asp|Tyr|Tyr|Arg<br>175|Val|
|Gly|Gly|Arg|Thr<br>180|Met|Leu|Pro|Ile|Arg<br>185|Trp|Met|Pro|Pro|Glu<br>190|Ser|Ile|
|Leu|Tyr|Arg<br>195|Lys|Phe|Thr|Thr|Glu<br>200|Ser|Asp|Val|Trp|Ser<br>205|Phe|Gly|Val|
|Val|Leu<br>210|Trp|Glu|Ile|Phe|Thr<br>215|Tyr|Gly|Lys|Gln|Pro<br>220|Trp|Tyr|Gln|Leu|
|Ser<br>225|Asn|Thr|Glu|Ala|Ile<br>230|Asp|Cys|Ile|Thr|Gln<br>235|Gly|Arg|Glu|Leu|Glu<br>240|
|Arg|Pro|Arg|Ala|Cys<br>245|Pro|Pro|Glu|Val|Tyr<br>250|Ala|Ile|Met|Arg|Gly<br>255|Cys|
|Trp|Gln|Arg|Glu<br>260|Pro|Gln|Gln|Arg|His<br>265|Ser|Ile|Lys|Asp|Val<br>270|His|Ala|
|Arg|Leu|Gln<br>275|Ala|Leu|Ala|Gln|Ala|Pro| | | | | | | |

(2) INFORMATION FOR SEQ ID NO:53:

(i) SEQUENCE CHARACTERISTICS:
        (A) LENGTH: 272 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:53:

| | | | | | | | | | | | | | | |
|---|---|---|---|---|---|---|---|---|---|---|---|---|---|---|
|Glu<br>1|Lys|Ile|Thr|Leu<br>5|Leu|Arg|Glu|Leu|Gly<br>10|Gln|Gly|Ser|Phe|Gly<br>15|Met|
|Val|Tyr|Glu|Gly<br>20|Asn|Ala|Arg|Asp|Ile<br>25|Ile|Lys|Gly|Glu|Ala<br>30|Glu|Thr|
|Arg|Val|Ala<br>35|Val|Lys|Thr|Val|Asn<br>40|Glu|Ser|Ala|Ser|Leu<br>45|Arg|Glu|Arg|
|Ile|Glu<br>50|Phe|Leu|Asn|Glu|Ala<br>55|Ser|Val|Met|Lys|Gly<br>60|Phe|Thr|Cys|His|
|His<br>65|Val|Val|Arg|Leu|Leu<br>70|Gly|Val|Val|Ser|Lys<br>75|Gly|Gln|Pro|Thr|Leu<br>80|
|Val|Val|Met|Glu|Leu<br>85|Met|Ala|His|Gly|Asp<br>90|Leu|Lys|Ser|Tyr|Leu<br>95|Arg|
|Ser|Leu|Arg|Pro<br>100|Glu|Ala|Glu|Asn|Asn<br>105|Pro|Gly|Arg|Pro|Pro<br>110|Pro|Thr|
|Leu|Gln|Glu|Met<br>115|Ile|Gln|Met|Ala|Ala<br>120|Glu|Ile|Ala|Asp|Gly<br>125|Met|Ala|
|Tyr|Leu|Asn<br>130|Ala|Lys|Lys|Phe|His<br>135|Arg|Asp|Leu|Ala|Ala<br>140|Arg|Asn|
|Cys<br>145|Met|Val|Ala|His|Asp<br>150|Phe|Thr|Val|Lys|Ile<br>155|Gly|Asp|Phe|Gly|Met<br>160|
|Thr|Arg|Asp|Ile|Tyr<br>165|Glu|Thr|Asp|Tyr|Tyr<br>170|Arg|Lys|Gly|Gly|Lys<br>175|Gly|
|Leu|Leu|Pro|Val|Arg|Trp|Met|Ala|Pro|Glu|Ser|Leu|Lys|Asp|Gly|Val|

|     |     |     |     |     | 180 |     |     |     | 185 |     |     |     | 190 |     |
| --- | --- | --- | --- | --- | --- | --- | --- | --- | --- | --- | --- | --- | --- | --- |
| Phe | Thr | Thr 195 | Ser | Ser | Asp | Met | Trp 200 | Ser | Phe | Gly | Val | Val 205 | Leu | Trp | Glu |
| Ile | Thr 210 | Ser | Leu | Ala | Glu | Gln 215 | Pro | Tyr | Gln | Gly | Leu 220 | Ser | Asn | Glu | Gln |
| Val 225 | Leu | Lys | Phe | Val | Met 230 | Asp | Gly | Gly | Tyr | Leu 235 | Asp | Gln | Pro | Asp | Asn 240 |
| Cys | Pro | Glu | Arg | Val 245 | Thr | Asp | Leu | Met | Arg 250 | Met | Cys | Trp | Gln | Phe 255 | Asn |
| Pro | Lys | Met | Arg 260 | Pro | Thr | Phe | Leu | Glu 265 | Ile | Val | Asn | Leu | Leu 270 | Lys | Asp |

( 2 ) INFORMATION FOR SEQ ID NO:54:

( i ) SEQUENCE CHARACTERISTICS:
        ( A ) LENGTH: 266 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:54:

| Glu 1 | Lys | Ile | Thr | Met 5 | Ser | Arg | Glu | Leu | Gly 10 | Gln | Gly | Ser | Phe | Gly 15 | Met |
| --- | --- | --- | --- | --- | --- | --- | --- | --- | --- | --- | --- | --- | --- | --- | --- |
| Val | Tyr | Glu | Gly 20 | Val | Ala | Lys | Gly | Val 25 | Val | Lys | Asp | Glu | Pro 30 | Glu | Thr |
| Arg | Val | Ala 35 | Ile | Lys | Thr | Val | Asn 40 | Glu | Ala | Ala | Ser | Met 45 | Arg | Glu | Arg |
| Ile | Glu 50 | Phe | Leu | Asn | Glu | Ala 55 | Ser | Val | Met | Lys | Glu 60 | Phe | Asn | Cys | His |
| His 65 | Val | Val | Arg | Leu | Leu 70 | Gly | Val | Val | Ser | Gln 75 | Gly | Gln | Pro | Thr | Leu 80 |
| Val | Ile | Met | Glu | Leu 85 | Met | Thr | Arg | Gly | Asp 90 | Leu | Lys | Ser | Tyr | Leu 95 | Arg |
| Ser | Leu | Arg | Pro 100 | Glu | Met | Glu | Asn | Asn 105 | Pro | Val | Leu | Ala | Pro 110 | Pro | Ser |
| Leu | Ser | Lys 115 | Met | Ile | Gln | Met | Ala 120 | Gly | Glu | Ile | Ala | Asp 125 | Gly | Met | Ala |
| Tyr | Leu 130 | Asn | Ala | Asn | Lys | Phe 135 | Val | His | Arg | Asp | Leu 140 | Ala | Ala | Arg | Asn |
| Cys 145 | Met | Val | Ala | Glu | Asp 150 | Phe | Thr | Val | Lys | Ile 155 | Gly | Asp | Phe | Gly | Met 160 |
| Thr | Arg | Asp | Ile | Tyr 165 | Glu | Thr | Asp | Tyr | Tyr 170 | Arg | Lys | Gly | Gly | Lys 175 | Gly |
| Leu | Leu | Pro | Val 180 | Arg | Trp | Met | Ser | Pro 185 | Glu | Ser | Leu | Lys | Asp 190 | Gly | Val |
| Phe | Thr | Thr 195 | Tyr | Ser | Asp | Val | Trp 200 | Ser | Phe | Gly | Val | Val 205 | Leu | Trp | Glu |
| Ile | Ala 210 | Thr | Leu | Ala | Glu | Gln 215 | Pro | Tyr | Gln | Gly | Leu 220 | Ser | Asn | Glu | Gln |
| Val 225 | Leu | Arg | Phe | Val | Met 230 | Glu | Gly | Gly | Leu | Leu 235 | Asp | Lys | Pro | Asp | Asn 240 |
| Cys | Pro | Asp | Met | Leu 245 | Phe | Glu | Leu | Met | Arg 250 | Met | Cys | Trp | Gln | Tyr 255 | Asn |
| Pro | Lys | Met | Arg 260 | Pro | Ser | Phe | Leu | Glu 265 | Ile |

(2) INFORMATION FOR SEQ ID NO:55:

(i) SEQUENCE CHARACTERISTICS:
    (A) LENGTH: 274 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:55:

| Glu | Lys | Leu | Thr | Leu | Arg | Leu | Leu | Leu | Gly | Ser | Gly | Ala | Phe | Gly | Glu |
|---|---|---|---|---|---|---|---|---|---|---|---|---|---|---|---|
| 1 | | | | 5 | | | | | 10 | | | | | 15 | |
| Val | Tyr | Glu | Gly | Thr | Ala | Val | Asp | Ile | Leu | Gly | Val | Gly | Ser | Gly | Glu |
| | | | 20 | | | | | 25 | | | | | 30 | | |
| Ile | Lys | Val | Ala | Val | Lys | Thr | Leu | Lys | Lys | Gly | Ser | Thr | Asp | Gln | Glu |
| | | 35 | | | | | 40 | | | | | 45 | | | |
| Lys | Ile | Glu | Phe | Leu | Lys | Glu | Ala | His | Leu | Met | Ser | Lys | Phe | Asn | His |
| | 50 | | | | | 55 | | | | | 60 | | | | |
| Pro | Asn | Ile | Leu | Lys | Gln | Leu | Gly | Val | Cys | Leu | Leu | Asn | Glu | Pro | Gln |
| 65 | | | | | 70 | | | | | 75 | | | | | 80 |
| Tyr | Ile | Ile | Leu | Glu | Leu | Met | Glu | Gly | Gly | Asp | Leu | Leu | Thr | Tyr | Leu |
| | | | | 85 | | | | | 90 | | | | | 95 | |
| Arg | Lys | Ala | Arg | Met | Ala | Thr | Phe | Tyr | Gly | Pro | Leu | Leu | Thr | Leu | Val |
| | | | 100 | | | | | 105 | | | | | 110 | | |
| Asp | Leu | Val | Asp | Leu | Cys | Val | Asp | Ile | Ser | Lys | Gly | Cys | Val | Tyr | Leu |
| | | | 115 | | | | | 120 | | | | | 125 | | |
| Glu | Arg | Met | His | Phe | Ile | His | Arg | Asp | Leu | Ala | Ala | Arg | Asn | Cys | Leu |
| | | 130 | | | | | 135 | | | | | 140 | | | |
| Val | Ser | Val | Lys | Asp | Tyr | Thr | Ser | Pro | Arg | Ile | Val | Lys | Ile | Gly | Asp |
| 145 | | | | | 150 | | | | | 155 | | | | | 160 |
| Phe | Gly | Leu | Ala | Arg | Asp | Ile | Tyr | Lys | Asn | Asp | Tyr | Tyr | Arg | Lys | Arg |
| | | | | 165 | | | | | 170 | | | | | 175 | |
| Gly | Glu | Gly | Leu | Leu | Pro | Val | Arg | Trp | Met | Ala | Pro | Glu | Ser | Leu | Met |
| | | | | 180 | | | | | 185 | | | | | 190 | |
| Asp | Gly | Ile | Phe | Thr | Thr | Gln | Ser | Asp | Val | Trp | Ser | Phe | Gly | Ile | Leu |
| | | | 195 | | | | | 200 | | | | | 205 | | |
| Ile | Trp | Glu | Ile | Leu | Thr | Leu | Gly | His | Gln | Pro | Tyr | Pro | Ala | His | Ser |
| | 210 | | | | | 215 | | | | | 220 | | | | |
| Asn | Leu | Asp | Val | Leu | Asn | Tyr | Val | Gln | Thr | Gly | Gly | Arg | Leu | Glu | Pro |
| 225 | | | | | 230 | | | | | 235 | | | | | 240 |
| Pro | Arg | Asn | Cys | Pro | Asp | Asp | Leu | Trp | Asn | Leu | Met | Thr | Gln | Cys | Trp |
| | | | | 245 | | | | | 250 | | | | | 255 | |
| Ala | Gln | Glu | Pro | Asp | Gln | Arg | Pro | Thr | Phe | His | Arg | Ile | Gln | Asp | Gln |
| | | | 260 | | | | | 265 | | | | | 270 | | |
| Leu | Gln | | | | | | | | | | | | | | |

(2) INFORMATION FOR SEQ ID NO:56:

(i) SEQUENCE CHARACTERISTICS:
    (A) LENGTH: 282 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:56:

```
Glu  Asn  Ile  Ile  Gln  Leu  Ala  Pro  Leu  Gly  Gln  Gly  Ser  Phe  Gly  Met
1              5                        10                       15

Val  Tyr  Glu  Gly  Ile  Leu  Lys  Ser  Phe  Pro  Pro  Asn  Gly  Val  Asp  Arg
              20                       25                       30

Glu  Cys  Ala  Ile  Lys  Thr  Val  Asn  Glu  Asn  Ala  Thr  Asp  Arg  Glu  Arg
          35                       40                       45

Thr  Asn  Phe  Leu  Ser  Glu  Ala  Ser  Val  Met  Lys  Glu  Phe  Asp  Thr  Tyr
     50                       55                       60

His  Val  Val  Arg  Leu  Leu  Gly  Val  Cys  Ser  Arg  Gly  Gln  Pro  Ala  Leu
65                       70                       75                       80

Val  Val  Met  Glu  Leu  Met  Lys  Lys  Val  Glu  Leu  Lys  Ser  Tyr  Leu  Arg
               85                       90                       95

Ala  His  Arg  Pro  Arg  Ser  Gly  Met  Arg  Pro  Asp  Asp  Val  Ser  Leu  Ile
               100                      105                      110

Ala  Trp  Met  Thr  Gly  Asn  Val  Gln  Pro  Pro  Thr  Tyr  Gly  Arg  Ile  Tyr
          115                      120                      125

Gln  Val  Ala  Ile  Glu  Ile  Ala  Asp  Gly  Met  Ala  Tyr  Leu  Ala  Ala  Lys
     130                      135                      140

Lys  Phe  Val  His  Arg  Asp  Leu  Ala  Ala  Arg  Asn  Cys  Met  Val  Ala  Asp
145                      150                      155                      160

Asp  Leu  Thr  Val  Lys  Ile  Gly  Asp  Phe  Gly  Met  Thr  Arg  Asp  Ile  Tyr
                    165                      170                      175

Glu  Thr  Asp  Tyr  Tyr  Arg  Lys  Gly  Thr  Lys  Gly  Leu  Leu  Pro  Val  Arg
               180                      185                      190

Trp  Met  Pro  Pro  Glu  Ser  Leu  Arg  Asp  Gly  Val  Tyr  Ser  Ser  Ala  Ser
          195                      200                      205

Asp  Val  Phe  Ser  Phe  Gly  Val  Val  Leu  Trp  Glu  Met  Ala  Thr  Leu  Ala
     210                      215                      220

Ala  Gln  Pro  Tyr  Gln  Gly  Leu  Ser  Asn  Glu  Gln  Val  Leu  Arg  Tyr  Val
225                      230                      235                      240

Ile  Asp  Gly  Gly  Val  Met  Glu  Arg  Pro  Glu  Asn  Cys  Pro  Asp  Phe  Leu
                    245                      250                      255

His  Lys  Leu  Met  Gln  Arg  Cys  Trp  His  Arg  Ser  Ser  Ala  Arg  Pro
               260                      265                      270

Ser  Phe  Leu  Asp  Ile  Ile  Ala  Tyr  Leu  Glu
     275                      280
```

(2) INFORMATION FOR SEQ ID NO:57:

(i) SEQUENCE CHARACTERISTICS:
        (A) LENGTH: 277 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:57:

```
Ser  Gln  Leu  Lys  Leu  Leu  Arg  Phe  Leu  Gly  Ser  Gly  Ala  Phe  Gly  Glu
1              5                        10                       15

Val  Tyr  Glu  Gly  Gln  Leu  Lys  Thr  Glu  Asp  Ser  Glu  Glu  Pro  Gln  Arg
               20                       25                       30

Val  Ala  Ile  Lys  Ser  Leu  Arg  Lys  Gly  Ala  Ser  Glu  Phe  Ala  Glu  Leu
          35                       40                       45

Leu  Gln  Glu  Ala  Gln  Leu  Met  Ser  Asn  Phe  Lys  His  Glu  Asn  Ile  Val
     50                       55                       60

Arg  Leu  Val  Gly  Ile  Cys  Phe  Asp  Thr  Glu  Ser  Ile  Ser  Leu  Ile  Met
```

```
        65                      70                      75                      80
Glu   His   Met   Glu   Ala   Gly   Asp   Leu   Leu   Ser   Tyr   Leu   Arg   Ala   Ala   Arg
                        85                      90                            95

Ala   Thr   Ser   Thr   Gln   Glu   Pro   Gln   Pro   Thr   Ala   Gly   Leu   Ser   Leu   Ser
                  100                     105                           110

Glu   Leu   Leu   Ala   Met   Cys   Ile   Asp   Val   Ala   Asn   Gly   Cys   Ser   Tyr   Leu
            115                           120                           125

Glu   Asp   Met   His   Phe   Val   His   Arg   Asp   Leu   Ala   Cys   Arg   Asn   Cys   Leu
      130                                 135                     140

Val   Thr   Glu   Ser   Thr   Gly   Ser   Thr   Asp   Arg   Arg   Arg   Thr   Val   Lys   Ile
145                                 150                     155                           160

Gly   Asp   Phe   Gly   Leu   Ala   Arg   Asp   Ile   Tyr   Lys   Ser   Asp   Tyr   Tyr   Arg
                        165                     170                           175

Lys   Glu   Gly   Glu   Gly   Leu   Leu   Pro   Val   Arg   Trp   Met   Ser   Pro   Glu   Ser
                  180                     185                           190

Leu   Val   Asp   Gly   Leu   Phe   Thr   Thr   Gln   Ser   Asp   Val   Trp   Ala   Phe   Gly
            195                           200                           205

Val   Leu   Cys   Trp   Glu   Ile   Leu   Thr   Leu   Gly   Gln   Gln   Pro   Tyr   Ala   Ala
      210                                 215                     220

Arg   Asn   Asn   Phe   Glu   Val   Leu   Ala   His   Val   Lys   Glu   Gly   Gly   Arg   Leu
225                                 230                     235                           240

Gln   Gln   Pro   Pro   Met   Cys   Thr   Glu   Lys   Leu   Tyr   Ser   Leu   Leu   Leu   Cys
                        245                     250                           255

Trp   Arg   Thr   Asp   Pro   Trp   Glu   Arg   Pro   Ser   Phe   Arg   Arg   Cys   Tyr   Asn
                  260                     265                           270

Thr   Leu   His   Ala   Ile
                  275
```

( 2 ) INFORMATION FOR SEQ ID NO:58:

( i ) SEQUENCE CHARACTERISTICS:
        ( A ) LENGTH: 256 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:58:

```
Val   His   Phe   Asn   Glu   Val   Ile   Gly   Arg   Gly   His   Phe   Gly   Cys   Val   Tyr
1                       5                       10                            15

His   Gly   Thr   Leu   Leu   Asp   Asn   Asp   Gly   Lys   Lys   Ile   His   Cys   Ala   Val
                  20                      25                            30

Lys   Ser   Leu   Asn   Arg   Ile   Thr   Asp   Ile   Gly   Glu   Val   Ser   Gln   Phe   Leu
            35                            40                            45

Thr   Glu   Gly   Ile   Ile   Met   Lys   Asp   Phe   Ser   His   Pro   Asn   Val   Leu   Ser
      50                            55                      60

Leu   Leu   Gly   Ile   Cys   Leu   Arg   Ser   Glu   Gly   Ser   Pro   Leu   Val   Val   Leu
65                            70                      75                            80

Pro   Tyr   Met   Lys   His   Gly   Asp   Leu   Arg   Asn   Phe   Ile   Arg   Asn   Glu   Thr
                        85                      90                            95

His   Asn   Pro   Thr   Val   Lys   Asp   Leu   Ile   Gly   Phe   Gly   Leu   Gln   Val   Ala
                  100                     105                           110

Lys   Ala   Met   Lys   Tyr   Leu   Ala   Ser   Lys   Lys   Phe   Val   His   Arg   Asp   Leu
            115                           120                           125

Ala   Ala   Arg   Asn   Cys   Met   Leu   Asp   Glu   Lys   Phe   Thr   Val   Lys   Val   Ala
      130                           135                     140
```

-continued

```
        Asp   Phe   Gly   Leu   Ala   Arg   Asp   Met   Tyr   Asp   Lys   Glu   Tyr   Tyr   Ser   Val
        145                     150                     155                                         160

His   Asn   Lys   Thr   Gly   Ala   Lys   Leu   Pro   Val   Lys   Trp   Met   Ala   Leu   Glu
                                165                     170                                 175

Ser   Leu   Gln   Thr   Gln   Lys   Phe   Thr   Thr   Lys   Ser   Asp   Val   Trp   Ser   Phe
                                180                     185                                 190

Gly   Val   Val   Leu   Trp   Glu   Leu   Met   Thr   Arg   Gly   Ala   Pro   Pro   Tyr   Pro
                          195                     200                           205

Asp   Val   Asn   Thr   Phe   Asp   Ile   Thr   Val   Tyr   Leu   Leu   Gln   Gly   Arg   Arg
                          210                     215                           220

Leu   Ile   Gln   Pro   Glu   Tyr   Cys   Pro   Asp   Pro   Leu   Tyr   Glu   Val   Met   Leu
        225                     230                           235                                   240

Lys   Cys   Trp   His   Pro   Lys   Ala   Glu   Met   Arg   Pro   Ser   Phe   Ser   Glu   Leu
                                245                     250                           255
```

( 2 ) INFORMATION FOR SEQ ID NO:59:

( i ) SEQUENCE CHARACTERISTICS:
      ( A ) LENGTH: 144 base pairs
      ( B ) TYPE: nucleic acid
      ( C ) STRANDEDNESS: double
      ( D ) TOPOLOGY: unknown ( i i ) MOLECULE TYPE: cDNA ( i x ) FEATURE:
      ( A ) NAME/KEY: CDS
      ( B ) LOCATION: 1..144

( x i ) SEQUENCE DESCRIPTION: SEQ ID NO:59:

```
TCT   AGT   CAC   TTC   TTT   GTC   CAC   AAG   GAC   CTT   GCA   GCT   CGC   AAT   ATT   TTA         48
Ser   Ser   His   Phe   Phe   Val   His   Lys   Asp   Leu   Ala   Ala   Arg   Asn   Ile   Leu
1                       5                             10                            15

ATC   GGA   GAG   CAA   CTT   CAT   GTA   AAG   ATT   TCA   GAC   TTG   GGG   CTT   TCC   AGA         96
Ile   Gly   Glu   Gln   Leu   His   Val   Lys   Ile   Ser   Asp   Leu   Gly   Leu   Ser   Arg
                  20                            25                            30

GAA   ATT   TAC   TCC   GCT   GAT   TAC   TAC   AGG   GTC   CAG   AGT   AAG   TCC   TTG   CTG        144
Glu   Ile   Tyr   Ser   Ala   Asp   Tyr   Tyr   Arg   Val   Gln   Ser   Lys   Ser   Leu   Leu
            35                            40                            45
```

( 2 ) INFORMATION FOR SEQ ID NO:60:

( i ) SEQUENCE CHARACTERISTICS:
      ( A ) LENGTH: 48 amino acids
      ( B ) TYPE: amino acid
      ( D ) TOPOLOGY: linear ( i i ) MOLECULE TYPE: protein ( x i ) SEQUENCE DESCRIPTION: SEQ ID NO:60:

```
Ser   Ser   His   Phe   Phe   Val   His   Lys   Asp   Leu   Ala   Ala   Arg   Asn   Ile   Leu
1                       5                             10                            15

Ile   Gly   Glu   Gln   Leu   His   Val   Lys   Ile   Ser   Asp   Leu   Gly   Leu   Ser   Arg
                  20                            25                            30

Glu   Ile   Tyr   Ser   Ala   Asp   Tyr   Tyr   Arg   Val   Gln   Ser   Lys   Ser   Leu   Leu
            35                            40                            45
```

( 2 ) INFORMATION FOR SEQ ID NO:61:

( i ) SEQUENCE CHARACTERISTICS:
      ( A ) LENGTH: 144 base pairs
      ( B ) TYPE: nucleic acid
      ( C ) STRANDEDNESS: double
      ( D ) TOPOLOGY: unknown ( i i ) MOLECULE TYPE: cDNA ( i x ) FEATURE:
    ( A ) NAME/KEY: CDS
    ( B ) LOCATION: 1..144

( x i ) SEQUENCE DESCRIPTION: SEQ ID NO:61:

```
TCC AGC CAC CAC GTG GTT CAC AAG GAC CTG GCC ACC CGC AAT GTG CTA    48
Ser Ser His His Val Val His Lys Asp Leu Ala Thr Arg Asn Val Leu
 1               5                  10                  15

GTG TAC GAC AAG CTG AAC GTG AAG ATC TCA GAC TTG GGC CTC TTC CGA    96
Val Tyr Asp Lys Leu Asn Val Lys Ile Ser Asp Leu Gly Leu Phe Arg
             20                  25                  30

GAG GTG TAT GCC GCC GAT TAC TAC AAG CTG CTG GGG AAC TCG CTG CTG   144
Glu Val Tyr Ala Ala Asp Tyr Tyr Lys Leu Leu Gly Asn Ser Leu Leu
         35                  40                  45
```

( 2 ) INFORMATION FOR SEQ ID NO:62:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

```
Ser Ser His His Val Val His Lys Asp Leu Ala Thr Arg Asn Val Leu
 1               5                  10                  15

Val Tyr Asp Lys Leu Asn Val Lys Ile Ser Asp Leu Gly Leu Phe Arg
             20                  25                  30

Glu Val Tyr Ala Ala Asp Tyr Tyr Lys Leu Leu Gly Asn Ser Leu Leu
         35                  40                  45
```

( 2 ) INFORMATION FOR SEQ ID NO:63:

( i ) SEQUENCE CHARACTERISTICS:
        ( A ) LENGTH: 75 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..75

( x i ) SEQUENCE DESCRIPTION: SEQ ID NO:63:

```
CTC TCC AGG AAC ATC TAC TCA GCA GAC TAC TAC AAA GCT AAT GAA AAC    48
Leu Ser Arg Asn Ile Tyr Ser Ala Asp Tyr Tyr Lys Ala Asn Glu Asn
 1               5                  10                  15

GAC GCT ATC CCC ATT AGT TGG ATG CCT                                75
Asp Ala Ile Pro Ile Ser Trp Met Pro
             20                  25
```

( 2 ) INFORMATION FOR SEQ ID NO:64:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

```
Leu Ser Arg Asn Ile Tyr Ser Ala Asp Tyr Tyr Lys Ala Asn Glu Asn
```

```
                1               5                      10                     15
Asp  Ala  Ile  Pro  Ile  Ser  Trp  Met  Pro
                    20                      25
```

( 2 ) INFORMATION FOR SEQ ID NO:65:

( i ) SEQUENCE CHARACTERISTICS:
        ( A ) LENGTH: 81 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..81

( x i ) SEQUENCE DESCRIPTION: SEQ ID NO:65:

```
AAG  CGC  TTT  ATT  CAC  CGT  GAC  CTG  GCT  GCC  CGC  AAT  CTG  CTG  TTG  GCT         48
Lys  Arg  Phe  Ile  His  Arg  Asp  Leu  Ala  Ala  Arg  Asn  Leu  Leu  Leu  Ala
  1                 5                           10                      15

ACC  CGC  GAC  CTG  GTC  AAA  ATC  GGT  GAC  TTT  GGT                                   81
Thr  Arg  Asp  Leu  Val  Lys  Ile  Gly  Asp  Phe  Gly
                    20                      25
```

( 2 ) INFORMATION FOR SEQ ID NO:66:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

```
Lys  Arg  Phe  Ile  His  Arg  Asp  Leu  Ala  Ala  Arg  Asn  Leu  Leu  Leu  Ala
  1                 5                           10                      15

Thr  Arg  Asp  Leu  Val  Lys  Ile  Gly  Asp  Phe  Gly
                    20                      25
```

( 2 ) INFORMATION FOR SEQ ID NO:67:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:67:

```
Ala  Gly  Met  Val  Tyr  Leu  Ala  Gly  Leu  His  Phe  Val  His  Arg  Asp  Leu
  1                 5                           10                      15

Ala  Thr  Arg  Asn  Cys  Leu  Val  Gly  Gln  Gly  Leu  Val  Val  Lys  Ile  Gly
                    20                      25                      30

Asp  Phe  Gly  Met  Ser  Arg  Asp  Ile  Tyr  Ser  Thr  Asp  Tyr  Tyr  Arg  Val
                    35                      40                      45

Gly  Gly  Arg  Thr  Met  Leu  Pro  Ile  Arg  Trp  Met  Pro
                    50                      55                      60
```

( 2 ) INFORMATION FOR SEQ ID NO:68:

( i ) SEQUENCE CHARACTERISTICS:
        ( A ) LENGTH: 48 amino acids
        ( B ) TYPE: amino acid
        ( C ) STRANDEDNESS: single (D) TOPOLOGY: unknown (i i) MOLECULE TYPE: peptide (x i) SEQUENCE DESCRIPTION: SEQ ID NO:68:

```
Ser  Ser  His  Phe  Phe  Val  His  Lys  Asp  Leu  Ala  Ala  Arg  Asn  Ile  Leu
1              5                        10                           15

Ile  Gly  Glu  Gln  Leu  His  Val  Lys  Ile  Ser  Asp  Leu  Gly  Leu  Ser  Arg
               20                        25                      30

Glu  Ile  Tyr  Ser  Ala  Asp  Tyr  Tyr  Arg  Val  Gln  Ser  Lys  Ser  Leu  Leu
               35                  40                      45
```

(2) INFORMATION FOR SEQ ID NO:69:

(i) SEQUENCE CHARACTERISTICS:
        (A) LENGTH: 48 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:69:

```
Ser  Ser  His  His  Val  Val  His  Lys  Asp  Leu  Ala  Thr  Arg  Asn  Val  Leu
1              5                        10                           15

Val  Tyr  Asp  Lys  Leu  Asn  Val  Lys  Ile  Ser  Asp  Leu  Gly  Leu  Phe  Arg
               20                        25                      30

Glu  Val  Tyr  Ala  Ala  Asp  Tyr  Tyr  Lys  Leu  Leu  Gly  Asn  Ser  Leu  Leu
               35                  40                      45
```

(2) INFORMATION FOR SEQ ID NO:70:

(i) SEQUENCE CHARACTERISTICS:
        (A) LENGTH: 19 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:70:

```
Leu  Ser  Arg  Asn  Ile  Tyr  Ser  Ala  Asp  Tyr  Tyr  Lys  Ala  Asn  Glu  Asn
1              5                        10                           15

Asp  Ala  Ile
```

(2) INFORMATION FOR SEQ ID NO:71:

(i) SEQUENCE CHARACTERISTICS:
        (A) LENGTH: 21 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:71:

```
Lys  Arg  Phe  Ile  His  Arg  Asp  Leu  Ala  Ala  Arg  Asn  Leu  Leu  Leu  Ala
1              5                        10                           15

Thr  Arg  Asp  Leu  Val
               20
```

(2) INFORMATION FOR SEQ ID NO:72:

(i) SEQUENCE CHARACTERISTICS:
        (A) LENGTH: 800 amino acids
        (B) TYPE: amino acid (C) STRANDEDNESS: single
(D) TOPOLOGY: unknown (ii) MOLECULE TYPE: peptide (xi) SEQUENCE DESCRIPTION: SEQ ID NO:72:

```
Gly  Gly  Gly  Phe  Phe  His  Trp  Ser  Leu  Val  Cys  Gln  Val  Trp  Pro  Pro
 1              5                   10                      15

Ser  His  Ser  Lys  Ser  Arg  Tyr  Ser  Asp  Glu  Tyr  Glu  Glu  Asp  Gly  Phe
               20                   25                      30

Cys  Gln  Pro  Tyr  Arg  Gly  Ile  Ala  Cys  Ala  Arg  Phe  Ile  Gly  Asn  Arg
               35                   40                      45

Thr  Val  Tyr  Met  Glu  Ser  Leu  His  Met  Gln  Gly  Glu  Ile  Glu  Asn  Gln
          50                   55                      60

Ile  Thr  Ala  Ala  Phe  Thr  Met  Ile  Gly  Thr  Ser  Ser  His  Leu  Ser  Asp
 65                       70                   75                       80

Lys  Cys  Ser  Gln  Phe  Ala  Ile  Pro  Ser  Leu  Cys  His  Tyr  Ala  Phe  Pro
                    85                   90                       95

Tyr  Cys  Asp  Glu  Thr  Ser  Ser  Val  Pro  Lys  Pro  Arg  Asp  Leu  Cys  Arg
               100                  105                     110

Asp  Glu  Cys  Glu  Ile  Leu  Glu  Asn  Val  Leu  Cys  Gln  Thr  Glu  Tyr  Ile
               115                  120                     125

Phe  Ala  Arg  Ser  Asn  Pro  Met  Ile  Leu  Met  Arg  Leu  Lys  Leu  Pro  Asn
          130                  135                      140

Cys  Glu  Asp  Leu  Pro  Gln  Pro  Glu  Ser  Pro  Glu  Ala  Ala  Asn  Cys  Ile
145                       150                  155                      160

Arg  Ile  Gly  Ile  Pro  Met  Ala  Asp  Pro  Ile  Asn  Lys  Asn  His  Lys  Cys
               165                  170                     175

Tyr  Asn  Ser  Thr  Gly  Val  Asp  Tyr  Arg  Gly  Thr  Val  Ser  Val  Thr  Lys
               180                  185                     190

Ser  Gly  Arg  Gln  Cys  Gln  Pro  Trp  Asn  Ser  Gln  Tyr  Pro  His  Thr  His
          195                  200                      205

Thr  Phe  Thr  Ala  Leu  Arg  Phe  Pro  Glu  Leu  Asn  Gly  Gly  His  Ser  Tyr
     210                       215                  220

Cys  Arg  Asn  Pro  Gly  Asn  Gln  Lys  Glu  Ala  Pro  Trp  Cys  Phe  Thr  Leu
225                       230                  235                      240

Asp  Glu  Asn  Phe  Lys  Ser  Asp  Leu  Cys  Asp  Ile  Pro  Ala  Cys  Asp  Ser
               245                  250                     255

Lys  Asp  Ser  Lys  Glu  Lys  Asn  Lys  Met  Glu  Ile  Leu  Tyr  Ile  Leu  Val
               260                  265                     270

Pro  Ser  Val  Ala  Ile  Pro  Leu  Ala  Ile  Ala  Leu  Leu  Phe  Phe  Phe  Ile
          275                  280                      285

Cys  Val  Cys  Arg  Asn  Asn  Gln  Lys  Ser  Ser  Ser  Ala  Pro  Val  Gln  Arg
     290                       295                  300

Gln  Pro  Lys  His  Val  Arg  Gly  Gln  Asn  Val  Glu  Met  Ser  Met  Leu  Asn
305                       310                  315                      320

Ala  Tyr  Lys  Pro  Lys  Ser  Lys  Ala  Lys  Glu  Leu  Pro  Leu  Ser  Ala  Val
               325                  330                     335

Arg  Phe  Met  Glu  Glu  Leu  Gly  Glu  Cys  Ala  Phe  Gly  Lys  Ile  Tyr  Lys
               340                  345                     350

Gly  His  Leu  Tyr  Leu  Pro  Gly  Met  Asp  His  Ala  Gln  Leu  Val  Ala  Ile
          355                  360                      365

Lys  Thr  Leu  Lys  Asp  Tyr  Asn  Asn  Pro  Gln  Gln  Trp  Met  Glu  Phe  Gln
     370                       375                  380

Gln  Glu  Ala  Ser  Leu  Met  Ala  Glu  Leu  His  His  Pro  Asn  Ile  Val  Cys
```

-continued

```
                385                           390                           395                           400
 Leu   Leu   Gly   Ala   Val   Thr   Gln   Glu   Gln   Pro   Val   Cys   Met   Leu   Phe   Glu
                         405                           410                           415
 Tyr   Ile   Asn   Gln   Gly   Asp   Leu   His   Glu   Phe   Leu   Ile   Met   Arg   Ser   Pro
                   420                           425                           430
 His   Ser   Asp   Val   Gly   Cys   Ser   Ser   Asp   Glu   Asp   Gly   Thr   Val   Lys   Ser
             435                           440                           445
 Ser   Leu   Asp   His   Gly   Asp   Phe   Leu   His   Ile   Ala   Ile   Gln   Ile   Ala   Ala
       450                           455                           460
 Gly   Met   Glu   Tyr   Leu   Ser   Ser   His   Phe   Phe   Val   His   Lys   Asp   Leu   Ala
 465                           470                           475                           480
 Ala   Arg   Asn   Ile   Leu   Ile   Gly   Glu   Gln   Leu   His   Val   Lys   Ile   Ser   Asp
                         485                           490                           495
 Leu   Gly   Leu   Ser   Arg   Glu   Ile   Tyr   Ser   Ala   Asp   Tyr   Tyr   Arg   Val   Gln
                   500                           505                           510
 Ser   Lys   Ser   Leu   Leu   Pro   Ile   Arg   Trp   Met   Pro   Pro   Glu   Ala   Ile   Met
             515                           520                           525
 Tyr   Gly   Lys   Phe   Ser   Ser   Asp   Ser   Asp   Ile   Trp   Ser   Phe   Gly   Val   Val
       530                           535                           540
 Leu   Trp   Glu   Ile   Phe   Ser   Phe   Gly   Leu   Gln   Pro   Tyr   Tyr   Gly   Phe   Ser
 545                           550                           555                           560
 Asn   Gln   Glu   Val   Ile   Glu   Met   Val   Arg   Lys   Arg   Gln   Leu   Leu   Pro   Cys
                         565                           570                           575
 Ser   Glu   Asp   Cys   Pro   Pro   Arg   Met   Tyr   Ser   Leu   Met   Thr   Glu   Cys   Trp
                   580                           585                           590
 Asn   Glu   Ile   Pro   Ser   Arg   Arg   Pro   Arg   Phe   Lys   Asp   Ile   His   Val   Arg
             595                           600                           605
 Leu   Arg   Ser   Trp   Glu   Gly   Leu   Ser   Ser   His   Thr   Ser   Ser   Thr   Thr   Pro
       610                           615                           620
 Ser   Gly   Gly   Asn   Ala   Thr   Thr   Gln   Thr   Thr   Ser   Leu   Ser   Ala   Ser   Pro
 625                           630                           635                           640
 Val   Ser   Asn   Leu   Ser   Asn   Pro   Arg   Tyr   Pro   Asn   Tyr   Met   Phe   Pro   Ser
                         645                           650                           655
 Gln   Gly   Ile   Thr   Pro   Gln   Gly   Gln   Ile   Ala   Gly   Phe   Ile   Gly   Pro   Pro
                   660                           665                           670
 Ile   Pro   Gln   Asn   Gln   Arg   Phe   Ile   Pro   Ile   Asn   Gly   Tyr   Pro   Ile   Pro
             675                           680                           685
 Pro   Gly   Tyr   Ala   Ala   Phe   Pro   Ala   Ala   His   Tyr   Gln   Pro   Thr   Gly   Pro
       690                           695                           700
 Pro   Arg   Val   Ile   Gln   His   Cys   Pro   Pro   Pro   Lys   Ser   Arg   Ser   Pro   Ser
 705                           710                           715                           720
 Ser   Ala   Ser   Gly   Ser   Thr   Ser   Thr   Gly   His   Val   Thr   Ser   Leu   Pro   Ser
                         725                           730                           735
 Ser   Gly   Ser   Asn   Gln   Glu   Ala   Asn   Ile   Pro   Leu   Leu   Pro   His   Met   Ser
                   740                           745                           750
 Ile   Pro   Asn   His   Pro   Gly   Gly   Met   Gly   Ile   Thr   Val   Phe   Gly   Asn   Lys
             755                           760                           765
 Ser   Gln   Lys   Pro   Tyr   Lys   Ile   Asp   Ser   Lys   Gln   Ala   Ser   Leu   Leu   Gly
       770                           775                           780
 Asp   Ala   Asn   Ile   His   Gly   His   Thr   Glu   Ser   Met   Ile   Ser   Ala   Glu   Leu
 785                           790                           795                           800
```

( 2 ) INFORMATION FOR SEQ ID NO:73:

( i ) SEQUENCE CHARACTERISTICS:
  ( A ) LENGTH: 285 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:73:

```
Lys Pro Asp Thr Phe Val Gln His Ile Lys Arg His Asn Ile Val Leu
  1               5                  10                  15
Lys Arg Glu Leu Gly Glu Gly Ala Phe Gly Lys Val Phe Leu Ala Glu
                 20                  25                  30
Cys Tyr Asn Leu Cys Pro Glu Gln Asp Lys Ile Leu Val Ala Val Lys
             35                  40                  45
Thr Leu Lys Asp Ala Ser Asp Asn Ala Arg Lys Asp Phe His Arg Glu
         50                  55                  60
Ala Glu Leu Leu Thr Asn Leu Gln His Glu His Ile Val Lys Phe Tyr
 65                  70                  75                  80
Gly Val Cys Val Glu Gly Asp Pro Leu Ile Met Val Phe Glu Tyr Met
                 85                  90                  95
Lys His Gly Asp Leu Asn Lys Phe Leu Arg Ala His Gly Pro Asp Ala
             100                 105                 110
Val Leu Met Ala Glu Gly Asn Pro Thr Glu Leu Thr Gln Ser Gln
             115                 120                 125
Met Leu His Ile Ala Gln Gln Ile Ala Ala Gly Met Val Tyr Leu Ala
         130                 135                 140
Ser Gln His Phe Val His Arg Asp Leu Ala Thr Arg Asn Cys Leu Val
 145                 150                 155                 160
Gly Glu Asn Leu Leu Val Lys Ile Gly Asp Phe Gly Met Ser Arg Asp
                 165                 170                 175
Val Tyr Ser Thr Asp Tyr Tyr Arg Val Gly Gly His Thr Met Leu Pro
             180                 185                 190
Ile Arg Trp Met Pro Pro Glu Ser Ile Met Tyr Arg Lys Phe Thr Thr
         195                 200                 205
Glu Ser Asp Val Trp Ser Leu Gly Val Val Leu Trp Glu Ile Phe Thr
     210                 215                 220
Tyr Gly Lys Gln Pro Trp Tyr Gln Leu Ser Asn Asn Glu Val Ile Glu
 225                 230                 235                 240
Cys Ile Thr Gln Gly Arg Val Leu Gln Arg Pro Arg Thr Cys Pro Gln
             245                 250                 255
Glu Val Tyr Glu Leu Met Leu Gly Cys Trp Gln Arg Glu Pro His Thr
             260                 265                 270
Arg Lys Asn Ile Lys Asn Ile His Thr Leu Leu Gln Asn
         275                 280                 285
```

( 2 ) INFORMATION FOR SEQ ID NO:74:

( i ) SEQUENCE CHARACTERISTICS:
  ( A ) LENGTH: 310 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:74:

```
Ser Ser Leu Ser Pro Thr Glu Gly Lys Gly Ser Gly Leu Gln Gly His
  1               5                  10                  15
```

```
Ile  Ile  Glu  Asn  Pro  Gln  Tyr  Phe  Ser  Asp  Ala  Cys  Val  His  His  Ile
              20                       25                      30

Lys  Arg  Arg  Asp  Ile  Val  Leu  Lys  Trp  Glu  Leu  Gly  Glu  Gly  Ala  Phe
              35                       40                      45

Gly  Lys  Val  Phe  Leu  Ala  Glu  Cys  His  Asn  Leu  Leu  Pro  Glu  Gln  Asp
     50                            55                      60

Lys  Met  Leu  Val  Ala  Val  Lys  Ala  Leu  Lys  Glu  Ala  Ser  Glu  Ser  Ala
65                            70                      75                       80

Arg  Gln  Asp  Phe  Gln  Arg  Glu  Ala  Glu  Leu  Leu  Thr  Met  Leu  Gln  His
                    85                       90                      95

Gln  His  Ile  Val  Arg  Phe  Phe  Gly  Val  Cys  Thr  Glu  Gly  Arg  Pro  Leu
               100                      105                     110

Leu  Met  Val  Phe  Glu  Tyr  Met  Arg  His  Gly  Asp  Leu  Asn  Arg  Phe  Leu
               115                      120                     125

Arg  Ser  His  Gly  Pro  Asp  Ala  Lys  Leu  Leu  Ala  Gly  Gly  Glu  Asp  Val
               130                      135                     140

Ala  Pro  Gly  Pro  Leu  Gly  Leu  Gly  Gln  Leu  Leu  Ala  Val  Ala  Ser  Gln
145                           150                      155                    160

Val  Ala  Ala  Gly  Met  Val  Tyr  Leu  Ala  Gly  Leu  His  Phe  Val  His  Arg
                    165                      170                     175

Asp  Leu  Ala  Thr  Arg  Asn  Cys  Leu  Val  Gly  Gln  Gly  Leu  Val  Val  Lys
               180                      185                     190

Ile  Gly  Asp  Phe  Gly  Met  Ser  Arg  Asp  Ile  Tyr  Ser  Thr  Asp  Tyr  Tyr
               195                      200                     205

Arg  Val  Gly  Gly  Arg  Thr  Met  Leu  Pro  Ile  Arg  Trp  Met  Pro  Pro  Glu
          210                      215                      220

Ser  Ile  Leu  Tyr  Arg  Lys  Phe  Thr  Thr  Glu  Ser  Asp  Val  Trp  Ser  Phe
225                           230                      235                    240

Gly  Val  Val  Leu  Trp  Glu  Ile  Phe  Thr  Tyr  Gly  Lys  Gln  Pro  Trp  Tyr
                    245                      250                     255

Gln  Leu  Ser  Asn  Thr  Glu  Ala  Ile  Asp  Cys  Ile  Thr  Gln  Gly  Arg  Glu
               260                      265                     270

Leu  Glu  Arg  Pro  Arg  Ala  Cys  Pro  Pro  Glu  Val  Tyr  Ala  Ile  Met  Arg
               275                      280                     285

Gly  Cys  Trp  Gln  Arg  Glu  Pro  Gln  Gln  Arg  His  Ser  Ile  Lys  Asp  Val
     290                           295                     300

His  Ala  Arg  Leu  Gln  Ala
305                      310
```

(2) INFORMATION FOR SEQ ID NO:75:

(i) SEQUENCE CHARACTERISTICS:
        (A) LENGTH: 332 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:75:

```
Leu  Ile  Ile  Ala  Leu  Pro  Val  Ala  Val  Leu  Leu  Ile  Val  Gly  Gly  Leu
1                   5                       10                      15

Val  Ile  Met  Leu  Tyr  Val  Phe  His  Arg  Lys  Arg  Asn  Asn  Ser  Arg  Leu
               20                       25                      30

Gly  Asn  Gly  Val  Leu  Tyr  Ala  Ser  Val  Asn  Pro  Glu  Tyr  Phe  Ser  Ala
               35                       40                      45

Ala  Asp  Val  Tyr  Val  Pro  Asp  Glu  Trp  Glu  Val  Ala  Arg  Glu  Lys  Ile
```

|     |     |     |     | 50  |     |     |     |     | 55  |     |     |     |     | 60  |
|-----|-----|-----|-----|-----|-----|-----|-----|-----|-----|-----|-----|-----|-----|-----|

Thr Met Ser Arg Glu Leu Gly Gln Gly Ser Phe Gly Met Val Tyr
65              70                  75                  80

Gly Val Ala Lys Gly Val Val Lys Asp Glu Pro Glu Thr Arg Val Ala
                85                  90                  95

Ile Lys Thr Val Asn Glu Ala Ala Ser Met Arg Glu Arg Ile Glu Phe
            100             105                 110

Leu Asn Glu Ala Ser Val Met Lys Glu Phe Asn Cys His His Val Val
            115             120                 125

Arg Leu Leu Gly Val Val Ser Gln Gly Gln Pro Thr Leu Val Ile Met
            130             135                 140

Glu Leu Met Thr Arg Gly Asp Leu Lys Ser Tyr Leu Arg Ser Leu Arg
145                 150                 155                 160

Pro Glu Met Glu Asn Asn Pro Val Leu Ala Pro Pro Ser Leu Ser Lys
                165             170                 175

Met Ile Gln Met Ala Gly Glu Ile Ala Asp Gly Met Ala Tyr Leu Asn
                180             185                 190

Ala Asn Lys Phe Val His Arg Asp Leu Ala Ala Arg Asn Cys Met Val
            195             200                 205

Ala Glu Asp Phe Thr Val Lys Ile Gly Asp Phe Gly Met Thr Arg Asp
            210             215                 220

Ile Tyr Glu Thr Asp Tyr Tyr Arg Lys Gly Gly Lys Gly Leu Leu Pro
225                 230                 235                 240

Val Arg Trp Met Ser Pro Glu Ser Leu Lys Asp Gly Val Phe Thr Thr
                245             250                 255

Tyr Ser Asp Val Trp Ser Phe Gly Val Val Leu Trp Glu Ile Ala Thr
            260             265                 270

Leu Ala Glu Gln Pro Tyr Gln Gly Leu Ser Asn Glu Gln Val Leu Arg
            275             280                 285

Phe Val Met Glu Gly Gly Leu Leu Asp Lys Pro Asp Asn Cys Pro Asp
            290             295                 300

Met Leu Phe Glu Leu Met Arg Met Cys Trp Gln Tyr Asn Pro Lys Met
305                 310                 315                 320

Arg Pro Ser Phe Leu Glu Ile Ile Ser Ser Ile Lys
                325                 330

( 2 ) INFORMATION FOR SEQ ID NO:76:

( i ) SEQUENCE CHARACTERISTICS:
        ( A ) LENGTH: 340 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:76:

Lys Ile Ile Ile Gly Pro Leu Ile Phe Val Phe Leu Phe Ser Val Val
1               5                   10                  15

Ile Gly Ser Ile Tyr Leu Phe Leu Arg Lys Arg Gln Pro Asp Gly Pro
            20                  25                  30

Leu Gly Pro Leu Tyr Ala Ser Ser Asn Pro Glu Tyr Leu Ser Ala Ser
            35                  40                  45

Asp Val Phe Pro Cys Ser Val Tyr Val Pro Asp Glu Trp Glu Val Ser
            50                  55                  60

Arg Glu Lys Ile Thr Leu Leu Arg Glu Leu Gly Gln Gly Ser Phe Gly
65                  70                  75                  80

```
          Gly   Met   Val   Tyr   Glu   Gly   Asn   Ala   Arg   Asp   Ile   Ile   Lys   Gly   Glu   Ala
                            85                            90                             95

Glu   Thr   Arg   Val   Ala   Val   Lys   Thr   Val   Asn   Glu   Ser   Ala   Ser   Leu   Arg
                            100                           105                            110

Glu   Arg   Ile   Glu   Phe   Leu   Asn   Glu   Ala   Ser   Val   Met   Lys   Gly   Phe   Thr
                      115                           120                     125

Cys   His   His   Val   Val   Arg   Leu   Leu   Gly   Val   Val   Ser   Lys   Gly   Gln   Pro
                      130                           135                     140

Thr   Leu   Val   Val   Met   Glu   Leu   Met   Ala   His   Gly   Asp   Leu   Lys   Ser   Tyr
          145                           150                           155                            160

Leu   Arg   Ser   Leu   Arg   Pro   Glu   Ala   Glu   Asn   Asn   Pro   Gly   Arg   Pro   Pro
                                  165                           170                            175

Pro   Thr   Leu   Gln   Glu   Met   Ile   Gln   Met   Ala   Ala   Glu   Ile   Ala   Asp   Gly
                            180                           185                            190

Met   Ala   Tyr   Leu   Asn   Ala   Lys   Lys   Phe   Val   His   Arg   Asp   Leu   Ala   Ala
                      195                           200                     205

Arg   Asn   Cys   Met   Val   Ala   His   Asp   Phe   Thr   Val   Lys   Ile   Gly   Asp   Phe
                      210                           215                     220

Gly   Met   Thr   Arg   Asp   Ile   Tyr   Glu   Thr   Asp   Tyr   Tyr   Arg   Lys   Gly   Gly
          225                           230                           235                            240

Lys   Gly   Leu   Leu   Pro   Val   Arg   Trp   Met   Ala   Pro   Glu   Ser   Leu   Lys   Asp
                                  245                           250                            255

Gly   Val   Phe   Thr   Thr   Ser   Ser   Asp   Met   Trp   Ser   Phe   Gly   Val   Val   Leu
                            260                           265                            270

Trp   Glu   Ile   Thr   Ser   Leu   Ala   Glu   Gln   Pro   Tyr   Gln   Gly   Leu   Ser   Asn
                      275                           280                     285

Glu   Gln   Val   Leu   Lys   Phe   Val   Met   Asp   Gly   Gly   Tyr   Leu   Asp   Gln   Pro
                290                           295                            300

Asp   Asn   Cys   Pro   Glu   Arg   Val   Thr   Asp   Leu   Met   Arg   Met   Cys   Trp   Gln
          305                           310                           315                            320

Phe   Asn   Pro   Asn   Met   Arg   Pro   Thr   Phe   Leu   Glu   Ile   Val   Asn   Leu   Leu
                            325                           330                            335

Lys   Asp   Asp   Leu
                            340

( 2 ) INFORMATION FOR SEQ ID NO:77:

( i ) SEQUENCE CHARACTERISTICS:
                ( A ) LENGTH: 2595 base pairs
                ( B ) TYPE: nucleic acid
                ( C ) STRANDEDNESS: double
                ( D ) TOPOLOGY: unknown ( i i ) MOLECULE TYPE: DNA (genomic)

( i x ) FEATURE:
                ( A ) NAME/KEY: CDS
                ( B ) LOCATION: 3..2402

( x i ) SEQUENCE DESCRIPTION: SEQ ID NO:77:

AA   GGA   GGT   GGT   TTC   TTC   CAC   TGG   AGT   CTT   GTT   TGT   CAA   GTT   TGG   CCC              47
     Gly   Gly   Gly   Phe   Phe   His   Trp   Ser   Leu   Val   Cys   Gln   Val   Trp   Pro
     1                 5                             10                            15

CCC   TCC   CAC   AGC   AAG   TCC   AGA   TAC   TCA   GAT   GAG   TAT   GAA   GAA   GAT   GGA           95
Pro   Ser   His   Ser   Lys   Ser   Arg   Tyr   Ser   Asp   Glu   Tyr   Glu   Glu   Asp   Gly
                        20                            25                            30

TTC   TGT   CAG   CCA   TAC   AGA   GGG   ATT   GCA   TGT   GCA   AGA   TTT   ATT   GGC   AAC          143
Phe   Cys   Gln   Pro   Tyr   Arg   Gly   Ile   Ala   Cys   Ala   Arg   Phe   Ile   Gly   Asn
                        35                            40                            45
```

| | | | | | | | | | | | | | | | | |
|---|---|---|---|---|---|---|---|---|---|---|---|---|---|---|---|---|
| CGC | ACC | GTC | TAT | ATG | GAG | TCT | TTG | CAC | ATG | CAA | GGG | GAA | ATA | GAA | AAT | 191 |
| Arg | Thr | Val | Tyr | Met | Glu | Ser | Leu | His | Met | Gln | Gly | Glu | Ile | Glu | Asn | |
| | | 50 | | | | 55 | | | | | 60 | | | | | |
| CAG | ATC | ACA | GCT | GCC | TTC | ACT | ATG | ATT | GGC | ACT | TCC | AGT | CAC | TTA | TCT | 239 |
| Gln | Ile | Thr | Ala | Ala | Phe | Thr | Met | Ile | Gly | Thr | Ser | Ser | His | Leu | Ser | |
| | 65 | | | | | 70 | | | | | 75 | | | | | |
| GAT | AAG | TGT | TCT | CAG | TTC | GCC | ATT | CCT | TCC | CTG | TGC | CAC | TAT | GCC | TTC | 287 |
| Asp | Lys | Cys | Ser | Gln | Phe | Ala | Ile | Pro | Ser | Leu | Cys | His | Tyr | Ala | Phe | |
| 80 | | | | | 85 | | | | | 90 | | | | | 95 | |
| CCG | TAC | TGC | GAT | GAA | ACT | TCA | TCC | GTC | CCA | AAG | CCC | CGT | GAC | TTG | TGT | 335 |
| Pro | Tyr | Cys | Asp | Glu | Thr | Ser | Ser | Val | Pro | Lys | Pro | Arg | Asp | Leu | Cys | |
| | | | | 100 | | | | | 105 | | | | | 110 | | |
| CGC | GAT | GAA | TGT | GAA | ATC | CTG | GAG | AAT | GTC | CTG | TGT | CAA | ACA | GAG | TAC | 383 |
| Arg | Asp | Glu | Cys | Glu | Ile | Leu | Glu | Asn | Val | Leu | Cys | Gln | Thr | Glu | Tyr | |
| | | | 115 | | | | | 120 | | | | | 125 | | | |
| ATT | TTT | GCA | AGA | TCA | AAT | CCC | ATG | ATT | CTG | ATG | AGG | CTG | AAA | CTG | CCA | 431 |
| Ile | Phe | Ala | Arg | Ser | Asn | Pro | Met | Ile | Leu | Met | Arg | Leu | Lys | Leu | Pro | |
| | | 130 | | | | | 135 | | | | | 140 | | | | |
| AAC | TGT | GAA | GAT | CTC | CCC | CAG | CCA | GAG | AGC | CCA | GAA | GCT | GCG | AAC | TGT | 479 |
| Asn | Cys | Glu | Asp | Leu | Pro | Gln | Pro | Glu | Ser | Pro | Glu | Ala | Ala | Asn | Cys | |
| | 145 | | | | | 150 | | | | | 155 | | | | | |
| ATC | CGG | ATT | GGA | ATT | CCC | ATG | GCA | GAT | CCT | ATA | AAT | AAA | AAT | CAC | AAG | 527 |
| Ile | Arg | Ile | Gly | Ile | Pro | Met | Ala | Asp | Pro | Ile | Asn | Lys | Asn | His | Lys | |
| 160 | | | | | 165 | | | | | 170 | | | | | 175 | |
| TGT | TAT | AAC | AGC | ACA | GGT | GTG | GAC | TAC | CGG | GGG | ACC | GTC | AGT | GTG | ACC | 575 |
| Cys | Tyr | Asn | Ser | Thr | Gly | Val | Asp | Tyr | Arg | Gly | Thr | Val | Ser | Val | Thr | |
| | | | | 180 | | | | | 185 | | | | | 190 | | |
| AAA | TCA | GGG | CGC | CAG | TGC | CAG | CCA | TGG | AAT | TCC | CAG | TAT | CCC | CAC | ACA | 623 |
| Lys | Ser | Gly | Arg | Gln | Cys | Gln | Pro | Trp | Asn | Ser | Gln | Tyr | Pro | His | Thr | |
| | | | 195 | | | | | 200 | | | | | 205 | | | |
| CAC | ACT | TTC | ACC | GCC | CTT | CGT | TTC | CCA | GAG | CTG | AAT | GGA | GGC | CAT | TCC | 671 |
| His | Thr | Phe | Thr | Ala | Leu | Arg | Phe | Pro | Glu | Leu | Asn | Gly | Gly | His | Ser | |
| | | 210 | | | | | 215 | | | | | 220 | | | | |
| TAC | TGC | CGC | AAC | CCA | GGG | AAT | CAA | AAG | GAA | GCT | CCC | TGG | TGC | TTC | ACC | 719 |
| Tyr | Cys | Arg | Asn | Pro | Gly | Asn | Gln | Lys | Glu | Ala | Pro | Trp | Cys | Phe | Thr | |
| | 225 | | | | | 230 | | | | | 235 | | | | | |
| TTG | GAT | GAA | AAC | TTT | AAG | TCT | GAT | CTG | TGT | GAC | ATC | CCA | GCT | TGC | GAT | 767 |
| Leu | Asp | Glu | Asn | Phe | Lys | Ser | Asp | Leu | Cys | Asp | Ile | Pro | Ala | Cys | Asp | |
| 240 | | | | | 245 | | | | | 250 | | | | | 255 | |
| TCA | AAG | GAT | TCC | AAG | GAG | AAG | AAT | AAA | ATG | GAA | ATC | CTG | TAC | ATA | CTA | 815 |
| Ser | Lys | Asp | Ser | Lys | Glu | Lys | Asn | Lys | Met | Glu | Ile | Leu | Tyr | Ile | Leu | |
| | | | | 260 | | | | | 265 | | | | | 270 | | |
| GTG | CCA | AGT | GTG | GCC | ATT | CCC | CTG | GCC | ATT | GCT | TTA | CTC | TTC | TTC | TTC | 863 |
| Val | Pro | Ser | Val | Ala | Ile | Pro | Leu | Ala | Ile | Ala | Leu | Leu | Phe | Phe | Phe | |
| | | | 275 | | | | | 280 | | | | | 285 | | | |
| ATT | TGC | GTC | TGT | CGG | AAT | AAC | CAG | AAG | TCA | TCG | TCG | GCA | CCA | GTC | CAG | 911 |
| Ile | Cys | Val | Cys | Arg | Asn | Asn | Gln | Lys | Ser | Ser | Ser | Ala | Pro | Val | Gln | |
| | | 290 | | | | | 295 | | | | | 300 | | | | |
| AGG | CAA | CCA | AAA | CAC | GTC | AGA | GGT | CAA | AAT | GTG | GAG | ATG | TCA | ATG | CTG | 959 |
| Arg | Gln | Pro | Lys | His | Val | Arg | Gly | Gln | Asn | Val | Glu | Met | Ser | Met | Leu | |
| | 305 | | | | | 310 | | | | | 315 | | | | | |
| AAT | GCA | TAT | AAA | CCC | AAG | AGC | AAG | GCT | AAG | GAG | CTA | CCT | CTT | TCT | GCT | 1007 |
| Asn | Ala | Tyr | Lys | Pro | Lys | Ser | Lys | Ala | Lys | Glu | Leu | Pro | Leu | Ser | Ala | |
| 320 | | | | | 325 | | | | | 330 | | | | | 335 | |
| GTA | CGC | TTT | ATG | GAA | GAA | TTG | GGT | GAG | TGT | GCC | TTT | GGA | AAA | ATC | TAT | 1055 |
| Val | Arg | Phe | Met | Glu | Glu | Leu | Gly | Glu | Cys | Ala | Phe | Gly | Lys | Ile | Tyr | |
| | | | | 340 | | | | | 345 | | | | | 350 | | |
| AAA | GGC | CAT | CTC | TAT | CTC | CCA | GGC | ATG | GAC | CAT | GCT | CAG | CTG | GTT | GCT | 1103 |
| Lys | Gly | His | Leu | Tyr | Leu | Pro | Gly | Met | Asp | His | Ala | Gln | Leu | Val | Ala | |
| | | | 355 | | | | | 360 | | | | | 365 | | | |

```
ATC  AAG  ACC  TTG  AAA  GAC  TAT  AAC  AAC  CCC  CAG  CAA  TGG  ATG  GAA  TTT    1151
Ile  Lys  Thr  Leu  Lys  Asp  Tyr  Asn  Asn  Pro  Gln  Gln  Trp  Met  Glu  Phe
          370                      375                     380

CAA  CAA  GAA  GCC  TCC  CTA  ATG  GCA  GAA  CTG  CAC  CAC  CCC  AAT  ATT  GTC    1199
Gln  Gln  Glu  Ala  Ser  Leu  Met  Ala  Glu  Leu  His  His  Pro  Asn  Ile  Val
     385                      390                     395

TGC  CTT  CTA  GGT  GCC  GTC  ACT  CAG  GAA  CAA  CCT  GTG  TGC  ATG  CTT  TTT    1247
Cys  Leu  Leu  Gly  Ala  Val  Thr  Gln  Glu  Gln  Pro  Val  Cys  Met  Leu  Phe
400                      405                     410                     415

GAG  TAT  ATT  AAT  CAG  GGG  GAT  CTC  CAT  GAG  TTC  CTC  ATC  ATG  AGA  TCC    1295
Glu  Tyr  Ile  Asn  Gln  Gly  Asp  Leu  His  Glu  Phe  Leu  Ile  Met  Arg  Ser
                    420                     425                     430

CCA  CAC  TCT  GAT  GTT  GGC  TGC  AGC  AGT  GAT  GAA  GAT  GGG  ACT  GTG  AAA    1343
Pro  His  Ser  Asp  Val  Gly  Cys  Ser  Ser  Asp  Glu  Asp  Gly  Thr  Val  Lys
               435                     440                     445

TCC  AGC  CTG  GAC  CAC  GGA  GAT  TTT  CTG  CAC  ATT  GCA  ATT  CAG  ATT  GCA    1391
Ser  Ser  Leu  Asp  His  Gly  Asp  Phe  Leu  His  Ile  Ala  Ile  Gln  Ile  Ala
          450                     455                     460

GCT  GGC  ATG  GAA  TAC  CTG  TCT  AGT  CAC  TTC  TTT  GTC  CAC  AAG  GAC  CTT    1439
Ala  Gly  Met  Glu  Tyr  Leu  Ser  Ser  His  Phe  Phe  Val  His  Lys  Asp  Leu
     465                     470                     475

GCA  GCT  CGC  AAT  ATT  TTA  ATC  GGA  GAG  CAA  CTT  CAT  GTA  AAG  ATT  TCA    1487
Ala  Ala  Arg  Asn  Ile  Leu  Ile  Gly  Glu  Gln  Leu  His  Val  Lys  Ile  Ser
480                      485                     490                     495

GAC  TTG  GGG  CTT  TCC  AGA  GAA  ATT  TAC  TCC  GCT  GAT  TAC  TAC  AGG  GTC    1535
Asp  Leu  Gly  Leu  Ser  Arg  Glu  Ile  Tyr  Ser  Ala  Asp  Tyr  Tyr  Arg  Val
                    500                     505                     510

CAG  AGT  AAG  TCC  TTG  CTG  CCC  ATT  CGC  TGG  ATG  CCC  CCT  GAA  GCC  ATC    1583
Gln  Ser  Lys  Ser  Leu  Leu  Pro  Ile  Arg  Trp  Met  Pro  Pro  Glu  Ala  Ile
               515                     520                     525

ATG  TAT  GGC  AAA  TTC  TCT  TCT  GAT  TCA  GAT  ATC  TGG  TCC  TTT  GGG  GTT    1631
Met  Tyr  Gly  Lys  Phe  Ser  Ser  Asp  Ser  Asp  Ile  Trp  Ser  Phe  Gly  Val
          530                     535                     540

GTC  TTG  TGG  GAG  ATT  TTC  AGT  TTT  GGA  CTC  CAG  CCA  TAT  TAT  GGA  TTC    1679
Val  Leu  Trp  Glu  Ile  Phe  Ser  Phe  Gly  Leu  Gln  Pro  Tyr  Tyr  Gly  Phe
     545                     550                     555

AGT  AAC  CAG  GAA  GTG  ATT  GAG  ATG  GTG  AGA  AAA  CGG  CAG  CTC  TTA  CCA    1727
Ser  Asn  Gln  Glu  Val  Ile  Glu  Met  Val  Arg  Lys  Arg  Gln  Leu  Leu  Pro
560                      565                     570                     575

TGC  TCT  GAA  GAC  TGC  CCA  CCC  AGA  ATG  TAC  AGC  CTC  ATG  ACA  GAG  TGC    1775
Cys  Ser  Glu  Asp  Cys  Pro  Pro  Arg  Met  Tyr  Ser  Leu  Met  Thr  Glu  Cys
                    580                     585                     590

TGG  AAT  GAG  ATT  CCT  TCT  AGG  AGA  CCA  AGA  TTT  AAA  GAT  ATT  CAC  GTC    1823
Trp  Asn  Glu  Ile  Pro  Ser  Arg  Arg  Pro  Arg  Phe  Lys  Asp  Ile  His  Val
               595                     600                     605

CGG  CTT  CGG  TCC  TGG  GAG  GGA  CTC  TCA  AGT  CAC  ACA  AGC  TCT  ACT  ACT    1871
Arg  Leu  Arg  Ser  Trp  Glu  Gly  Leu  Ser  Ser  His  Thr  Ser  Ser  Thr  Thr
          610                     615                     620

CCT  TCA  GGG  GGA  AAT  GCC  ACC  ACA  CAG  ACA  ACC  TCC  CTC  AGT  GCC  AGC    1919
Pro  Ser  Gly  Gly  Asn  Ala  Thr  Thr  Gln  Thr  Thr  Ser  Leu  Ser  Ala  Ser
     625                     630                     635

CCA  GTG  AGT  AAT  CTC  AGT  AAC  CCC  AGA  TAT  CCT  AAT  TAC  ATG  TTC  CCG    1967
Pro  Val  Ser  Asn  Leu  Ser  Asn  Pro  Arg  Tyr  Pro  Asn  Tyr  Met  Phe  Pro
640                      645                     650                     655

AGC  CAG  GGT  ATT  ACA  CCA  CAG  GGC  CAG  ATT  GCT  GGT  TTC  ATT  GGC  CCG    2015
Ser  Gln  Gly  Ile  Thr  Pro  Gln  Gly  Gln  Ile  Ala  Gly  Phe  Ile  Gly  Pro
                    660                     665                     670

CCA  ATA  CCT  CAG  AAC  CAG  CGA  TTC  ATT  CCC  ATC  AAT  GGA  TAC  CCA  ATA    2063
Pro  Ile  Pro  Gln  Asn  Gln  Arg  Phe  Ile  Pro  Ile  Asn  Gly  Tyr  Pro  Ile
               675                     680                     685
```

```
CCT  CCT  GGA  TAT  GCA  GCG  TTT  CCA  GCT  GCC  CAC  TAC  CAG  CCA  ACA  GGT      2111
Pro  Pro  Gly  Tyr  Ala  Ala  Phe  Pro  Ala  Ala  His  Tyr  Gln  Pro  Thr  Gly
          690                      695                     700

CCT  CCC  AGA  GTG  ATT  CAG  CAC  TGC  CCA  CCT  CCC  AAG  AGT  CGG  TCC  CCA      2159
Pro  Pro  Arg  Val  Ile  Gln  His  Cys  Pro  Pro  Pro  Lys  Ser  Arg  Ser  Pro
     705                      710                     715

AGC  AGT  GCC  AGT  GGG  TCG  ACT  AGC  ACT  GGC  CAT  GTG  ACT  AGC  TTG  CCC      2207
Ser  Ser  Ala  Ser  Gly  Ser  Thr  Ser  Thr  Gly  His  Val  Thr  Ser  Leu  Pro
720                      725                     730                          735

TCA  TCA  GGA  TCC  AAT  CAG  GAA  GCA  AAT  ATT  CCT  TTA  CTA  CCA  CAC  ATG      2255
Ser  Ser  Gly  Ser  Asn  Gln  Glu  Ala  Asn  Ile  Pro  Leu  Leu  Pro  His  Met
                    740                      745                     750

TCA  ATT  CCA  AAT  CAT  CCT  GGT  GGA  ATG  GGT  ATC  ACC  GTT  TTT  GGC  AAC      2303
Ser  Ile  Pro  Asn  His  Pro  Gly  Gly  Met  Gly  Ile  Thr  Val  Phe  Gly  Asn
                    755                      760                     765

AAA  TCT  CAA  AAA  CCC  TAC  AAA  ATT  GAC  TCA  AAG  CAA  GCA  TCT  TTA  CTA      2351
Lys  Ser  Gln  Lys  Pro  Tyr  Lys  Ile  Asp  Ser  Lys  Gln  Ala  Ser  Leu  Leu
          770                      775                     780

GGA  GAC  GCC  AAT  ATT  CAT  GGA  CAC  ACC  GAA  TCT  ATG  ATT  TCT  GCA  GAA      2399
Gly  Asp  Ala  Asn  Ile  His  Gly  His  Thr  Glu  Ser  Met  Ile  Ser  Ala  Glu
          785                      790                     795

CTG  TAAAATGCAC  AACTTTTGTA  AATGTGGTAT  ACAGGACAAA  CTAGACGGCC                     2452
Leu
800

GTAGAAAAGA  TTTATATTCA  AATGTTTTTA  TTAAAGTAAG  GTTCTCATTT  AGCAGACATC              2512

GCAACAAGTA  CCTTCTGTGA  AGTTTCACTG  TGTCTTACCA  AGCAGGACAG  ACACTCGGCC              2572

AGAAAAAAGA  AAAAAAAAAA  AAA                                                         2595
```

( 2 ) INFORMATION FOR SEQ ID NO:78:

( i ) SEQUENCE CHARACTERISTICS:
        ( A ) LENGTH: 800 amino acids
        ( B ) TYPE: amino acid
        ( D ) TOPOLOGY: linear ( i i ) MOLECULE TYPE: protein ( x i ) SEQUENCE DESCRIPTION: SEQ ID NO:78:

```
Gly  Gly  Gly  Phe  Phe  His  Trp  Ser  Leu  Val  Cys  Gln  Val  Trp  Pro  Pro
  1                 5                     10                         15

Ser  His  Ser  Lys  Ser  Arg  Tyr  Ser  Asp  Glu  Tyr  Glu  Glu  Asp  Gly  Phe
               20                     25                         30

Cys  Gln  Pro  Tyr  Arg  Gly  Ile  Ala  Cys  Ala  Arg  Phe  Ile  Gly  Asn  Arg
               35                     40                         45

Thr  Val  Tyr  Met  Glu  Ser  Leu  His  Met  Gln  Gly  Glu  Ile  Glu  Asn  Gln
     50                     55                         60

Ile  Thr  Ala  Ala  Phe  Thr  Met  Ile  Gly  Thr  Ser  Ser  His  Leu  Ser  Asp
 65                      70                     75                         80

Lys  Cys  Ser  Gln  Phe  Ala  Ile  Pro  Ser  Leu  Cys  His  Tyr  Ala  Phe  Pro
               85                     90                         95

Tyr  Cys  Asp  Glu  Thr  Ser  Ser  Val  Pro  Lys  Pro  Arg  Asp  Leu  Cys  Arg
              100                    105                        110

Asp  Glu  Cys  Glu  Ile  Leu  Glu  Asn  Val  Leu  Cys  Gln  Thr  Glu  Tyr  Ile
              115                    120                        125

Phe  Ala  Arg  Ser  Asn  Pro  Met  Ile  Leu  Met  Arg  Leu  Lys  Leu  Pro  Asn
              130                    135                        140

Cys  Glu  Asp  Leu  Pro  Gln  Pro  Glu  Ser  Pro  Glu  Ala  Ala  Asn  Cys  Ile
145                     150                    155                        160
```

-continued

| Arg | Ile | Gly | Ile | Pro | Met | Ala | Asp | Pro | Ile | Asn | Lys | Asn | His | Lys | Cys |
|-----|-----|-----|-----|-----|-----|-----|-----|-----|-----|-----|-----|-----|-----|-----|-----|
|     |     |     |     | 165 |     |     |     | 170 |     |     |     |     |     | 175 |     |

| Tyr | Asn | Ser | Thr | Gly | Val | Asp | Tyr | Arg | Gly | Thr | Val | Ser | Val | Thr | Lys |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ser | Gly | Arg | Gln | Cys | Gln | Pro | Trp | Asn | Ser | Gln | Tyr | Pro | His | Thr | His |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Thr | Phe | Thr | Ala | Leu | Arg | Phe | Pro | Glu | Leu | Asn | Gly | Gly | His | Ser | Tyr |
|     | 210 |     |     |     |     | 215 |     |     |     |     |     | 220 |     |     |     |

| Cys | Arg | Asn | Pro | Gly | Asn | Gln | Lys | Glu | Ala | Pro | Trp | Cys | Phe | Thr | Leu |
| 225 |     |     |     |     | 230 |     |     |     |     | 235 |     |     |     |     | 240 |

| Asp | Glu | Asn | Phe | Lys | Ser | Asp | Leu | Cys | Asp | Ile | Pro | Ala | Cys | Asp | Ser |
|     |     |     |     | 245 |     |     |     |     | 250 |     |     |     |     | 255 |     |

| Lys | Asp | Ser | Lys | Glu | Lys | Asn | Lys | Met | Glu | Ile | Leu | Tyr | Ile | Leu | Val |
|     |     |     | 260 |     |     |     |     | 265 |     |     |     |     | 270 |     |     |

| Pro | Ser | Val | Ala | Ile | Pro | Leu | Ala | Ile | Ala | Leu | Leu | Phe | Phe | Phe | Ile |
|     |     | 275 |     |     |     |     | 280 |     |     |     |     | 285 |     |     |     |

| Cys | Val | Cys | Arg | Asn | Asn | Gln | Lys | Ser | Ser | Ser | Ala | Pro | Val | Gln | Arg |
|     | 290 |     |     |     |     | 295 |     |     |     |     | 300 |     |     |     |     |

| Gln | Pro | Lys | His | Val | Arg | Gly | Gln | Asn | Val | Glu | Met | Ser | Met | Leu | Asn |
| 305 |     |     |     |     | 310 |     |     |     |     | 315 |     |     |     |     | 320 |

| Ala | Tyr | Lys | Pro | Lys | Ser | Lys | Ala | Lys | Glu | Leu | Pro | Leu | Ser | Ala | Val |
|     |     |     |     | 325 |     |     |     |     | 330 |     |     |     |     | 335 |     |

| Arg | Phe | Met | Glu | Glu | Leu | Gly | Glu | Cys | Ala | Phe | Gly | Lys | Ile | Tyr | Lys |
|     |     |     | 340 |     |     |     |     | 345 |     |     |     |     | 350 |     |     |

| Gly | His | Leu | Tyr | Leu | Pro | Gly | Met | Asp | His | Ala | Gln | Leu | Val | Ala | Ile |
|     |     | 355 |     |     |     |     | 360 |     |     |     |     | 365 |     |     |     |

| Lys | Thr | Leu | Lys | Asp | Tyr | Asn | Asn | Pro | Gln | Gln | Trp | Met | Glu | Phe | Gln |
|     | 370 |     |     |     |     | 375 |     |     |     |     | 380 |     |     |     |     |

| Gln | Glu | Ala | Ser | Leu | Met | Ala | Glu | Leu | His | His | Pro | Asn | Ile | Val | Cys |
| 385 |     |     |     |     | 390 |     |     |     |     | 395 |     |     |     |     | 400 |

| Leu | Leu | Gly | Ala | Val | Thr | Gln | Glu | Gln | Pro | Val | Cys | Met | Leu | Phe | Glu |
|     |     |     |     | 405 |     |     |     |     | 410 |     |     |     |     | 415 |     |

| Tyr | Ile | Asn | Gln | Gly | Asp | Leu | His | Glu | Phe | Leu | Ile | Met | Arg | Ser | Pro |
|     |     |     | 420 |     |     |     |     | 425 |     |     |     |     | 430 |     |     |

| His | Ser | Asp | Val | Gly | Cys | Ser | Ser | Asp | Glu | Asp | Gly | Thr | Val | Lys | Ser |
|     |     | 435 |     |     |     |     | 440 |     |     |     |     | 445 |     |     |     |

| Ser | Leu | Asp | His | Gly | Asp | Phe | Leu | His | Ile | Ala | Ile | Gln | Ile | Ala | Ala |
|     | 450 |     |     |     |     | 455 |     |     |     |     | 460 |     |     |     |     |

| Gly | Met | Glu | Tyr | Leu | Ser | Ser | His | Phe | Phe | Val | His | Lys | Asp | Leu | Ala |
| 465 |     |     |     |     | 470 |     |     |     |     | 475 |     |     |     |     | 480 |

| Ala | Arg | Asn | Ile | Leu | Ile | Gly | Glu | Gln | Leu | His | Val | Lys | Ile | Ser | Asp |
|     |     |     |     | 485 |     |     |     |     | 490 |     |     |     |     | 495 |     |

| Leu | Gly | Leu | Ser | Arg | Glu | Ile | Tyr | Ser | Ala | Asp | Tyr | Tyr | Arg | Val | Gln |
|     |     |     | 500 |     |     |     |     | 505 |     |     |     |     | 510 |     |     |

| Ser | Lys | Ser | Leu | Leu | Pro | Ile | Arg | Trp | Met | Pro | Pro | Glu | Ala | Ile | Met |
|     |     | 515 |     |     |     |     | 520 |     |     |     |     | 525 |     |     |     |

| Tyr | Gly | Lys | Phe | Ser | Ser | Asp | Ser | Asp | Ile | Trp | Ser | Phe | Gly | Val | Val |
|     |     | 530 |     |     |     |     | 535 |     |     |     |     | 540 |     |     |     |

| Leu | Trp | Glu | Ile | Phe | Ser | Phe | Gly | Leu | Gln | Pro | Tyr | Tyr | Gly | Phe | Ser |
| 545 |     |     |     |     | 550 |     |     |     |     | 555 |     |     |     |     | 560 |

| Asn | Gln | Glu | Val | Ile | Glu | Met | Val | Arg | Lys | Arg | Gln | Leu | Leu | Pro | Cys |
|     |     |     |     | 565 |     |     |     |     | 570 |     |     |     |     | 575 |     |

| Ser | Glu | Asp | Cys | Pro | Pro | Arg | Met | Tyr | Ser | Leu | Met | Thr | Glu | Cys | Trp |

|     |     |     |     | 580 |     |     |     |     | 585 |     |     |     |     | 590 |     |
|-----|-----|-----|-----|-----|-----|-----|-----|-----|-----|-----|-----|-----|-----|-----|-----|
| Asn | Glu | Ile | Pro | Ser | Arg | Arg | Pro | Arg | Phe | Lys | Asp | Ile | His | Val | Arg |
|     |     | 595 |     |     |     | 600 |     |     |     |     |     | 605 |     |     |     |
| Leu | Arg | Ser | Trp | Glu | Gly | Leu | Ser | Ser | His | Thr | Ser | Ser | Thr | Thr | Pro |
|     | 610 |     |     |     |     | 615 |     |     |     |     | 620 |     |     |     |     |
| Ser | Gly | Gly | Asn | Ala | Thr | Thr | Gln | Thr | Thr | Ser | Leu | Ser | Ala | Ser | Pro |
| 625 |     |     |     |     | 630 |     |     |     |     | 635 |     |     |     |     | 640 |
| Val | Ser | Asn | Leu | Ser | Asn | Pro | Arg | Tyr | Pro | Asn | Tyr | Met | Phe | Pro | Ser |
|     |     |     |     | 645 |     |     |     |     | 650 |     |     |     |     | 655 |     |
| Gln | Gly | Ile | Thr | Pro | Gln | Gly | Gln | Ile | Ala | Gly | Phe | Ile | Gly | Pro | Pro |
|     |     |     | 660 |     |     |     |     | 665 |     |     |     |     | 670 |     |     |
| Ile | Pro | Gln | Asn | Gln | Arg | Phe | Ile | Pro | Ile | Asn | Gly | Tyr | Pro | Ile | Pro |
|     |     | 675 |     |     |     |     | 680 |     |     |     |     | 685 |     |     |     |
| Pro | Gly | Tyr | Ala | Ala | Phe | Pro | Ala | Ala | His | Tyr | Gln | Pro | Thr | Gly | Pro |
|     | 690 |     |     |     |     | 695 |     |     |     |     | 700 |     |     |     |     |
| Pro | Arg | Val | Ile | Gln | His | Cys | Pro | Pro | Pro | Lys | Ser | Arg | Ser | Pro | Ser |
| 705 |     |     |     |     | 710 |     |     |     |     | 715 |     |     |     |     | 720 |
| Ser | Ala | Ser | Gly | Ser | Thr | Ser | Thr | Gly | His | Val | Thr | Ser | Leu | Pro | Ser |
|     |     |     |     | 725 |     |     |     |     | 730 |     |     |     |     | 735 |     |
| Ser | Gly | Ser | Asn | Gln | Glu | Ala | Asn | Ile | Pro | Leu | Leu | Pro | His | Met | Ser |
|     |     |     | 740 |     |     |     |     | 745 |     |     |     |     | 750 |     |     |
| Ile | Pro | Asn | His | Pro | Gly | Gly | Met | Gly | Ile | Thr | Val | Phe | Gly | Asn | Lys |
|     |     | 755 |     |     |     |     | 760 |     |     |     |     | 765 |     |     |     |
| Ser | Gln | Lys | Pro | Tyr | Lys | Ile | Asp | Ser | Lys | Gln | Ala | Ser | Leu | Leu | Gly |
|     | 770 |     |     |     |     | 775 |     |     |     |     | 780 |     |     |     |     |
| Asp | Ala | Asn | Ile | His | Gly | His | Thr | Glu | Ser | Met | Ile | Ser | Ala | Glu | Leu |
| 785 |     |     |     |     | 790 |     |     |     |     | 795 |     |     |     |     | 800 |

( 2 ) INFORMATION FOR SEQ ID NO:79:

( i ) SEQUENCE CHARACTERISTICS:
        ( A ) LENGTH: 755 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..753

( x i ) SEQUENCE DESCRIPTION: SEQ ID NO:79:

| TCG | CCG | CAC | TCG | GAC | GTG | GGG | AGC | ACC | GAT | GAT | GAC | CGC | ACG | GTG | AAG | 48 |
|-----|-----|-----|-----|-----|-----|-----|-----|-----|-----|-----|-----|-----|-----|-----|-----|----|
| Ser | Pro | His | Ser | Asp | Val | Gly | Ser | Thr | Asp | Asp | Asp | Arg | Thr | Val | Lys |    |
| 1   |     |     |     | 5   |     |     |     |     | 10  |     |     |     |     | 15  |     |    |
| TCC | GCC | CTG | GAG | CCC | CCC | GAC | TTC | GTG | CAC | CTT | GTG | GCA | CAG | ATC | GCG | 96 |
| Ser | Ala | Leu | Glu | Pro | Pro | Asp | Phe | Val | His | Leu | Val | Ala | Gln | Ile | Ala |    |
|     |     |     | 20  |     |     |     |     | 25  |     |     |     |     | 30  |     |     |    |
| GCG | GGG | ATG | GAG | TAC | CTA | TCC | AGC | CAC | CAC | GTG | GTT | CAC | AAG | GAC | CTG | 144 |
| Ala | Gly | Met | Glu | Tyr | Leu | Ser | Ser | His | His | Val | Val | His | Lys | Asp | Leu |    |
|     |     | 35  |     |     |     |     | 40  |     |     |     |     | 45  |     |     |     |    |
| GCC | ACC | CGC | AAT | GTG | CTA | GTG | TAC | GAC | AAG | CTG | AAC | GTG | AAG | ATC | TCA | 192 |
| Ala | Thr | Arg | Asn | Val | Leu | Val | Tyr | Asp | Lys | Leu | Asn | Val | Lys | Ile | Ser |    |
|     | 50  |     |     |     |     | 55  |     |     |     |     | 60  |     |     |     |     |    |
| GAC | TTG | GGC | CTC | TTC | CGA | GAG | GTG | TAT | GCC | GCC | GAT | TAC | TAC | AAG | CTG | 240 |
| Asp | Leu | Gly | Leu | Phe | Arg | Glu | Val | Tyr | Ala | Ala | Asp | Tyr | Tyr | Lys | Leu |    |
| 65  |     |     |     |     | 70  |     |     |     |     | 75  |     |     |     |     | 80  |    |
| CTG | GGG | AAC | TCG | CTG | CTG | CCT | ATC | CGC | TGG | ATG | GCC | CCA | GAG | GCC | ATC | 288 |
| Leu | Gly | Asn | Ser | Leu | Leu | Pro | Ile | Arg | Trp | Met | Ala | Pro | Glu | Ala | Ile |    |

-continued

|  |  |  |  |  | 85 |  |  |  | 90 |  |  |  |  | 95 |  |  |
|---|---|---|---|---|---|---|---|---|---|---|---|---|---|---|---|---|
| ATG | TAC | GGC | AAG | TTC | TCC | ATC | GAC | TCA | GAC | ATC | TGG | TCC | TAC | GGT | GTG | 336 |
| Met | Tyr | Gly | Lys 100 | Phe | Ser | Ile | Asp | Ser 105 | Asp | Ile | Trp | Ser | Tyr 110 | Gly | Val |  |
| GTC | CTG | TGG | GAG | GTC | TTC | AGC | TAC | GGC | CTG | CAG | CCC | TAC | TGC | GGG | TAT | 384 |
| Val | Leu | Trp 115 | Glu | Val | Phe | Ser | Tyr 120 | Gly | Leu | Gln | Pro | Tyr 125 | Cys | Gly | Tyr |  |
| TCC | AAC | CAG | GAT | GTG | GTG | GAG | ATG | ATC | CGG | AAC | CGG | CAG | GTG | CTG | CCT | 432 |
| Ser | Asn 130 | Gln | Asp | Val | Val | Glu 135 | Met | Ile | Arg | Asn | Arg 140 | Gln | Val | Leu | Pro |  |
| TGC | CCC | GAT | GAC | TGT | CCC | GCC | TGG | GTG | TAT | GCC | CTC | ATG | ATC | GAG | TGC | 480 |
| Cys 145 | Pro | Asp | Asp | Cys | Pro 150 | Ala | Trp | Val | Tyr | Ala 155 | Leu | Met | Ile | Glu | Cys 160 |  |
| TGG | AAC | GAG | TTC | CCC | AGC | CGG | CGG | CCC | CGC | TTC | AAG | GAC | ATC | CAC | AGC | 528 |
| Trp | Asn | Glu | Phe | Pro 165 | Ser | Arg | Arg | Pro | Arg 170 | Phe | Lys | Asp | Ile | His 175 | Ser |  |
| CGG | CTC | CGA | GCC | TGG | GGC | AAC | CTT | TCC | AAC | TAC | AAC | AGC | TCG | GCG | CAG | 576 |
| Arg | Leu | Arg | Ala 180 | Trp | Gly | Asn | Leu | Ser 185 | Asn | Tyr | Asn | Ser | Ser 190 | Ala | Gln |  |
| ACC | TCG | GGG | GCC | AGC | AAC | ACC | ACG | CAG | ACC | AGC | TCC | CTG | AGC | ACC | AGC | 624 |
| Thr | Ser | Gly 195 | Ala | Ser | Asn | Thr | Thr 200 | Gln | Thr | Ser | Ser | Leu 205 | Ser | Thr | Ser |  |
| CCA | GTG | AGC | AAT | GTG | AGC | AAC | GCC | CGC | TAC | GTG | GGG | CCC | AAG | CAG | TTG | 672 |
| Pro | Val 210 | Ser | Asn | Val | Ser 215 | Asn | Ala | Arg | Tyr | Val 220 | Gly | Pro | Lys | Gln | Leu |  |
| GCC | CCG | CCC | TTC | CCA | CAG | CCC | CAG | TTC | ATC | CCC | ATG | AAG | GGC | CAG | ATC | 720 |
| Ala 225 | Pro | Pro | Phe | Pro | Gln 230 | Pro | Gln | Phe | Ile | Pro 235 | Met | Lys | Gly | Gln | Ile 240 |  |
| AGA | CCC | ATG | GTG | CCC | GCG | CCG | CAG | CTC | TAC | ATC | CC |  |  |  |  | 755 |
| Arg | Pro | Met | Val | Pro 245 | Ala | Pro | Gln | Leu | Tyr 250 | Ile |  |  |  |  |  |  |

( 2 ) INFORMATION FOR SEQ ID NO:80:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:80:

| Ser 1 | Pro | His | Ser | Asp 5 | Val | Gly | Ser | Thr | Asp 10 | Asp | Arg | Thr | Val | Lys 15 |
|---|---|---|---|---|---|---|---|---|---|---|---|---|---|---|
| Ser | Ala | Leu | Glu 20 | Pro | Pro | Asp | Phe | Val 25 | His | Leu | Val | Ala | Gln 30 | Ile | Ala |
| Ala | Gly | Met 35 | Glu | Tyr | Leu | Ser | Ser 40 | His | His | Val | Val | His 45 | Lys | Asp | Leu |
| Ala | Thr 50 | Arg | Asn | Val | Leu | Val 55 | Tyr | Asp | Lys | Leu | Asn 60 | Val | Lys | Ile | Ser |
| Asp 65 | Leu | Gly | Leu | Phe | Arg 70 | Glu | Val | Tyr | Ala | Ala 75 | Asp | Tyr | Tyr | Lys | Leu 80 |
| Leu | Gly | Asn | Ser | Leu 85 | Leu | Pro | Ile | Arg | Trp 90 | Met | Ala | Pro | Glu | Ala 95 | Ile |
| Met | Tyr | Gly | Lys 100 | Phe | Ser | Ile | Asp | Ser 105 | Asp | Ile | Trp | Ser | Tyr 110 | Gly | Val |
| Val | Leu | Trp 115 | Glu | Val | Phe | Ser | Tyr 120 | Gly | Leu | Gln | Pro | Tyr 125 | Cys | Gly | Tyr |
| Ser | Asn 130 | Gln | Asp | Val | Val | Glu 135 | Met | Ile | Arg | Asn | Arg 140 | Gln | Val | Leu | Pro |

| Cys | Pro | Asp | Asp | Cys | Pro | Ala | Trp | Val | Tyr | Ala | Leu | Met | Ile | Glu | Cys |
| 145 | | | | 150 | | | | | 155 | | | | | | 160 |

| Trp | Asn | Glu | Phe | Pro | Ser | Arg | Arg | Pro | Arg | Phe | Lys | Asp | Ile | His | Ser |
| | | | | 165 | | | | | 170 | | | | | 175 | |

| Arg | Leu | Arg | Ala | Trp | Gly | Asn | Leu | Ser | Asn | Tyr | Asn | Ser | Ser | Ala | Gln |
| | | | 180 | | | | | 185 | | | | | 190 | | |

| Thr | Ser | Gly | Ala | Ser | Asn | Thr | Thr | Gln | Thr | Ser | Ser | Leu | Ser | Thr | Ser |
| | | 195 | | | | | 200 | | | | | 205 | | | |

| Pro | Val | Ser | Asn | Val | Ser | Asn | Ala | Arg | Tyr | Val | Gly | Pro | Lys | Gln | Leu |
| | 210 | | | | | 215 | | | | | 220 | | | | |

| Ala | Pro | Pro | Phe | Pro | Gln | Pro | Gln | Phe | Ile | Pro | Met | Lys | Gly | Gln | Ile |
| 225 | | | | | 230 | | | | | 235 | | | | | 240 |

| Arg | Pro | Met | Val | Pro | Ala | Pro | Gln | Leu | Tyr | Ile |
| | | | | 245 | | | | | 250 | |

( 2 ) INFORMATION FOR SEQ ID NO:81:

( i ) SEQUENCE CHARACTERISTICS:
        ( A ) LENGTH: 251 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:81:

| Ser | Pro | His | Ser | Asp | Val | Gly | Ser | Thr | Asp | Asp | Arg | Thr | Val | Lys |
| 1 | | | | 5 | | | | | 10 | | | | | 15 |

| Ser | Ala | Leu | Glu | Pro | Pro | Asp | Phe | Val | His | Leu | Val | Ala | Gln | Ile | Ala |
| | | | 20 | | | | | 25 | | | | | 30 | | |

| Ala | Gly | Met | Glu | Tyr | Leu | Ser | Ser | His | His | Val | Val | His | Lys | Asp | Leu |
| | | 35 | | | | | 40 | | | | | 45 | | | |

| Ala | Thr | Arg | Asn | Val | Leu | Val | Tyr | Asp | Lys | Leu | Asn | Val | Lys | Ile | Ser |
| | 50 | | | | | 55 | | | | | 60 | | | | |

| Asp | Leu | Gly | Leu | Phe | Arg | Glu | Val | Tyr | Ala | Ala | Asp | Tyr | Tyr | Lys | Leu |
| 65 | | | | | 70 | | | | | 75 | | | | | 80 |

| Leu | Gly | Asn | Ser | Leu | Leu | Pro | Ile | Arg | Trp | Met | Ala | Pro | Glu | Ala | Ile |
| | | | | 85 | | | | | 90 | | | | | 95 | |

| Met | Tyr | Gly | Lys | Phe | Ser | Ile | Asp | Ser | Asp | Ile | Trp | Ser | Tyr | Gly | Val |
| | | | 100 | | | | | 105 | | | | | 110 | | |

| Val | Leu | Trp | Glu | Val | Phe | Ser | Tyr | Gly | Leu | Gln | Pro | Tyr | Cys | Gly | Tyr |
| | | | 115 | | | | | 120 | | | | | 125 | | |

| Ser | Asn | Gln | Asp | Val | Val | Glu | Met | Ile | Arg | Asn | Arg | Gln | Val | Leu | Pro |
| | | | 130 | | | | | 135 | | | | | 140 | | |

| Cys | Pro | Asp | Asp | Cys | Pro | Ala | Trp | Val | Tyr | Ala | Leu | Met | Ile | Glu | Cys |
| 145 | | | | 150 | | | | | 155 | | | | | | 160 |

| Trp | Asn | Glu | Phe | Pro | Ser | Arg | Arg | Pro | Arg | Phe | Lys | Asp | Ile | His | Ser |
| | | | | 165 | | | | | 170 | | | | | 175 | |

| Arg | Leu | Arg | Ala | Trp | Gly | Asn | Leu | Ser | Asn | Tyr | Asn | Ser | Ser | Ala | Gln |
| | | | 180 | | | | | 185 | | | | | 190 | | |

| Thr | Ser | Gly | Ala | Ser | Asn | Thr | Thr | Gln | Thr | Ser | Ser | Leu | Ser | Thr | Ser |
| | | 195 | | | | | 200 | | | | | 205 | | | |

| Pro | Val | Ser | Asn | Val | Ser | Asn | Ala | Arg | Tyr | Val | Gly | Pro | Lys | Gln | Leu |
| | 210 | | | | | 215 | | | | | 220 | | | | |

| Ala | Pro | Pro | Phe | Pro | Gln | Pro | Gln | Phe | Ile | Pro | Met | Lys | Gly | Gln | Ile |
| 225 | | | | | 230 | | | | | 235 | | | | | 240 |

Arg  Pro  Met  Val  Pro  Ala  Pro  Gln  Leu  Tyr  Ile
                               245                      250

( 2 ) INFORMATION FOR SEQ ID NO:82:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:82:

Ser  Pro  His  Ser  Asp  Val  Gly  Cys  Ser  Ser  Asp  Glu  Asp  Gly  Thr  Val
        1                    5                        10                       15

Lys  Ser  Ser  Leu  Asp  His  Gly  Asp  Phe  Leu  His  Ile  Ala  Ile  Gln  Ile
                          20                       25                       30

Ala  Ala  Gly  Met  Glu  Tyr  Leu  Ser  Ser  His  Phe  Phe  Val  His  Lys  Asp
                     35                       40                       45

Leu  Ala  Ala  Arg  Asn  Ile  Leu  Ile  Gly  Glu  Gln  Leu  His  Val  Lys  Ile
                50                       55                       60

Ser  Asp  Leu  Gly  Leu  Ser  Arg  Glu  Ile  Tyr  Ser  Ala  Asp  Tyr  Tyr  Arg
        65                       70                       75                       80

Val  Gln  Ser  Lys  Ser  Leu  Leu  Pro  Ile  Arg  Trp  Met  Pro  Pro  Glu  Ala
                          85                       90                       95

Ile  Met  Tyr  Gly  Lys  Phe  Ser  Ser  Asp  Ser  Asp  Ile  Trp  Ser  Phe  Gly
                          100                      105                      110

Val  Val  Leu  Trp  Glu  Ile  Phe  Ser  Phe  Gly  Leu  Gln  Pro  Tyr  Tyr  Gly
                     115                      120                      125

Phe  Ser  Asn  Gln  Glu  Val  Ile  Glu  Met  Val  Arg  Lys  Arg  Gln  Leu  Leu
             130                      135                      140

Pro  Cys  Ser  Glu  Asp  Cys  Pro  Pro  Arg  Met  Tyr  Ser  Leu  Met  Thr  Glu
        145                      150                      155                      160

Cys  Trp  Asn  Glu  Ile  Pro  Ser  Arg  Arg  Pro  Arg  Phe  Lys  Asp  Ile  His
                          165                      170                      175

Val  Arg  Leu  Arg  Ser  Trp  Glu  Gly  Leu  Ser  Ser  His  Thr  Ser  Ser  Thr
                     180                      185                      190

Thr  Pro  Ser  Gly  Gly  Asn  Ala  Thr  Thr  Gln  Thr  Thr  Ser  Leu  Ser  Ala
                     195                      200                      205

Ser  Pro  Val  Ser  Asn  Leu  Ser  Asn  Pro  Arg  Tyr  Pro  Asn  Tyr  Met  Phe
                210                      215                      220

Pro  Ser  Gln  Gly  Ile  Thr  Pro  Gln  Gly  Gln  Ile  Ala  Gly  Phe  Ile  Gly
        225                      230                      235                      240

Pro  Pro  Ile  Pro  Gln  Asn  Gln  Arg  Phe  Ile
                               245                      250

( 2 ) INFORMATION FOR SEQ ID NO:83:

( i ) SEQUENCE CHARACTERISTICS:
        ( A ) LENGTH: 163 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:83:

Thr  Glu  Leu  Thr  Gln  Ser  Gln  Met  Leu  His  Ile  Ala  Gln  Gln  Ile  Ala
        1                    5                        10                       15

|     |     |     |     |     |     |     |     |     |     |     |     |     |     |     |
|-----|-----|-----|-----|-----|-----|-----|-----|-----|-----|-----|-----|-----|-----|-----|
| Ala | Gly | Met | Val<br>20 | Tyr | Leu | Ala | Ser | Gln<br>25 | His | Phe | Val | His | Arg<br>30 | Asp | Leu |
| Ala | Thr | Arg<br>35 | Asn | Cys | Leu | Val | Gly<br>40 | Glu | Asn | Leu | Leu | Val<br>45 | Lys | Ile | Gly |
| Asp | Phe<br>50 | Gly | Met | Ser | Arg | Asp<br>55 | Val | Tyr | Ser | Thr | Asp<br>60 | Tyr | Tyr | Arg | Val |
| Gly<br>65 | Gly | His | Thr | Met | Leu<br>70 | Pro | Ile | Arg | Trp | Met<br>75 | Pro | Pro | Glu | Ser | Ile<br>80 |
| Met | Tyr | Arg | Lys | Phe<br>85 | Thr | Thr | Glu | Ser | Asp<br>90 | Val | Trp | Ser | Leu | Gly<br>95 | Val |
| Val | Leu | Trp | Glu<br>100 | Ile | Phe | Thr | Tyr | Gly<br>105 | Lys | Gln | Pro | Trp | Tyr<br>110 | Gln | Leu |
| Ser | Asn | Asn<br>115 | Glu | Val | Ile | Glu | Cys<br>120 | Ile | Thr | Gln | Gly | Arg<br>125 | Val | Leu | Gln |
| Arg | Pro<br>130 | Arg | Thr | Cys | Pro | Gln<br>135 | Glu | Val | Tyr | Glu | Leu<br>140 | Met | Leu | Gly | Cys |
| Trp<br>145 | Gln | Arg | Glu | Pro | His<br>150 | Thr | Arg | Lys | Asn | Ile<br>155 | Lys | Asn | Ile | His | Thr<br>160 |
| Leu | Leu | Gln |

(2) INFORMATION FOR SEQ ID NO:84:

(i) SEQUENCE CHARACTERISTICS:
        (A) LENGTH: 179 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:84:

|     |     |     |     |     |     |     |     |     |     |     |     |     |     |     |     |
|-----|-----|-----|-----|-----|-----|-----|-----|-----|-----|-----|-----|-----|-----|-----|-----|
| Gly<br>1 | Pro | Asp | Ala | Lys<br>5 | Leu | Leu | Ala | Gly | Glu<br>10 | Asp | Val | Ala | Pro<br>15 | Gly |
| Pro | Leu | Gly | Leu<br>20 | Gly | Gln | Leu | Leu | Ala<br>25 | Val | Ala | Ser | Gln | Val<br>30 | Ala | Ala |
| Gly | Met | Val<br>35 | Tyr | Leu | Ala | Gly | Leu<br>40 | His | Phe | Val | His | Arg<br>45 | Asp | Leu | Ala |
| Thr | Arg<br>50 | Asn | Cys | Leu | Val | Gly<br>55 | Gln | Gly | Leu | Val | Val<br>60 | Lys | Ile | Gly | Asp |
| Phe<br>65 | Gly | Met | Ser | Arg | Asp<br>70 | Ile | Tyr | Ser | Thr | Asp<br>75 | Tyr | Tyr | Arg | Val | Gly<br>80 |
| Gly | Arg | Thr | Met | Leu<br>85 | Pro | Ile | Arg | Trp | Met<br>90 | Pro | Pro | Glu | Ser | Ile<br>95 | Leu |
| Tyr | Arg | Lys | Phe<br>100 | Thr | Thr | Glu | Ser | Asp<br>105 | Val | Trp | Ser | Phe | Gly<br>110 | Val | Val |
| Leu | Trp | Glu | Ile<br>115 | Phe | Thr | Tyr | Gly | Lys<br>120 | Gln | Pro | Trp | Tyr | Gln<br>125 | Leu | Ser |
| Asn | Thr | Glu<br>130 | Ala | Ile | Asp | Cys | Ile<br>135 | Thr | Gln | Gly | Arg | Glu<br>140 | Leu | Glu | Arg |
| Pro | Arg<br>145 | Ala | Cys | Pro | Pro | Glu<br>150 | Val | Tyr | Ala | Ile | Met<br>155 | Arg | Gly | Cys | Trp<br>160 |
| Gln | Arg | Glu | Pro | Gln<br>165 | Gln | Arg | His | Ser | Ile<br>170 | Lys | Asp | Val | His | Ala<br>175 | Arg |
| Leu | Gln | Ala<br>180 |

(2) INFORMATION FOR SEQ ID NO:85:

( i ) SEQUENCE CHARACTERISTICS:
   ( A ) LENGTH: 237 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO:85:

```
Glu Asn Asn Pro Val Leu Ala Pro Pro Ser Leu Ser Lys Met Ile Gln
1               5                   10                  15
Met Ala Gly Glu Ile Ala Asp Gly Met Ala Tyr Leu Asn Ala Asn Lys
            20                  25                  30
Phe Val His Arg Asp Leu Ala Ala Arg Asn Cys Met Val Ala Glu Asp
            35                  40                  45
Phe Thr Val Lys Ile Gly Asp Phe Gly Met Thr Arg Asp Ile Tyr Glu
        50                  55                  60
Thr Asp Tyr Tyr Arg Lys Gly Gly Lys Gly Leu Leu Pro Val Arg Trp
65                  70                  75                  80
Met Ser Pro Glu Ser Leu Lys Asp Gly Val Phe Thr Thr Tyr Ser Asp
                85                  90                  95
Val Trp Ser Phe Gly Val Val Leu Trp Glu Ile Ala Thr Leu Ala Glu
                100                 105                 110
Gln Pro Tyr Gln Gly Leu Ser Asn Glu Gln Val Leu Arg Phe Val Met
            115                 120                 125
Glu Gly Gly Leu Leu Asp Lys Pro Asp Asn Cys Pro Asp Met Leu Phe
    130                 135                 140
Glu Leu Met Arg Met Cys Trp Gln Tyr Asn Pro Lys Met Arg Pro Ser
145                 150                 155                 160
Phe Leu Glu Ile Ile Ser Ser Ile Lys Glu Glu Met Glu Pro Gly Phe
                165                 170                 175
Arg Glu Val Ser Phe Tyr Tyr Ser Glu Glu Asn Lys Leu Pro Glu Pro
            180                 185                 190
Glu Glu Leu Asp Leu Glu Pro Glu Asn Met Glu Ser Val Pro Leu Asp
        195                 200                 205
Pro Ser Ala Ser Ser Ser Ser Leu Pro Leu Pro Asp Arg His Ser Gly
    210                 215                 220
His Lys Ala Glu Asn Gly Pro Gly Pro Gly Val Leu Val
225                 230                 235
```

( 2 ) INFORMATION FOR SEQ ID NO:86:

( i ) SEQUENCE CHARACTERISTICS:
   ( A ) LENGTH: 172 amino acids
   ( B ) TYPE: amino acid
   ( C ) STRANDEDNESS: single
   ( D ) TOPOLOGY: unknown ( i i ) MOLECULE TYPE: peptide ( x i ) SEQUENCE DESCRIPTION: SEQ ID NO:86:

```
Pro Glu Ala Glu Asn Asn Pro Gly Arg Pro Pro Pro Thr Leu Gln Glu
1               5                   10                  15
Met Ile Gln Met Ala Ala Glu Ile Ala Asp Gly Met Ala Tyr Leu Asn
            20                  25                  30
Ala Lys Lys Phe Val His Arg Asp Leu Ala Ala Arg Asn Cys Met Val
            35                  40                  45
Ala His Asp Phe Thr Val Lys Ile Gly Asp Phe Gly Met Thr Arg Asp
        50                  55                  60
```

```
Ile  Tyr  Glu  Thr  Asp  Tyr  Tyr  Arg  Lys  Gly  Gly  Lys  Gly  Leu  Leu  Pro
 65                  70                       75                             80

Val  Arg  Trp  Met  Ala  Pro  Glu  Ser  Leu  Lys  Asp  Gly  Val  Phe  Thr  Thr
                     85                       90                        95

Ser  Ser  Asp  Met  Trp  Ser  Phe  Gly  Val  Val  Leu  Trp  Glu  Ile  Thr  Ser
               100                      105                     110

Leu  Ala  Glu  Gln  Pro  Tyr  Gln  Gly  Leu  Ser  Asn  Glu  Gln  Val  Leu  Lys
          115                      120                     125

Phe  Val  Met  Asp  Gly  Gly  Tyr  Leu  Asp  Gln  Pro  Asp  Asn  Cys  Pro  Glu
     130                      135                     140

Arg  Val  Thr  Asp  Leu  Met  Arg  Met  Cys  Trp  Gln  Phe  Asn  Pro  Asn  Met
145                      150                     155                          160

Arg  Pro  Thr  Phe  Leu  Glu  Ile  Val  Asn  Leu  Leu  Lys
                    165                      170
```

( 2 ) INFORMATION FOR SEQ ID NO:87:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: modified_base
        ( B ) LOCATION: 13
        ( D ) OTHER INFORMATION: /mod_base=OTHER
            / label= N
            / note= "N = G,A,C or T"

( i x ) FEATURE:
        ( A ) NAME/KEY: modified_base
        ( B ) LOCATION: 16
        ( D ) OTHER INFORMATION: /mod_base=OTHER
            / label= N
            / note= "N = G,A,C or T"

( i x ) FEATURE:
        ( A ) NAME/KEY: modified_base
        ( B ) LOCATION: 22
        ( D ) OTHER INFORMATION: /mod_base=OTHER
            / label= N
            / note= "N = G,A,C or T"

( i x ) FEATURE:
        ( A ) NAME/KEY: modified_base
        ( B ) LOCATION: 25
        ( D ) OTHER INFORMATION: /mod_base=OTHER
            / label= Y
            / note= "Y = C or T"

( i x ) FEATURE:
        ( A ) NAME/KEY: modified_base
        ( B ) LOCATION: 26
        ( D ) OTHER INFORMATION: /mod_base=OTHER
            / label= Y
            / note= "Y = C or T"

( x i ) SEQUENCE DESCRIPTION: SEQ ID NO:87:

ACGTCTCGAG GCNGGNATGG TNTAYYT                    27

( 2 ) INFORMATION FOR SEQ ID NO:88:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
    ( A ) NAME/KEY: modified_base
    ( B ) LOCATION: 19
    ( D ) OTHER INFORMATION: /mod_base=OTHER
        / label= N
        / note= "N = G,A,C or T"

( i x ) FEATURE:
    ( A ) NAME/KEY: modified_base
    ( B ) LOCATION: 21
    ( D ) OTHER INFORMATION: /mod_base=OTHER
        / label= K
        / note= "K = G or T"

( i x ) FEATURE:
    ( A ) NAME/KEY: modified_base
    ( B ) LOCATION: 22
    ( D ) OTHER INFORMATION: /mod_base=OTHER
        / label= D
        / note= "D = G, A or T"

( i x ) FEATURE:
    ( A ) NAME/KEY: modified_base
    ( B ) LOCATION: 25
    ( D ) OTHER INFORMATION: /mod_base=OTHER
        / label= Y
        / note= "Y = C or T"

( x i ) SEQUENCE DESCRIPTION: SEQ ID NO:88:

CATGTCTAGA GGCATCCANC KDATNGG    27

( 2 ) INFORMATION FOR SEQ ID NO:89:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: modified_base
        ( B ) LOCATION: 13
        ( D ) OTHER INFORMATION: /mod_base=OTHER
            / label= R
            / note= "R = A or G"

( i x ) FEATURE:
        ( A ) NAME/KEY: modified_base
        ( B ) LOCATION: 16
        ( D ) OTHER INFORMATION: /mod_base=OTHER
            / label= H
            / note= "H = A, C or T"

( i x ) FEATURE:
        ( A ) NAME/KEY: modified_base
        ( B ) LOCATION: 19
        ( D ) OTHER INFORMATION: /mod_base=OTHER
            / label= N
            / note= "N = G,A,C or T"

( i x ) FEATURE:
        ( A ) NAME/KEY: modified_base
        ( B ) LOCATION: 22
        ( D ) OTHER INFORMATION: /mod_base=OTHER
            / label= Y
            / note= "Y = C or T"

( i x ) FEATURE:
        ( A ) NAME/KEY: modified_base
        ( B ) LOCATION: 25
        ( D ) OTHER INFORMATION: /mod_base=OTHER
            / label= Y
            / note= "Y = C or T"

(x i) SEQUENCE DESCRIPTION: SEQ ID NO:89:

ACGTCTCGAG AARATHGGNG AYTTYGG 27

(2) INFORMATION FOR SEQ ID NO:90:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (i i) MOLECULE TYPE: cDNA (i x) FEATURE:
        (A) NAME/KEY: modified_base
        (B) LOCATION: 13
        (D) OTHER INFORMATION: /mod_base=OTHER
            / label= R
            / note= "R = A or G"

(i x) FEATURE:
        (A) NAME/KEY: modified_base
        (B) LOCATION: 16
        (D) OTHER INFORMATION: /mod_base=OTHER
            / label= R
            / note= "R = A or G"

(i x) FEATURE:
        (A) NAME/KEY: modified_base
        (B) LOCATION: 19
        (D) OTHER INFORMATION: /mod_base=OTHER
            / label= N
            / note= "N = G,A,C or T"

(i x) FEATURE:
        (A) NAME/KEY: modified_base
        (B) LOCATION: 22
        (D) OTHER INFORMATION: /mod_base=OTHER
            / label= D
            / note= "D = G, A or T"

(i x) FEATURE:
        (A) NAME/KEY: modified_base
        (B) LOCATION: 25
        (D) OTHER INFORMATION: /mod_base=OTHER
            / label= Y
            / note= "Y = C or T"

(x i) SEQUENCE DESCRIPTION: SEQ ID NO:90:

CATGTCTAGA CCRAARTCNC CDATYTT 27

(2) INFORMATION FOR SEQ ID NO:91:

(i) SEQUENCE CHARACTERISTICS:
        (A) LENGTH: 6 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:91:

Asp Leu Ala Thr Arg Asn (2) INFORMATION FOR SEQ ID NO:92:

(i) SEQUENCE CHARACTERISTICS:
        (A) LENGTH: 6 amino acids
        (B) TYPE: amino acid
        (C) STRANDEDNESS: single
        (D) TOPOLOGY: unknown (i i) MOLECULE TYPE: peptide ( x i ) SEQUENCE DESCRIPTION: SEQ ID NO:92:

Asp Leu Ala Ala Arg Asn ( 2 ) INFORMATION FOR SEQ ID NO:93:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:93:

Asp Val Trp Ser Leu Gly ( 2 ) INFORMATION FOR SEQ ID NO:94:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:94:

Asp Val Trp Ser Phe Gly ( 2 ) INFORMATION FOR SEQ ID NO:95:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:95:

Asp Val Trp Ser Tyr Gly ( 2 ) INFORMATION FOR SEQ ID NO:96:

( i ) SEQUENCE CHARACTERISTICS:
        ( A ) LENGTH: 1101 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:96:

```
Val Glu Gly Ala Met Asp Leu Ile Leu Ile Asn Ser Leu Pro Leu Val
 1               5                  10                  15

Ser Asp Ala Glu Thr Ser Leu Thr Cys Ile Ala Ser Gly Trp His Pro
                20                  25                  30

His Glu Pro Ile Thr Ile Gly Arg Asp Phe Glu Ala Leu Met Asn Gln
            35                  40                  45

His Gln Asp Pro Leu Glu Val Thr Gln Asp Val Thr Arg Glu Trp Ala
        50                  55                  60

Lys Lys Val Val Trp Lys Arg Glu Lys Ala Ser Lys Ile Asn Gly Ala
65                  70                  75                  80

Tyr Phe Cys Glu Gly Arg Val Arg Gly Gln Ala Ile Arg Ile Arg Thr
                85                  90                  95
```

```
Met Lys Met Arg Gln Gln Ala Ser Phe Leu Pro Ala Thr Leu Thr Met
        100                     105                     110
Thr Val Asp Arg Gly Asp Asn Val Asn Ile Ser Phe Lys Lys Val Leu
            115                 120                 125
Ile Lys Glu Glu Asp Ala Val Ile Tyr Lys Asn Gly Ser Phe Ile His
    130                 135                 140
Ser Val Pro Arg His Glu Val Pro Asp Ile Leu Glu Val His Leu Pro
145                     150                 155                 160
His Ala Gln Pro Gln Asp Ala Gly Val Tyr Ser Ala Arg Tyr Ile Gly
                    165                 170                 175
Gly Asn Leu Phe Thr Ser Ala Phe Thr Arg Leu Ile Val Arg Arg Cys
                180                 185                 190
Glu Ala Gln Lys Trp Gly Pro Asp Cys Asn Arg Pro Cys Thr Thr Cys
            195                 200                 205
Lys Asn Asn Gly Val Cys His Glu Asp Thr Gly Glu Cys Ile Cys Pro
    210                 215                 220
Pro Gly Phe Met Gly Arg Thr Cys Glu Lys Ala Cys Glu Pro His Thr
225                 230                 235                 240
Phe Gly Arg Thr Cys Lys Glu Arg Cys Ser Gly Ser Glu Gly Cys Lys
                245                 250                 255
Ser Tyr Val Phe Cys Leu Pro Asp Pro Tyr Gly Cys Ser Cys Ala Thr
                260                 265                 270
Gly Trp Arg Gly Leu Gln Cys Asn Glu Ala Cys Pro Tyr Gly His Tyr
        275                 280                 285
Gly Pro Asp Cys Lys Leu Arg Cys His Cys Thr Asn Glu Glu Met Cys
        290                 295                 300
Asp Arg Phe Gln Gly Cys Leu Cys Ser Gln Gly Trp Gln Gly Leu Gln
305                 310                 315                 320
Cys Glu Lys Glu Gly Arg Pro Arg Met Thr Pro Gln Ile Glu Asp Leu
                325                 330                 335
Pro Asp His Ile Glu Val Asn Ser Gly Lys Phe Asn Pro Ile Cys Lys
            340                 345                 350
Ala Ser Gly Trp Pro Leu Pro Thr Ser Glu Glu Met Thr Leu Val Lys
        355                 360                 365
Pro Asp Gly Thr Val Leu Gln Pro Asn Asp Phe Asn His Thr Asp His
    370                 375                 380
Phe Ser Val Ala Ile Phe Thr Val Asn Arg Ile Leu Pro Pro Asp Ser
385                 390                 395                 400
Gly Val Trp Val Cys Ser Val Asn Thr Val Ala Gly Met Val Glu Lys
                405                 410                 415
Pro Phe Asn Ile Ser Val Lys Val Leu Pro Glu Pro Leu His Ala Pro
            420                 425                 430
Asn Val Ile Asp Thr Gly His Asn Phe Ala Ile Ile Asn Ile Ser Ser
        435                 440                 445
Glu Pro Tyr Phe Gly Asp Gly Pro Ile Lys Ser Lys Lys Leu Phe Tyr
    450                 455                 460
Lys Pro Val Asn Gln Ala Trp Lys Tyr Ile Gln Val Met Asn Glu Ile
465                 470                 475                 480
Val Thr Leu Asn Tyr Leu Glu Pro Arg Thr Asp Tyr Glu Leu Cys Val
                485                 490                 495
Gln Leu Val Arg Pro Gly Glu Gly Gly Glu Gly His Pro Gly Pro Val
            500                 505                 510
Arg Arg Phe Thr Thr Ala Ser Ile Gly Leu Pro Pro Pro Arg Gly Leu
```

-continued

|  |  | 515 |  |  |  | 520 |  |  |  | 525 |  |  |  |  |
|---|---|---|---|---|---|---|---|---|---|---|---|---|---|---|
| Ser | Leu 530 | Leu | Pro | Lys | Ser 535 | Gln | Thr | Ala | Leu | Asn 540 | Leu | Thr | Trp | Gln | Pro |
| Ile 545 | Phe | Thr | Ser | Ser | Glu 550 | Asp | Glu | Phe | Tyr | Val 555 | Glu | Val | Glu | Arg | Trp 560 |
| Ser | Gln | Gln | Thr | Arg 565 | Ser | Asp | Gln | Gln | Asn 570 | Ile | Lys | Val | Pro | Gly 575 | Asn |
| Leu | Thr | Ser | Val 580 | Leu | Leu | Asn | Asn | Leu 585 | Leu | Pro | Arg | Glu | Gln 590 | Tyr | Ser |
| Val | Arg | Ala 595 | Arg | Val | Asn | Thr 600 | Lys | Ala | Gln | Gly | Glu 605 | Trp | Ser | Glu | Glu |
| Leu | Arg | Ala 610 | Trp | Thr | Leu | Ser 615 | Asp | Ile | Leu | Pro | Pro 620 | Gln | Pro | Glu | Asn |
| Ile 625 | Lys | Ile | Thr | Asn | Ile 630 | Thr | Asp | Tyr | Thr | Ala 635 | Leu | Val | Ser | Trp | Thr 640 |
| Ile | Val | Asp | Gly | Tyr 645 | Ser | Ile | Ser | Ser | Ile 650 | Ile | Arg | Tyr | Lys 655 | Val |
| Gln | Gly | Lys | Asn 660 | Glu | Asp | Gln | His | Ile 665 | Asp | Val | Lys | Ile | Lys 670 | Asn | Ala |
| Thr | Ile | Thr 675 | Gln | Tyr | Gln | Leu | Lys 680 | Gly | Leu | Glu | Pro | Glu 685 | Thr | Thr | Tyr |
| His | Val 690 | Asp | Ile | Phe | Ala | Glu 695 | Asn | Asn | Ile | Gly | Ser 700 | Ser | Asn | Pro | Ala |
| Phe 705 | Ser | Gln | Glu | Ile | Arg 710 | Thr | Leu | Pro | Ala | Pro 715 | Lys | Asp | Leu | Gly | Gly 720 |
| Gly | Lys | Met | Leu | Leu 725 | Ile | Ala | Ile | Leu | Gly 730 | Ser | Ala | Gly | Met | Thr 735 | Cys |
| Ile | Thr | Val | Leu 740 | Leu | Ala | Phe | Leu | Ile 745 | Met | Leu | Gln | Leu | Lys 750 | Arg | Ala |
| Asn | Val | Gln 755 | Arg | Arg | Met | Ala | Gln 760 | Ala | Phe | Gln | Asn | Val 765 | Arg | Glu | Glu |
| Pro | Ala | Val 770 | Gln | Phe | Asn | Ser 775 | Gly | Thr | Leu | Ala | Leu 780 | Asn | Arg | Lys | Ala |
| Lys 785 | Asn | Asn | Pro | Asp | Pro 790 | Thr | Ile | Tyr | Pro | Val 795 | Leu | Asp | Trp | Asn | Asp 800 |
| Ile | Lys | Phe | Gln | Asp 805 | Val | Ile | Gly | Glu | Gly 810 | Asn | Phe | Gly | Gln | Val 815 | Leu |
| Lys | Ala | Arg | Ile 820 | Lys | Lys | Asp | Gly | Leu 825 | Arg | Met | Asp | Ala | Ala 830 | Ile | Lys |
| Arg | Met | Lys 835 | Glu | Tyr | Ala | Ser | Lys 840 | Asp | Asp | His | Arg | Asp 845 | Phe | Ala | Gly |
| Glu | Leu 850 | Glu | Val | Leu | Cys | Lys 855 | Leu | Gly | His | His | Pro 860 | Asn | Ile | Ile | Asn |
| Leu 865 | Leu | Gly | Ala | Cys | Glu 870 | His | Arg | Gly | Tyr | Leu 875 | Tyr | Leu | Ala | Ile | Glu 880 |
| Tyr | Ala | Pro | His | Gly 885 | Asn | Leu | Leu | Asp | Phe 890 | Leu | Arg | Lys | Ser | Arg 895 | Val |
| Leu | Glu | Thr | Asp 900 | Pro | Ala | Phe | Ala | Ile 905 | Ala | Asn | Ser | Thr | Ala 910 | Ser | Thr |
| Leu | Ser | Ser 915 | Gln | Gln | Leu | Leu | His 920 | Phe | Ala | Ala | Asp | Val 925 | Ala | Arg | Gly |
| Met | Asp 930 | Tyr | Leu | Ser | Gln | Lys 935 | Gln | Phe | Ile | His | Arg 940 | Asp | Leu | Ala | Ala |

```
Arg  Asn  Ile  Leu  Val  Gly  Glu  Asn  Tyr  Ile  Ala  Lys  Ile  Ala  Asp  Phe
945                      950                      955                      960

Gly  Leu  Ser  Arg  Gly  Gln  Glu  Val  Tyr  Val  Lys  Lys  Thr  Met  Gly  Arg
                    965                      970                      975

Leu  Pro  Val  Arg  Trp  Met  Ala  Ile  Glu  Ser  Leu  Asn  Tyr  Ser  Val  Tyr
                980                      985                      990

Thr  Thr  Asn  Ser  Asp  Val  Trp  Ser  Tyr  Gly  Val  Leu  Leu  Trp  Glu  Ile
          995                      1000                     1005

Val  Ser  Leu  Gly  Gly  Thr  Pro  Tyr  Cys  Gly  Met  Thr  Cys  Ala  Glu  Leu
          1010                     1015                     1020

Tyr  Glu  Lys  Leu  Pro  Gln  Gly  Tyr  Arg  Leu  Glu  Lys  Pro  Leu  Asn  Cys
1025                     1030                     1035                     1040

Asp  Asp  Glu  Val  Tyr  Asp  Leu  Met  Arg  Gln  Cys  Trp  Arg  Glu  Lys  Pro
                1045                     1050                     1055

Tyr  Glu  Arg  Pro  Ser  Phe  Ala  Gln  Ile  Leu  Val  Ser  Leu  Asn  Arg  Met
                1060                     1065                     1070

Leu  Glu  Glu  Arg  Lys  Thr  Tyr  Val  Asn  Thr  Thr  Leu  Tyr  Glu  Lys  Phe
          1075                     1080                     1085

Thr  Tyr  Ala  Gly  Ile  Asp  Cys  Ser  Ala  Glu  Glu  Ala  Ala
          1090                     1095                     1100
```

( 2 ) INFORMATION FOR SEQ ID NO:97:

( i ) SEQUENCE CHARACTERISTICS:
        ( A ) LENGTH: 1135 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:97:

```
Met  Val  Trp  Trp  Gly  Ser  Pro  Phe  Leu  Leu  Pro  Ile  Leu  Phe  Leu  Ala
1                   5                        10                       15

Ser  His  Val  Gly  Ala  Ser  Val  Asp  Leu  Thr  Leu  Leu  Ala  Asn  Leu  Arg
               20                       25                       30

Ile  Thr  Glu  Pro  Gln  Arg  Phe  Phe  Leu  Thr  Cys  Val  Ser  Gly  Glu  Ala
          35                       40                       45

Gly  Gln  Gly  Arg  Ser  Ser  Asp  Val  Trp  Ala  Arg  Leu  Leu  Leu  Glu  Lys
     50                       55                       60

Asp  Asp  Arg  Ile  Val  Arg  Thr  Phe  Pro  Pro  Gly  Gln  Pro  Leu  His  Leu
65                       70                       75                       80

Thr  Arg  Asn  Gly  Ser  His  Gln  Val  Thr  Leu  Arg  Gly  Phe  Ser  Lys  Pro
                85                       90                       95

Ser  Asp  Leu  Val  Gly  Val  Phe  Ser  Cys  Val  Gly  Gly  Ala  Gly  Thr  Arg
               100                      105                      110

Arg  Thr  Arg  Val  Leu  Tyr  Val  His  Asn  Ser  Pro  Gly  Ala  His  Leu  Phe
          115                      120                      125

Pro  Asp  Lys  Val  Thr  His  Thr  Val  Asn  Lys  Gly  Asp  Thr  Ala  Val  Leu
          130                      135                      140

Ser  Ala  Arg  Val  His  Lys  Glu  Lys  Gln  Thr  Asp  Val  Ile  Trp  Lys  Asn
145                      150                      155                      160

Asn  Gly  Ser  Tyr  Phe  His  Thr  Leu  Asp  Trp  His  Glu  Ala  His  Asp  Ala
                165                      170                      175

Gly  Phe  Gln  Leu  Gln  Leu  Gln  Asn  Val  Gln  Pro  Pro  Ser  Ser  Ala  Ile
               180                      185                      190

Tyr  Ala  Ala  Thr  Tyr  Leu  Glu  Ala  Ser  Pro  Phe  Glu  Cys  Phe  Phe  Arg
```

-continued

```
                  195                              200                              205

Leu   Ile   Val   Arg   Gly   Cys   Glu   Ala   Gly   Arg   Trp   Gly   Pro   Gly   Cys   Val
          210                           215                           220

Lys   Asp   Cys   Pro   Gly   Cys   Leu   His   Gly   Gly   Val   Cys   His   Asp   His   Asp
    225                           230                           235                           240

Gly   Glu   Cys   Val   Cys   Pro   Pro   Gly   Phe   Thr   Gly   Thr   Arg   Cys   Glu   Gln
                            245                           250                           255

Ala   Cys   Arg   Glu   Gly   Arg   Phe   Gly   Gln   Ser   Cys   Gln   Glu   Pro   Cys   Pro
                      260                           265                           270

Gly   Thr   Ala   Gly   Cys   Arg   Gly   Leu   Thr   Phe   Cys   Leu   Pro   Asp   Pro   Tyr
                      275                           280                           285

Gly   Cys   Ser   Cys   Gly   Cys   Gly   Trp   Arg   Gly   Ser   Gln   Cys   Gln   Glu   Ala
          290                           295                           300

Cys   Ala   Pro   Gly   His   Phe   Gly   Ala   Asp   Cys   Arg   Leu   Gln   Cys   Gln   Cys
    305                           310                           315                           320

Gln   Asn   Gly   Gly   Tyr   Cys   Asp   Arg   Phe   Ser   Gly   Cys   Val   Cys   Pro   Ser
                            325                           330                           335

Gly   Trp   His   Gly   Val   His   Cys   Glu   Lys   Ser   Asp   Arg   Ile   Pro   Gln   Ile
                      340                           345                           350

Leu   Asn   Val   Ala   Thr   Glu   Leu   Glu   Phe   Gln   Leu   Arg   Thr   Met   Pro   Arg
                      355                           360                           365

Ile   Asn   Cys   Ala   Ala   Ala   Gly   Asn   Pro   Phe   Pro   Val   Arg   Gly   Ser   Met
                      370                           375                           380

Glu   Leu   Arg   Lys   Pro   Asp   Gly   Thr   Met   Leu   Leu   Ser   Thr   Lys   Ala   Ile
    385                           390                           395                           400

Val   Glu   Pro   Asp   Arg   Thr   Thr   Ala   Glu   Phe   Glu   Val   Pro   Arg   Leu   Thr
                            405                           410                           415

Leu   Gly   Asp   Ser   Gly   Phe   Trp   Glu   Cys   Arg   Val   Ser   Thr   Ser   Gly   Gly
                      420                           425                           430

Gln   Asp   Ser   Arg   Arg   Phe   Lys   Val   Asn   Val   Lys   Val   Pro   Pro   Val   Pro
                      435                           440                           445

Leu   Thr   Ala   Pro   Arg   Leu   Leu   Ala   Lys   Gln   Ser   Arg   Gln   Leu   Val   Val
                      450                           455                           460

Ser   Pro   Leu   Val   Ser   Phe   Gly   Gly   Asp   Gly   Pro   Ile   Ser   Ser   Val   Arg
    465                           470                           475                           480

Leu   His   Tyr   Arg   Pro   Gln   Asp   Ser   Met   Ile   Thr   Trp   Ser   Ala   Ile   Val
                      485                           490                           495

Val   Asp   Pro   Ser   Glu   Asn   Val   Thr   Leu   Met   Asn   Leu   Lys   Pro   Arg   Thr
                      500                           505                           510

Gly   Tyr   Asn   Val   Arg   Val   Gln   Leu   Ser   Arg   Pro   Gly   Glu   Gly   Gly   Glu
                      515                           520                           525

Gly   Ala   Trp   Gly   Pro   Ser   Thr   Leu   Met   Thr   Thr   Asp   Cys   Pro   Glu   Pro
                      530                           535                           540

Leu   Leu   Gln   Pro   Trp   Val   Glu   Ser   Trp   Asn   Val   Glu   Gly   Pro   Asp   Arg
    545                           550                           555                           560

Leu   Arg   Val   Ser   Trp   Ser   Leu   Pro   Ser   Val   Pro   Leu   Ser   Gly   Asp   Gly
                            565                           570                           575

Phe   Leu   Leu   Arg   Leu   Trp   Asp   Gly   Ala   Arg   Gly   Gln   Glu   Arg   Arg   Glu
                      580                           585                           590

Asn   Ile   Ser   Ser   Pro   Gln   Ala   Arg   Thr   Ala   Leu   Leu   Thr   Gly   Leu   Thr
                      595                           600                           605

Pro   Gly   Thr   His   Tyr   Gln   Leu   Asp   Val   Arg   Leu   Tyr   His   Cys   Thr   Leu
    610                           615                           620
```

```
Leu  Gly  Pro  Ala  Ser  Pro  Ser  Ala  His  Val  His  Leu  Pro  Leu  Ser  Gly
625                 630                 635                 640

Pro  Pro  Ala  Pro  Arg  His  Leu  Arg  Ala  Gln  Ala  Leu  Ser  Asp  Ser  Glu
                    645                 650                 655

Ile  Arg  Leu  Met  Trp  Gln  His  Pro  Glu  Ala  Pro  Pro  Gly  Pro  Ile  Ser
               660                 665                 670

Lys  Tyr  Ile  Val  Glu  Ile  Gln  Val  Ala  Gly  Gly  Ser  Gly  Asp  Pro  Gln
          675                 680                 685

Trp  Met  Asp  Val  Asp  Lys  Pro  Glu  Glu  Thr  Ser  Thr  Thr  Val  Arg  Gly
690                 695                 700

Leu  Asn  Ala  Ser  Thr  Arg  Tyr  Leu  Phe  Arg  Val  Arg  Ala  Ser  Val  Gln
705                 710                 715                 720

Gly  Leu  Gly  Asp  Trp  Ser  Asn  Thr  Val  Glu  Glu  Thr  Thr  Leu  Gly  Asn
                    725                 730                 735

Gly  Leu  Gln  Ser  Ala  Ser  Pro  Val  Gln  Glu  Ser  Arg  Val  Ala  Glu  Asp
               740                 745                 750

Gly  Leu  Asp  Gln  Gln  Leu  Val  Leu  Ala  Val  Val  Gly  Ser  Val  Ser  Ala
          755                 760                 765

Thr  Cys  Leu  Thr  Ile  Leu  Ala  Ala  Leu  Leu  Ala  Leu  Val  Cys  Ile  Arg
770                 775                 780

Arg  Ser  Cys  Leu  His  Arg  Arg  His  Thr  Phe  Thr  Tyr  Gln  Ser  Gly  Ser
785                 790                 795                 800

Gly  Glu  Glu  Thr  Ile  Leu  Gln  Phe  Ser  Ser  Gly  Thr  Leu  Thr  Leu  Thr
                    805                 810                 815

Arg  Arg  Pro  Lys  Pro  Gln  Pro  Glu  Pro  Leu  Ser  Tyr  Pro  Val  Leu  Glu
               820                 825                 830

Trp  Glu  Asp  Ile  Thr  Phe  Glu  Asp  Leu  Ile  Gly  Glu  Gly  Asn  Phe  Gly
          835                 840                 845

Gln  Val  Ile  Arg  Ala  Met  Ile  Lys  Lys  Asp  Gly  Leu  Lys  Met  Asn  Ala
850                 855                 860

Ala  Ile  Lys  Met  Leu  Lys  Glu  Tyr  Ala  Ser  Glu  Asn  Asp  His  Arg  Asp
865                 870                 875                 880

Phe  Ala  Gly  Glu  Leu  Glu  Val  Leu  Cys  Lys  Leu  Gly  His  His  Pro  Asn
                    885                 890                 895

Ile  Ile  Asn  Leu  Leu  Gly  Ala  Cys  Glu  Asn  Arg  Gly  Tyr  Leu  Tyr  Ile
               900                 905                 910

Ala  Ile  Glu  Tyr  Ala  Pro  Tyr  Gly  Asn  Leu  Leu  Asp  Phe  Leu  Arg  Lys
          915                 920                 925

Ser  Arg  Val  Leu  Glu  Thr  Asp  Pro  Ala  Phe  Ala  Arg  Glu  His  Gly  Thr
930                 935                 940

Ala  Ser  Thr  Leu  Ser  Ser  Arg  Gln  Leu  Leu  Arg  Phe  Ala  Ser  Asp  Ala
945                 950                 955                 960

Ala  Asn  Gly  Met  Gln  Tyr  Leu  Ser  Glu  Lys  Gln  Phe  Ile  His  Arg  Asp
                    965                 970                 975

Leu  Ala  Ala  Arg  Asn  Val  Leu  Val  Gly  Glu  Asn  Leu  Ala  Ser  Lys  Ile
               980                 985                 990

Ala  Asp  Phe  Gly  Leu  Ser  Arg  Gly  Glu  Glu  Val  Tyr  Val  Lys  Lys  Thr
          995                 1000                1005

Met  Gly  Arg  Leu  Pro  Val  Arg  Trp  Met  Ala  Ile  Glu  Ser  Leu  Asn  Tyr
          1010                1015                1020

Ser  Val  Tyr  Thr  Thr  Lys  Ser  Asp  Val  Trp  Ser  Phe  Gly  Val  Leu  Leu
1025                1030                1035                1040

Trp  Glu  Ile  Val  Ser  Leu  Gly  Gly  Thr  Pro  Tyr  Cys  Gly  Met  Thr  Cys
                    1045                1050                1055
```

```
         Ala  Glu  Leu  Tyr  Glu  Lys  Leu  Pro  Gln  Gly  Tyr  Arg  Met  Glu  Gln  Pro
                        1060                1065                1070

Arg  Asn  Cys  Asp  Asp  Glu  Val  Tyr  Glu  Leu  Met  Arg  Gln  Cys  Trp  Arg
                   1075                     1080                1085

Asp  Arg  Pro  Tyr  Glu  Arg  Pro  Pro  Phe  Ala  Gln  Ile  Ala  Leu  Gln  Leu
              1090                     1095                     1100

Gly  Arg  Met  Leu  Glu  Ala  Arg  Lys  Ala  Tyr  Val  Asn  Met  Ser  Leu  Phe
         1105                     1110                1115                          1120

Glu  Asn  Phe  Thr  Tyr  Ala  Gly  Ile  Asp  Ala  Thr  Ala  Glu  Glu  Ala
                             1125                    1130                     1135
```

( 2 ) INFORMATION FOR SEQ ID NO:98:

( i ) SEQUENCE CHARACTERISTICS:
        ( A ) LENGTH: 1138 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:98:

```
         Met  Val  Trp  Arg  Val  Pro  Pro  Phe  Leu  Leu  Pro  Ile  Leu  Phe  Leu  Ala
         1                   5                        10                       15

Ser  His  Val  Gly  Ala  Ala  Val  Asp  Leu  Thr  Leu  Leu  Ala  Asn  Leu  Arg
                        20                      25                      30

Leu  Thr  Asp  Pro  Gln  Arg  Phe  Phe  Leu  Thr  Cys  Val  Ser  Gly  Glu  Ala
                   35                      40                      45

Gly  Ala  Gly  Arg  Gly  Ser  Asp  Ala  Trp  Gly  Pro  Leu  Leu  Leu  Glu
              50                      55                      60

Lys  Asp  Asp  Arg  Ile  Val  Arg  Thr  Pro  Pro  Gly  Pro  Pro  Leu  Arg  Leu
         65                       70                      75                       80

Ala  Arg  Asn  Gly  Ser  His  Gln  Val  Thr  Leu  Arg  Gly  Phe  Ser  Lys  Pro
                             85                      90                      95

Ser  Asp  Leu  Val  Gly  Val  Phe  Ser  Cys  Val  Gly  Gly  Ala  Gly  Ala  Arg
                        100                     105                     110

Arg  Thr  Arg  Val  Ile  Tyr  Val  His  Asn  Ser  Pro  Gly  Ala  His  Leu  Leu
                        115                     120                     125

Pro  Asp  Lys  Val  Thr  His  Thr  Val  Asn  Lys  Gly  Asp  Thr  Ala  Val  Leu
              130                     135                     140

Ser  Ala  Arg  Val  His  Lys  Glu  Lys  Gln  Thr  Asp  Val  Ile  Trp  Lys  Ser
         145                     150                     155                          160

Asn  Gly  Ser  Tyr  Phe  Tyr  Thr  Leu  Asp  Trp  His  Glu  Ala  Gln  Asp  Gly
                             165                     170                     175

Arg  Phe  Leu  Leu  Gln  Leu  Pro  Asn  Val  Gln  Pro  Pro  Ser  Ser  Gly  Ile
                        180                     185                     190

Tyr  Ser  Ala  Thr  Tyr  Leu  Glu  Ala  Ser  Pro  Leu  Gly  Ser  Ala  Phe  Phe
                   195                     200                     205

Arg  Leu  Ile  Val  Arg  Gly  Cys  Gly  Ala  Gly  Arg  Trp  Gly  Pro  Gly  Cys
              210                     215                     220

Thr  Lys  Glu  Cys  Pro  Gly  Cys  Leu  His  Gly  Gly  Val  Cys  His  Asp  His
         225                     230                     235                          240

Asp  Gly  Glu  Cys  Val  Cys  Pro  Pro  Gly  Phe  Thr  Gly  Thr  Arg  Cys  Glu
                        245                     250                     255

Gln  Ala  Cys  Arg  Glu  Gly  Arg  Phe  Gly  Gln  Ser  Cys  Gln  Glu  Gln  Cys
                        260                     265                     270
```

```
Pro Gly Ile Ser Gly Cys Arg Gly Leu Thr Phe Cys Leu Pro Asp Pro
        275                 280                 285

Tyr Gly Cys Ser Cys Gly Ser Gly Trp Arg Gly Ser Gln Cys Gln Glu
        290                 295                 300

Ala Cys Ala Pro Gly His Phe Gly Ala Asp Cys Arg Leu Gln Cys Gln
305                     310                 315                 320

Cys Gln Asn Gly Gly Thr Cys Asp Arg Phe Ser Gly Cys Val Cys Pro
                325                 330                 335

Ser Gly Trp His Gly Val His Cys Glu Lys Ser Asp Arg Ile Pro Gln
            340             345                 350

Ile Leu Asn Met Ala Ser Glu Leu Glu Phe Asn Leu Glu Thr Met Pro
            355             360             365

Arg Ile Asn Cys Ala Ala Ala Gly Asn Pro Phe Pro Val Arg Gly Ser
        370                 375             380

Ile Glu Leu Arg Lys Pro Asp Gly Thr Val Leu Leu Ser Thr Lys Ala
385                 390                 395                 400

Ile Val Glu Pro Glu Lys Thr Thr Ala Glu Phe Glu Val Pro Arg Leu
                405                 410                 415

Val Leu Ala Asp Ser Gly Phe Trp Glu Cys Arg Val Ser Thr Ser Gly
            420                 425                 430

Gly Gln Asp Ser Arg Arg Phe Lys Val Asn Val Lys Val Pro Pro Val
        435                 440                 445

Pro Leu Ala Ala Pro Arg Leu Leu Thr Lys Gln Ser Arg Gln Leu Val
    450                 455                 460

Val Ser Pro Leu Val Ser Phe Ser Gly Asp Gly Pro Ile Ser Thr Val
465                 470                 475                 480

Arg Leu His Tyr Arg Pro Gln Asp Ser Thr Met Asp Trp Ser Thr Ile
                485                 490                 495

Val Val Asp Pro Ser Glu Asn Val Thr Leu Met Asn Leu Arg Pro Lys
            500                 505                 510

Thr Gly Tyr Ser Val Arg Val Gln Leu Ser Arg Pro Gly Glu Gly Gly
            515                 520             525

Glu Gly Ala Trp Gly Pro Pro Thr Leu Met Thr Thr Asp Cys Pro Glu
    530                 535                 540

Pro Leu Leu Gln Pro Trp Leu Glu Gly Trp His Val Glu Gly Thr Asp
545                 550                 555                 560

Arg Leu Arg Val Ser Trp Ser Leu Pro Leu Val Pro Gly Pro Leu Val
                565             570             575

Gly Asp Gly Phe Leu Leu Arg Leu Trp Asp Gly Thr Arg Gly Gln Glu
            580                 585                 590

Arg Arg Glu Asn Val Ser Ser Pro Gln Ala Arg Thr Ala Leu Leu Thr
        595                 600                 605

Gly Leu Thr Pro Gly Thr His Tyr Gln Leu Asp Val Gln Leu Tyr His
    610                 615                 620

Cys Thr Leu Leu Gly Pro Ala Ser Pro Ala His Val Leu Leu Pro
625                 630                 635                 640

Pro Ser Gly Pro Pro Ala Pro Arg His Leu His Ala Gln Ala Leu Ser
                645                 650                 655

Asp Ser Glu Ile Gln Leu Thr Trp Lys His Pro Glu Ala Leu Pro Gly
            660                 665                 670

Pro Ile Ser Lys Tyr Val Val Glu Val Gln Val Ala Gly Gly Ala Gly
            675                 680                 685

Asp Pro Leu Trp Ile Asp Val Asp Arg Pro Glu Glu Thr Ser Thr Ile
            690                 695             700
```

-continued

```
Ile Arg Gly Leu Asn Ala Ser Thr Arg Tyr Leu Phe Arg Met Arg Ala
705                 710                 715                 720

Ser Ile Gln Gly Leu Gly Asp Trp Ser Asn Thr Val Glu Glu Ser Thr
                725                 730                 735

Leu Gly Asn Gly Leu Gln Ala Glu Gly Pro Val Gln Glu Ser Arg Ala
                740                 745                 750

Ala Glu Glu Gly Leu Asp Gln Gln Leu Ile Leu Ala Val Val Gly Ser
            755                 760                 765

Val Ser Ala Thr Cys Leu Thr Ile Leu Ala Ala Leu Leu Thr Leu Val
            770                 775                 780

Cys Ile Arg Arg Ser Cys Leu His Arg Arg Arg Thr Phe Thr Tyr Gln
785                 790                 795                 800

Ser Gly Ser Gly Glu Glu Thr Ile Leu Gln Phe Ser Ser Gly Thr Leu
                805                 810                 815

Thr Leu Thr Arg Arg Pro Lys Leu Gln Pro Glu Pro Leu Ser Tyr Pro
                820                 825                 830

Val Leu Glu Trp Glu Asp Ile Thr Phe Glu Asp Leu Ile Gly Glu Gly
            835                 840                 845

Asn Phe Gly Gln Val Ile Arg Ala Met Ile Lys Lys Asp Gly Leu Lys
850                 855                 860

Met Asn Ala Ala Ile Lys Met Leu Lys Glu Tyr Ala Ser Glu Asn Asp
865                 870                 875                 880

His Arg Asp Phe Ala Gly Glu Leu Glu Val Leu Cys Lys Leu Gly His
                885                 890                 895

His Pro Asn Ile Ile Asn Leu Leu Gly Ala Cys Lys Asn Arg Gly Tyr
                900                 905                 910

Leu Tyr Ile Ala Ile Glu Tyr Ala Pro Tyr Gly Asn Leu Leu Asp Phe
            915                 920                 925

Leu Arg Lys Ser Arg Val Leu Glu Thr Asp Pro Ala Phe Ala Arg Glu
            930                 935                 940

His Gly Thr Ala Ser Thr Leu Ser Ser Arg Gln Leu Leu Arg Phe Ala
945                 950                 955                 960

Ser Asp Ala Ala Asn Gly Met Gln Tyr Leu Ser Glu Lys Gln Phe Ile
                965                 970                 975

His Arg Asp Leu Ala Ala Arg Asn Val Leu Val Gly Glu Asn Leu Ala
            980                 985                 990

Ser Lys Ile Ala Asp Phe Gly Leu Ser Arg Gly Glu Glu Val Tyr Val
            995                 1000                1005

Lys Lys Thr Met Gly Arg Leu Pro Val Arg Trp Met Ala Ile Glu Ser
1010                1015                1020

Leu Asn Tyr Ser Val Tyr Thr Thr Lys Ser Asp Val Trp Ser Phe Gly
1025                1030                1035                1040

Val Leu Leu Trp Glu Ile Val Ser Leu Gly Gly Thr Pro Tyr Cys Gly
                1045                1050                1055

Met Thr Cys Ala Glu Leu Tyr Glu Lys Leu Pro Gln Ala Asp Arg Met
                1060                1065                1070

Glu Gln Pro Arg Asn Cys Asp Asp Glu Val Tyr Glu Leu Met Arg Gln
            1075                1080                1085

Cys Trp Arg Asp Arg Pro Tyr Glu Arg Pro Pro Phe Ala Gln Ile Ala
            1090                1095                1100

Leu Gln Leu Gly Arg Met Leu Glu Ala Arg Lys Ala Tyr Val Asn Met
1105                1110                1115                1120

Ser Leu Phe Glu Asn Phe Thr Tyr Ala Gly Ile Asp Ala Thr Ala Glu
```

(2) INFORMATION FOR SEQ ID NO:99:

(i) SEQUENCE CHARACTERISTICS:
        (A) LENGTH: 301 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:99:

```
Ile Lys Phe Gln Asp Val Ile Gly Glu Gly Asn Phe Gly Gln Val Leu
 1               5                  10                  15
Lys Ala Arg Ile Lys Lys Asp Gly Leu Arg Met Asp Ala Ala Ile Lys
                20                  25                  30
Arg Met Lys Glu Tyr Ala Ser Lys Asp Asp His Arg Asp Phe Ala Gly
            35                  40                  45
Glu Leu Glu Val Leu Cys Lys Leu Gly His His Pro Asn Ile Ile Asn
        50                  55                  60
Leu Leu Gly Ala Cys Glu His Arg Gly Tyr Leu Tyr Leu Ala Ile Glu
65                  70                  75                  80
Tyr Ala Pro His Gly Asn Leu Leu Asp Phe Leu Arg Lys Ser Arg Val
                85                  90                  95
Leu Glu Thr Asp Pro Ala Phe Ala Ile Ala Asn Ser Thr Ala Ser Thr
               100                 105                 110
Leu Ser Ser Gln Gln Leu Leu His Phe Ala Ala Asp Val Ala Arg Gly
           115                 120                 125
Met Asp Tyr Leu Ser Gln Lys Gln Phe Ile His Arg Asp Leu Ala Ala
       130                 135                 140
Arg Asn Ile Leu Val Gly Glu Asn Tyr Ile Ala Lys Ile Ala Asp Phe
145                 150                 155                 160
Gly Leu Ser Arg Gly Gln Glu Val Tyr Val Lys Lys Thr Met Gly Arg
               165                 170                 175
Leu Pro Val Arg Trp Met Ala Ile Glu Ser Leu Asn Tyr Ser Val Tyr
           180                 185                 190
Thr Thr Asn Ser Asp Val Trp Ser Tyr Gly Val Leu Leu Trp Glu Ile
       195                 200                 205
Val Ser Leu Gly Gly Thr Pro Tyr Cys Gly Met Thr Cys Ala Glu Leu
210                 215                 220
Tyr Glu Lys Leu Pro Gln Gly Tyr Arg Leu Glu Lys Pro Leu Asn Cys
225                 230                 235                 240
Asp Asp Glu Val Tyr Asp Leu Met Arg Gln Cys Trp Arg Glu Lys Pro
                245                 250                 255
Tyr Glu Arg Pro Ser Phe Ala Gln Ile Leu Val Ser Leu Asn Arg Met
            260                 265                 270
Leu Glu Glu Arg Lys Thr Tyr Val Asn Thr Thr Leu Tyr Glu Lys Phe
        275                 280                 285
Thr Tyr Ala Gly Ile Asp Cys Ser Ala Glu Glu Ala Ala
    290                 295                 300
```

(2) INFORMATION FOR SEQ ID NO:100:

(i) SEQUENCE CHARACTERISTICS:
        (A) LENGTH: 3592 base pairs
        (B) TYPE: nucleic acid (C) STRANDEDNESS: unknown
(D) TOPOLOGY: unknown (i i) MOLECULE TYPE: DNA (i x) FEATURE:
    (A) NAME/KEY: CDS
    (B) LOCATION: 598..3444

(i x) FEATURE:
    (A) NAME/KEY: modified_base
    (B) LOCATION: 56
    (D) OTHER INFORMATION: /mod_base=OTHER
        / label= N
        / note= "Where N = G, A, C or T"

(i x) FEATURE:
    (A) NAME/KEY: modified_base
    (B) LOCATION: 3538
    (D) OTHER INFORMATION: /mod_base=OTHER
        / label= N
        / note= "Where N = G, A, C or T"

(x i) SEQUENCE DESCRIPTION: SEQ ID NO:100:

```
GACCTCGTTC TGGGGTTTCT GAGACACAAG ACACAGGAAA GTTCTGGATG CCCAGNCTAC      60
CCTTGCAATC TGCTGTGCCT CCTCTGATCT GGGCTCTGCA AGTGCCCACT TGGGTCCAAA     120
GAGGAACTTG GGTCCCAAGA ACTGCACCTT CACTACCCGC CGGGATGTCC CTACCCACCC     180
CCAGGAACCT CCTAGAGGCA CCCTCCCCCG TCCACAATCC CCTCCCCCAA ACTACAGCCT     240
GAGCTCGCTC TTGCGCGCGC GCTCTCCTGG GCCCAAGTGA ATAGTCCTAG CTCGAGCGGG     300
ACACGGTGGT GGATACAATT CCCCTCGCCT CCAGCCGCCA GGAGCTCTCC GGCGGCGCAG     360
GCAGCATCGT CCCCTCAAGC AGCCGCTCCT GCACCTGGGC AGCCTGGACC CTCGTGCCCT     420
GCTCACGGGG CCTCGCGCGG GGGGCGCCCC GGGACTTCCC CTGCGGACCG GGTGGAGGAG     480
GAAGAGGAGG AGGAGGAAGA AGAGGGCTTG GTTCAGGACC CCCACCCCAC TAGGAACACC     540
TGGCTTCGCT GCTGCGGCCA CTTCTTTTTA AGGAGGAGAA GAGAACCAGC GAGAGCCATG     600
GGGGGCTGCG AAGTCCGGGA ATTTCTTTTG CAATTTGGTT TCTTCTTGCC CCTGCTGACA     660
GCTTGGACCG GCGACTGCAG TCACGTCTCC AACCAAGTTG TGTTGCTTGA TACATCTACA     720
GTGATGGGAG AACTAGGATG GAAAACATAT CCACTGAATG GGTGGGATGC CATTACTGAA     780
ATGGATGAAC ACAACAGGCC CATACATACA TACCAGGTAT GCAATGTCAT GGAACCAAAC     840
CAGAACAACT GGCTTCGTAC TAACTGGATC TCTCGTGATG CTGCTCAGAA AATCTATGTG     900
GAAATGAAGT TCACATTGAG AGATTGTAAC AGCATCCCAT GGGTCTTGGG AACGTGTAAA     960
GAAACATTTA CTCTGTATTA TATTGAATCT GACGAATCCC ACGGAACTAA ATTCAAGCCA    1020
AGCCAATATA TAAAGATTGA CACAATTGCT GCGGATGAGA GTTTTACTCA GATGGATTTG    1080
GGTGATCGCA TCCTTAAACT CAACACTGAA GTTCGTGAGG TGGGGCCAAT AGAAAGGAAA    1140
GGATTCTATT TGGCTTTTCA AGATATTGGA GCATGCATTG CTCTGGTCTC AGTCCGTGTG    1200
TTCTACAAAA AATGCCCCTT CACTGTGCGG AACTTGGCTA TGTTTCCGGA TACCATCCCA    1260
AGGGTTGACT CTTCCTCTTT GGTTGAAGTG CGGGGCTCAT GCGTGAAGAG TTCTGAGGAG    1320
CGAGATACTC CTAAACTCTA CTGTGGAGCT GATGGAGACT GGCTCGTCCC TCTTGGAAGG    1380
TGTATCTGCA CTACAGGGTA TGAAGAAATC GAGGGTTCTT GCCATGCTTG CCGGCCAGGA    1440
TTCTATAAAG CATTTGCTGG GAACACAAAA TGTTCCAAAT GCCCTCCCCA CAGCTCAACC    1500
TTCGTGGAAG CAACTTCGGT CTGCCATTGT GAAAAGGGTT ACTTCCGGGC AGAAAAAGAC    1560
CCACCTTCTA TGGCGTGTAC TAGACCACCT TCAGCTCCTA GAAATGTGGC TTTTAACATT    1620
AATGAAACAG CCCTTATTTT GGAATGGAGC CCACCCAGTG ACACAGGAGG GAGAAAAGAT    1680
```

-continued

```
CTCACATATA GTGTAATCTG TAAGAAATGT GGCGTAGACG CTAGCCAGTG TGAAGACTGC    1740
GGTGCAGGAC TTCGATTCAT CCCAAGACCC ACCGGACTTA TCAACAATTC CGTGGTAGTA    1800
CTTGACTTTG TGTCTCACGT CAATTATACC TTTGAAATAG AAGCCATGAA TGGAGTTTCT    1860
GAGTTGAGCA TTTCTCCCAA GCCATTCACA GCTATTACAG TGACCACAGA TCAAGATGCA    1920
CCTTCTCTGA TAGGTATGAT GAGGAAGGAC TGGGCATCCC AGAACAGCCT TGCCCTATCA    1980
TGGCAAGCAC CTGCATTTTC CAATGGAGCC ATTCTGGACT ATGAGATCAA GTACTATGAG    2040
AAAGAGCATG AACAGCTCAC CTATTCCTCC ACGAGGTCCA AGGCCCAAG  TGTCATCATC    2100
ACAGGCCTCA AGCCAGCCAC CACGTACATA TTTCATATCC GAGTGAGGAC TGCGACAGGA    2160
TACAGTGGCT ACAGTCAGAA GTTTGAATTT GAAACAGGAG ACGAAACTTC TGACATGGCA    2220
GCGGAACAAG GGCAGATCCT GGTCATAGCC ACGGCAGCCG TCGGGGATT  CACTCTCCTA    2280
GTTATCCTCA CTTTGTTCTT CCTCATCACT GGGAGGTGTC AATGGTACAT CAAGGCCAAA    2340
ATGAAGTCAG AAGAGAAGAG AAGAACACAC TTACAGAACA GCCACCTGCG CTTCCCAGGA    2400
ATCAAAACCT ACATTGATCC AGATACTTAT GAAGACCCAT CTCTAGCTGT CCACGAATTT    2460
GAAAAGAGA  TTGACCCTTC AAGAATTCGC ATTGAGAGAG TGATTGGAGC AGGTGAATTT    2520
GGAGAAGTCT GCAGTGGGCG TTTAAAGACA CCAGGGAAAA GGGAAATCCC AGTTGCCATT    2580
AAAACCTTGA AAGGTGGCCA TATGGACCGA CAAAGAAGAG ATTTTCTAAG AGAAGCTAGC    2640
ATCATGGGTC AGTTTGACCA CCCAAACATC ATTCGCCTAG AAGGTGTTGT TACTAAAAGA    2700
TCCTTCCCAG CGATTGGGGT GGAAGCCTTC TGCCCCAGCT TCCTAAGGGC TGGGTTTTTA    2760
AATGGCATCC AAGCACCACA TCCAGTGACT GCAGGAGGCT CTCTCCCCCC CAGGATCCCT    2820
GCAGGCCGGC CAGTAATGAT CGTGGTAGAG TATATGGAGA ATGGATCTCT AGACTCCTTT    2880
TTGCGGAAGC ACGATGGCCA CTTCACCGTC ATCCAGTTGG TCGGCATGCT TCGGGGCATT    2940
GCATCAGGCA TGAAGTATCT TTCCGACATG GGATACGTTC ATCGAGACCT AGCAGCTAGG    3000
AACATCTTGG TGAACAGCAA CTTGGTATGC AAAGTCTCTG ATTTCGGCCT CTCCCGAGTG    3060
CTGGAAGACG ACCCAGAAGC AGCTTATACA ACAACTGGTG GAAAAATACC TATAAGGTGG    3120
ACAGCCCCAG AAGCTATCGC CTACAGGAAA TTCTCCTCAG CGAGTGATGT CTGGAGCTAC    3180
GGGATTGTCA TGTGGGAGGT GATGTCCTAT GGAGAGAGAC CATACTGGGA AATGTCCAAC    3240
CAGGATGTTA TTTTATCCAT TGAAGAAGGT TACCGACTTC CTGCTCCAAT GGGCTGCCCA    3300
CCGTCGCTGC ACCAGCTGAT GCTCCACTGC TGGCAGAAGG AGAGAAACCA CAGGCCAAAA    3360
TTCACTGACA TCGTCAGCTT CCTGGACAAA CTGATTCGCA ACCCCAGCGC CCTTCACACG    3420
CTGGTGGAGG ACATCCTCGT GTAAGATGCA TAATGTTGGT ACTTTCTCCC CGACAGTCAC    3480
AATCGTTCAG GCTGCAGGCA AGAGGAACAG ATAGGGGGAA CGAGCTTGCC TTAGTAGNTG    3540
TCCAATTATC AACCCTCTAT AACTCTTATC GGGTTCATTA GCTCATCAGA TT            3592
```

( 2 ) INFORMATION FOR SEQ ID NO:101:

( i ) SEQUENCE CHARACTERISTICS:
        ( A ) LENGTH: 948 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:101:

```
Met Gly Gly Cys Glu Val Arg Glu Phe Leu Leu Gln Phe Gly Phe Phe
1               5                   10                  15
```

| | | | | | | | | | | | | | | |
|---|---|---|---|---|---|---|---|---|---|---|---|---|---|---|
| Leu | Pro | Leu | Leu<br>20 | Thr | Ala | Trp | Thr | Gly<br>25 | Asp | Cys | Ser | His | Val<br>30 | Ser | Asn |
| Gln | Val | Val<br>35 | Leu | Leu | Asp | Thr | Ser<br>40 | Thr | Val | Met | Gly | Glu<br>45 | Leu | Gly | Trp |
| Lys | Thr<br>50 | Tyr | Pro | Leu | Asn | Gly<br>55 | Trp | Asp | Ala | Ile | Thr<br>60 | Glu | Met | Asp | Glu |
| His<br>65 | Asn | Arg | Pro | Ile | His<br>70 | Thr | Tyr | Gln | Val | Cys<br>75 | Asn | Val | Met | Glu | Pro<br>80 |
| Asn | Gln | Asn | Asn | Trp<br>85 | Leu | Arg | Thr | Asn | Trp<br>90 | Ile | Ser | Arg | Asp | Ala<br>95 | Ala |
| Gln | Lys | Ile | Tyr<br>100 | Val | Glu | Met | Lys | Phe<br>105 | Thr | Leu | Arg | Asp | Cys<br>110 | Asn | Ser |
| Ile | Pro | Trp<br>115 | Val | Leu | Gly | Thr | Cys<br>120 | Lys | Glu | Thr | Phe | Thr<br>125 | Leu | Tyr | Tyr |
| Ile | Glu<br>130 | Ser | Asp | Glu | Ser | His<br>135 | Gly | Thr | Lys | Phe | Lys<br>140 | Pro | Ser | Gln | Tyr |
| Ile<br>145 | Lys | Ile | Asp | Thr | Ile<br>150 | Ala | Ala | Asp | Glu | Ser<br>155 | Phe | Thr | Gln | Met | Asp<br>160 |
| Leu | Gly | Asp | Arg | Ile<br>165 | Leu | Lys | Leu | Asn | Thr<br>170 | Glu | Val | Arg | Glu | Val<br>175 | Gly |
| Pro | Ile | Glu | Arg<br>180 | Lys | Gly | Phe | Tyr | Leu<br>185 | Ala | Phe | Gln | Asp | Ile<br>190 | Gly | Ala |
| Cys | Ile | Ala<br>195 | Leu | Val | Ser | Val | Arg<br>200 | Val | Phe | Tyr | Lys | Lys<br>205 | Cys | Pro | Phe |
| Thr | Val<br>210 | Arg | Asn | Leu | Ala | Met<br>215 | Phe | Pro | Asp | Thr | Ile<br>220 | Pro | Arg | Val | Asp |
| Ser<br>225 | Ser | Ser | Leu | Val | Glu<br>230 | Val | Arg | Gly | Ser | Cys<br>235 | Val | Lys | Ser | Ser | Glu<br>240 |
| Glu | Arg | Asp | Thr | Pro<br>245 | Lys | Leu | Tyr | Cys | Gly<br>250 | Ala | Asp | Gly | Asp | Trp<br>255 | Leu |
| Val | Pro | Leu | Gly<br>260 | Arg | Cys | Ile | Cys | Thr<br>265 | Thr | Gly | Tyr | Glu | Glu<br>270 | Ile | Glu |
| Gly | Ser | Cys<br>275 | His | Ala | Cys | Arg | Pro<br>280 | Gly | Phe | Tyr | Lys | Ala<br>285 | Phe | Ala | Gly |
| Asn | Thr<br>290 | Lys | Cys | Ser | Lys | Cys<br>295 | Pro | Pro | His | Ser | Ser<br>300 | Thr | Phe | Val | Glu |
| Ala<br>305 | Thr | Ser | Val | Cys | His<br>310 | Cys | Glu | Lys | Gly | Tyr<br>315 | Phe | Arg | Ala | Glu | Lys<br>320 |
| Asp | Pro | Pro | Ser | Met<br>325 | Ala | Cys | Thr | Arg | Pro<br>330 | Pro | Ser | Ala | Pro | Arg<br>335 | Asn |
| Val | Ala | Phe | Asn<br>340 | Ile | Asn | Glu | Thr | Ala<br>345 | Leu | Ile | Leu | Glu | Trp<br>350 | Ser | Pro |
| Pro | Ser | Asp<br>355 | Thr | Gly | Gly | Arg | Lys<br>360 | Asp | Leu | Thr | Tyr | Ser<br>365 | Val | Ile | Cys |
| Lys | Lys<br>370 | Cys | Gly | Val | Asp | Ala<br>375 | Ser | Gln | Cys | Glu | Asp<br>380 | Cys | Gly | Ala | Gly |
| Leu<br>385 | Arg | Phe | Ile | Pro | Arg<br>390 | Pro | Thr | Gly | Leu | Ile<br>395 | Asn | Asn | Ser | Val | Val<br>400 |
| Val | Leu | Asp | Phe | Val<br>405 | Ser | His | Val | Asn | Tyr<br>410 | Thr | Phe | Glu | Ile | Glu<br>415 | Ala |
| Met | Asn | Gly | Val<br>420 | Ser | Glu | Leu | Ser | Ile<br>425 | Ser | Pro | Lys | Pro | Phe<br>430 | Thr | Ala |
| Ile | Thr | Val | Thr | Thr | Asp | Gln | Asp | Ala | Pro | Ser | Leu | Ile | Gly | Met | Met |

|     |     |     |     |     | 435 |     |     |     |     | 440 |     |     |     |     | 445 |     |     |     |
| --- | --- | --- | --- | --- | --- | --- | --- | --- | --- | --- | --- | --- | --- | --- | --- | --- | --- | --- |
| Arg | Lys 450 | Asp | Trp | Ala | Ser | Gln 455 | Asn | Ser | Leu | Ala | Leu 460 | Ser | Trp | Gln | Ala |
| Pro 465 | Ala | Phe | Ser | Asn | Gly 470 | Ala | Ile | Leu | Asp | Tyr 475 | Glu | Ile | Lys | Tyr | Tyr 480 |
| Glu | Lys | Glu | His | Gln 485 | Leu | Thr | Tyr | Ser | Ser 490 | Thr | Arg | Ser | Lys 495 | Ala |
| Pro | Ser | Val | Ile 500 | Ile | Thr | Gly | Leu | Lys 505 | Pro | Ala | Thr | Thr | Tyr 510 | Ile | Phe |
| His | Ile | Arg 515 | Val | Arg | Thr | Ala | Thr 520 | Gly | Tyr | Ser | Gly | Tyr 525 | Ser | Gln | Lys |
| Phe | Glu 530 | Phe | Glu | Thr | Gly | Asp 535 | Glu | Thr | Ser | Asp | Met 540 | Ala | Ala | Glu | Gln |
| Gly 545 | Gln | Ile | Leu | Val | Ile 550 | Ala | Thr | Ala | Ala | Val 555 | Gly | Gly | Phe | Thr | Leu 560 |
| Leu | Val | Ile | Leu | Thr 565 | Leu | Phe | Phe | Leu | Ile 570 | Thr | Gly | Arg | Cys | Gln 575 | Trp |
| Tyr | Ile | Lys | Ala 580 | Lys | Met | Lys | Ser | Glu 585 | Glu | Lys | Arg | Arg | Thr 590 | His | Leu |
| Gln | Asn | Ser 595 | His | Leu | Arg | Phe | Pro 600 | Gly | Ile | Lys | Thr | Tyr 605 | Ile | Asp | Pro |
| Asp | Thr 610 | Tyr | Glu | Asp | Pro | Ser 615 | Leu | Ala | Val | His | Glu 620 | Phe | Glu | Lys | Glu |
| Ile 625 | Asp | Pro | Ser | Arg | Ile 630 | Arg | Ile | Glu | Arg | Val 635 | Ile | Gly | Ala | Gly | Glu 640 |
| Phe | Gly | Glu | Val | Cys 645 | Ser | Gly | Arg | Leu | Lys 650 | Thr | Pro | Gly | Lys | Arg 655 | Glu |
| Ile | Pro | Val | Ala 660 | Ile | Lys | Thr | Leu | Lys 665 | Gly | Gly | His | Met | Asp 670 | Arg | Gln |
| Arg | Arg | Asp 675 | Phe | Leu | Arg | Glu | Ala 680 | Ser | Ile | Met | Gly | Gln 685 | Phe | Asp | His |
| Pro | Asn 690 | Ile | Ile | Arg | Leu | Glu 695 | Gly | Val | Val | Thr | Lys 700 | Arg | Ser | Phe | Pro |
| Ala 705 | Ile | Gly | Val | Glu | Ala 710 | Phe | Cys | Pro | Ser | Phe 715 | Leu | Arg | Ala | Gly | Phe 720 |
| Leu | Asn | Gly | Ile | Gln 725 | Ala | Pro | His | Pro | Val 730 | Thr | Ala | Gly | Gly | Ser 735 | Leu |
| Pro | Pro | Arg | Ile 740 | Pro | Ala | Gly | Arg | Pro 745 | Val | Met | Ile | Val | Glu 750 | Tyr |
| Met | Glu | Asn 755 | Gly | Ser | Leu | Asp | Ser 760 | Phe | Leu | Arg | Lys | His 765 | Asp | Gly | His |
| Phe | Thr 770 | Val | Ile | Gln | Leu | Val 775 | Gly | Met | Leu | Arg | Gly 780 | Ile | Ala | Ser | Gly |
| Met 785 | Lys | Tyr | Leu | Ser | Asp 790 | Met | Gly | Tyr | Val | His 795 | Arg | Asp | Leu | Ala | Ala 800 |
| Arg | Asn | Ile | Leu | Val 805 | Asn | Ser | Asn | Leu | Val 810 | Cys | Lys | Val | Ser | Asp 815 | Phe |
| Gly | Leu | Ser | Arg 820 | Val | Leu | Glu | Asp | Asp 825 | Pro | Glu | Ala | Ala | Tyr 830 | Thr | Thr |
| Thr | Gly | Gly 835 | Lys | Ile | Pro | Ile | Arg 840 | Trp | Thr | Ala | Pro | Glu 845 | Ala | Ile | Ala |
| Tyr | Arg 850 | Lys | Phe | Ser | Ser | Ala 855 | Ser | Asp | Val | Trp | Ser 860 | Tyr | Gly | Ile | Val |

|  |  |  |  |  |  |  |  |  |  |  |  |  |  |  |  |
|---|---|---|---|---|---|---|---|---|---|---|---|---|---|---|---|
| Met | Trp | Glu | Val | Met | Ser | Tyr | Gly | Glu | Arg | Pro | Tyr | Trp | Glu | Met | Ser |
| 865 |  |  |  | 870 |  |  |  |  | 875 |  |  |  |  | 880 |  |
| Asn | Gln | Asp | Val | Ile | Leu | Ser | Ile | Glu | Glu | Gly | Tyr | Arg | Leu | Pro | Ala |
|  |  |  |  | 885 |  |  |  |  | 890 |  |  |  |  | 895 |  |
| Pro | Met | Gly | Cys | Pro | Pro | Ser | Leu | His | Gln | Leu | Met | Leu | His | Cys | Trp |
|  |  |  | 900 |  |  |  |  | 905 |  |  |  |  | 910 |  |  |
| Gln | Lys | Glu | Arg | Asn | His | Arg | Pro | Lys | Phe | Thr | Asp | Ile | Val | Ser | Phe |
|  |  | 915 |  |  |  |  | 920 |  |  |  |  | 925 |  |  |  |
| Leu | Asp | Lys | Leu | Ile | Arg | Asn | Pro | Ser | Ala | Leu | His | Thr | Leu | Val | Glu |
|  | 930 |  |  |  |  | 935 |  |  |  |  | 940 |  |  |  |  |
| Asp | Ile | Leu | Val |
| 945 |

( 2 ) INFORMATION FOR SEQ ID NO:102:

( i ) SEQUENCE CHARACTERISTICS:
        ( A ) LENGTH: 3906 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 476..3493

( x i ) SEQUENCE DESCRIPTION: SEQ ID NO:102:

```
CGGAAAACAT  CATCTAGATT  TAAGATGACT  CGTCTTCTTT  AATCTCGTCC  GTATCAGCAC        60

TGAAGACTGA  AAGGGAACCT  TCACCACCAC  TCCAACCCTG  GTGGCACTTA  AAAAAAAAAA       120

ATAACAGTTC  TAAAAAAGAA  AGGGGGACCA  AAAAACAGAA  AAAGGAAAGT  CTTAAGAGCC       180

AAAGGAGCGG  GACTCGGGAC  CCTCTGCAGA  CCCTTGACTC  AGCCCACCCA  GGACCGTACT       240

AGCCATCCGA  ACTTCTAATT  CATCTTATCC  AACTGAAAGG  GAGGGCGGCA  CAAGCCAGAA       300

GCAAACTTCG  GCGGTCTCTG  CGGATCTGTG  ATTCCCACAT  TGAGAGGGGT  CGAGAGCCAG       360

AAGGCACAGG  ACCCCACCAG  GAGGAGGAGT  TCCGCGCCTC  TCTCGCCCCT  TCCACCAAGC       420

CTGAACCTTA  GACTGAACCA  CGCGGGACCT  AAGAGGCAGA  AGAGGGTAGT  AGAAA ATG        478
                                                                 Met
                                                                   1
```

|  |  |  |  |  |  |  |  |  |  |  |  |  |  |  |  |
|---|---|---|---|---|---|---|---|---|---|---|---|---|---|---|---|
| CGG | GGC | TCC | GGG | CCC | CGC | GGT | GCG | GGA | CGC | CGA | CGG | ACC | CAG | GGC | AGA | 526 |
| Arg | Gly | Ser | Gly | Pro | Arg | Gly | Ala | Gly | Arg | Arg | Arg | Thr | Gln | Gly | Arg |
|  |  | 5 |  |  |  |  | 10 |  |  |  |  | 15 |  |  |  |
| GGT | GGC | GGC | GGC | GAC | ACC | CCC | CGC | GTC | CCT | GCC | TCT | CTG | GCA | GGC | TGC | 574 |
| Gly | Gly | Gly | Gly | Asp | Thr | Pro | Arg | Val | Pro | Ala | Ser | Leu | Ala | Gly | Cys |
|  |  | 20 |  |  |  |  | 25 |  |  |  |  | 30 |  |  |  |
| TAT | TCC | GCA | CCT | CTA | AAG | GGG | CCC | CTC | TGG | ACG | TGC | CTT | CTC | CTG | TGT | 622 |
| Tyr | Ser | Ala | Pro | Leu | Lys | Gly | Pro | Leu | Trp | Thr | Cys | Leu | Leu | Leu | Cys |
|  | 35 |  |  |  |  | 40 |  |  |  |  | 45 |  |  |  |  |
| GCG | GCG | CTC | CGG | ACC | CTT | TTG | GCC | AGC | CCC | AGT | AAC | GAA | GTG | AAT | TTA | 670 |
| Ala | Ala | Leu | Arg | Thr | Leu | Leu | Ala | Ser | Pro | Ser | Asn | Glu | Val | Asn | Leu |
| 50 |  |  |  |  | 55 |  |  |  |  | 60 |  |  |  |  | 65 |
| TTG | GAT | TCG | CGC | ACT | GTC | CTG | GGA | GAC | CTT | GGA | TGG | ATT | GCT | TTT | CCA | 718 |
| Leu | Asp | Ser | Arg | Thr | Val | Leu | Gly | Asp | Leu | Gly | Trp | Ile | Ala | Phe | Pro |
|  |  |  | 70 |  |  |  |  | 75 |  |  |  |  | 80 |  |  |
| AAG | AAT | GGG | TGG | GAA | GAG | ATT | GGT | GAA | GTT | GAT | GAA | AAC | TAT | GCC | CCC | 766 |
| Lys | Asn | Gly | Trp | Glu | Glu | Ile | Gly | Glu | Val | Asp | Glu | Asn | Tyr | Ala | Pro |
|  |  |  | 85 |  |  |  |  | 90 |  |  |  |  | 95 |  |  |
| ATC | CAC | ACC | TAT | CAA | GTG | TGC | AAA | GTT | ATG | GAA | CAG | AAT | CAG | AAT | AAT | 814 |
| Ile | His | Thr | Tyr | Gln | Val | Cys | Lys | Val | Met | Glu | Gln | Asn | Gln | Asn | Asn |
|  |  | 100 |  |  |  |  | 105 |  |  |  |  | 110 |  |  |  |

| | | | | | | | | | | | | | | | | |
|---|---|---|---|---|---|---|---|---|---|---|---|---|---|---|---|---|
| TGG | CTG | TTG | ACC | AGT | TGG | ATC | TCT | AAC | GAA | GGT | GCT | TCC | AGA | ATT | TTT | 862 |
| Trp | Leu | Leu | Thr | Ser | Trp | Ile | Ser | Asn | Glu | Gly | Ala | Ser | Arg | Ile | Phe | |
| | 115 | | | | | 120 | | | | | 125 | | | | | |
| ATT | GAA | CTC | AAG | TTT | ACT | CTG | AGG | GAT | TGC | AAC | AGC | CTT | CCT | GGA | GGA | 910 |
| Ile | Glu | Leu | Lys | Phe | Thr | Leu | Arg | Asp | Cys | Asn | Ser | Leu | Pro | Gly | Gly | |
| 130 | | | | | 135 | | | | 140 | | | | | | 145 | |
| CTG | GGG | ACT | TGC | AAG | GAG | ACC | TTT | AAC | ATG | TAT | TAT | TTT | GAG | TCG | GAT | 958 |
| Leu | Gly | Thr | Cys | Lys | Glu | Thr | Phe | Asn | Met | Tyr | Tyr | Phe | Glu | Ser | Asp | |
| | | | | 150 | | | | | 155 | | | | | | 160 | |
| GAT | GAG | AAT | GGG | AGA | AAT | ATC | AAA | GAG | AAC | CAG | TAC | ATC | AAG | ATC | GAT | 1006 |
| Asp | Glu | Asn | Gly | Arg | Asn | Ile | Lys | Glu | Asn | Gln | Tyr | Ile | Lys | Ile | Asp | |
| | | | 165 | | | | | 170 | | | | | 175 | | | |
| ACC | ATT | GCT | GCT | GAT | GAG | AGC | TTC | ACC | GAA | CTT | GAC | CTT | GGA | GAC | CGG | 1054 |
| Thr | Ile | Ala | Ala | Asp | Glu | Ser | Phe | Thr | Glu | Leu | Asp | Leu | Gly | Asp | Arg | |
| | | 180 | | | | | 185 | | | | | 190 | | | | |
| GTC | ATG | AAG | CTG | AAT | ACG | GAG | GTC | AGA | GAT | GTA | GGA | CCT | CTG | AGC | AAA | 1102 |
| Val | Met | Lys | Leu | Asn | Thr | Glu | Val | Arg | Asp | Val | Gly | Pro | Leu | Ser | Lys | |
| | 195 | | | | | 200 | | | | | 205 | | | | | |
| AAG | GGA | TTT | TAT | CTT | GCT | TTC | CAA | GAT | GTC | GGT | GCT | TGC | ATC | GCT | CTG | 1150 |
| Lys | Gly | Phe | Tyr | Leu | Ala | Phe | Gln | Asp | Val | Gly | Ala | Cys | Ile | Ala | Leu | |
| 210 | | | | | 215 | | | | 220 | | | | | | 225 | |
| GTT | TCT | GTC | CGT | GTC | TAC | TAT | AAA | AAA | TGT | CCT | TCT | GTA | GTT | AGA | CAT | 1198 |
| Val | Ser | Val | Arg | Val | Tyr | Tyr | Lys | Lys | Cys | Pro | Ser | Val | Val | Arg | His | |
| | | | | 230 | | | | | 235 | | | | | | 240 | |
| TTG | GCT | GTT | TTC | CCT | GAC | ACG | ATC | ACT | GGA | GCA | GAT | TCT | TCC | CAG | TTG | 1246 |
| Leu | Ala | Val | Phe | Pro | Asp | Thr | Ile | Thr | Gly | Ala | Asp | Ser | Ser | Gln | Leu | |
| | | | 245 | | | | | 250 | | | | | 255 | | | |
| CTA | GAG | GTG | TCA | GGC | TCC | TGC | GTC | AAC | CAT | TCT | GTG | ACA | GAC | GAT | CCT | 1294 |
| Leu | Glu | Val | Ser | Gly | Ser | Cys | Val | Asn | His | Ser | Val | Thr | Asp | Asp | Pro | |
| | | 260 | | | | | 265 | | | | | 270 | | | | |
| CCC | AAA | ATG | CAT | TGC | AGT | GCT | GAA | GGG | GAG | TGG | CTG | GTT | CCC | ATC | GGG | 1342 |
| Pro | Lys | Met | His | Cys | Ser | Ala | Glu | Gly | Glu | Trp | Leu | Val | Pro | Ile | Gly | |
| | 275 | | | | | 280 | | | | | 285 | | | | | |
| AAA | TGC | ATG | TGC | AAG | GCC | GGA | TAT | GAA | GAG | AAA | AAT | GGT | ACC | TGT | CAA | 1390 |
| Lys | Cys | Met | Cys | Lys | Ala | Gly | Tyr | Glu | Glu | Lys | Asn | Gly | Thr | Cys | Gln | |
| 290 | | | | | 295 | | | | 300 | | | | | | 305 | |
| GTG | TGC | AGA | CCT | GGG | TTC | TTC | AAA | GCC | TCT | CCT | CAC | AGC | CAG | ACC | TGC | 1438 |
| Val | Cys | Arg | Pro | Gly | Phe | Phe | Lys | Ala | Ser | Pro | His | Ser | Gln | Thr | Cys | |
| | | | | 310 | | | | | 315 | | | | | | 320 | |
| AGC | AAA | TGT | CCA | CCT | CAC | AGT | TAC | ACC | CAT | GAG | GAA | GCT | TCC | ACC | TCT | 1486 |
| Ser | Lys | Cys | Pro | Pro | His | Ser | Tyr | Thr | His | Glu | Glu | Ala | Ser | Thr | Ser | |
| | | | 325 | | | | | 330 | | | | | 335 | | | |
| TGT | GTC | TGT | GAA | AAG | GAT | TAT | TTC | AGG | AGG | GAA | TCT | GAT | CCG | CCC | ACA | 1534 |
| Cys | Val | Cys | Glu | Lys | Asp | Tyr | Phe | Arg | Arg | Glu | Ser | Asp | Pro | Pro | Thr | |
| | | 340 | | | | | 345 | | | | | 350 | | | | |
| ATG | GCA | TGC | ACA | AGA | CCC | CCC | TCA | GCT | CCT | CGG | AAT | GCC | ATC | TCA | AAT | 1582 |
| Met | Ala | Cys | Thr | Arg | Pro | Pro | Ser | Ala | Pro | Arg | Asn | Ala | Ile | Ser | Asn | |
| | 355 | | | | | 360 | | | | | 365 | | | | | |
| GTT | AAT | GAA | ACT | AGT | GTC | TTT | CTG | GAG | TGG | ATT | CCT | CCT | GCT | GAC | ACT | 1630 |
| Val | Asn | Glu | Thr | Ser | Val | Phe | Leu | Glu | Trp | Ile | Pro | Pro | Ala | Asp | Thr | |
| 370 | | | | | 375 | | | | 380 | | | | | | 385 | |
| GGT | GGA | GGG | AAA | GAT | GTG | TCC | TAT | TAC | ATT | TTA | TGC | AAG | AAG | TGC | AAC | 1678 |
| Gly | Gly | Gly | Lys | Asp | Val | Ser | Tyr | Tyr | Ile | Leu | Cys | Lys | Lys | Cys | Asn | |
| | | | | 390 | | | | | 395 | | | | | | 400 | |
| TCC | CAT | GCA | GGT | GTG | TGT | GAG | GAG | TGT | GGC | GGT | CAT | GTC | AGG | TAC | CTC | 1726 |
| Ser | His | Ala | Gly | Val | Cys | Glu | Glu | Cys | Gly | Gly | His | Val | Arg | Tyr | Leu | |
| | | | 405 | | | | | 410 | | | | | 415 | | | |
| CCC | CAG | CAA | ATC | GGC | CTG | AAA | AAT | ACC | TCT | GTC | ATG | ATG | GCG | GAC | CCC | 1774 |
| Pro | Gln | Gln | Ile | Gly | Leu | Lys | Asn | Thr | Ser | Val | Met | Met | Ala | Asp | Pro | |
| | | 420 | | | | | 425 | | | | | 430 | | | | |

| | | | | | | | | | | | | | | | | |
|---|---|---|---|---|---|---|---|---|---|---|---|---|---|---|---|---|
| CTT | GCT | CAC | ACA | AAC | TAT | ACC | TTT | GAA | ATT | GAG | GCA | GTG | AAC | GGA | GTT | 1822 |
| Leu | Ala | His | Thr | Asn | Tyr | Thr | Phe | Glu | Ile | Glu | Ala | Val | Asn | Gly | Val | |
| | | 435 | | | | 440 | | | | | 445 | | | | | |
| TCC | GAC | TTG | AGT | CCA | GGC | ACC | CGG | CAG | TAT | GTG | TCT | GTA | AAT | GTA | ACC | 1870 |
| Ser | Asp | Leu | Ser | Pro | Gly | Thr | Arg | Gln | Tyr | Val | Ser | Val | Asn | Val | Thr | |
| 450 | | | | | 455 | | | | 460 | | | | | | 465 | |
| ACG | AAC | CAA | GCA | GCT | CCT | TCT | CCA | GTC | ACC | AAC | GTG | AAG | AAG | GGG | AAG | 1918 |
| Thr | Asn | Gln | Ala | Ala | Pro | Ser | Pro | Val | Thr | Asn | Val | Lys | Lys | Gly | Lys | |
| | | | | 470 | | | | | 475 | | | | | 480 | | |
| ATC | GCA | AAG | AAC | AGC | ATT | TCT | TTG | TCT | TGG | CAA | GAG | CCA | GAT | CGC | CCC | 1966 |
| Ile | Ala | Lys | Asn | Ser | Ile | Ser | Leu | Ser | Trp | Gln | Glu | Pro | Asp | Arg | Pro | |
| | | | 485 | | | | | 490 | | | | | 495 | | | |
| AAT | GGG | ATC | ATC | CTG | GAG | TAC | GAA | ATC | AAG | TAC | TTT | GAA | AAG | GAC | CAA | 2014 |
| Asn | Gly | Ile | Ile | Leu | Glu | Tyr | Glu | Ile | Lys | Tyr | Phe | Glu | Lys | Asp | Gln | |
| | | | 500 | | | | 505 | | | | | 510 | | | | |
| GAG | ACC | AGC | TAC | ACA | ATT | ATC | AAG | TCT | AAA | GAG | ACC | ACT | ATT | ACG | GCA | 2062 |
| Glu | Thr | Ser | Tyr | Thr | Ile | Ile | Lys | Ser | Lys | Glu | Thr | Thr | Ile | Thr | Ala | |
| | 515 | | | | | 520 | | | | | 525 | | | | | |
| GAG | GGC | CTG | AAA | CCT | GCG | TCT | GTG | TAT | GTC | TTC | CAA | ATT | CGA | GCA | CGT | 2110 |
| Glu | Gly | Leu | Lys | Pro | Ala | Ser | Val | Tyr | Val | Phe | Gln | Ile | Arg | Ala | Arg | |
| 530 | | | | | 535 | | | | 540 | | | | | | 545 | |
| ACA | GCA | GCA | GGC | TAC | GGC | GTC | TTC | AGT | CGA | CGG | TTT | GAG | TTT | GAA | ACC | 2158 |
| Thr | Ala | Ala | Gly | Tyr | Gly | Val | Phe | Ser | Arg | Arg | Phe | Glu | Phe | Glu | Thr | |
| | | | | 550 | | | | | 555 | | | | | 560 | | |
| ACA | CCA | GTG | TTT | GGA | GCA | TCT | AAT | GAT | CAA | AGC | CAG | ATT | CCC | ATC | ATT | 2206 |
| Thr | Pro | Val | Phe | Gly | Ala | Ser | Asn | Asp | Gln | Ser | Gln | Ile | Pro | Ile | Ile | |
| | | | 565 | | | | | 570 | | | | | 575 | | | |
| GGG | GTG | TCA | GTG | ACG | GTG | GGA | GTC | ATC | TTG | TTG | GCA | GTG | ATG | ATC | GGC | 2254 |
| Gly | Val | Ser | Val | Thr | Val | Gly | Val | Ile | Leu | Leu | Ala | Val | Met | Ile | Gly | |
| | | 580 | | | | | 585 | | | | | 590 | | | | |
| TTC | CTC | CTC | AGT | GGC | AGT | TGC | TGC | GAA | TGT | GGC | TGT | GGG | AGG | GCT | TCT | 2302 |
| Phe | Leu | Leu | Ser | Gly | Ser | Cys | Cys | Glu | Cys | Gly | Cys | Gly | Arg | Ala | Ser | |
| | 595 | | | | | 600 | | | | | 605 | | | | | |
| TCC | CTG | TGC | GCT | GTT | GCC | CAT | CCA | AGC | CTA | ATA | TGG | CGG | TGT | GGC | TAC | 2350 |
| Ser | Leu | Cys | Ala | Val | Ala | His | Pro | Ser | Leu | Ile | Trp | Arg | Cys | Gly | Tyr | |
| 610 | | | | | 615 | | | | | 620 | | | | | 625 | |
| AGC | AAA | GCA | AAG | CAG | GAT | CCA | GAA | GAG | GAA | AAG | ATG | CAC | TTT | CAT | AAC | 2398 |
| Ser | Lys | Ala | Lys | Gln | Asp | Pro | Glu | Glu | Glu | Lys | Met | His | Phe | His | Asn | |
| | | | | 630 | | | | | 635 | | | | | 640 | | |
| GGG | CAC | ATT | AAA | CTG | CCA | GGA | GTA | AGA | ACG | TAC | ATT | GAT | CCA | CAC | ACC | 2446 |
| Gly | His | Ile | Lys | Leu | Pro | Gly | Val | Arg | Thr | Tyr | Ile | Asp | Pro | His | Thr | |
| | | | 645 | | | | | 650 | | | | | 655 | | | |
| TAC | GAA | GAT | CCC | ACT | CAA | GCC | GTT | CAT | GAA | TTT | GGC | AAG | GAG | ATC | GAG | 2494 |
| Tyr | Glu | Asp | Pro | Thr | Gln | Ala | Val | His | Glu | Phe | Gly | Lys | Glu | Ile | Glu | |
| | | 660 | | | | | 665 | | | | | 670 | | | | |
| GCC | TCA | TGC | ATC | ACC | ATT | GAG | AGA | GTT | ATT | GGA | GCA | GGT | GAA | TTT | GGT | 2542 |
| Ala | Ser | Cys | Ile | Thr | Ile | Glu | Arg | Val | Ile | Gly | Ala | Gly | Glu | Phe | Gly | |
| | 675 | | | | | 680 | | | | | 685 | | | | | |
| GAA | GTT | TGT | AGT | GGA | CGT | TTG | AAA | CTA | CCC | GGA | AAA | AGA | GAA | TTG | CCT | 2590 |
| Glu | Val | Cys | Ser | Gly | Arg | Leu | Lys | Leu | Pro | Gly | Lys | Arg | Glu | Leu | Pro | |
| 690 | | | | | 695 | | | | | 700 | | | | | 705 | |
| GTG | GCT | ACC | AAA | ACT | CTT | AAA | GTA | GGC | TAC | ACT | GAA | AAG | CAG | CGC | AGA | 2638 |
| Val | Ala | Thr | Lys | Thr | Leu | Lys | Val | Gly | Tyr | Thr | Glu | Lys | Gln | Arg | Arg | |
| | | | | 710 | | | | | 715 | | | | | | 720 | |
| GAT | TTT | CTG | AGT | GAA | GCG | AGT | ATC | ATG | GGG | CAG | TTT | GAT | CAT | CCA | AAC | 2686 |
| Asp | Phe | Leu | Ser | Glu | Ala | Ser | Ile | Met | Gly | Gln | Phe | Asp | His | Pro | Asn | |
| | | | 725 | | | | | 730 | | | | | 735 | | | |
| ATC | ATC | CAT | CTA | GAA | GGC | GTT | GTG | ACT | AAA | AGT | AAA | CCT | GTG | ATG | ATA | 2734 |
| Ile | Ile | His | Leu | Glu | Gly | Val | Val | Thr | Lys | Ser | Lys | Pro | Val | Met | Ile | |
| | | 740 | | | | | 745 | | | | | 750 | | | | |

```
GTG  ACA  GAG  TAC  ATG  GAG  AAT  GGC  TCC  TTA  GAC  ACA  TTT  TTA  AAG  AAA      2782
Val  Thr  Glu  Tyr  Met  Glu  Asn  Gly  Ser  Leu  Asp  Thr  Phe  Leu  Lys  Lys
755                           760                           765

AAC  GAT  GGC  CAG  TTC  ACT  GTG  ATT  CAG  CTT  GTT  GGC  ATG  CTG  AGA  GGC      2830
Asn  Asp  Gly  Gln  Phe  Thr  Val  Ile  Gln  Leu  Val  Gly  Met  Leu  Arg  Gly
770                      775                           780                      785

ATC  GCT  GCA  GGA  ATG  AAG  TAC  CTT  TCT  GAC  ATG  GGC  TAC  GTG  CAC  AGA      2878
Ile  Ala  Ala  Gly  Met  Lys  Tyr  Leu  Ser  Asp  Met  Gly  Tyr  Val  His  Arg
                    790                      795                           800

GAC  CTT  GCT  GCT  AGA  AAC  ATC  TTA  ATC  AAC  AGT  AAC  CTT  GTG  TGC  AAA      2926
Asp  Leu  Ala  Ala  Arg  Asn  Ile  Leu  Ile  Asn  Ser  Asn  Leu  Val  Cys  Lys
               805                      810                           815

GTG  TCT  GAC  TTT  GGA  CTT  TCC  AGG  GTG  CTG  GAA  GAT  GAT  CCT  GAG  GCA      2974
Val  Ser  Asp  Phe  Gly  Leu  Ser  Arg  Val  Leu  Glu  Asp  Asp  Pro  Glu  Ala
          820                      825                           830

GCC  TAT  ACC  ACA  AGG  GGA  GGC  AAA  ATT  CCA  ATC  AGG  TGG  ACT  GCT  CCA      3022
Ala  Tyr  Thr  Thr  Arg  Gly  Gly  Lys  Ile  Pro  Ile  Arg  Trp  Thr  Ala  Pro
     835                           840                      845

GAA  GCA  ATA  GCT  TTT  CGA  AAG  TTT  ACC  TCT  GCC  AGT  GAT  GTC  TGG  AGC      3070
Glu  Ala  Ile  Ala  Phe  Arg  Lys  Phe  Thr  Ser  Ala  Ser  Asp  Val  Trp  Ser
850                           855                      860                      865

TAT  GGA  ATC  GTA  ATG  TGG  GAA  GTT  GTG  TCC  TAT  GGA  GAG  AGA  CCG  TAC      3118
Tyr  Gly  Ile  Val  Met  Trp  Glu  Val  Val  Ser  Tyr  Gly  Glu  Arg  Pro  Tyr
                    870                      875                           880

TGG  GAG  ATG  ACC  AAT  CAG  GAT  GTG  ATC  AAG  GCA  GTG  GAA  GAA  GGC  TAC      3166
Trp  Glu  Met  Thr  Asn  Gln  Asp  Val  Ile  Lys  Ala  Val  Glu  Glu  Gly  Tyr
               885                      890                           895

CGC  CTG  CCA  AGC  CCC  ATG  GAT  TGT  CCT  GCT  GCC  CTC  TAT  CAA  TTA  ATG      3214
Arg  Leu  Pro  Ser  Pro  Met  Asp  Cys  Pro  Ala  Ala  Leu  Tyr  Gln  Leu  Met
          900                      905                           910

CTG  GAT  TGC  TGG  CAG  AAA  GAT  CGC  AAC  AGC  AGG  CCC  AAG  TTT  GAT  GAC      3262
Leu  Asp  Cys  Trp  Gln  Lys  Asp  Arg  Asn  Ser  Arg  Pro  Lys  Phe  Asp  Asp
     915                           920                      925

ATA  GTC  AAC  ATG  CTG  GAT  AAG  CTG  ATA  CGA  AAC  CCA  AGT  AGT  TTG  AAG      3310
Ile  Val  Asn  Met  Leu  Asp  Lys  Leu  Ile  Arg  Asn  Pro  Ser  Ser  Leu  Lys
930                           935                      940                      945

ACA  CTG  GTG  AAC  GCG  TCA  AGC  AGG  GTA  TCT  ACT  TTG  TTG  GCA  GAA  CAT      3358
Thr  Leu  Val  Asn  Ala  Ser  Ser  Arg  Val  Ser  Thr  Leu  Leu  Ala  Glu  His
                    950                      955                           960

GGA  TCT  TTG  GGG  TCT  GGG  GCC  TAC  AGA  TCA  GTA  GGT  GAA  TGG  CTA  GAA      3406
Gly  Ser  Leu  Gly  Ser  Gly  Ala  Tyr  Arg  Ser  Val  Gly  Glu  Trp  Leu  Glu
               965                      970                           975

GCA  ACC  AAA  ATG  GGC  CGG  TAC  ACA  GAG  ATT  TTC  ATG  GAA  AAT  GGA  TAC      3454
Ala  Thr  Lys  Met  Gly  Arg  Tyr  Thr  Glu  Ile  Phe  Met  Glu  Asn  Gly  Tyr
          980                           985                      990

AGT  TCA  ATG  GAC  GCT  GTG  GCT  CAG  GTG  ACC  TTG  GAG  TGAGTAGTTT               3500
Ser  Ser  Met  Asp  Ala  Val  Ala  Gln  Val  Thr  Leu  Glu
     995                      1000                     1005

TTCTGATAAT  TTTTACATAG  CTGTTGGGGC  AAGAAAAGTA  TATTCAGACA  ACAGAGTGGA             3560

TGCAATCAAG  GGAAAACAGT  TTACCTGTGT  CCATATGTGT  CAGCTTCCAA  AGAAGCCTCA             3620

TCTTTTTTTA  GCCTGTGCTG  TTAACAGCTG  CATGGTTCCT  GCTTCTTGTG  TCCAGAATCT             3680

TTGCTATTTT  GTTCACAAAC  AGCACTTGAG  AGTTTGGATA  ATTGGATTAC  AACCCTTGGC             3740

AAAGTACTGG  TACTTTGTGT  TGTGAAAAAA  AAGACATTTC  CTTGAGTTTT  TATACTGGTA             3800

CTTATGTTAC  ATGAATGTAA  ATATAAAACA  AACAAGCTG   TAAGCACAAT  TGGTGTGGTT             3860

AGTCTTGTGT  AACAAAAACA  TAAAAAGATT  AAAAAAAAAA  AAAAA                             3906
```

( 2 ) INFORMATION FOR SEQ ID NO:103:

( i ) SEQUENCE CHARACTERISTICS:
        ( A ) LENGTH: 1005 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

```
Met Arg Gly Ser Gly Pro Arg Gly Ala Gly Arg Arg Thr Gln Gly
  1               5                  10                  15
Arg Gly Gly Gly Gly Asp Thr Pro Arg Val Pro Ala Ser Leu Ala Gly
                 20                  25                  30
Cys Tyr Ser Ala Pro Leu Lys Gly Pro Leu Trp Thr Cys Leu Leu Leu
             35                  40                  45
Cys Ala Ala Leu Arg Thr Leu Leu Ala Ser Pro Ser Asn Glu Val Asn
         50                  55                  60
Leu Leu Asp Ser Arg Thr Val Leu Gly Asp Leu Gly Trp Ile Ala Phe
 65                  70                  75                  80
Pro Lys Asn Gly Trp Glu Glu Ile Gly Glu Val Asp Glu Asn Tyr Ala
                 85                  90                  95
Pro Ile His Thr Tyr Gln Val Cys Lys Val Met Glu Gln Asn Gln Asn
            100                 105                 110
Asn Trp Leu Leu Thr Ser Trp Ile Ser Asn Glu Gly Ala Ser Arg Ile
            115                 120                 125
Phe Ile Glu Leu Lys Phe Thr Leu Arg Asp Cys Asn Ser Leu Pro Gly
        130                 135                 140
Gly Leu Gly Thr Cys Lys Glu Thr Phe Asn Met Tyr Tyr Phe Glu Ser
145                 150                 155                 160
Asp Asp Glu Asn Gly Arg Asn Ile Lys Glu Asn Gln Tyr Ile Lys Ile
                165                 170                 175
Asp Thr Ile Ala Ala Asp Glu Ser Phe Thr Glu Leu Asp Leu Gly Asp
            180                 185                 190
Arg Val Met Lys Leu Asn Thr Glu Val Arg Asp Val Gly Pro Leu Ser
        195                 200                 205
Lys Lys Gly Phe Tyr Leu Ala Phe Gln Asp Val Gly Ala Cys Ile Ala
210                 215                 220
Leu Val Ser Val Arg Val Tyr Tyr Lys Lys Cys Pro Ser Val Val Arg
225                 230                 235                 240
His Leu Ala Val Phe Pro Asp Thr Ile Thr Gly Ala Asp Ser Ser Gln
                245                 250                 255
Leu Leu Glu Val Ser Gly Ser Cys Val Asn His Ser Val Thr Asp Asp
            260                 265                 270
Pro Pro Lys Met His Cys Ser Ala Glu Gly Glu Trp Leu Val Pro Ile
        275                 280                 285
Gly Lys Cys Met Cys Lys Ala Gly Tyr Glu Glu Lys Asn Gly Thr Cys
    290                 295                 300
Gln Val Cys Arg Pro Gly Phe Phe Lys Ala Ser Pro His Ser Gln Thr
305                 310                 315                 320
Cys Ser Lys Cys Pro Pro His Ser Tyr Thr His Glu Glu Ala Ser Thr
                325                 330                 335
Ser Cys Val Cys Glu Lys Asp Tyr Phe Arg Arg Glu Ser Asp Pro Pro
            340                 345                 350
Thr Met Ala Cys Thr Arg Pro Pro Ser Ala Pro Arg Asn Ala Ile Ser
        355                 360                 365
```

```
Asn Val Asn Glu Thr Ser Val Phe Leu Glu Trp Ile Pro Pro Ala Asp
    370             375                 380

Thr Gly Gly Gly Lys Asp Val Ser Tyr Tyr Ile Leu Cys Lys Lys Cys
385             390             395                         400

Asn Ser His Ala Gly Val Cys Glu Glu Cys Gly Gly His Val Arg Tyr
            405                 410                     415

Leu Pro Gln Gln Ile Gly Leu Lys Asn Thr Ser Val Met Met Ala Asp
        420             425                     430

Pro Leu Ala His Thr Asn Tyr Thr Phe Glu Ile Glu Ala Val Asn Gly
        435             440                 445

Val Ser Asp Leu Ser Pro Gly Thr Arg Gln Tyr Val Ser Val Asn Val
    450             455             460

Thr Thr Asn Gln Ala Ala Pro Ser Pro Val Thr Asn Val Lys Lys Gly
465             470             475                         480

Lys Ile Ala Lys Asn Ser Ile Ser Leu Ser Trp Gln Glu Pro Asp Arg
            485             490                     495

Pro Asn Gly Ile Ile Leu Glu Tyr Glu Ile Lys Tyr Phe Glu Lys Asp
            500             505             510

Gln Glu Thr Ser Tyr Thr Ile Ile Lys Ser Lys Glu Thr Ile Thr
        515             520             525

Ala Glu Gly Leu Lys Pro Ala Ser Val Tyr Val Phe Gln Ile Arg Ala
530             535             540

Arg Thr Ala Ala Gly Tyr Gly Val Phe Ser Arg Arg Phe Glu Phe Glu
545             550             555                     560

Thr Thr Pro Val Phe Gly Ala Ser Asn Asp Gln Ser Gln Ile Pro Ile
                565             570             575

Ile Gly Val Ser Val Thr Val Gly Val Ile Leu Leu Ala Val Met Ile
            580             585             590

Gly Phe Leu Leu Ser Gly Ser Cys Cys Glu Cys Gly Cys Gly Arg Ala
            595             600             605

Ser Ser Leu Cys Ala Val Ala His Pro Ser Leu Ile Trp Arg Cys Gly
    610             615             620

Tyr Ser Lys Ala Lys Gln Asp Pro Glu Glu Glu Lys Met His Phe His
625             630             635                     640

Asn Gly His Ile Lys Leu Pro Gly Val Arg Thr Tyr Ile Asp Pro His
            645             650             655

Thr Tyr Glu Asp Pro Thr Gln Ala Val His Glu Phe Gly Lys Glu Ile
            660             665             670

Glu Ala Ser Cys Ile Thr Ile Glu Arg Val Ile Gly Ala Gly Glu Phe
        675             680             685

Gly Glu Val Cys Ser Gly Arg Leu Lys Leu Pro Gly Lys Arg Glu Leu
    690             695             700

Pro Val Ala Thr Lys Thr Leu Lys Val Gly Tyr Thr Glu Lys Gln Arg
705             710             715                     720

Arg Asp Phe Leu Ser Glu Ala Ser Ile Met Gly Gln Phe Asp His Pro
            725             730             735

Asn Ile Ile His Leu Glu Gly Val Val Thr Lys Ser Lys Pro Val Met
            740             745             750

Ile Val Thr Glu Tyr Met Glu Asn Gly Ser Leu Asp Thr Phe Leu Lys
        755             760             765

Lys Asn Asp Gly Gln Phe Thr Val Ile Gln Leu Val Gly Met Leu Arg
    770             775             780

Gly Ile Ala Ala Gly Met Lys Tyr Leu Ser Asp Met Gly Tyr Val His
785             790             795             800
```

| Arg | Asp | Leu | Ala | Ala | Arg | Asn | Ile | Leu | Ile | Asn | Ser | Asn | Leu | Val | Cys |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

| Lys | Val | Ser | Asp | Phe | Gly | Leu | Ser | Arg | Val | Leu | Glu | Asp | Asp | Pro | Glu |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Ala | Ala | Tyr | Thr | Thr | Arg | Gly | Gly | Lys | Ile | Pro | Ile | Arg | Trp | Thr | Ala |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| Pro | Glu | Ala | Ile | Ala | Phe | Arg | Lys | Phe | Thr | Ser | Ala | Ser | Asp | Val | Trp |
|-----|-----|-----|-----|-----|-----|-----|-----|-----|-----|-----|-----|-----|-----|-----|-----|
|     | 850 |     |     |     |     | 855 |     |     |     |     | 860 |     |     |     |     |

| Ser | Tyr | Gly | Ile | Val | Met | Trp | Glu | Val | Val | Ser | Tyr | Gly | Glu | Arg | Pro |
|-----|-----|-----|-----|-----|-----|-----|-----|-----|-----|-----|-----|-----|-----|-----|-----|
| 865 |     |     |     |     | 870 |     |     |     |     | 875 |     |     |     |     | 880 |

| Tyr | Trp | Glu | Met | Thr | Asn | Gln | Asp | Val | Ile | Lys | Ala | Val | Glu | Glu | Gly |
|-----|-----|-----|-----|-----|-----|-----|-----|-----|-----|-----|-----|-----|-----|-----|-----|
|     |     |     |     | 885 |     |     |     |     | 890 |     |     |     |     | 895 |     |

| Tyr | Arg | Leu | Pro | Ser | Pro | Met | Asp | Cys | Pro | Ala | Ala | Leu | Tyr | Gln | Leu |
|-----|-----|-----|-----|-----|-----|-----|-----|-----|-----|-----|-----|-----|-----|-----|-----|
|     |     |     | 900 |     |     |     |     | 905 |     |     |     |     | 910 |     |     |

| Met | Leu | Asp | Cys | Trp | Gln | Lys | Asp | Arg | Asn | Ser | Arg | Pro | Lys | Phe | Asp |
|-----|-----|-----|-----|-----|-----|-----|-----|-----|-----|-----|-----|-----|-----|-----|-----|
|     |     | 915 |     |     |     |     | 920 |     |     |     |     | 925 |     |     |     |

| Asp | Ile | Val | Asn | Met | Leu | Asp | Lys | Leu | Ile | Arg | Asn | Pro | Ser | Ser | Leu |
|-----|-----|-----|-----|-----|-----|-----|-----|-----|-----|-----|-----|-----|-----|-----|-----|
|     | 930 |     |     |     |     | 935 |     |     |     |     | 940 |     |     |     |     |

| Lys | Thr | Leu | Val | Asn | Ala | Ser | Ser | Arg | Val | Ser | Thr | Leu | Leu | Ala | Glu |
|-----|-----|-----|-----|-----|-----|-----|-----|-----|-----|-----|-----|-----|-----|-----|-----|
| 945 |     |     |     |     | 950 |     |     |     |     | 955 |     |     |     |     | 960 |

| His | Gly | Ser | Leu | Gly | Ser | Gly | Ala | Tyr | Arg | Ser | Val | Gly | Glu | Trp | Leu |
|-----|-----|-----|-----|-----|-----|-----|-----|-----|-----|-----|-----|-----|-----|-----|-----|
|     |     |     |     | 965 |     |     |     |     | 970 |     |     |     |     | 975 |     |

| Glu | Ala | Thr | Lys | Met | Gly | Arg | Tyr | Thr | Glu | Ile | Phe | Met | Glu | Asn | Gly |
|-----|-----|-----|-----|-----|-----|-----|-----|-----|-----|-----|-----|-----|-----|-----|-----|
|     |     |     | 980 |     |     |     |     | 985 |     |     |     |     | 990 |     |     |

| Tyr | Ser | Ser | Met | Asp | Ala | Val | Ala | Gln | Val | Thr | Leu | Glu |
|-----|-----|-----|-----|-----|-----|-----|-----|-----|-----|-----|-----|-----|
|     |     | 995 |     |     |     |     | 1000 |     |     |     |     | 1005 |

( 2 ) INFORMATION FOR SEQ ID NO:104:

( i ) SEQUENCE CHARACTERISTICS:
        ( A ) LENGTH: 3358 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Coding Sequence
        ( B ) LOCATION: 376...3186
        ( D ) OTHER INFORMATION:
        ( A ) NAME/KEY: Human ROR1
        ( B ) LOCATION: 1...3358
        ( D ) OTHER INFORMATION:

( x i ) SEQUENCE DESCRIPTION: SEQ ID NO:104:

| GAGCTGGAGC | AGCCGCCACC | GCCGCCGCCG | AGGGAGCCCC | GGGACGGCAG | CCCCTGGGCG | 60 |
| CAGGGTGCGC | TGTTCTCGGA | GTCCGACCCA | GGGCGACTCA | CGCCCACTGG | TGCGACCCGG | 120 |
| ACAGCCTGGG | ACTGACCCGC | CGGCCCAGGC | GAGGCTGCAG | CCAGAGGGCT | GGGAAGGGAT | 180 |
| CGCGCTCGCG | GCATCCAGAG | GCGGCCAGGC | GGAGGCGAGG | GAGCAGGTTA | GAGGGACAAA | 240 |
| GAGCTTTGCA | GACGTCCCCG | GCGTCCTGCG | AGCGCCAGCG | GCCGGGACGA | GGCGGCCGGG | 300 |
| AGCCCGGGAA | GAGCCCGTGG | ATGTTCTGCG | CGCGGCCTGG | GAGCCGCCGC | CGCCGCCGCC | 360 |

| TCAGCGAGAG | GAGGA | ATG | CAC | CGG | CCG | CGC | CGC | CGC | GGG | ACG | CGC | CCG | CCG | 411 |
|            |       | Met | His | Arg | Pro | Arg | Arg | Arg | Gly | Thr | Arg | Pro | Pro |     |
|            |       | 1   |     |     | 5   |     |     |     |     | 10  |     |     |     |     |

| CTC | CTG | GCG | CTG | CTG | GCC | GCG | CTG | CTG | CTG | GCC | GCA | CGC | GGG | GCT | GCT | 459 |
| Leu | Leu | Ala | Leu | Leu | Ala | Ala | Leu | Leu | Leu | Ala | Ala | Arg | Gly | Ala | Ala |     |
|     |     | 15  |     |     |     |     | 20  |     |     |     |     | 25  |     |     |     |     |

| | | | | | | | | | | | | | | | | |
|---|---|---|---|---|---|---|---|---|---|---|---|---|---|---|---|---|
| GCC | CAA | GAA | ACA | GAG | CTG | TCA | GTC | AGT | GCT | GAA | TTA | GTG | CCT | ACC | TCA | 507 |
| Ala | Gln | Glu | Thr | Glu | Leu | Ser | Val | Ser | Ala | Glu | Leu | Val | Pro | Thr | Ser | |
| | 30 | | | | | 35 | | | | | 40 | | | | | |
| TCA | TGG | AAC | ATC | TCA | AGT | GAA | CTC | AAC | AAA | GAT | TCT | TAC | CTG | ACC | CTT | 555 |
| Ser | Trp | Asn | Ile | Ser | Ser | Glu | Leu | Asn | Lys | Asp | Ser | Tyr | Leu | Thr | Leu | |
| 45 | | | | | 50 | | | | | 55 | | | | | 60 | |
| GAT | GAA | CCA | ATG | AAT | AAC | ATC | ACC | ACG | TCT | CTG | GGC | CAG | ACA | GCA | GAA | 603 |
| Asp | Glu | Pro | Met | Asn | Asn | Ile | Thr | Thr | Ser | Leu | Gly | Gln | Thr | Ala | Glu | |
| | | | | 65 | | | | | 70 | | | | | 75 | | |
| CTG | CAC | TGC | AAA | GTC | TCT | GGG | AAT | CCA | CCT | CCC | ACC | ATC | CGC | TGG | TTC | 651 |
| Leu | His | Cys | Lys | Val | Ser | Gly | Asn | Pro | Pro | Pro | Thr | Ile | Arg | Trp | Phe | |
| | | | 80 | | | | | 85 | | | | | 90 | | | |
| AAA | AAT | GAT | GCT | CCT | GTG | GTC | CAG | GAG | CCC | CGG | AGG | CTC | TCC | TTT | CGG | 699 |
| Lys | Asn | Asp | Ala | Pro | Val | Val | Gln | Glu | Pro | Arg | Arg | Leu | Ser | Phe | Arg | |
| | | | 95 | | | | | 100 | | | | | 105 | | | |
| TCC | ACC | ATC | TAT | GGC | TCT | CGG | CTG | CGG | ATT | AGA | AAC | CTC | GAC | ACC | ACA | 747 |
| Ser | Thr | Ile | Tyr | Gly | Ser | Arg | Leu | Arg | Ile | Arg | Asn | Leu | Asp | Thr | Thr | |
| | | 110 | | | | | 115 | | | | | 120 | | | | |
| GAC | ACA | GGC | TAC | TTC | CAG | TGC | GTG | GCA | ACA | AAC | GGC | AAG | GAG | GTG | GTT | 795 |
| Asp | Thr | Gly | Tyr | Phe | Gln | Cys | Val | Ala | Thr | Asn | Gly | Lys | Glu | Val | Val | |
| 125 | | | | | 130 | | | | | 135 | | | | | 140 | |
| TCT | TCC | ACT | GGA | GTC | TTG | TTT | GTC | AAG | TTT | GGC | CCC | CCT | CCC | ACT | GCA | 843 |
| Ser | Ser | Thr | Gly | Val | Leu | Phe | Val | Lys | Phe | Gly | Pro | Pro | Pro | Thr | Ala | |
| | | | | 145 | | | | | 150 | | | | | 155 | | |
| AGT | CCA | GGA | TAC | TCA | GAT | GAG | TAT | GAA | GAA | GAT | GGA | TTC | TGT | CAG | CCA | 891 |
| Ser | Pro | Gly | Tyr | Ser | Asp | Glu | Tyr | Glu | Glu | Asp | Gly | Phe | Cys | Gln | Pro | |
| | | | 160 | | | | | 165 | | | | | 170 | | | |
| TAC | AGA | GGG | ATT | GCA | TGT | GCA | AGA | TTT | ATT | GGC | AAC | CGC | ACC | GTC | TAT | 939 |
| Tyr | Arg | Gly | Ile | Ala | Cys | Ala | Arg | Phe | Ile | Gly | Asn | Arg | Thr | Val | Tyr | |
| | | 175 | | | | | 180 | | | | | 185 | | | | |
| ATG | GAG | TCT | TTG | CAC | ATG | CAA | GGG | GAA | ATA | GAA | AAT | CAG | ATC | ACA | GCT | 987 |
| Met | Glu | Ser | Leu | His | Met | Gln | Gly | Glu | Ile | Glu | Asn | Gln | Ile | Thr | Ala | |
| | 190 | | | | | 195 | | | | | 200 | | | | | |
| GCC | TTC | ACT | ATG | ATT | GGC | ACT | TCC | AGT | CAC | TTA | TCT | GAT | AAG | TGT | TCT | 1035 |
| Ala | Phe | Thr | Met | Ile | Gly | Thr | Ser | Ser | His | Leu | Ser | Asp | Lys | Cys | Ser | |
| 205 | | | | | 210 | | | | | 215 | | | | | 220 | |
| CAG | TTC | GCC | ATT | CCT | TCC | CTG | TGC | CAC | TAT | GCC | TTC | CCG | TAC | TGC | GAT | 1083 |
| Gln | Phe | Ala | Ile | Pro | Ser | Leu | Cys | His | Tyr | Ala | Phe | Pro | Tyr | Cys | Asp | |
| | | | | 225 | | | | | 230 | | | | | 235 | | |
| GAA | ACT | TCA | TCC | GTC | CCA | AAG | CCC | CGT | GAC | TTG | TGT | CGC | GAT | GAA | TGT | 1131 |
| Glu | Thr | Ser | Ser | Val | Pro | Lys | Pro | Arg | Asp | Leu | Cys | Arg | Asp | Glu | Cys | |
| | | | 240 | | | | | 245 | | | | | 250 | | | |
| GAA | ATC | CTG | GAG | AAT | GTC | CTG | TGT | CAA | ACA | GAG | TAC | ATT | TTT | GCA | AGA | 1179 |
| Glu | Ile | Leu | Glu | Asn | Val | Leu | Cys | Gln | Thr | Glu | Tyr | Ile | Phe | Ala | Arg | |
| | | 255 | | | | | 260 | | | | | 265 | | | | |
| TCA | AAT | CCC | ATG | ATT | CTG | ATG | AGG | CTG | AAA | CTG | CCA | AAC | TGT | GAA | GAT | 1227 |
| Ser | Asn | Pro | Met | Ile | Leu | Met | Arg | Leu | Lys | Leu | Pro | Asn | Cys | Glu | Asp | |
| | 270 | | | | | 275 | | | | | 280 | | | | | |
| CTC | CCC | CAG | CCA | GAG | AGC | CCA | GAA | GCT | GCG | AAC | TGT | ATC | CGG | ATT | GGA | 1275 |
| Leu | Pro | Gln | Pro | Glu | Ser | Pro | Glu | Ala | Ala | Asn | Cys | Ile | Arg | Ile | Gly | |
| 285 | | | | | 290 | | | | | 295 | | | | | 300 | |
| ATT | CCC | ATG | GCA | GAT | CCT | ATA | AAT | AAA | AAT | CAC | AAG | TGT | TAT | AAC | AGC | 1323 |
| Ile | Pro | Met | Ala | Asp | Pro | Ile | Asn | Lys | Asn | His | Lys | Cys | Tyr | Asn | Ser | |
| | | | | 305 | | | | | 310 | | | | | 315 | | |
| ACA | GGT | GTG | GAC | TAC | CGG | GGG | ACC | GTC | AGT | GTG | ACC | AAA | TCA | GGG | CGC | 1371 |
| Thr | Gly | Val | Asp | Tyr | Arg | Gly | Thr | Val | Ser | Val | Thr | Lys | Ser | Gly | Arg | |
| | | | 320 | | | | | 325 | | | | | 330 | | | |
| CAG | TGC | CAG | CCA | TGG | AAT | TCC | CAG | TAT | CCC | CAC | ACA | CAC | ACT | TTC | ACC | 1419 |
| Gln | Cys | Gln | Pro | Trp | Asn | Ser | Gln | Tyr | Pro | His | Thr | His | Thr | Phe | Thr | |
| | | 335 | | | | | 340 | | | | | 345 | | | | |

```
GCC CTT CGT TTC CCA GAG CTG AAT GGA GGC CAT TCC TAC TGC CGC AAC    1467
Ala Leu Arg Phe Pro Glu Leu Asn Gly Gly His Ser Tyr Cys Arg Asn
350             355             360

CCA GGG AAT CAA AAG GAA GCT CCC TGG TGC TTC ACC TTG GAT GAA AAC    1515
Pro Gly Asn Gln Lys Glu Ala Pro Trp Cys Phe Thr Leu Asp Glu Asn
365             370             375             380

TTT AAG TCT GAT CTG TGT GAC ATC CCA GCT TGC GAT TCA AAG GAT TCC    1563
Phe Lys Ser Asp Leu Cys Asp Ile Pro Ala Cys Asp Ser Lys Asp Ser
            385             390             395

AAG GAG AAG AAT AAA ATG GAA ATC CTG TAC ATA CTA GTG CCA AGT GTG    1611
Lys Glu Lys Asn Lys Met Glu Ile Leu Tyr Ile Leu Val Pro Ser Val
        400             405             410

GCC ATT CCC CTG GCC ATT GCT TTA CTC TTC TTC TTC ATT TGC GTC TGT    1659
Ala Ile Pro Leu Ala Ile Ala Leu Leu Phe Phe Phe Ile Cys Val Cys
        415             420             425

CGG AAT AAC CAG AAG TCA TCG TCG GCA CCA GTC CAG AGG CAA CCA AAA    1707
Arg Asn Asn Gln Lys Ser Ser Ser Ala Pro Val Gln Arg Gln Pro Lys
        430             435             440

CAC GTC AGA GGT CAA AAT GTG GAG ATG TCA ATG CTG AAT GCA TAT AAA    1755
His Val Arg Gly Gln Asn Val Glu Met Ser Met Leu Asn Ala Tyr Lys
445             450             455             460

CCC AAG AGC AAG GCT AAA GAG CTA CCT CTT TCT GCT GTA CGC TTT ATG    1803
Pro Lys Ser Lys Ala Lys Glu Leu Pro Leu Ser Ala Val Arg Phe Met
            465             470             475

GAA GAA TTG GGT GAG TGT GCC TTT GGA AAA ATC TAT AAA GGC CAT CTC    1851
Glu Glu Leu Gly Glu Cys Ala Phe Gly Lys Ile Tyr Lys Gly His Leu
        480             485             490

TAT CTC CCA GGC ATG GAC CAT GCT CAG CTG GTT GCT ATC AAG ACC TTG    1899
Tyr Leu Pro Gly Met Asp His Ala Gln Leu Val Ala Ile Lys Thr Leu
        495             500             505

AAA GAC TAT AAC AAC CCC CAG CAA TGG ATG GAA TTT CAA CAA GAA GCC    1947
Lys Asp Tyr Asn Asn Pro Gln Gln Trp Met Glu Phe Gln Gln Glu Ala
510             515             520

TCC CTA ATG GCA GAA CTG CAC CAC CCC AAT ATT GTC TGC CTT CTA GGT    1995
Ser Leu Met Ala Glu Leu His His Pro Asn Ile Val Cys Leu Leu Gly
525             530             535             540

GCC GTC ACT CAG GAA CAA CCT GTG TGC ATG CTT TTT GAG TAT ATT AAT    2043
Ala Val Thr Gln Glu Gln Pro Val Cys Met Leu Phe Glu Tyr Ile Asn
            545             550             555

CAG GGG GAT CTC CAT GAG TTC CTC ATC ATG AGA TCC CCA CAC TCT GAT    2091
Gln Gly Asp Leu His Glu Phe Leu Ile Met Arg Ser Pro His Ser Asp
            560             565             570

GTT GGC TGC AGC AGT GAT GAA GAT GGG ACT GTG AAA TCC AGC CTG GAC    2139
Val Gly Cys Ser Ser Asp Glu Asp Gly Thr Val Lys Ser Ser Leu Asp
        575             580             585

CAC GGA GAT TTT CTG CAC ATT GCA ATT CAG ATT GCA GCT GGC ATG GAA    2187
His Gly Asp Phe Leu His Ile Ala Ile Gln Ile Ala Ala Gly Met Glu
        590             595             600

TAC CTG TCT AGT CAC TTC TTT GTC CAC AAG GAC CTT GCA GCT CGC AAT    2235
Tyr Leu Ser Ser His Phe Phe Val His Lys Asp Leu Ala Ala Arg Asn
605             610             615             620

ATT TTA ATC GGA GAG CAA CTT CAT GTA AAG ATT TCA GAC TTG GGG CTT    2283
Ile Leu Ile Gly Glu Gln Leu His Val Lys Ile Ser Asp Leu Gly Leu
            625             630             635

TCC AGA GAA ATT TAC TCC GCT GAT TAC TAC AGG GTC CAG AGT AAG TCC    2331
Ser Arg Glu Ile Tyr Ser Ala Asp Tyr Tyr Arg Val Gln Ser Lys Ser
            640             645             650

TTG CTG CCC ATT CGC TGG ATG CCC CCT GAA GCC ATC ATG TAT GGC AAA    2379
Leu Leu Pro Ile Arg Trp Met Pro Pro Glu Ala Ile Met Tyr Gly Lys
            655             660             665
```

| | | | | | | | | | | | | | | | | |
|---|---|---|---|---|---|---|---|---|---|---|---|---|---|---|---|---|
| TTC | TCT | TCT | GAT | TCA | GAT | ATC | TGG | TCC | TTT | GGG | GTT | GTC | TTG | TGG | GAG | 2427 |
| Phe | Ser | Ser | Asp | Ser | Asp | Ile | Trp | Ser | Phe | Gly | Val | Val | Leu | Trp | Glu | |
| | 670 | | | | 675 | | | | | 680 | | | | | | |
| ATT | TTC | AGT | TTT | GGA | CTC | CAG | CCA | TAT | TAT | GGA | TTC | AGT | AAC | CAG | GAA | 2475 |
| Ile | Phe | Ser | Phe | Gly | Leu | Gln | Pro | Tyr | Tyr | Gly | Phe | Ser | Asn | Gln | Glu | |
| 685 | | | | | 690 | | | | | 695 | | | | | 700 | |
| GTG | ATT | GAG | ATG | GTG | AGA | AAA | CGG | CAG | CTC | TTA | CCA | TGC | TCT | GAA | GAC | 2523 |
| Val | Ile | Glu | Met | Val | Arg | Lys | Arg | Gln | Leu | Leu | Pro | Cys | Ser | Glu | Asp | |
| | | | | 705 | | | | | 710 | | | | | 715 | | |
| TGC | CCA | CCC | AGA | ATG | TAC | AGC | CTC | ATG | ACA | GAG | TGC | TGG | AAT | GAG | ATT | 2571 |
| Cys | Pro | Pro | Arg | Met | Tyr | Ser | Leu | Met | Thr | Glu | Cys | Trp | Asn | Glu | Ile | |
| | | | 720 | | | | | 725 | | | | | 730 | | | |
| CCT | TCT | AGG | AGA | CCA | AGA | TTT | AAA | GAT | ATT | CAC | GTC | CGG | CTT | CGG | TCC | 2619 |
| Pro | Ser | Arg | Arg | Pro | Arg | Phe | Lys | Asp | Ile | His | Val | Arg | Leu | Arg | Ser | |
| | | 735 | | | | | 740 | | | | | 745 | | | | |
| TGG | GAG | GGA | CTC | TCA | AGT | CAC | ACA | AGC | TCT | ACT | ACT | CCT | TCA | GGG | GGA | 2667 |
| Trp | Glu | Gly | Leu | Ser | Ser | His | Thr | Ser | Ser | Thr | Thr | Pro | Ser | Gly | Gly | |
| | 750 | | | | | 755 | | | | | 760 | | | | | |
| AAT | GCC | ACC | ACA | CAG | ACA | ACC | TCC | CTC | AGT | GCC | AGC | CCA | GTG | AGT | AAT | 2715 |
| Asn | Ala | Thr | Thr | Gln | Thr | Thr | Ser | Leu | Ser | Ala | Ser | Pro | Val | Ser | Asn | |
| 765 | | | | | 770 | | | | | 775 | | | | | 780 | |
| CTC | AGT | AAC | CCC | AGA | TAT | CCT | AAT | TAC | ATG | TTC | CCG | AGC | CAG | GGT | ATT | 2763 |
| Leu | Ser | Asn | Pro | Arg | Tyr | Pro | Asn | Tyr | Met | Phe | Pro | Ser | Gln | Gly | Ile | |
| | | | | 785 | | | | | 790 | | | | | 795 | | |
| ACA | CCA | CAG | GGC | CAG | ATT | GCT | GGT | TTC | ATT | GGC | CCG | CCA | ATA | CCT | CAG | 2811 |
| Thr | Pro | Gln | Gly | Gln | Ile | Ala | Gly | Phe | Ile | Gly | Pro | Pro | Ile | Pro | Gln | |
| | | | 800 | | | | | 805 | | | | | 810 | | | |
| AAC | CAG | CGA | TTC | ATT | CCC | ATC | AAT | GGA | TAC | CCA | ATA | CCT | CCT | GGA | TAT | 2859 |
| Asn | Gln | Arg | Phe | Ile | Pro | Ile | Asn | Gly | Tyr | Pro | Ile | Pro | Pro | Gly | Tyr | |
| | | 815 | | | | | 820 | | | | | 825 | | | | |
| GCA | GCG | TTT | CCA | GCT | GCC | CAC | TAC | CAG | CCA | ACA | GGT | CCT | CCC | AGA | GTG | 2907 |
| Ala | Ala | Phe | Pro | Ala | Ala | His | Tyr | Gln | Pro | Thr | Gly | Pro | Pro | Arg | Val | |
| | 830 | | | | | 835 | | | | | 840 | | | | | |
| ATT | CAG | CAC | TGC | CCA | CCT | CCC | AAG | AGT | CGG | TCC | CCA | AGC | AGT | GCC | AGT | 2955 |
| Ile | Gln | His | Cys | Pro | Pro | Pro | Lys | Ser | Arg | Ser | Pro | Ser | Ser | Ala | Ser | |
| 845 | | | | | 850 | | | | | 855 | | | | | 860 | |
| GGG | TCG | ACT | AGC | ACT | GGC | CAT | GTG | ACT | AGC | TTG | CCC | TCA | TCA | GGA | TCC | 3003 |
| Gly | Ser | Thr | Ser | Thr | Gly | His | Val | Thr | Ser | Leu | Pro | Ser | Ser | Gly | Ser | |
| | | | | 865 | | | | | 870 | | | | | 875 | | |
| AAT | CAG | GAA | GCA | AAT | ATT | CCT | TTA | CTA | CCA | CAC | ATG | TCA | ATT | CCA | AAT | 3051 |
| Asn | Gln | Glu | Ala | Asn | Ile | Pro | Leu | Leu | Pro | His | Met | Ser | Ile | Pro | Asn | |
| | | | 880 | | | | | 885 | | | | | 890 | | | |
| CAT | CCT | GGT | GGA | ATG | GGT | ATC | ACC | GTT | TTT | GGC | AAC | AAA | TCT | CAA | AAA | 3099 |
| His | Pro | Gly | Gly | Met | Gly | Ile | Thr | Val | Phe | Gly | Asn | Lys | Ser | Gln | Lys | |
| | | 895 | | | | | 900 | | | | | 905 | | | | |
| CCC | TAC | AAA | ATT | GAC | TCA | AAG | CAA | GCA | TCT | TTA | CTA | GGA | GAC | GCC | AAT | 3147 |
| Pro | Tyr | Lys | Ile | Asp | Ser | Lys | Gln | Ala | Ser | Leu | Leu | Gly | Asp | Ala | Asn | |
| | 910 | | | | | 915 | | | | | 920 | | | | | |
| ATT | CAT | GGA | CAC | ACC | GAA | TCT | ATG | ATT | TCT | GCA | GAA | CTG | TAAAATGCAC | AA | | 3198 |
| Ile | His | Gly | His | Thr | Glu | Ser | Met | Ile | Ser | Ala | Glu | Leu | | | | |
| 925 | | | | | 930 | | | | | 935 | | | | | | |
| CTTTTGTAAA | TGTGGTATAC | AGGACAAACT | AGACGGCCGT | AGAAAAGATT | TATATTCAAA | | | | | | | | | | | 3258 |
| TGTTTTTATT | AAAGTAAGGT | TCTCATTTAG | CAGACATCGC | AACAAGTACC | TTCTGTGAAG | | | | | | | | | | | 3318 |
| TTTCACTGTG | TCTTACCAAG | CAGGACAGAC | ACTCGGCCAG | | | | | | | | | | | | | 3358 |

( 2 ) INFORMATION FOR SEQ ID NO:105:

( i ) SEQUENCE CHARACTERISTICS:
        ( A ) LENGTH: 937 amino acids (B) TYPE: amino acid
(C) STRANDEDNESS: single
(D) TOPOLOGY: linear (ii) MOLECULE TYPE: protein (v) FRAGMENT TYPE: internal (ix) FEATURE:
(A) NAME/KEY: Human ROR1
(B) LOCATION: 1...937
(C) OTHER INFORMATION:

(xi) SEQUENCE DESCRIPTION: SEQ ID NO:105:

```
Met His Arg Pro Arg Arg Arg Gly Thr Arg Pro Pro Leu Leu Ala Leu
 1               5                  10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
                100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
                180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
            275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350
```

```
Pro  Glu  Leu  Asn  Gly  Gly  His  Ser  Tyr  Cys  Arg  Asn  Pro  Gly  Asn  Gln
          355                 360                      365

Lys  Glu  Ala  Pro  Trp  Cys  Phe  Thr  Leu  Asp  Glu  Asn  Phe  Lys  Ser  Asp
     370                 375                      380

Leu  Cys  Asp  Ile  Pro  Ala  Cys  Asp  Ser  Lys  Asp  Ser  Lys  Glu  Lys  Asn
385                      390                      395                      400

Lys  Met  Glu  Ile  Leu  Tyr  Ile  Leu  Val  Pro  Ser  Val  Ala  Ile  Pro  Leu
                    405                      410                      415

Ala  Ile  Ala  Leu  Leu  Phe  Phe  Phe  Ile  Cys  Val  Cys  Arg  Asn  Asn  Gln
               420                      425                      430

Lys  Ser  Ser  Ser  Ala  Pro  Val  Gln  Arg  Gln  Pro  Lys  His  Val  Arg  Gly
          435                      440                      445

Gln  Asn  Val  Glu  Met  Ser  Met  Leu  Asn  Ala  Tyr  Lys  Pro  Lys  Ser  Lys
     450                      455                      460

Ala  Lys  Glu  Leu  Pro  Leu  Ser  Ala  Val  Arg  Phe  Met  Glu  Glu  Leu  Gly
465                      470                      475                      480

Glu  Cys  Ala  Phe  Gly  Lys  Ile  Tyr  Lys  Gly  His  Leu  Tyr  Leu  Pro  Gly
                    485                      490                      495

Met  Asp  His  Ala  Gln  Leu  Val  Ala  Ile  Lys  Thr  Leu  Lys  Asp  Tyr  Asn
               500                      505                      510

Asn  Pro  Gln  Gln  Trp  Met  Glu  Phe  Gln  Gln  Glu  Ala  Ser  Leu  Met  Ala
          515                      520                      525

Glu  Leu  His  His  Pro  Asn  Ile  Val  Cys  Leu  Leu  Gly  Ala  Val  Thr  Gln
     530                      535                      540

Glu  Gln  Pro  Val  Cys  Met  Leu  Phe  Glu  Tyr  Ile  Asn  Gln  Gly  Asp  Leu
545                      550                      555                      560

His  Glu  Phe  Leu  Ile  Met  Arg  Ser  Pro  His  Ser  Asp  Val  Gly  Cys  Ser
                    565                      570                      575

Ser  Asp  Glu  Asp  Gly  Thr  Val  Lys  Ser  Ser  Leu  Asp  His  Gly  Asp  Phe
               580                      585                      590

Leu  His  Ile  Ala  Ile  Gln  Ile  Ala  Ala  Gly  Met  Glu  Tyr  Leu  Ser  Ser
          595                      600                      605

His  Phe  Phe  Val  His  Lys  Asp  Leu  Ala  Ala  Arg  Asn  Ile  Leu  Ile  Gly
     610                      615                      620

Glu  Gln  Leu  His  Val  Lys  Ile  Ser  Asp  Leu  Gly  Leu  Ser  Arg  Glu  Ile
625                      630                      635                      640

Tyr  Ser  Ala  Asp  Tyr  Tyr  Arg  Val  Gln  Ser  Lys  Ser  Leu  Leu  Pro  Ile
                    645                      650                      655

Arg  Trp  Met  Pro  Pro  Glu  Ala  Ile  Met  Tyr  Gly  Lys  Phe  Ser  Ser  Asp
               660                      665                      670

Ser  Asp  Ile  Trp  Ser  Phe  Gly  Val  Val  Leu  Trp  Glu  Ile  Phe  Ser  Phe
          675                      680                      685

Gly  Leu  Gln  Pro  Tyr  Tyr  Gly  Phe  Ser  Asn  Gln  Glu  Val  Ile  Glu  Met
     690                      695                      700

Val  Arg  Lys  Arg  Gln  Leu  Leu  Pro  Cys  Ser  Glu  Asp  Cys  Pro  Pro  Arg
705                      710                      715                      720

Met  Tyr  Ser  Leu  Met  Thr  Glu  Cys  Trp  Asn  Glu  Ile  Pro  Ser  Arg  Arg
                    725                      730                      735

Pro  Arg  Phe  Lys  Asp  Ile  His  Val  Arg  Leu  Arg  Ser  Trp  Glu  Gly  Leu
               740                      745                      750

Ser  Ser  His  Thr  Ser  Ser  Thr  Thr  Pro  Ser  Gly  Gly  Asn  Ala  Thr  Thr
          755                      760                      765

Gln  Thr  Thr  Ser  Leu  Ser  Ala  Ser  Pro  Val  Ser  Asn  Leu  Ser  Asn  Pro
```

|   |   |   |   |   | 770 |   |   |   |   | 775 |   |   |   |   | 780 |   |   |
|---|---|---|---|---|---|---|---|---|---|---|---|---|---|---|---|---|---|
| Arg | Tyr | Pro | Asn | Tyr | Met | Phe | Pro | Ser | Gln | Gly | Ile | Thr | Pro | Gln | Gly |
| 785 |   |   |   |   | 790 |   |   |   |   | 795 |   |   |   |   | 800 |

Gln Ile Ala Gly Phe Ile Gly Pro Pro Ile Pro Gln Asn Gln Arg Phe
                    805                 810                 815

Ile Pro Ile Asn Gly Tyr Pro Ile Pro Pro Gly Tyr Ala Ala Phe Pro
                820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
        850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
930                 935

( 2 ) INFORMATION FOR SEQ ID NO:106:

( i ) SEQUENCE CHARACTERISTICS:
        ( A ) LENGTH: 4092 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Coding Sequence
        ( B ) LOCATION: 200...3028
        ( D ) OTHER INFORMATION:
        ( A ) NAME/KEY: Human ROR2
        ( B ) LOCATION: 1...4092
        ( D ) OTHER INFORMATION:

( x i ) SEQUENCE DESCRIPTION: SEQ ID NO:106:

AGCCAGCCCT TGCCGTGGCC GGAGCCGAGC GGCGCATCCG GGCCGGAGAA GAGGACGACG    60

ACGAGGTCCT CGAAGTGGAC CCGTTTGCGA AGCGCCAGGG AGAAGGAGGA GCGGACGCAT   120

CGTAGAAAGG GGTGGTGGCG CCCGACCCCG CGCCCCGGCC CGAAGCTCTG AGGGCTTCCC   180

GGCCCCCACT GCCTGCGGC ATG GCC CGG GGC TCG GCG CTC CCG CGG CGG CCG   232
                        Met Ala Arg Gly Ser Ala Leu Pro Arg Arg Pro
                       1           5                  10

CTG CTG TGC ATC CCG GCC GTC TGG GCG GCC GCC GCG CTT CTG CTC TCA   280
Leu Leu Cys Ile Pro Ala Val Trp Ala Ala Ala Ala Leu Leu Leu Ser
        15                      20                 25

GTG TCC CGG ACT TCA GGT GAA GTG GAG GTT CTG GAT CCG AAC GAC CCT   328
Val Ser Arg Thr Ser Gly Glu Val Glu Val Leu Asp Pro Asn Asp Pro
        30                      35                 40

TTA GGA CCC CTT GAT GGG CAG GAC GGC CCG ATT CCA ACT CTG AAA GGT   376
Leu Gly Pro Leu Asp Gly Gln Asp Gly Pro Ile Pro Thr Leu Lys Gly
    45                      50                 55

TAC TTT CTG AAT TTT CTG GAG CCA GTA AAC AAT ATC ACC ATT GTC CAA   424
Tyr Phe Leu Asn Phe Leu Glu Pro Val Asn Asn Ile Thr Ile Val Gln
60                     65                 70                 75

GGC CAG ACG GCA ATT CTG CAC TGC AAG GTG GCA GGA AAC CCA CCC CCT   472

```
Gly Gln Thr Ala Ile Leu His Cys Lys Val Ala Gly Asn Pro Pro Pro
                80                    85                90

AAC GTG CGG TGG CTA AAG AAT GAT GCC CCG GTG GTG CAG GAG CCG CGG        520
Asn Val Arg Trp Leu Lys Asn Asp Ala Pro Val Val Gln Glu Pro Arg
            95                  100                 105

CGG ATC ATC ATC CGG AAG ACA GAA TAT GGT TCA CGA CTG CGA ATC CAG        568
Arg Ile Ile Ile Arg Lys Thr Glu Tyr Gly Ser Arg Leu Arg Ile Gln
            110                 115                 120

GAC CTG GAC ACG ACA GAC ACT GGC TAC TAC CAG TGC GTG GCC ACC AAC        616
Asp Leu Asp Thr Thr Asp Thr Gly Tyr Tyr Gln Cys Val Ala Thr Asn
        125                 130                 135

GGG ATG AAG ACC ATT ACC GCC ACT GGC GTC CTG TTT GTG CGG CTG GGT        664
Gly Met Lys Thr Ile Thr Ala Thr Gly Val Leu Phe Val Arg Leu Gly
140             145                 150                 155

CCA ACG CAC AGC CCA AAT CAT AAC TTT CAG GAT GAT TAC CAC GAG GAT        712
Pro Thr His Ser Pro Asn His Asn Phe Gln Asp Asp Tyr His Glu Asp
                160                 165                 170

GGG TTC TGC CAG CCT TAC CGG GGA ATT GCC TGT GCA CGC TTC ATT GGC        760
Gly Phe Cys Gln Pro Tyr Arg Gly Ile Ala Cys Ala Arg Phe Ile Gly
            175                 180                 185

AAC CGG ACC ATT TAT GTG GAC TCG CTT CAG ATG CAG GGG GAG ATT GAA        808
Asn Arg Thr Ile Tyr Val Asp Ser Leu Gln Met Gln Gly Glu Ile Glu
        190                 195                 200

AAC CGA ATC ACA GCG GCC TTC ACC ATG ATC GGC ACG TCT ACG CAC CTG        856
Asn Arg Ile Thr Ala Ala Phe Thr Met Ile Gly Thr Ser Thr His Leu
    205                 210                 215

TCG GAC CAG TGC TCA CAG TTC GCC ATC CCA TCC TTC TGC CAC TTC GTG        904
Ser Asp Gln Cys Ser Gln Phe Ala Ile Pro Ser Phe Cys His Phe Val
220             225                 230                 235

TTT CCT CTG TGC GAC GCG CGC TCC CGG GCA CCC AAG CCG CGT GAG CTG        952
Phe Pro Leu Cys Asp Ala Arg Ser Arg Ala Pro Lys Pro Arg Glu Leu
                240                 245                 250

TGC CGC GAC GAG TGC GAG GTG CTG GAG AGC GAC CTG TGC CGC CAG GAG        1000
Cys Arg Asp Glu Cys Glu Val Leu Glu Ser Asp Leu Cys Arg Gln Glu
            255                 260                 265

TAC ACC ATC GCC CGC TCC AAC CCG CTC ATC CTC ATG CGG CTT CAG CTG        1048
Tyr Thr Ile Ala Arg Ser Asn Pro Leu Ile Leu Met Arg Leu Gln Leu
        270                 275                 280

CCC AAG TGT GAG GCG CTG CCC ATG CCT GAG AGC CCC GAC GCT GCC AAC        1096
Pro Lys Cys Glu Ala Leu Pro Met Pro Glu Ser Pro Asp Ala Ala Asn
    285                 290                 295

TGC ATG CGC ATT GGC ATC CCA GCC GAG AGG CTG GGC CGC TAC CAT CAG        1144
Cys Met Arg Ile Gly Ile Pro Ala Glu Arg Leu Gly Arg Tyr His Gln
300             305                 310                 315

TGC TAT AAC GGC TCA GGC ATG GAT TAC AGA GGA ACG GCA AGC ACC ACC        1192
Cys Tyr Asn Gly Ser Gly Met Asp Tyr Arg Gly Thr Ala Ser Thr Thr
                320                 325                 330

AAG TCA GGC CAC CAG TGC CAG CCG TGG GCC CTG CAG CAC CCC CAC AGC        1240
Lys Ser Gly His Gln Cys Gln Pro Trp Ala Leu Gln His Pro His Ser
            335                 340                 345

CAC CAC CTG TCC AGC ACA GAC TTC CCT GAG CTT GGA GGG GGC CAC GCC        1288
His His Leu Ser Ser Thr Asp Phe Pro Glu Leu Gly Gly Gly His Ala
        350                 355                 360

TAC TGC CGG AAC CCC GGA GGC CAG ATG GAG GGC CCC TGG TGC TTT ACG        1336
Tyr Cys Arg Asn Pro Gly Gly Gln Met Glu Gly Pro Trp Cys Phe Thr
    365                 370                 375

CAG AAT AAA AAC GTA CGC ATG GAA CTG TGT GAC GTA CCC TCG TGT AGT        1384
Gln Asn Lys Asn Val Arg Met Glu Leu Cys Asp Val Pro Ser Cys Ser
380             385                 390                 395

CCC CGA GAC AGC AGC AAG ATG GGG ATT CTG TAC ATC TTG GTC CCC AGC        1432
```

| | | | | | | | | | | | | | | | | |
|---|---|---|---|---|---|---|---|---|---|---|---|---|---|---|---|---|
| Pro | Arg | Asp | Ser | Ser<br>400 | Lys | Met | Gly | Ile | Leu<br>405 | Tyr | Ile | Leu | Val | Pro<br>410 | Ser | |
| ATC<br>Ile | GCA<br>Ala | ATT<br>Ile | CCA<br>Pro<br>415 | CTG<br>Leu | GTC<br>Val | ATC<br>Ile | GCT<br>Ala | TGC<br>Cys<br>420 | CTT<br>Leu | TTC<br>Phe | TTC<br>Phe | TTG<br>Leu | GTT<br>Val<br>425 | TGC<br>Cys | ATG<br>Met | 1480 |
| TGC<br>Cys | CGG<br>Arg | AAT<br>Asn<br>430 | AAG<br>Lys | CAG<br>Gln | AAG<br>Lys | GCA<br>Ala | TCT<br>Ser<br>435 | GCG<br>Ala | TCC<br>Ser | ACA<br>Thr | CCG<br>Pro | CAG<br>Gln<br>440 | CGG<br>Arg | CGA<br>Arg | CAG<br>Gln | 1528 |
| CTG<br>Leu | ATG<br>Met<br>445 | GCC<br>Ala | TCG<br>Ser | CCC<br>Pro | AGC<br>Ser | CAA<br>Gln<br>450 | GAC<br>Asp | ATG<br>Met | GAA<br>Glu | ATG<br>Met | CCC<br>Pro<br>455 | CTC<br>Leu | ATT<br>Ile | AAC<br>Asn | CAG<br>Gln | 1576 |
| CAC<br>His<br>460 | AAA<br>Lys | CAG<br>Gln | GCC<br>Ala | AAA<br>Lys | CTC<br>Leu<br>465 | AAA<br>Lys | GAG<br>Glu | ATC<br>Ile | AGC<br>Ser | CTG<br>Leu<br>470 | TCT<br>Ser | GCG<br>Ala | GTG<br>Val | AGG<br>Arg | TTC<br>Phe<br>475 | 1624 |
| ATG<br>Met | GAG<br>Glu | GAG<br>Glu | CTG<br>Leu | GGA<br>Gly<br>480 | GAG<br>Glu | GAC<br>Asp | CGG<br>Arg | TTT<br>Phe | GGG<br>Gly<br>485 | AAA<br>Lys | GTC<br>Val | TAC<br>Tyr | AAA<br>Lys | GGT<br>Gly<br>490 | CAC<br>His | 1672 |
| CTG<br>Leu | TTC<br>Phe | GGC<br>Gly | CCT<br>Pro<br>495 | GCC<br>Ala | CCG<br>Pro | GGG<br>Gly | GAG<br>Glu | CAG<br>Gln<br>500 | ACC<br>Thr | CAG<br>Gln | GCT<br>Ala | GTG<br>Val | GCC<br>Ala<br>505 | ATC<br>Ile | AAA<br>Lys | 1720 |
| ACG<br>Thr | CTG<br>Leu | AAG<br>Lys<br>510 | GAC<br>Asp | AAA<br>Lys | GCG<br>Ala | GAG<br>Glu | GGG<br>Gly<br>515 | CCC<br>Pro | CTG<br>Leu | CGG<br>Arg | GAG<br>Glu | GAG<br>Glu<br>520 | TTC<br>Phe | CGG<br>Arg | CAT<br>His | 1768 |
| GAG<br>Glu | GCT<br>Ala<br>525 | ATG<br>Met | CTG<br>Leu | CGA<br>Arg | GCA<br>Ala | CGG<br>Arg<br>530 | CTG<br>Leu | CAA<br>Gln | CAC<br>His | CCC<br>Pro | AAC<br>Asn<br>535 | GTC<br>Val | GTC<br>Val | TGC<br>Cys | CTG<br>Leu | 1816 |
| CTG<br>Leu<br>540 | GGC<br>Gly | GTG<br>Val | GTG<br>Val | ACC<br>Thr | AAG<br>Lys<br>545 | GAC<br>Asp | CAG<br>Gln | CCC<br>Pro | CTG<br>Leu | AGC<br>Ser<br>550 | ATG<br>Met | ATC<br>Ile | TTC<br>Phe | AGC<br>Ser | TAC<br>Tyr<br>555 | 1864 |
| TGT<br>Cys | TCG<br>Ser | CAC<br>His | GGC<br>Gly | GAC<br>Asp<br>560 | CTC<br>Leu | CAC<br>His | GAA<br>Glu | TTC<br>Phe | CTG<br>Leu<br>565 | GTC<br>Val | ATG<br>Met | CGC<br>Arg | TCG<br>Ser | CCG<br>Pro<br>570 | CAC<br>His | 1912 |
| TCG<br>Ser | GAC<br>Asp | GTG<br>Val | GGC<br>Gly<br>575 | AGC<br>Ser | ACC<br>Thr | GAT<br>Asp | GAT<br>Asp | GAC<br>Asp<br>580 | CGC<br>Arg | ACG<br>Thr | GTG<br>Val | AAG<br>Lys | TCC<br>Ser<br>585 | GCC<br>Ala | CTG<br>Leu | 1960 |
| GAG<br>Glu | CCC<br>Pro | CCC<br>Pro<br>590 | GAC<br>Asp | TTC<br>Phe | GTG<br>Val | CAC<br>His | CTT<br>Leu<br>595 | GTG<br>Val | GCA<br>Ala | CAG<br>Gln | ATC<br>Ile | GCG<br>Ala<br>600 | GCG<br>Ala | GGG<br>Gly | ATG<br>Met | 2008 |
| GAG<br>Glu | TAC<br>Tyr<br>605 | CTA<br>Leu | TCC<br>Ser | AGC<br>Ser | CAC<br>His | CAC<br>His<br>610 | GTG<br>Val | GTT<br>Val | CAC<br>His | AAG<br>Lys | GAC<br>Asp<br>615 | CTG<br>Leu | GCC<br>Ala | ACC<br>Thr | CGC<br>Arg | 2056 |
| AAT<br>Asn<br>620 | GTG<br>Val | CTA<br>Leu | GTG<br>Val | TAC<br>Tyr | GAC<br>Asp<br>625 | AAG<br>Lys | CTG<br>Leu | AAC<br>Asn | GTG<br>Val | AAG<br>Lys<br>630 | ATC<br>Ile | TCA<br>Ser | GAC<br>Asp | TTG<br>Leu | GGC<br>Gly<br>635 | 2104 |
| CTC<br>Leu | TTC<br>Phe | CGA<br>Arg | GAG<br>Glu | GTG<br>Val<br>640 | TAT<br>Tyr | GCC<br>Ala | GCC<br>Ala | GAT<br>Asp | TAC<br>Tyr<br>645 | TAC<br>Tyr | AAG<br>Lys | CTG<br>Leu | CTG<br>Leu | GGG<br>Gly<br>650 | AAC<br>Asn | 2152 |
| TCG<br>Ser | CTG<br>Leu | CTG<br>Leu | CCT<br>Pro<br>655 | ATC<br>Ile | CGC<br>Arg | TGG<br>Trp | ATG<br>Met | GCC<br>Ala<br>660 | CCA<br>Pro | GAG<br>Glu | GCC<br>Ala | ATC<br>Ile | ATG<br>Met<br>665 | TAC<br>Tyr | GGC<br>Gly | 2200 |
| AAG<br>Lys | TTC<br>Phe | TCC<br>Ser<br>670 | ATC<br>Ile | GAC<br>Asp | TCA<br>Ser | GAC<br>Asp | ATC<br>Ile<br>675 | TGG<br>Trp | TCC<br>Ser | TAC<br>Tyr | GGT<br>Gly | GTG<br>Val<br>680 | GTC<br>Val | CTG<br>Leu | TGG<br>Trp | 2248 |
| GAG<br>Glu | GTC<br>Val<br>685 | TTC<br>Phe | AGC<br>Ser | TAC<br>Tyr | GGC<br>Gly | CTG<br>Leu<br>690 | CAG<br>Gln | CCC<br>Pro | TAC<br>Tyr | TGC<br>Cys | GGG<br>Gly<br>695 | TAC<br>Tyr | TCC<br>Ser | AAC<br>Asn | CAG<br>Gln | 2296 |
| GAT<br>Asp<br>700 | GTG<br>Val | GTG<br>Val | GAG<br>Glu | ATG<br>Met | ATC<br>Ile<br>705 | CGG<br>Arg | AAC<br>Asn | CGG<br>Arg | CAG<br>Gln | GTG<br>Val<br>710 | CTG<br>Leu | CCT<br>Pro | TGC<br>Cys | CCC<br>Pro | GAT<br>Asp<br>715 | 2344 |
| GAC<br>Asp | TGT<br>Cys | CCC<br>Pro | GCC<br>Ala | TGG<br>Trp | GTG<br>Val | TAT<br>Tyr | GCC<br>Ala | CTC<br>Leu | ATG<br>Met | ATC<br>Ile | GAG<br>Glu | TGC<br>Cys | TGG<br>Trp | AAC<br>Asn | GAG<br>Glu | 2392 |

```
Asp Cys Pro Ala Trp Val Tyr Ala Leu Met Ile Glu Cys Trp Asn Glu
            720                 725                 730

TTC CCC AGC CGG CGG CCC CGC TTC AAG GAC ATC CAC AGC CGG CTC CGA    2440
Phe Pro Ser Arg Arg Pro Arg Phe Lys Asp Ile His Ser Arg Leu Arg
            735                 740                 745

GCC TGG GGC AAC CTT TCC AAC TAC AAC AGC TCG GCG CAG ACC TCG GGG    2488
Ala Trp Gly Asn Leu Ser Asn Tyr Asn Ser Ser Ala Gln Thr Ser Gly
            750                 755                 760

GCC AGC AAC ACC ACG CAG ACC AGC TCC CTG AGC ACC AGC CCA GTG AGC    2536
Ala Ser Asn Thr Thr Gln Thr Ser Ser Leu Ser Thr Ser Pro Val Ser
765                 770                 775

AAT GTG AGC AAC GCC CGC TAC GTG GGG CCC AAG CAG AAG GCC CCG CCC    2584
Asn Val Ser Asn Ala Arg Tyr Val Gly Pro Lys Gln Lys Ala Pro Pro
780                 785                 790                 795

TTC CCA CAG CCC CAG TTC ATC CCC ATG AAG GGC CAG ATC AGA CCC ATG    2632
Phe Pro Gln Pro Gln Phe Ile Pro Met Lys Gly Gln Ile Arg Pro Met
                800                 805                 810

GTG CCC CCG CCG CAG CTC TAC GTC CCC GTC AAC GGC TAC CAG CCG GTG    2680
Val Pro Pro Pro Gln Leu Tyr Val Pro Val Asn Gly Tyr Gln Pro Val
            815                 820                 825

CCG GCC TAT GGG GCC TAC CTG CCC AAC TTC TAC CCG GTG CAG ATC CCA    2728
Pro Ala Tyr Gly Ala Tyr Leu Pro Asn Phe Tyr Pro Val Gln Ile Pro
            830                 835                 840

ATG CAG ATG GCC CCG CAG CAG GTG CCT CCT CAG ATG GTC CCC AAG CCC    2776
Met Gln Met Ala Pro Gln Gln Val Pro Pro Gln Met Val Pro Lys Pro
845                 850                 855

AGC TCA CAC CAC AGT GGC AGT GGC TCC ACC AGC ACA GGC TAC GTC ACC    2824
Ser Ser His His Ser Gly Ser Gly Ser Thr Ser Thr Gly Tyr Val Thr
860                 865                 870                 875

ACG GCC CCC TCC AAC ACA TCC ATG GCA GAC AGG GCA GCC CTG CTC TCA    2872
Thr Ala Pro Ser Asn Thr Ser Met Ala Asp Arg Ala Ala Leu Leu Ser
                880                 885                 890

GAG GGC GCT GAT GAC ACA CAG AAC GCC CCA GAA GAT GGG GCC CAG AGC    2920
Glu Gly Ala Asp Asp Thr Gln Asn Ala Pro Glu Asp Gly Ala Gln Ser
            895                 900                 905

ACC GTG CAG GAA GCA GAG GAG GAG GAA GGC TCT GTC CCA GAG ACT        2968
Thr Val Gln Glu Ala Glu Glu Glu Glu Gly Ser Val Pro Glu Thr
            910                 915                 920

GAG CTG CTG GGG GAC TGT GAC ACT CTG CAG GTG GAC GAG GCC CAA GTC    3016
Glu Leu Leu Gly Asp Cys Asp Thr Leu Gln Val Asp Glu Ala Gln Val
925                 930                 935

CAG CTG GAA GCT TGAGTGGCAC CAGGGCCCGG GGTTCGGGGA TAGAAGCCCC GCCGA  3073
Gln Leu Glu Ala
940

GACCCCACAG GGACCTCAGT CACCTTTGAG AAGACACCAT ACTCAGCAAT CACAAGAGCC  3133

CGCCGGCCAG TGGGCTTGTT TGCAGACTGG GTGAGGTGGA GCCCTGCTCC TCTCTGTCCT  3193

CTGACACAGA GAGCTGCCCT GCCTAGGAGC ACCCAAGCCA GGCAGGGGGT CTGGCAGCAC  3253

GGCGTCCTGG GGAGCAGGAC ACATGGTCAT CCCCAGGGCT GTATACATTG ATTCTGGTGG  3313

TAGACTGGTA GTGAGCAGCA AATGCCTTTC AAGAAAATAG GTGGCAGCTT CACTCCATGT  3373

CATATATGGA GTGAATATTT CAAAACGTTG GAATAAGGG CCTGCAAAAG GCAGCGAGGA   3433

GGCACCTCGG GTCTTGAGGT TCCTGACAAC CGATCTGGTC TGTTGGTTTG AGGATGAAGG  3493

GGCTCCATTT CTGCTGCCTC CCTGCTGAGA ATATTCTCCC TTTAGCAGCC AAAGATTCGC  3553

TGGAACGGAG GCTGCCCTCT GCTGCCTGTT GGGGTCGGAA GACAAGGGGC TTCTGAAATG  3613

GGAGTTCCTG AGATACAACA AAATGTGTGC CTTCAAGAA ACTGACAGCT TTGTATTTGG   3673

TGAAATGGTT TTAATTATAC TCCATGTGTA TTTTGCCCAC TTTTTTTGGG AATTCAAGGG  3733
```

| | | | | | |
|---|---|---|---|---|---|
| AAAGTGTTTC | TTGGGTTTGG | AATGTTCAGA | GGAAGCAGTA | TTGTACAGAA | CACGGTATTG 3793 |
| TTATTTTTGT | TAAGAATCAT | GTACAGAGCT | TAAATGTAAT | TTATATGTTT | TTAATATGCC 3853 |
| ATTTTCATTG | AAGTATTTTG | GTCTTAAGAT | GACTTTAGTA | ATTTAACTGT | TTATGTTACC 3913 |
| CACGTTGGGA | TCCAGTTGGT | CTTGGTTTGC | TTCTCTCTGT | ACCACGTGCA | CATGAGGTCC 3973 |
| ATTCATTTTA | CAGCCCCTGT | TACACACAGA | CCCACAGGCA | GCCGTCTGTG | CCCGCACACA 4033 |
| TTGTTGGTCC | TATTTGTAAA | TCCCACACCC | GGTGTATCCA | ATAAAGTGAA | ACCAACCCC 4092 |

( 2 ) INFORMATION FOR SEQ ID NO:107:

( i ) SEQUENCE CHARACTERISTICS:
        ( A ) LENGTH: 943 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( i x ) FEATURE:
        ( A ) NAME/KEY: Human ROR2
        ( B ) LOCATION: 1...943
        ( C ) OTHER INFORMATION:

( x i ) SEQUENCE DESCRIPTION: SEQ ID NO:107:

```
Met Ala Arg Gly Ser Ala Leu Pro Arg Arg Pro Leu Leu Cys Ile Pro
 1               5                  10                  15

Ala Val Trp Ala Ala Ala Leu Leu Leu Ser Val Ser Arg Thr Ser
                20              25                  30

Gly Glu Val Glu Val Leu Asp Pro Asn Asp Pro Leu Gly Pro Leu Asp
            35                  40                  45

Gly Gln Asp Gly Pro Ile Pro Thr Leu Lys Gly Tyr Phe Leu Asn Phe
        50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Met Lys Thr Ile
        130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
        210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
                245                 250                 255
```

```
Glu  Val  Leu  Glu  Ser  Asp  Leu  Cys  Arg  Gln  Glu  Tyr  Thr  Ile  Ala  Arg
               260                 265                 270

Ser  Asn  Pro  Leu  Ile  Leu  Met  Arg  Leu  Gln  Leu  Pro  Lys  Cys  Glu  Ala
          275                 280                 285

Leu  Pro  Met  Pro  Glu  Ser  Pro  Asp  Ala  Ala  Asn  Cys  Met  Arg  Ile  Gly
          290                 295                 300

Ile  Pro  Ala  Glu  Arg  Leu  Gly  Arg  Tyr  His  Gln  Cys  Tyr  Asn  Gly  Ser
305                      310                 315                           320

Gly  Met  Asp  Tyr  Arg  Gly  Thr  Ala  Ser  Thr  Thr  Lys  Ser  Gly  His  Gln
                    325                 330                      335

Cys  Gln  Pro  Trp  Ala  Leu  Gln  His  Pro  His  Ser  His  His  Leu  Ser  Ser
               340                 345                      350

Thr  Asp  Phe  Pro  Glu  Leu  Gly  Gly  Gly  His  Ala  Tyr  Cys  Arg  Asn  Pro
          355                      360                 365

Gly  Gly  Gln  Met  Glu  Gly  Pro  Trp  Cys  Phe  Thr  Gln  Asn  Lys  Asn  Val
     370                      375                 380

Arg  Met  Glu  Leu  Cys  Asp  Val  Pro  Ser  Cys  Ser  Pro  Arg  Asp  Ser  Ser
385                      390                 395                           400

Lys  Met  Gly  Ile  Leu  Tyr  Ile  Leu  Val  Pro  Ser  Ile  Ala  Ile  Pro  Leu
               405                 410                      415

Val  Ile  Ala  Cys  Leu  Phe  Phe  Leu  Val  Cys  Met  Cys  Arg  Asn  Lys  Gln
               420                 425                 430

Lys  Ala  Ser  Ala  Ser  Thr  Pro  Gln  Arg  Arg  Gln  Leu  Met  Ala  Ser  Pro
               435                 440                 445

Ser  Gln  Asp  Met  Glu  Met  Pro  Leu  Ile  Asn  Gln  His  Lys  Gln  Ala  Lys
          450                 455                 460

Leu  Lys  Glu  Ile  Ser  Leu  Ser  Ala  Val  Arg  Phe  Met  Glu  Glu  Leu  Gly
465                      470                 475                           480

Glu  Asp  Arg  Phe  Gly  Lys  Val  Tyr  Lys  Gly  His  Leu  Phe  Gly  Pro  Ala
               485                 490                      495

Pro  Gly  Glu  Gln  Thr  Gln  Ala  Val  Ala  Ile  Lys  Thr  Leu  Lys  Asp  Lys
               500                 505                      510

Ala  Glu  Gly  Pro  Leu  Arg  Glu  Glu  Phe  Arg  His  Glu  Ala  Met  Leu  Arg
          515                 520                 525

Ala  Arg  Leu  Gln  His  Pro  Asn  Val  Val  Cys  Leu  Leu  Gly  Val  Val  Thr
     530                 535                 540

Lys  Asp  Gln  Pro  Leu  Ser  Met  Ile  Phe  Ser  Tyr  Cys  Ser  His  Gly  Asp
545                 550                 555                           560

Leu  His  Glu  Phe  Leu  Val  Met  Arg  Ser  Pro  His  Ser  Asp  Val  Gly  Ser
               565                 570                      575

Thr  Asp  Asp  Asp  Arg  Thr  Val  Lys  Ser  Ala  Leu  Glu  Pro  Pro  Asp  Phe
               580                 585                 590

Val  His  Leu  Val  Ala  Gln  Ile  Ala  Ala  Gly  Met  Glu  Tyr  Leu  Ser  Ser
          595                 600                 605

His  His  Val  Val  His  Lys  Asp  Leu  Ala  Thr  Arg  Asn  Val  Leu  Val  Tyr
     610                 615                 620

Asp  Lys  Leu  Asn  Val  Lys  Ile  Ser  Asp  Leu  Gly  Leu  Phe  Arg  Glu  Val
625                 630                 635                           640

Tyr  Ala  Ala  Asp  Tyr  Tyr  Lys  Leu  Leu  Gly  Asn  Ser  Leu  Leu  Pro  Ile
               645                 650                      655

Arg  Trp  Met  Ala  Pro  Glu  Ala  Ile  Met  Tyr  Gly  Lys  Phe  Ser  Ile  Asp
               660                 665                      670

Ser  Asp  Ile  Trp  Ser  Tyr  Gly  Val  Val  Leu  Trp  Glu  Val  Phe  Ser  Tyr
```

```
                675                         680                         685
Gly  Leu  Gln  Pro  Tyr  Cys  Gly  Tyr  Ser  Asn  Gln  Asp  Val  Val  Glu  Met
     690                      695                      700

Ile  Arg  Asn  Arg  Gln  Val  Leu  Pro  Cys  Pro  Asp  Asp  Cys  Pro  Ala  Trp
705                      710                      715                      720

Val  Tyr  Ala  Leu  Met  Ile  Glu  Cys  Trp  Asn  Glu  Phe  Pro  Ser  Arg  Arg
               725                      730                           735

Pro  Arg  Phe  Lys  Asp  Ile  His  Ser  Arg  Leu  Arg  Ala  Trp  Gly  Asn  Leu
               740                 745                      750

Ser  Asn  Tyr  Asn  Ser  Ser  Ala  Gln  Thr  Ser  Gly  Ala  Ser  Asn  Thr  Thr
          755                      760                      765

Gln  Thr  Ser  Ser  Leu  Ser  Thr  Ser  Pro  Val  Ser  Asn  Val  Ser  Asn  Ala
     770                      775                      780

Arg  Tyr  Val  Gly  Pro  Lys  Gln  Lys  Ala  Pro  Pro  Phe  Pro  Gln  Pro  Gln
785                      790                      795                      800

Phe  Ile  Pro  Met  Lys  Gly  Gln  Ile  Arg  Pro  Met  Val  Pro  Pro  Pro  Gln
                    805                      810                      815

Leu  Tyr  Val  Pro  Val  Asn  Gly  Tyr  Gln  Pro  Val  Pro  Ala  Tyr  Gly  Ala
               820                      825                      830

Tyr  Leu  Pro  Asn  Phe  Tyr  Pro  Val  Gln  Ile  Pro  Met  Gln  Met  Ala  Pro
          835                      840                 845

Gln  Gln  Val  Pro  Pro  Gln  Met  Val  Pro  Lys  Pro  Ser  Ser  His  His  Ser
     850                      855                      860

Gly  Ser  Gly  Ser  Thr  Ser  Thr  Gly  Tyr  Val  Thr  Thr  Ala  Pro  Ser  Asn
865                      870                      875                      880

Thr  Ser  Met  Ala  Asp  Arg  Ala  Ala  Leu  Leu  Ser  Glu  Gly  Ala  Asp  Asp
               885                           890                      895

Thr  Gln  Asn  Ala  Pro  Glu  Asp  Gly  Ala  Gln  Ser  Thr  Val  Gln  Glu  Ala
               900                 905                      910

Glu  Glu  Glu  Glu  Glu  Gly  Ser  Val  Pro  Glu  Thr  Glu  Leu  Leu  Gly  Asp
          915                 920                      925

Cys  Asp  Thr  Leu  Gln  Val  Asp  Glu  Ala  Gln  Val  Gln  Leu  Glu  Ala
     930                 935                      940
```

EHK AND ROR TYROSINE KINASES

This is a continuation of application Ser. No. 08/406,247 filed Mar. 17, 1995, now abandoned, entitled "Ehk and Ror Tyrosine Kinases", which is a continuation-in-part of U.S. patent application Ser. No. 08/144,992 filed on Oct. 28, 1993, now abandoned, entitled "Assay Systems for Neurotrophin Activity" which is a continuation-in-part of U.S. patent application Ser. No. 07/736,559 filed on Jul. 26, 1991, now abandoned, entitled "Assay Systems for Neurotrophin Activity".

1. INTRODUCTION

The present invention provides for assay systems that may be used to detect and/or measure neurotrophin activity or to identify agents that exhibit neurotrophin-like activity. It is based, at least in part, on the discovery that the trkB proto-oncogene encodes a tyrosine kinase receptor that may serve as a functional binding protein for BDNF and NT-3. The present invention also provides for diagnostic and therapeutic methods based on the interaction between BDNF and/or NT-3 and trkB, and for a number of orphan receptor molecules, including members of the TIE and EHK family of receptor tyrosine kinases.

2. BACKGROUND OF THE INVENTION

The development and maintenance of the vertebrate nervous system depends on specific proteins, termed neurotrophic factors, originally defined by their ability to support the survival of neuronal populations (Snider and Johnson, 1989, Ann. Neurol. 26:489). Neurotrophic factors have also been implicated in processes involving the proliferation and differentiation of neurons (Cattaneo and McKay, 1990, Nature 347: 762–765; Lindsay and Harmar, 1989, Nature 337: 362–364), and they may play additional, thus far unexplored, roles both within as well as outside of the nervous system. Brain-derived neurotrophic factor (BDNF) and neurotrophin-3 (NT-3) have recently been molecularly cloned and shown to be structurally related to the prototypical neuronal survival molecule, nerve growth factor (NGF; Leibrock, et al., 1989, Nature 341:149–152; Hohn, et al., 1990, Nature 344:339–341; Maisonpierre, et al., 1990a, Science 247:1446–1451; Rosenthal, et al., 1990, Neuron 4:767–773; Ernfors, et al., 1990, Proc. Natl. Acad. Sci. U.S.A. 87:5454–5458; Jones and Reichardt, 1990, Proc. Natl. Acad. Sci. U.S.A. 87:8060–8064). These three related factors (designated "neurotrophins") do not display any structural homology to a fourth neurotrophic factor, ciliary neurotrophic factor (CNTF; Lin, et al., 1989, Science 246:1023–1025; Stockli, et al., 1989, Nature 342:920–923).

The receptor and signal transduction pathways utilized by NGF have been extensively studied, in large part due to the availability of a pheochromocytoma cell line (PC12) which differentiates in response to NGF (Greene and Tischler, 1976, Proc. Natl. Acad. Sci. U.S.A. 73:2424). These studies have resulted in the cloning of a transmembrane protein (designated "LNGFR" for low-affinity NGF receptor) which binds NGF with relatively low affinity (Chao, et al., 1986, Science 232:518–521; Radeke, et al., 1987, Nature 325:593–597). In addition to the LNGFR another protein (designated "HNGFR" for high-affinity NGF receptor), which is involved in forming a higher affinity binding site for NGF, is apparently required to initiate NGF-induced signal transduction (Zimmerman, et al., 1978, J. Supramol. Struc. 9:351–361; Sutter, et al., 1979 in Transmembrane Signalling (N.Y. Alan Liss) pp. 659–667; Bernd and Greene, 1984, J. Bio. Chem. 259:15509–15516; Hempstead, et al., 1989, Science 243:373–375). This HNGFR is phosphorylated on tyrosine in response to NGF, and apparently contains intrinsic tyrosine kinase activity (Meakin and Shooter, 1991a, Neuron 6:153–163). Furthermore, the ERK kinases (also known as the MAP2 kinases), early intermediates in tyrosine kinase activated signal cascades, are rapidly activated and phosphorylated on tyrosine in response to NGF. Thus, like many other growth factor responses, NGF signal transduction may be initiated by the activation of a receptor-linked tyrosine kinase.

Recent studies have revealed that the product of the trk proto-oncogene, which resembles a growth factor receptor (i.e., it is a transmembrane protein containing an intracytoplasmic tyrosine kinase domain) for which no ligand had been identified, is rapidly phosphorylated in response to NGF treatment in PC12 cells (Kaplan, et al., 1991, Nature 350:156–160; Klein, et al., 1991, Cell 65:189–197) and to directly bind NGF with relatively high affinity when expressed in heterologous cells (Klein, et al. supra). This finding, together with the restricted neuronal distribution of the trk protein in vivo, suggests that trk may be the component of the HNGFR responsible for initiating NGF signal transduction.

In contrast to the extensive study of NGF receptors and signal transduction pathways, the receptors and signal transduction pathways utilized by the other neurotrophic factors have only recently begun to be explored. However, BDNF appears to bind to the LNGFR with an affinity similar to that of NGF (Rodriguez-Tebar, et al., 1990, Neuron 4:487–492). Although both low and high affinity receptors for BDNF exist on neurons responsive to BDNF, the findings that BDNF and NGF act on different neurons and that NGF-responsive neurons do not express high-affinity BDNF receptors suggest that BDNF utilizes a different high affinity receptor than NGF (Rodriguez-Tebar and Barde, 1988, J. Neurosc. 8:3337–3342).

A variety of findings seem to link BDNF and NT-3, while distinguishing both of these neurotrophins from NGF. NT-3 and BDNF (but not NGF) expression displays striking reciprocal relationships during development, with NT-3 being expressed more prominently early and BDNF more prominently late during the development of some of the same brain regions (Maisonpierre et al., 1990, Neuron 5: 501–509). Interestingly, the distribution profiles that BDNF and NT-3 (but not NGF) ultimately achieve in various adult brain regions are quite similar. Id. In peripheral ganglia both BDNF and NT-3 (but not NGF) have their major effects on dorsal root ganglia and nodose ganglia, although NT-3 does seem to have minor effects on sympathetic ganglia (Maisonpierre et al. 1990a, Science 247: 1446–1451). NGF, in contrast, predominantly affects dorsal root ganglia and sympathetic ganglia.

These findings led to the suggestion that BDNF and NT-3 might in some cases act on the same neuronal populations, and that an early effect of NT-3 on these neurons might be replaced by a later effect of BDNF (Maisonpierre, et al., 1990b, Neurons 5:501–509). Furthermore, the finding that BDNF and NT-3 (but not NGF) are the most highly conserved growth factors yet described led to the suggestion that both these factors might be interacting with multiple receptors and that their strict conservation was required to maintain the specificity of their interactions with these multiple receptors.

Klein et al. (1989, EMBO J. 8:3701–3709) reported the isolation of trkB, which encodes a new member of the tyrosine protein kinase family of receptors found to be highly related to the human trk protooncogene. At the amino acid level, the products of trk and trkB were found to share 57 percent homology in their extracellular regions, including 9 of the 11 cysteines present in trk. This homology was found to increase to 88 percent within their respective tyrosine kinase catalytic domains. In adult mice, trkB was found to be preferentially expressed in brain tissue, although significant levels of trkB RNAs were also observed in lung, muscle, and ovaries. Further, trkB transcripts were detected in mid and late gestation embryos. In situ hybridization analysis of 14 and 18 day old mouse embryos indicated that trkB transcripts were localized in the central and peripheral nervous systems, including brain, spinal cord, spinal and cranial ganglia, paravertebral trunk of the sympathetic nervous system and various innervation pathways, suggesting that the trkB gene product may be a receptor involved in neurogenesis and early neural development as well as playing a role in the adult nervous system.

In 1990, Klein et al. (Cell 61:647–656) reported that the mouse trkB locus codes for at least two classes of receptor-like molecules, which they designated $gp145^{trkB}$ and $gp95^{trkB}$. These molecules appear to have identical extracellular and transmembrane domains, but only $gp145^{trkB}$ was found to contain a long cytoplasmic region that included a catalytic protein kinase domain. TrkB transcripts coding for this protein were observed in the cerebral cortex and the pyramidal cell layer of the hippocampus, whereas transcripts encoding $gp95^{trkB}$ were found in the ependymal linings of the cerebral ventricles and in the choroid plexus. Further, Middlemas, et al. (1991, Mol. Cell. Biol. 11:143– 153) reported the existence of two distinct C-terminally truncated receptors which share the complete extracellular region and transmembrane domain with $gp145^{trkB}$ but which differ from $gp145^{trkB}$ (hitherto referred to simply as trkB) in their short cytoplasmic tails.

3. SUMMARY OF THE INVENTION

The present invention provides for assay systems that may be used to detect and/or measure neurotrophin activity or to identify agents that exhibit neurotrophin-like activity, and for methods of using such assay systems. It is based, at least in part, on the discovery that the trkB proto-oncogene encodes a tyrosine kinase receptor that may serve as a functional binding protein for BDNF and NT-3. Such assay systems may be of particular value in identifying new neurotrophins or agents with neurotrophin-like activity. In various embodiments, the assay systems and methods of the invention may be used to detect and/or measure the binding of neurotrophin to the trkB protein, either using direct binding studies or the detection of the secondary effects of trkB/neurotrophin binding.

The present invention also provides for systems that may be used in both the assay of pre-defined agents, as well as the discovery of novel agents, that act on receptor tyrosine kinases. In a related aspect of this invention, the same system can be used to discover unknown receptors that mediate responses to known factors. This invention is based, at least in part, on the discovery that the trkB proto-oncogene encodes a tyrosine kinase receptor that is able not only to mediate BDNF/NT-3 dependent neuronal survival and differentiation (and not proliferation) in the neuronal cells in which it is normally expressed, but also is able to confer BDNF/NT-3 dependent survival and proliferation when stably expressed in a particular clone of the NIH3T3 fibroblast cell line.

Thus, according to the invention, the expression of receptor tyrosine kinases in fibroblasts allows for the use of these cells in survival/proliferation assays that may be used in both the assay of pre-defined agents, (such as the neurotrophins) as well as the discovery of novel agents, that act on these receptor tyrosine kinases; or other receptor tyrosine kinases for which no known ligand exists; these systems can be used even with receptor/ligand systems (such as the trk receptors and the neurotrophins) which may not normally act to mediate cellular proliferation. Once a particular receptor/ligand system is defined (as is done here with trkB and BDNF/NT-3), a variety of additional specific assay systems can be utilized.

The present invention further provides for a number of orphan tyrosine kinase receptor-like molecules, including five such molecules that are homologous to trk receptor and the insulin receptor family, and another four molecules that are homologous to, respectively, CSF1R/PDGFR/kit; ret; eck (now known as ehk) alpha; and eck beta. The invention also provides for a method for identifying receptor molecules, which can be orphan receptor molecules, as well as for additional species of receptor identified by this method.

The present invention also has diagnostic and therapeutic utilities. In particular embodiments of the invention, methods of detecting aberrancies in trkB function or expression may be used in the diagnosis of neurological disorders. In other embodiments, manipulation of the trkB/neurotrophin interaction may be used in the treatment of neurological disorders, including Alzheimer's disease, Parkinson's disease, and amyotrophic lateral sclerosis (Lou Gehrig's disease).

In other embodiments of the invention, novel tyrosine kinases are utilized to identify ligands useful for promoting the survival, growth or differentiation of various cell types.

1. ABBREVIATIONS

| | |
|---|---|
| BDNF | brain derived neurotrophic factor |
| BSA | bovine serum albumin |
| CNTF | ciliary neurotrophic factor |
| DSSD | isuccinimidyl suberate |
| HNGFR | high affinity nerve growth factor receptor |
| LNGFR | low affinity nerve growth factor receptor |
| NGF | nerve growth factor |
| NT-3 | neurotrophin-3 |
| pCMX-LNGFR | pCMX expression vector for expression of low affinity nerve growth factor receptor |
| pCMX-trkB | pCMX expression vector modified for expression of full length rat trkB cDNA |
| pCMX-trkB(del) | modified form of pCMX-trkB designed to express truncated form of trkB lacking most of the intracytoplasmic tyrosine kinase domain |
| pT24-ras | plasmid containing mutated (activated) version of ras oncogen |

4. DESCRIPTION OF THE FIGURES

FIG. 1. All three neurotrophins specifically cross-link to the LNGFR expressed in COS cells.

A. None of the neurotrophins display computable crosslinking to COS cells transfected with control vector, pCMX. The radiolabeled ligand utilized for each pair of lanes is indicated at the top of the lanes (each radiolabeled ligand is estimated to be at a concentration between 0.1 and 0.25 nM); "−" indicates absence and "+" indicates presence of unlabeled homologous ligand at a concentration of 500 nM. Notable bands seen with radiolabeled NGF varied from experiment to experiment and were not computable with unlabeled NGF, as indicated.

B. All three radiolabeled neurotrophins display computable cross-linking (resulting in a complex of approximately 100 kD, as expected for LNGFR) in COS cells transfected with pCMX-LNGFR; lanes marked as in panel A. C. Cross-linked species in COS cells transfected with pCMX-LNGFR co-migrates with cross-linked species in human A875 melanoma cells. Radiolabeled ligand used in this panel was BDNF; cells used for cross-linking indicated at top of each pair of lanes, and "−" and "+" as in panel A.

Figure 2A:
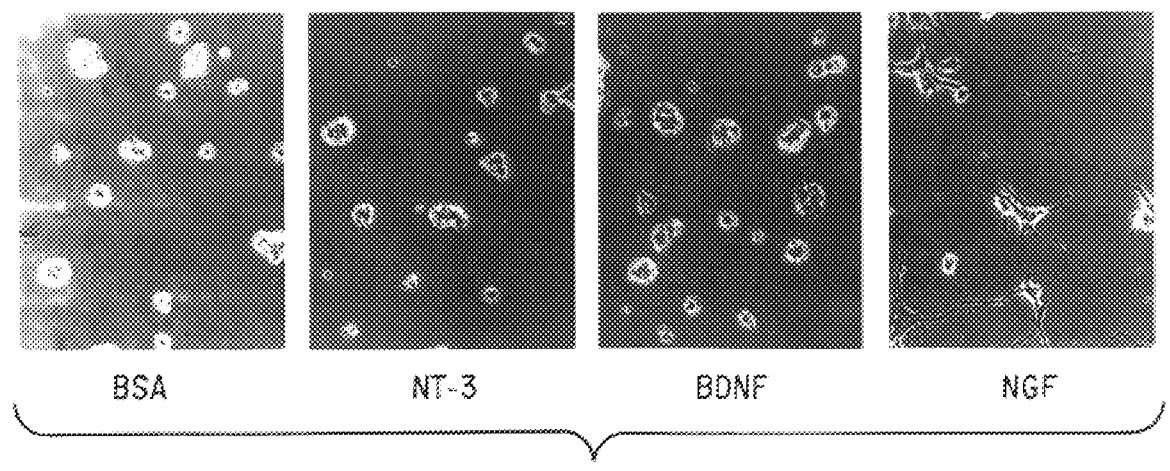
Figure 2B:
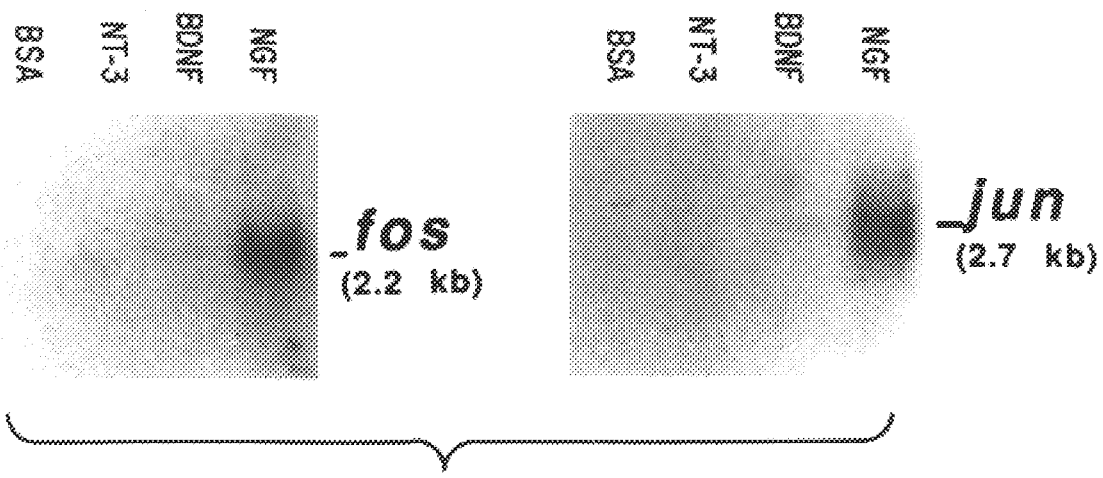

FIG. 2. Induction of neurite outgrowth and immediate-early gene expression in PC12 cells in response to NGF but not BDNF or NT-3.

A. PC12 cells cultured as recommended by Greene et al., 1987, Methods Enzymol. 147:, 207–216 in the presence of 100 ng/ml of BSA, NT-3, BDNF or NGF, as indicated. Varying concentrations of neurotrophins were tried; concentrations deemed saturating for NGF are depicted.

B. fos and jun transcripts (2.2 and 2.7 kb, respectively) identified by Northern analysis of total cellular RNA prepared from PC12 cells cultured as above in the absence of exogenous neurotrophic factors, and then treated for 30 minutes with 100 ng/ml BSA, NT-3, BDNF or NGF as indicated.

FIG. 3. BDNF and NT-3, but not NGF, bind specifically to trkB expressed in COS cells.

A. COS cells transfected with pCMX-trkB and chemically cross-linked to each of the three radiolabeled neurotrophins. Radiolabeled ligand utilized for each pair of lanes is indicated at top of lanes (each radiolabeled ligand is estimated to be at a concentration between 0.1 and 0.25 nM); "−" indicates absence and "+" indicates presence of unlabeled homologous ligand at a concentration of 500 nM. Bracket and asterisk indicate cross-linked species corresponding to trkB protein (approximately 160 to 180 kD).

B. Cross-linking of radiolabeled NT-3, in the absence ("−") or presence ("+") of unlabeled NT-3 at 500 nM, to COS cells transfected with an expression vector for a truncated form (lacking the tyrosine kinase domain) of trkB (pCMX-trkB(del)). Bracket and asterisk indicate cross-linked species corresponding to truncated version of trkB (120 to 150 kD, as expected for this deletion mutant).

FIG. 4. Cross-linking and binding of $^{125}$I-NT-3 to LNGFR is specifically blocked by all three neurotrophins, while cross-linking and binding of NT-3 to trkB is specifically blocked only by BDNF and NT-3.

A. COS cells transfected with pCMX-LNGFR and cross-linked to radiolabeled NT-3 (estimated concentration between 0.1 to 0.25 nM); the unlabeled neurotrophin used as cold competitor is indicated at the top of each triplet of lanes, with the concentration used per lane (in nM) indicated.

B. COS cells transfected with pCMX-trkB and cross-linked to radiolabeled NT-3; ligand concentrations and lane markings as in panel A.

C. COS cells transfected with pCMX-LNGFR used in solution binding experiments with radiolabeled NT-3 (at a concentration estimated to be between 0.1 and 0.25 nM) competed with varying concentrations of unlabeled NT-3, BDNF and NGF, as indicated.

D. COS cells transfected with pCMX-trkB used in solution binding experiments with radiolabeled NT-3 (at a concentration estimated to be between 0.1 and 0.25 nM) competed with varying concentrations of unlabeled NT-3, BDNF and NGF, as indicated. Date represent the percentage of total cpm bound and are the average of duplicate assays.

Figure 5C:
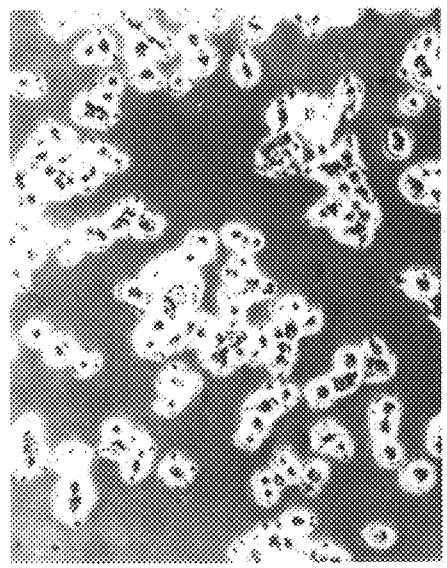
Figure 5D:
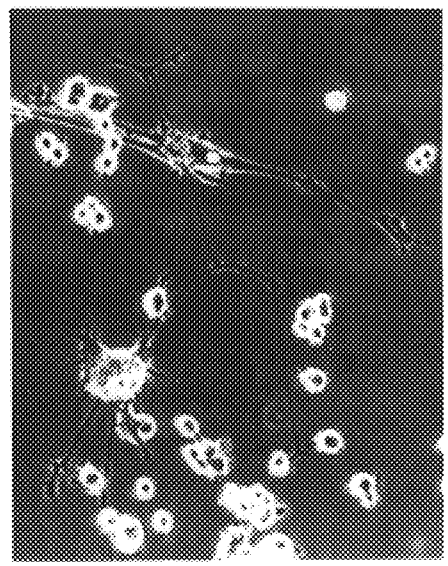
Figure 5E:
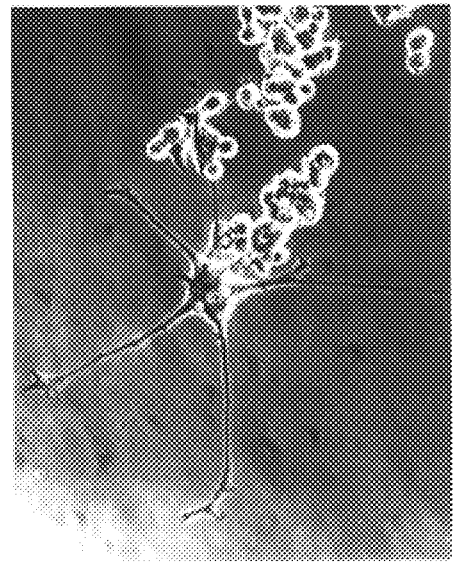

FIG. 5. PC12 cells transfected with pCMX-trkB differentiate in the presence of BDNF and NT-3.

A. PC12 cells transiently transfected with control plasmid pT24-ras and treated with 100 ng/ml BSA, used to determine number of transiently transfected cells in each experiment (see text for details).

B, C, D and E. PC12 cells transiently transfected with pCMX-trkB and treated with 100 ng/ml NGF (panel B), BSA (panel C), NT-3 (panel D) or BDNF (panel E). Numbers (in parentheses) at the bottom of each panel indicate the number of differentiated PC12 cells (i.e. cells having neurites more than twice the length of the cell body) observed per 35 mm well following each treatment; although absolute numbers varied in the three transfections performed, the ratios of differentiated cells observed following the different treatments remained constant for three independent experiments. No differentiated cells were observed in pCMX-trkB transfected PC12 cells treated with BSA (three separate experiments); after electroporation the cells were plated directly on plastic without pre-coating to eliminate any background neurite outgrowth, as described in text and in the Experimental Procedures.

FIG. 6. The human neuroblastoma SH-SY5Y responds to NGF and BDNF but not NT-3, and does not express trkB.

A. fos transcripts identified by Northern analysis of total cellular RNA prepared from SH-SY5Y cells cultured in the absence of added factor, and then treated for 30 minutes with 100 ng/ml BSA, NGF, NT-3, or BDNF as indicated.

B. trkB transcripts are detected by Northern analysis using ten micrograms of total cellular RNA from adult rat cerebellum (designated CB), but are not detectable in ten micrograms of total cellular RNA from SH-SY5Y. The complete coding region of trkB was used as a probe which identifies multiple trkB transcripts (Klein et al., 1989, EMBO J. 8: 3701–3709); the cerebellum lane appears as a smear because of gross over-exposure in the attempt to detect transcripts in SH-SY5Y.

FIG. 7. Expression of LNGFR and trkB in parental and pLTR-trkB transfected NIH3T3 cells.

A. Chemical cross-linking of radiolabelled NT-3 to COS cells transfected with an LNGFR expression vector (Squinto et al., 1991, Cell 65:1–20) in lanes 1 and 2, to parental NIH3T3 cells in lanes 3 and 4, and to pLTR-trkB transfected NIH3T3 cells in lanes 5 and 6; "−" indicates absence and "+" indicates presence of unlabeled NT-3 at 500 nM. Cross-linked LNGFR and trkB species are indicated by brackets, and appear similar to detected cross-linked species (Squinto et al., 1991, Cell 65:1–20).

B. Northern blot analysis of LNGFR expression in trkB-expressing NIH3T3 cells, in the parental NIH3T3 cells, in PC12 cells, and in SH-SY5Y cells. Ten micrograms of total RNA prepared from each of the indicated cell lines (except for the lane signified by PC12 in parenthesis, in which 0.5 micrograms of PC12 cell RNA was diluted in ten micrograms of NIH3T3 cell RNA) was fractionated by formaldehyde gel electrophoresis, transferred to a nylon membrane and hybridized with radiolabelled probes for the LNGFR (top) or trkB (bottom).

Figure 8:
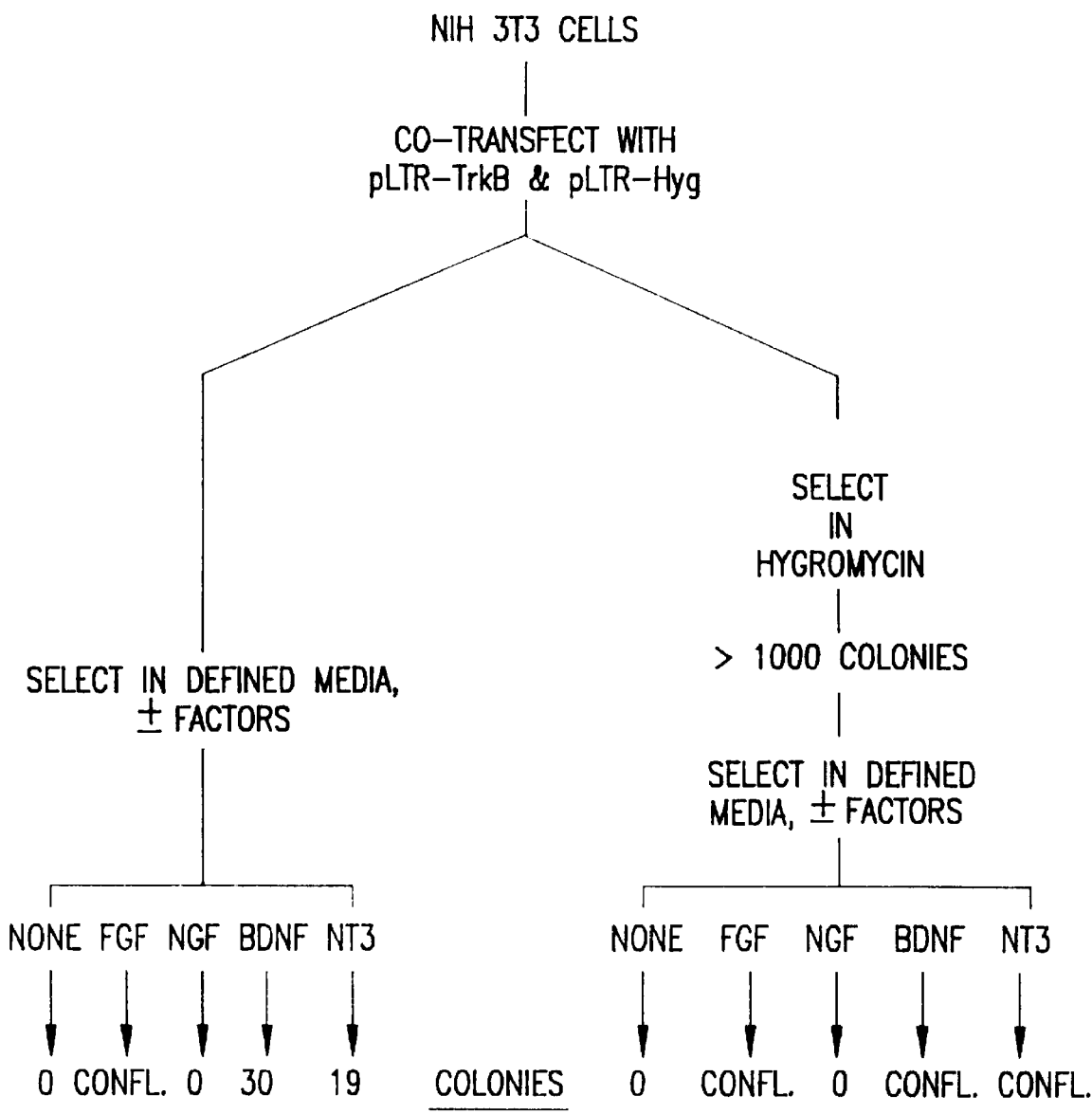

FIG. 8. Flow chart depicting transfection and selection strategies used to establish and assay trkB-expressing NIH3T3 cells. NIH3T3 cells transfected with 5 micrograms of pLTR-trkB, 1 microgram of pLTR-Hyg and 20 micrograms of human carrier DNA as described in the experimental procedures. Equal aliquots of transfected cells were plated in defined media containing the factors indicated (at 5 nM) or selected in medium containing 10% calf serum and hygromycin. Pooled hygromycin-resistant cells were subsequently placed in defined media as above. While only a small number of colonies were detected by direct selection in defined media supplemented with BDNF or NT-3, confluent survival with BDNF or NT-3 was seen using hygromycin-selected cells ("Conf." signifies confluent survival).

FIG. 9. Survival of parental and trkB-expressing NIH3T3 cells in defined media supplemented with bFGF or neurotrophins.

A. Parental (top row) or trkB-expressing NIH3T3 cells (bottom row) plated at 20% confluency, and maintained in defined media (with or without indicated factors at 5 nM) for 5 days.

B. TrkB-expressing NIH3T3 cells maintained in various concentrations of BDNF, NT-3 or bFGF. "–" indicates nearly complete cell death similar to parental NIH3T3 cells maintained in the absence of added factors (see panel A), "+++" indicates confluent survival similar to parental NIH3T3. cell maintained with 5 nM bFGF (see panel A), and "+" or "++" represent intermediate degrees of survival.

FIG. 10. Thymidine Incorporation and Proliferation Assays in TrkB-Expressing Fibroblasts Display Similar Neurotrophin Dose Dependency as Do Survival Assays in Primary Neurons.

A. Thymidine incorporation assay on NIH 3T3 fibroblasts, in response to indicated concentrations of bFGF, NGF, BDNF, and NT-3. Thymidine incorporation indicates counts per minute harvested from a single well of a 24-well plate; error bars are not provided for data points using a 5 pM concentration of each ligand because these points were not performed in duplicate.

B. Thymidine incorporation assay on trkB-expressing NIH 3T3 fibroblasts, in response to indicated concentrations of bFGF, NGF, BDNF, and NT-3; ordinate units and error bars are as in A.

C. Proliferation assay of trkB-expressing NIH 3T3 cells in response to differing concentrations of bFGF, BDNF, and NT-3; 5000 cells initially plated for each point, final cell number per well indicated.

D. Survival assay of primary neurons in dissociated cultures in response to differing concentrations of BDNF (neurons were isolated from dorsal root ganglions of embryonic day 9 chicks), performed as described (Lindsay and Rohrer, 1985 Dev. Biol, 112:30–48).

FIG. 11. Rapid induction of tyrosine phosphorylation in trkB-expressing fibroblasts stimulated with BDNF and NT-3.

A. Tyrosine phosphorylation of a 145 kD protein, presumed to be trkB (indicated by arrow), is rapidly induced in trkB-expressing NIH3T3 cells stimulated with BDNF or NT-3. Total cell lysates from parental or trkB-expressing NIH3T3 cells, exposed to the indicated factors for five minutes, were immunoprecipitated using an anti-phosphotyrosine monoclonal antibody conjugated to agarose beads, fractionated by acrylamide gel electrophoresis and then immunoblotted with a monoclonal antibody specific for phosphotyrosine.

B. Tyrosine phosphorylation of a 41 kD protein (presumed to be ERK2) is rapidly induced by bFGF in parental NIH3T3 cells, and by bFGF, NT-3 and BDNF in trkB-expressing NIH3T3 cells. Total cell lysates from parental or trkB-expressing NIH3T3 cells, exposed to the indicated factors for five minutes, were fractionated by acrylamide gel electrophoresis and then immunoblotted with a monoclonal antibody specific for phosphotyrosine.

Figure 12A:
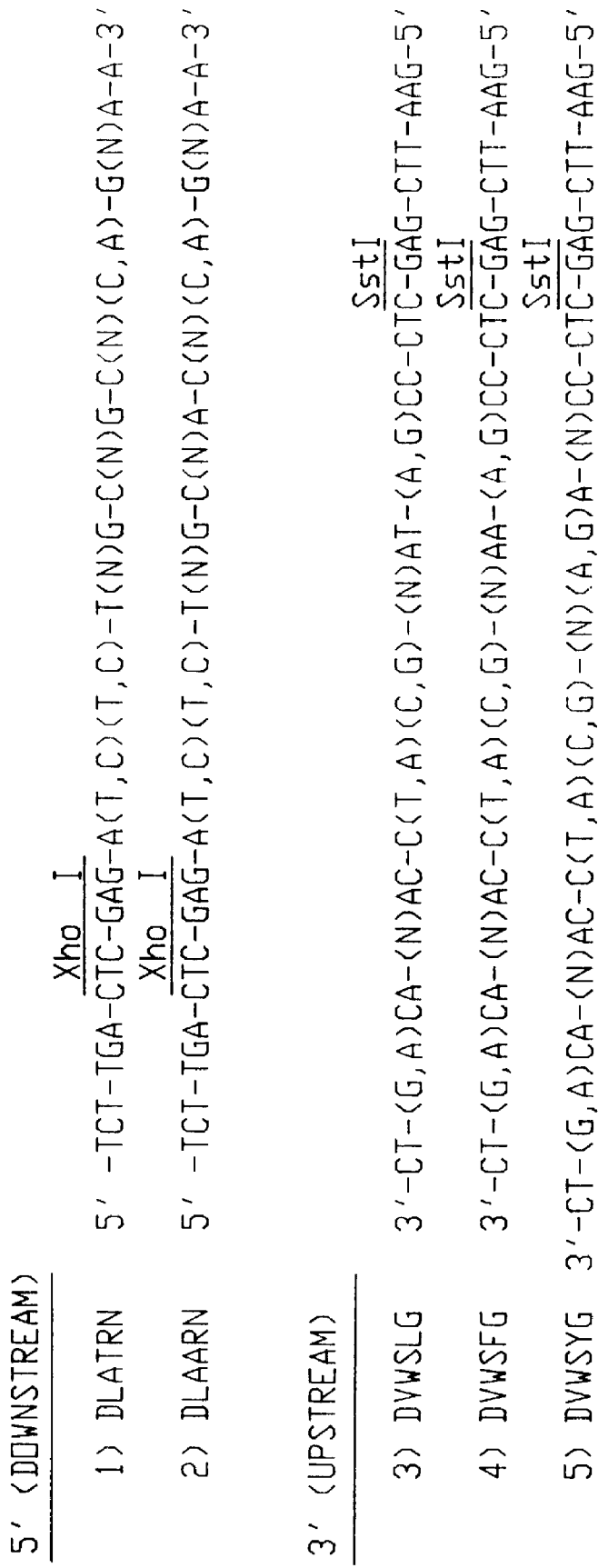

FIG. 12. A. PCR primers used to amplify sequences homologous to known tyrosine kinase molecules DLATRN= SEQ ID NO:91 and corresponds to nucleic acid SEQ ID NO:1; DLAARN=SEQ ID NO:92 and corresponds to nucleic acid SEQ ID NO:2; DVWSKG=SEQ ID NO:93 abd corresponds to nucleic acid SEQ ID NO:3; DVWSFG=SEQ ID NO:94 and corresponds to nucleic acid SEQ ID NO:4; DVWSYG=SEQ ID NO:95 and corresponds to nucleic acid sequence SEQ ID NO:5.

B. Amino acid sequences of novel cloned tyrosine kinases RTK-1=SEQ ID NO:6; RTK-6=SEQ ID NO:7, RTK-7=SEQ ID NO:8, RTK-8=SEQ ID NO:9, RTK-9=SEQ ID NO:10.

C. Nucleic acid and amino acid sequences of tyrosine kinase clones, namely Rtk-1, (SEQ ID NO:11 and SEQ ID NO:12) Rtk-6, (SEQ ID NO:19 and SEQ ID NO:20) Rtk-7, (SEQ ID NO:25 and SEQ ID NO:26) Rtk-8 (SEQ ID NO:32 and SEQ ID NO:33) and Rtk-9 (SEQ ID NO:30 and (SEQ ID NO:31), cDNA source and primers used in PCR reaction, and comparison with homologous molecules rtrkB=SEQ ID NO:13 and SEQ ID NO:14, mtrkB=SEQ ID NO:16, htrkA=SEQ ID NO:17 and SEQ ID NO:18, hkit=SEQ ID NO:21, hCSF1R=SEQ ID NO:22, hPDGFαR=SEQ ID NO:23, mCSF1R=SEQ ID NO:24, hret=SEQ ID NO:27, heck= SEQ ID NO:28 and SEQ ID NO:29.

D. Alignment of Rtk-1 (SEQ ID NO:34) rat cDNA protein sequence with trk A and trkB rtrkB=SEQ ID NO:35, mtrkB=SEQ ID NO:36, htrkA=SEQ ID NO:37.

E. Tyrosine Kinase homology domains as identified by Hanks et al., 1988, Science 241: 42–52 c-Src=SEQ ID NO:38, c-Yes=SEQ ID NO:39, HCK=SEQ ID NO:40, C-Fes=SEQ ID NO:41, c-Abl=SEQ ID NO:42, EGFR= SEQ ID NO:43, Neu=SEQ ID NO:44, CSF1R=SEQ ID NO:45, PDGFR=SEQ ID NO:46, IR=SEQ ID NO:47, 1GF1R=SEQ ID NO:48, c-Met=SEQ ID NO:49, c-Trk=SEQ ID NO:50.

FIG. 13. A. Comparison of the tyrosine kinase domain of the trk receptors and the insulin receptor subfamily trkB= SEQ ID NO:51, TRK=SEQ ID NO:52, INS.R=SEQ ID NO:53, IGF1R=SEQ ID NO:54, Ros=SEQ ID NO:55, DILR=SEQ ID NO:56, 7less=SEQ ID NO:57, MET=SEQ ID NO:58.

B. Nucleic acid and amino acid sequences of Rtk-2, (SEQ ID NO:59 and SEQ ID NO:60), Rtk-3, (SEQ ID NO:61 and SEQ ID NO:62) Rtk-4 (SEQ ID NO:63 and SEQ ID NO:64), and Rtk-5 (SEQ ID NO:65 and SEQ ID NO:66).

C. Comparison of deduced amino acid sequences of Rtk-2SEQ ID NO:68, Rtk-3 (SEQ ID NO:69) Rtk-4 (SEQ ID NO:70), and Rtk-5 (SEQ ID NO:71) with human trk (SEQ ID NO:67).

D. Comparison of the deduced amino acid sequence of Rtk-2 with human trk (SEQ ID NO:74) rat trkB (SEQ ID NO:73), insulin related growth factor receptor (SEQ ID NO:75), and insulin receptor (SEQ ID NO:76).

FIG. 14. Nucleotide (SEQ ID NO:77) and deduced amino acid sequence (SEQ ID NO:78) of Rtk-2.

FIG. 15. Nucleotide and deduced amino acid sequence of Rtk-3 (SEQ ID NOS:79 and 80).

FIG. 16. Alignment of sequences of Rtk-3 (SEQ ID NO:81) with sequences from Rtk-2 (SEQ ID NO: 82), trk (htrk=SEQ ID NO:84), trkB (rtrkB=SEQ ID NO:83), insulin-like growth factor receptor (IGF-R [hIGF-R=SEQ ID NO:85] and the insulin receptor (INS-R [hIns-R=SEQ ID NO:86]).

Figure 17:
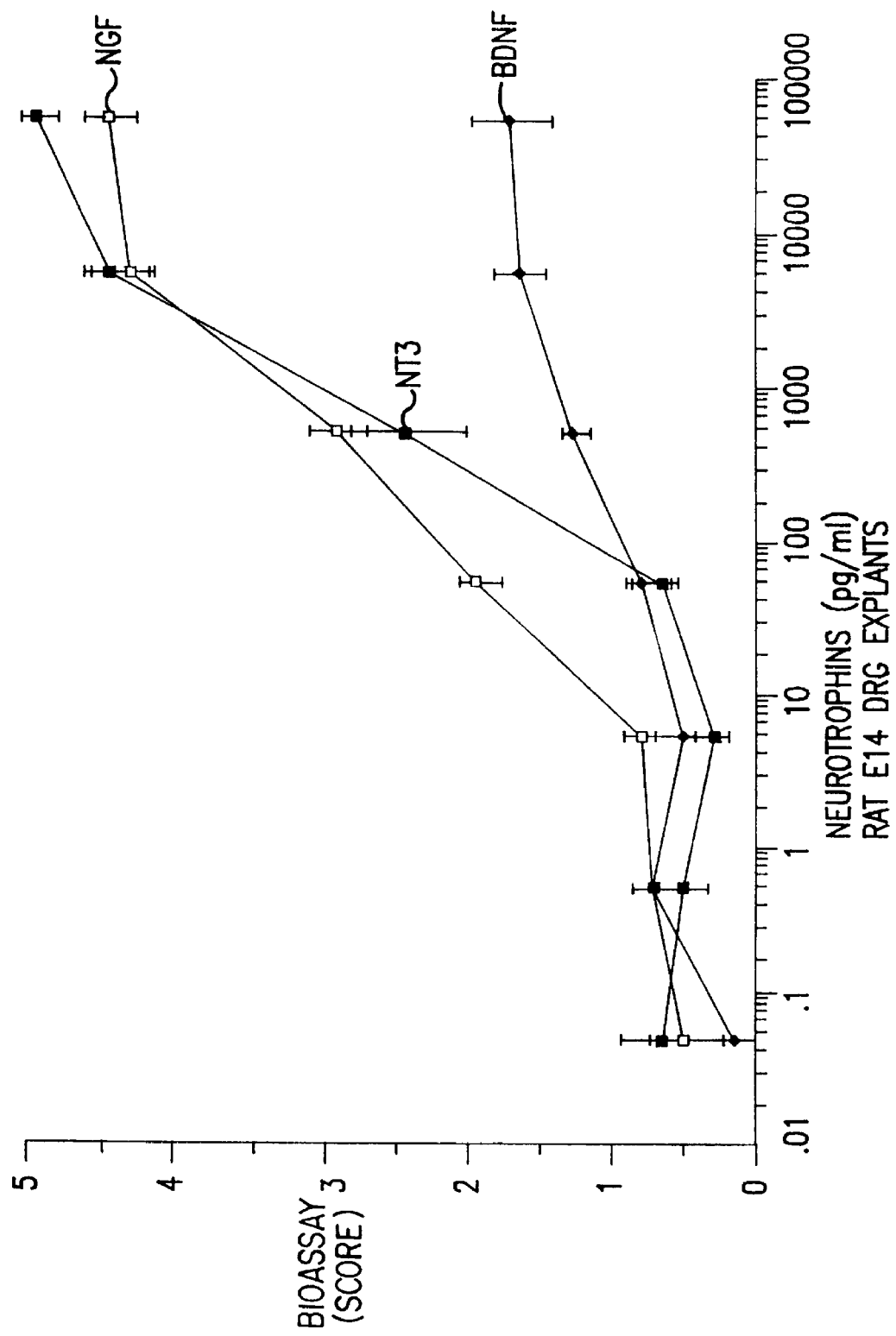

FIG. 17. Effects of neurotrophins (NGF, BDNF and NT-3) on neurite outgrowth in dorsal root ganglia of embryonic rat (E14). Concentrations of neurotrophins examined are in the range of 0.05 pg/ml to 50 ng/ml, and culture period was for 24 hr.

FIG. 18. Embryonic DRG were cultured for 24 hr. in the presence of NGF (50 ng/ml), following which mRNA level for trkA and B were examined. As a control, DRG was taken from rat and not cultured.

FIG. 19. Embryonic DRG were cultured in the presence of BDNF (50 ng/ml) or NT3 (50 ng/ml) for 24 hr, following which mRNA level for trkA, B and C were examined. Trks message were also examined in mediodorsal and ventral spinal cord from embryonic rat (E14).

Figure 20A:
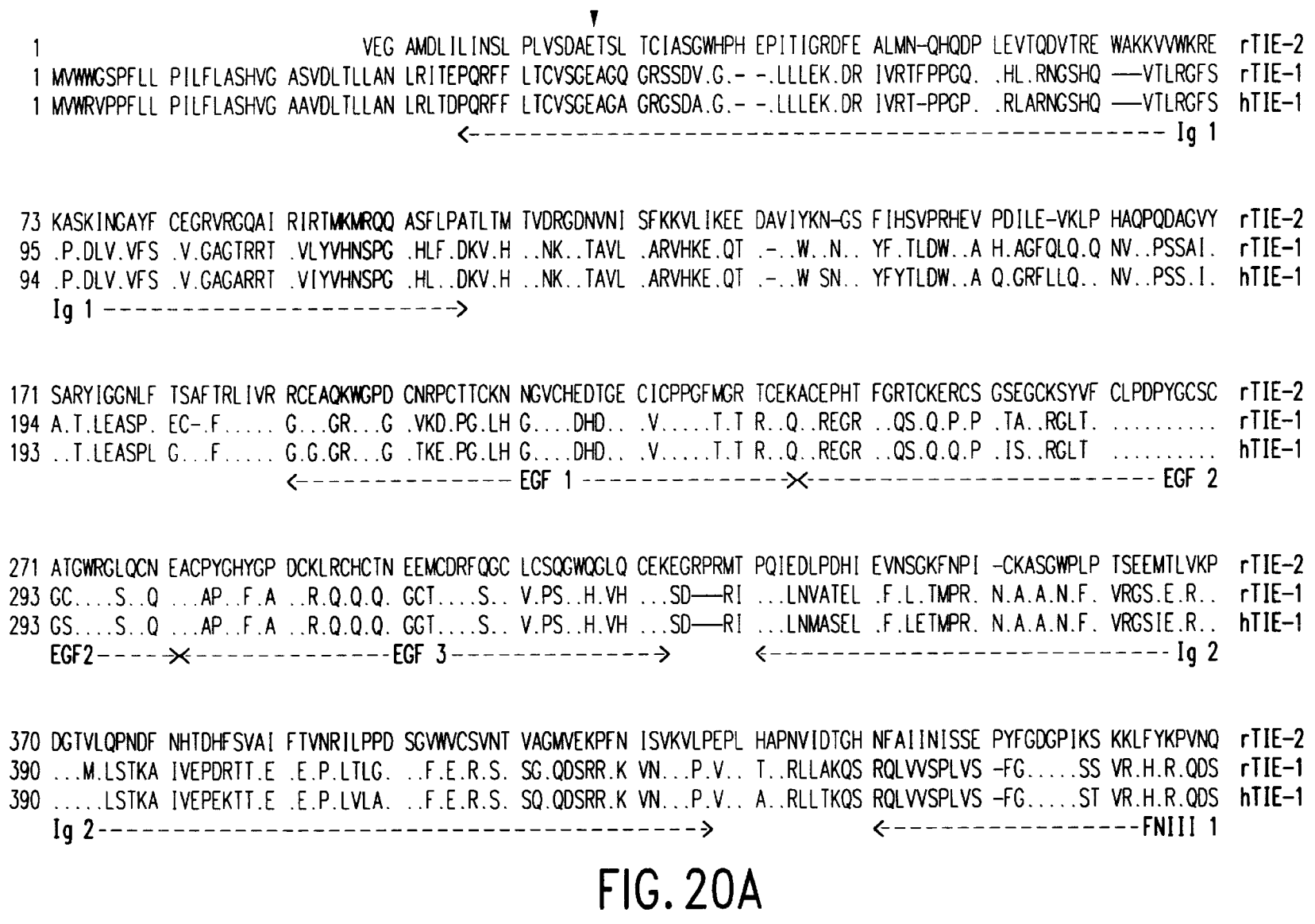

FIG. 20. Deduced amino acid sequence [rTIE SEQ ID NO:96] of Rtk-7 (now known as TIE-2). Arrowhead indicates position at which rat tie-2 genomic and RACE-PCR derived N terminal sequences diverge from one another. ig, IG-like loop; E, EGF-like repeat; FN, FN (fibronectin) III-like repeat; TK, tyrosine kinase domain, divided by short kinase insert region. Also shown are the amino acid sequences of rat Tie-1 (SEQ ID NO:97), HUMAN tIE-1 (SEQ ID NO:98) and mouse TEK (SEQ ID NO:99).

Figure 21B:
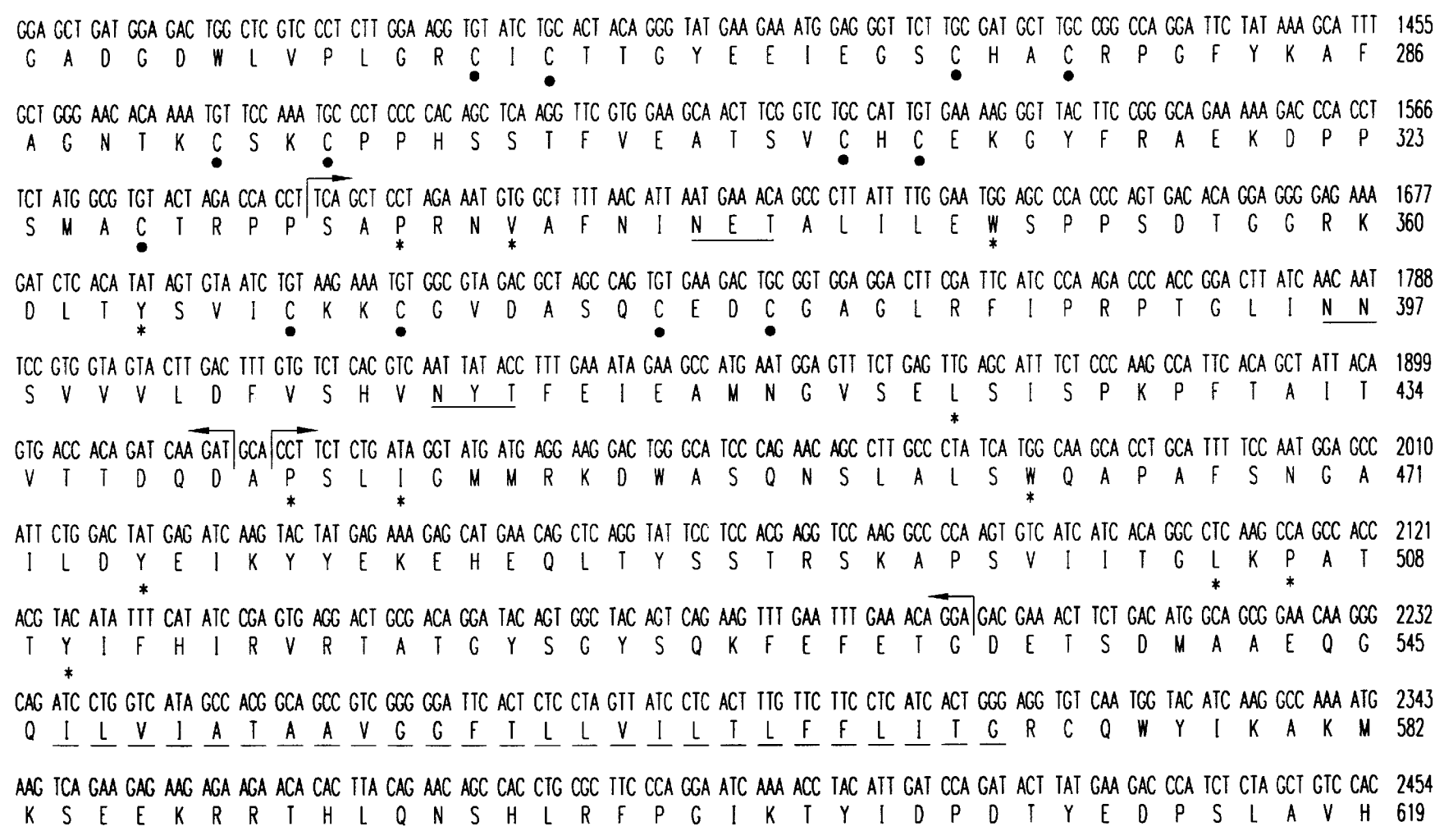

FIG. 21. Nucleotide [rEHK-2=SEQ ID NO: 100] and deduced amino acid sequence [rEHK-2=SEQ ID NO:101] of Rtk-8 (now known as EHK-2)(SEQ ID NOS:100 and 101). The inferred Ehk-2 sequence is 948 residues, beginning from the first Met condon in an open reading frame (ORF) that extends considerably further 5'. The 42 amino acid insert that interrupts the tyrosine kinase domain is boxed. In both sequence panels, bold, dashed underlining indicates the inferred transmembrane regions. Tandem FN III domains are confined by arrows, with key FN III consensus residues indicated by a large asterisk (*) Potential sites for Asn-linked glycosylation in the ectodomain are underlined and extracellular cysteines are highlighted with a closed circle (●). Stop condons that close the ehk ORFs are indicated by a small asterisk (⁺).

Figure 22B:
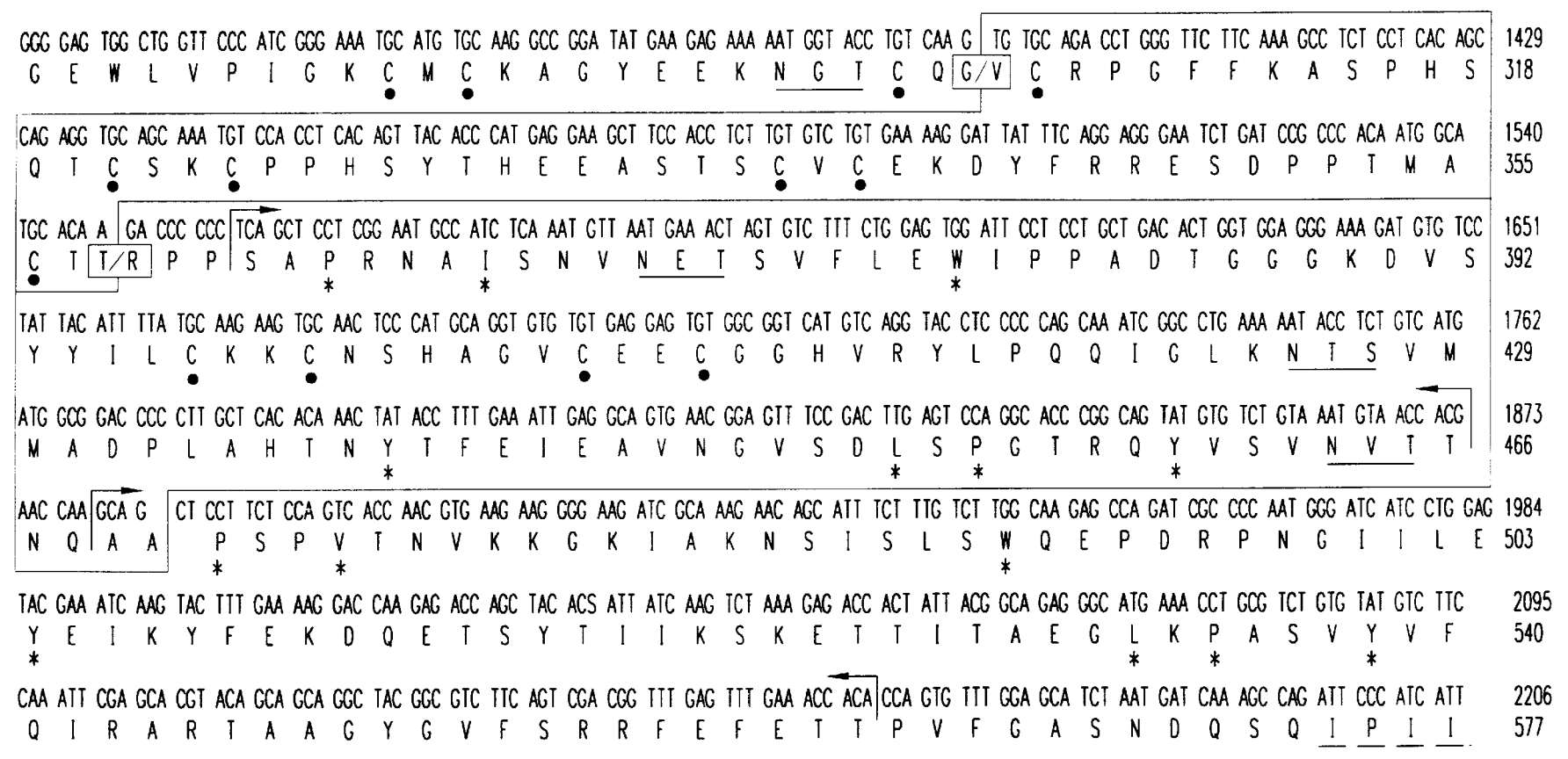
Figure 22C:
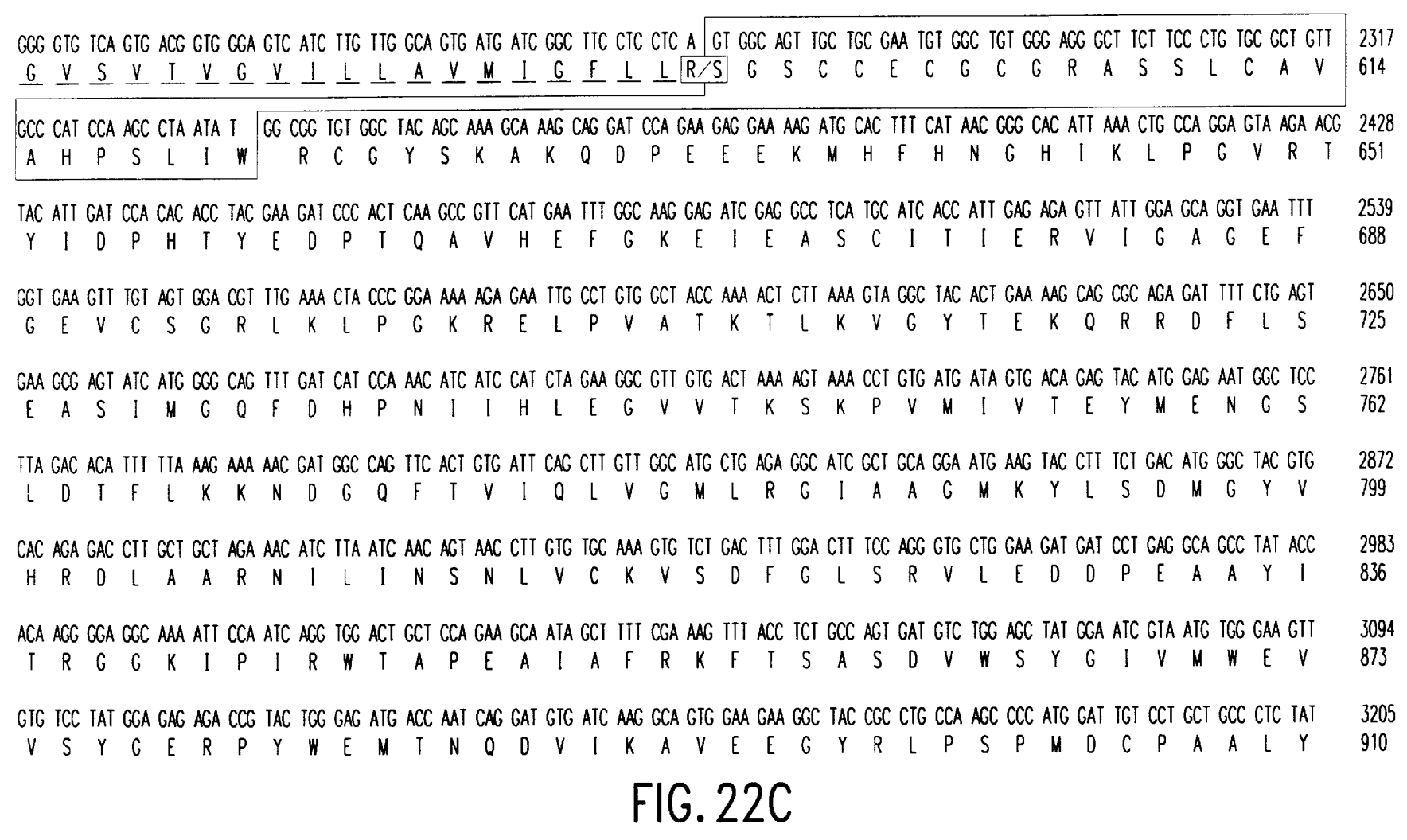
Figure 22E:
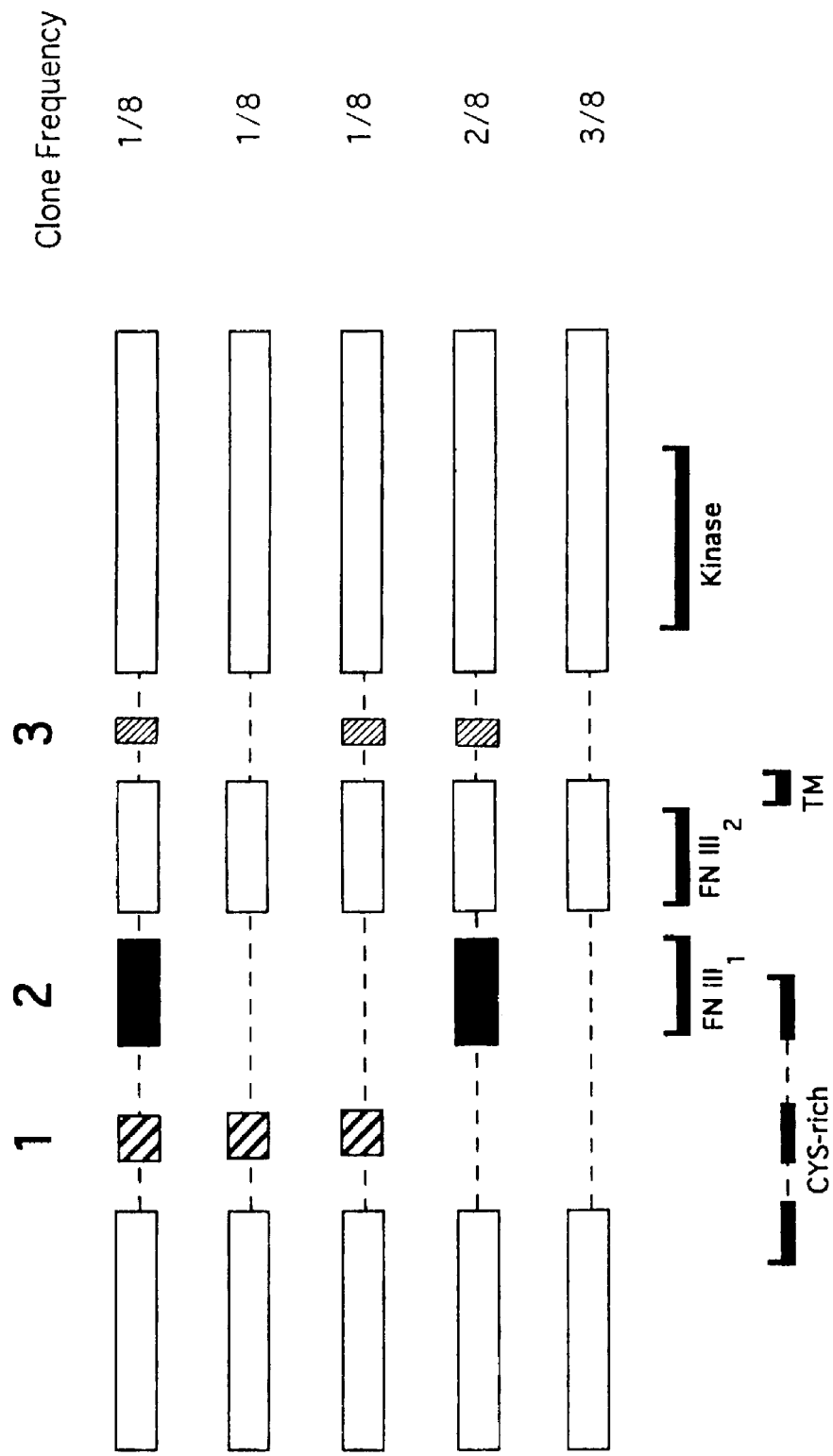

FIG. 22(a). Nucleotide [rEHK-2=SEQ ID NO:102] and deduced amino acid sequence [rEHK-1=SEQ ID NO:103] of Rtk-9 (now known as Ehk-1)(SEQ ID NOS:102 and 103). The inferred Ehk-1 sequence, including all differentially spliced exon sequences, is 1005 residues. The three variably-spliced exons are enclosed by lines and numbered along the left margin. Individual boxed residues at the N-terminal borders of these exons indicate the amino acid that is generated by splicing of the 5' exon donor junction to the alternative, downstream acceptor site. Differential splicing of three exons generate five forms of Ehk-1 in newborn brain. (b) Five types of ehk-1 cDNAs recovered are depicted, with three alternatively spliced exons numbered as shown above.

Figure 23:
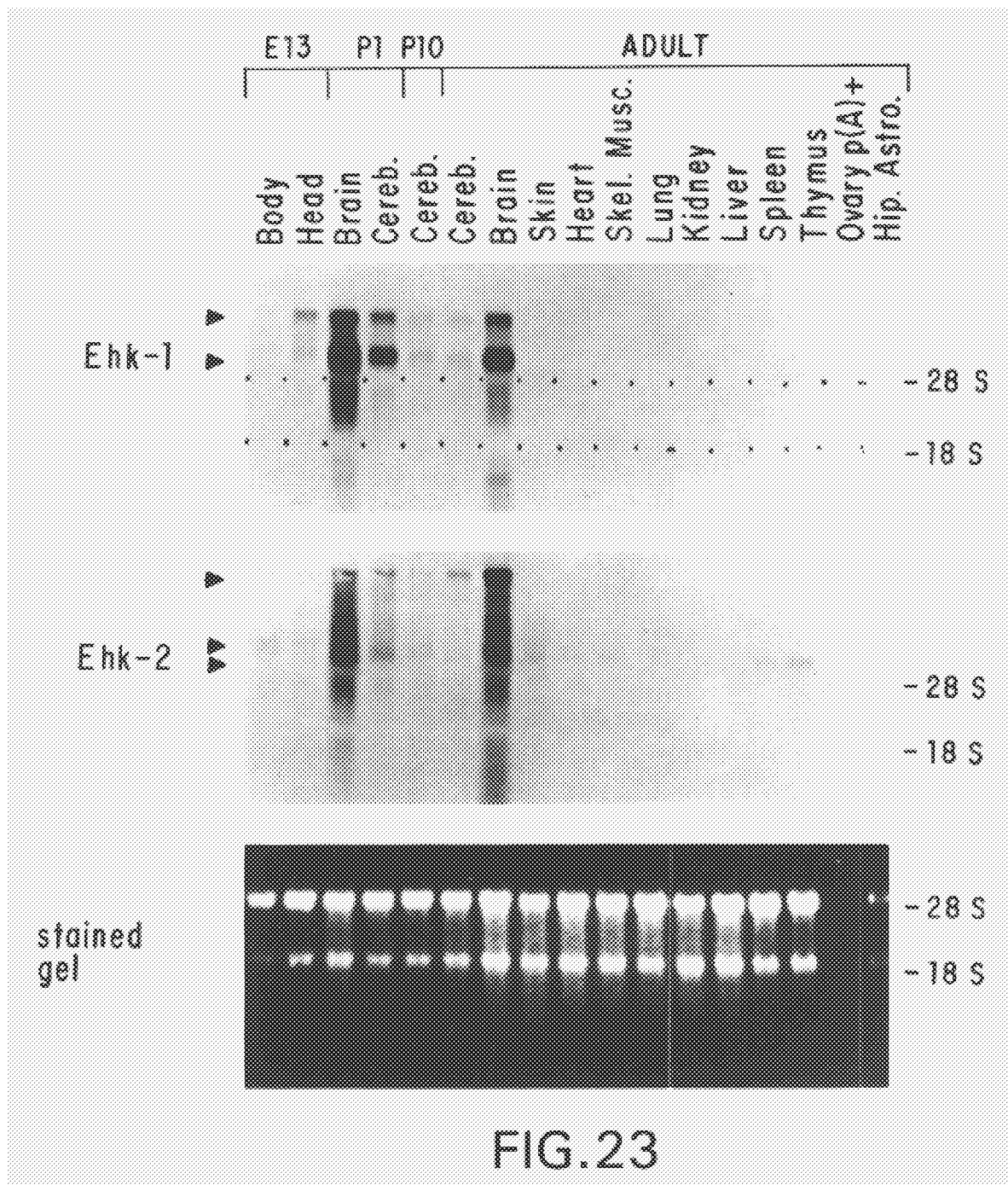

FIG. 23. Northern blot analysis of ehk gene expression in rat tissues. Ten microgram aliquots of total RNA from various E13, P1 and P10 and adult stage Sprague-Dawley rat tissues, 10 μg total RNA from newborn rat hippocampal astrocytes cultured for 28 days and 1 μg poly (A) +RNA from adult rat ovary were separated on duplicate formaldehyde-agarose gels, blotted to nylon and hybridized with $^{32}$P-labeled PCR fragments derived from the ehk-1 and ehk-2 tyrosine kinase domains. Embryonic day 1 (E1) is the day of maternal sperm positivity and post-natal day 0 (P0) is the day of birth; adults were about 10 weeks old.

FIG. 24. Comparison of Ehk-1 and Ehk-2 RNA distribution in adult rat brain. Pairs of nearly adjacent fresh frozen coronal brain sections were hybridized with $^{35}$S-labeled ehk-1 (a, c, eg, g, i) and with ehk-2 (b, d, f, h, j) antisense riboprobes, processed for emulsion autoradiography (5 week exposure) and viewed in a dark field. (a, b) Ventral forebrain (arrows demarcate transition between piriform cortex and olfactory tubercle). (c.d) Rostral septal region of the forebrain. (e,f) Hippocampus (upper left arrows demarcate CA2-CA1 boundary; lower right: arrows contrast elevated ehk-2 signal over dentate gyrus). (g,h) Dorsal midbrain. (i,j) Medial region of the hindbrain. CPu, caudate-putamen; DG, dentate gyrus; HDB, horizontal limb of the diagonal band; IG, indusium griseum; LC, locus coeruleus; Ox, optic Chiasm; Pt. pineal gland; Pir. piriform cortex; RS, retrosplenial cortex; Th, thalamus; TT, tenia tecta; Tu, olfactory tubercle. All magnifications as in a: Scale bar=100 μm.

FIG. 25. Ehk RNA distribution in select brain regions. (a) Ehk-1 hybridization to substantia nigra. (b) Ehk-1 hybridization to lateral and basolateral amydala (c) Ehk-1 hybridization to olfactory bulb (arrow highlights mitral cell). BL. basolateral amygdala; DR. dorsal raphe; GI, glomerular layer; IP, interpeduncular region; Mi, mitral cell layer; Pir. piriform cortex; SNC, Compacta of the substantia nigra. All magnifications as in a: Scale bar=100 μm.

5. DETAILED DESCRIPTION OF THE INVENTION

For purposes of clarity of disclosure, and not by way of limitation, the detailed description of the invention is divided into the following subsections:

(i) assay systems and methods;

(ii) experimental model systems;

(iii) diagnostic methods;

(iv) therapeutic methods; and (v) systems for the assay and discovery of agents that act on receptor tyrosine kinases and of novel tyrosine kinase receptors

1. Assay Methods and Systems

1. Methods

The present invention provides for assay systems and methods utilizing the TrkB receptor that may be used to detect and/or measure neurotrophin activity or to identify agents that exhibit neurotrophin-like activity. The assay systems and methods may also be used to identify agents that bind to the other receptors described herein, including, but not limited to Tie-2, Ehk-1 and Ehk-2, which may have activity on neuronal, muscle or epithelial cells. Thus, although several of the examples in this application are directed to TrkB, the methods and assay systems described herein apply with respect to any tyrosine kinase described herein.

The term "neurotrophin activity," as used herein, should be construed to refer to the activity of BDNF or NT-3, or of other, hitherto unidentified neurotrophic factors, or of non-neurotrophic factors (including peptide and nonpeptide molecules) which are capable of binding to trkB. Agents that exhibit neurotrophin activity include but are not limited to neurotrophic and non-neurotrophic factors, including peptide and non-peptide molecules, that have biological activity similar to BDNF and/or NT-3 with respect to immediate early gene induction, cell types affected, phenomena induced, etc. Biological activities of BDNF and NT-3 are described, respectively, in PCT application numbers PCT/US90/04915 and PCT/US90/04916, which are incorporated by reference in their entirety herein. Henceforth, both neurotrophins and agents with neurotrophin activity will be collectively referred to as test agents.

Accordingly, the present invention provides for a method of detecting or measuring neurotrophin activity comprising (i) exposing a cell that expresses trkB to a test agent; and (ii) detecting or measuring the specific binding of the test agent to trkB, in which specific binding to trkB positively correlates with neurotrophin activity.

A cell that expresses trkB may either naturally express trkB or be genetically engineered to do so. For example, trkB-encoding nucleic acid sequences obtained as described in section 6.1.2., infra, may be introduced into a cell by transfection, transduction, microinjection, electroporation, via a transgenic animal, etc., using any method known in the art. See for example, the transfection of COS and PC12 cells as described in section 6, infra, and the description of assay systems provided in Section 5.1.2., infra.

The specific binding of test agent to trkB may be measured in a number of ways. For example, the actual binding of test agent to cells expressing trkB may be detected or measured, by detecting or measuring (i) test agent bound to the surface of intact cells; (ii) test agent cross-linked to trkB protein in cell lysates; or (iii) test agent bound to trkB in vitro. The specific interaction between test agent and trkB may be evaluated by using reagents that demonstrate the unique properties of that interaction. For example, it has been demonstrated, according to the present invention (see section 6) that BDNF and NT-3, but not NGF, bind to trkB. Therefore, the specific binding of test agent to trkB may be competitively inhibited by BDNF or NT-3, but not NGF.

As a specific, nonlimiting example, the methods of the invention may be used as follows. Consider a case in which the neurotrophin level (for instance, BDNF) in a sample is to be measured. Varying dilutions of the sample (the test agent), in parallel with a negative control (NC) containing no BDNF activity, and a positive control (PC) containing a known amount of BDNF, may be exposed to cells that express trkB in the presence of detectably labeled BDNF (in this example, radioiodinated BDNF). The amount of BDNF in the test sample may be evaluated by determining the amount of $^{125}$I-labeled BDNF that binds to the controls and in each of the dilutions, and comparing the sample values to a standard curve. The more BDNF in the sample, the less $^{125}$I-BDNF that will bind to trkB. The amount of $^{125}$I-BDNF bound may be determined by measuring the amount of radioactivity per cell, or by cross-linking the BDNF to cell surface proteins using DSS, as described in Meakin and Shooter, 1991, Neuron 6:153–163, and detecting the amount of labeled protein in cell extracts, using, for example, SDS polyacrylamide gel electrophoresis, which may reveal a labeled protein having a size corresponding to BDNF-bound trkB. The specific test agent/trkB interaction may further be tested by adding various dilutions of unlabeled NGF to the assays; such unlabeled NGF should have no substantial affect on the competition between labeled BDNF and test agent for trkB binding. Alternatively, an agent known to be able to disrupt neurotrophin/trkB binding, such as, but not limited to, unlabeled NT-3 or anti-trkB antibody, may be expected to interfere with the competition between $^{125}$I-BDNF and test agent for trkB binding.

Detectably labeled neurotrophin includes, but is not limited to, neurotrophin linked covalently or noncovalently to a radioactive substance, a fluorescent substance, a substance that has enzymatic activity, a substance that may serve as a substrate for an enzyme (enzymes and substrates associated with calorimetrically detectable reactions are preferred) or to a substance that can be recognized by an antibody molecule that is preferably a detectably labeled antibody molecule.

Alternatively, the specific binding of test agent to trkB may be measured by evaluating the secondary biological effects of neurotrophin/trkB binding, including, but not limited to, the induction of neurite sprouting, immediate early gene expression or phosphorylation of trkB (see FIG. 11). For example, the ability of the test agent to induce neurite sprouting can be tested in cells that lack trkB and in comparable cells that express trkB; neurite sprouting in trkB-expressing cells but not in comparable cells that lack trkB would be indicative of a specific test agent/trkB interaction. A similar analysis could be performed by detecting immediate early gene (e.g. fos and jun) induction in trkB-minus and trkB-plus cells, or by detecting phosphorylation of trkB using standard phosphorylation assays known in the art. Such analysis might be useful in identifying neurotrophin agonists or antagonists that do not competitively bind to trkB.

For example, and not by way of limitation, it may be desirable to determine whether a particular sample contains BDNF. PC12 cells, a well characterized neuroblastoma cell line, do not sprout neurites in response to BDNF treatment (see section 6, infra, and FIG. 2A). However, PC12 cells transfected with trkB do sprout neurites in response to BDNF (see section 6, infra, and FIG. 5). Therefore, normal PC12 cells (trkB-minus cells) and PC12 cells transfected with trkB (trkB-plus cells) may be exposed to the sample (the test agent) and the presence or absence of neurite sprouting may be evaluated microscopically. In other embodiments, the amount of BDNF in the sample may be measured by determining the amount of neurite sprouting (or immediate early gene induction) and then comparing this value with a dose response curve for the particular neurotrophin being tested, here, BDNF.

Similarly, the present invention provides for a method of identifying an agent that has neurotrophin activity comprising (i) exposing a cell that expresses trkB to a test agent and (ii) detecting the specific binding of the test agent to trkB, in which specific binding to trkB positively correlates with neurotrophin-like activity. Specific binding may be detected by either assaying for direct binding or the secondary biological effects of binding, as discussed supra. Such a method may be particularly useful in identifying new members of the neurotrophin family or, in the pharmaceutical industry, in screening a large array of peptide and non-peptide agents (e.g., peptidomimetics) for neurotrophin-like activity. In a preferred, specific, nonlimiting embodiment of the invention, a large grid of culture wells may be prepared that contain, in alternate rows, PC12 (or fibroblasts, see infra) cells that are either trkB-minus or engineered to be trkB-plus. A variety of test agents may then be added such that each column of the grid, or a portion thereof, contains a different test agent. Each well could then be scored for the presence or absence of neurite sprouting. An extremely large number of test agents could be screened for neurotrophin activity in this manner.

In additional embodiments, the invention provides for methods of detecting or measuring neurotrophin activity or identifying an agent as having neurotrophin activity comprising (i) exposing a test agent to a trkB protein in vitro under conditions that permit binding to occur and (ii) detecting binding of the test agent to the trkB protein, in which binding of test agent to trkB correlates with neurotrophin or neurotrophin-like activity. According to such methods, the trkB may or may not be substantially purified, may be affixed to a solid support (e.g. as an affinity column or as an ELISA assay), or may be incorporated into an artificial membrane. Binding of test agent to trkB may be evaluated by any method known in the art. In preferred embodiments, the binding of test agent may be detected or measured by evaluating its ability to compete with detectably labeled known trkB ligands for trkB binding.

The present invention also provides for a method of detecting the ability of a test agent compound to function as an antagonist of neurotrophin activity comprising detecting the ability of the compound to inhibit an effect of neurotrophin binding to trkB on a cell that expresses trkB. Such an antagonist may or may not interfere with trkB/neurotrophin binding. Effects of neurotrophin binding to trkB are preferably biological or biochemical effects, including, but not limited to, neurite sprouting, cell survival or proliferation, cell transformation, immediate early gene induction, or trkB phosphorylation. For example, and not by way of limitation, PC12 cells (or fibroblasts, etc.) transfected with trkB may be exposed to effective amounts of either BDNF or BDNF plus a test agent suspected of being a BDNF antagonist. Neurite sprouting in these two groups of cells may be compared to sprouting in non-transfected cells exposed to BDNF, or BDNF plus the test agent, or NGF, or NGF plus the test agent. If the antagonist specifically inhibits BDNF, neurite sprouting should be inhibited only in trkB-plus cells treated with BDNF plus test agent compared to trkB-plus cells exposed to BDNF, and there should be little or no inhibition of sprouting of trkB-minus cells treated with NGF plus test agent relative to trkB-minus PC12 cells treated with NGF alone.

5.1.2. Systems

The present invention also provides for assay systems that may be used according to the methods described supra. Such assay systems comprise in vitro preparations of trkB, Tie-2, Ehk-1 or Ehk-2, e.g. affixed to a solid support, or may, preferably, comprise cells that express these proteins.

Cells that express trkB protein may do so naturally or may be genetically engineered to produce trkB, as described supra, by transfection, transduction, electroporation, microinjection, via a transgenic animal, etc. of nucleic acid encoding trkB in a suitable expression vector.

Any of the methods known to one skilled in the art for the insertion of DNA fragments into a vector may be used to construct expression vectors encoding trkB containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding trkB protein or peptide fragment may be regulated by a second nucleic acid sequence so that trkB protein or peptide is expressed in a host transformed with the recombinant DNA molecule. For example, expression of trkB may be controlled by any promoter/enhancer element known in the art. Promoters which may be used to control trkB expression include, but are not limited to, the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothioein gene (Brinster, et al., 1982, Nature 296:39–42); prokaryotic expression vectors such as the *I704*12*b*I704*10*-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl, et al., 1984, Cell 38:647–658; Adames, et al., 1985, Nature 318:533–538; Alexander et al., 1987, Mol. Cell. Biol. 7:1436–1444), mouse mammary tumor virus control region which is active in testicular, breast, lymphoid and mast cells (Leder, et al., 1986, Cell 45:485–495), albumin gene control region which is active in liver (Pinkert, et al., 1987, Genes and Devel. 1:268–276), alpha-fetoprotein gene control region which is active in liver (Krumlauf, et al., 1985, Mol. Cell. Biol. 5:1639–1648; Hammer et al., 1987, Science 235:53–58); alpha 1-antitrypsin gene control region which is active in the liver (Kelsey, et al, 1987, Genes and Devel. 1:161–171), beta-globin gene control region which is active in myeloid cells (Mogram, et al., 1985, Nature 315:338–340; et al., 1986, Cell 46:89–94); myelin basic protein gene control region which is active in oligodendrocyte cells in the brain (Readhead, et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing trkB gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted trkB gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the trkB gene is inserted within the marker gene sequence of the vector, recombinants containing the trkB insert can be identified by the absence of the marker gene function. In the third approach, recombinant expression vectors can be identified by assaying the foreign gene product expressed by the recombinant. Such assays can be based, for example, on the physical or functional properties of the trkB gene product, for example, by binding of the receptor to neurotrophic factor or to an antibody which directly recognizes the trkB. Cells of the present invention may transiently or, preferably, constitutively and permanently express trkB.

In preferred embodiments, the present invention provides for cells that express trkB and that also contain recombinant nucleic acid comprising an immediate early gene promoter (e.g. the fos or jun promoters (Gilman et al., 1986, Mol. Cell. Biol. 6:4305–4316). When such a cell is exposed to a neurotrophin, the neurotrophin may be expected to bind to trkB and secondarily induce transcription off the immediate early promoter. Such a cell may be used to detect neurotrophin/trkB binding by measuring the transcriptional activity of the immediate early gene promoter, for example, by nuclear run-off analysis, Northern blot analysis, or by measuring levels of a gene controlled by the promoter. The immediate early promoter may be used to control the expression of fos or jun or any detectable gene product, including, but not limited to, any of the known reporter genes, such as a gene that confers hygromycin resistance (Murphy and Efstratiadis, 1987, Proc. Natl. Acad. Sci. U.S.A. 84:8277–8281) chloramphenicol acetyltransferase (CAT), neomycin phosphotransferase (neo), beta-galactosidase beta-glucuronidase, beta-galactosidase, etc. In a specific embodiment, neurotrophin/trkB binding in a cell that expresses trkB and contains the human growth hormone gene under the control of the fos gene promoter may be expected to produce recombinant human growth hormone, as measured by Seldon, et al., 1986, Mol. Cell. Biol. 6:3173–3179. In another embodiment, trkB expression may also be used as a reporter gene and be placed under the control of an immediate early promoter in addition to constitutively expressed trkB to produce an amplified response to neurotrophin. Such trkB-expression reporter gene containing cell lines may provide an exceptionally sensitive and efficient method of detecting or measuring neurotrophin activity.

Furthermore, the cells used in the assay systems of the invention may or may not be cells of the nervous system. For example, in a specific, nonlimiting embodiment of the invention, growth-factor dependent fibroblasts may be used as the basis for a neurotrophin assay system. See Section 7, infra. A fibroblast cell line that is growth factor dependent in serum-free media (e.g. as described in Zham and Goldfarb, 1986, Mol. Cell. Biol. 6:3541–3544) may be transfected with the trkB gene, for instance by using a $CaPO_4$ transfection protocol with 5 micrograms of DNA of CMV-promoter-based expression vector comprising the rat trkB gene and one microgram of hygromycin-resistance gene-containing expression vector. After about 48 hours, the cells may then be selected for hygromycin resistance to identify positive transfectants. The cells may then be cultured for about three weeks in the presence of hygromycin, and then resistant colonies may be pooled. These cells may then be plated on tissue culture plates coated with poly-D-lysine and human fibronectin, and allowed to grow in DMEM plus 10% bovine calf serum for about four hours to allow the cells to bind to the plates. The serum-containing media may then be aspirated and the cells may be washed about three times with PBS to remove any residual serum. The cells may then be taken up with either serum free defined media (A 3:1 mixture of DMEM and Hams F12, supplemented with 8 mM sodium bicarbonate, 15 mM HEPES, $4 \times 10^{-6}$M $MnCl_2$, 3 mM histidine, $10^{-5}$M ethanolamine, $10^{-7}$M sodium selenite, 5 mg transferrin per liter, 200 mg bovine serum albumin-linoleic acid complex per liter gentamicin, penicillin, and streptomycin, 20 mM L-glutamine). Cells produced in this manner, then incubated with neurotrophin (e.g. 100 ng/ml NT-3 or BDNF), may, after about 5 days in culture (replacing media and growth factors every 48 hours), be expected to be growing and proliferating; cells treated with NGF at 100 ng/ml or in serum free-medium should not, however, proliferate (see also FIG. 7). As discussed in Section 6, infra, data suggests that there is another, non-trkB receptor for BDNF expressed on SH-SY5Y cells (see also FIG. 6). The present invention also provides for assay systems and methods utilizing the non-trkB receptor in a manner analogous to those utilizing the trkB receptor, as described herein.

2. Experimental Model Systems

The present invention also provides for experimental model systems for studying the physiological role of the neurotrophin gene family. In these model systems, trkB protein, peptide fragment, or a derivative thereof, may be either supplied to the system or produced within the system. Such model systems could be used to study the effects of neurotrophin excess or neurotrophin depletion. The experimental model systems may be used to study the effects of increased or decreased response to neurotrophin in cell or tissue cultures, in whole animals, in particular cells or tissues within whole animals or tissue culture systems, or over specified time intervals (including during embryogenesis) in embodiments in which trkB expression is controlled by an inducible or developmentally regulated promoter. In particular embodiments of the invention, the CMV promoter may be used to control expression of trkB in transgenic animals. The term "transgenic animals," as used herein, refers to non-human transgenic animals, including transgenic mosaics, which carry a transgene in some or all of their cells, which include any non-human species, and which are produced by any method known in the art, including, but not limited to microinjection, cell fusion, transfection, electroporation, etc. For example, the animals may be produced by a microinjection of zygotes by a method such as that set forth in "Brinster, et al.", 1989, Proc. Natl. Acad. Sci. U.S.A. 82:4438–4442.

The present invention also provides for model systems for autoimmune disease in which an autoimmune response is directed toward trkB. Such models comprise animals which have been immunized with immunogenic amounts of trkB and preferably found to produce anti-trkB antibodies and/or cell-mediated immunity. To produce such a model system, it may be desirable to administer the trkB in conjunction with an immune adjuvant, such as Bacille Calmette Guerin (BCG).

1. Models for Increased Neurotrophin Activity

For example, and not by way of limitation, an experimental model system may be created which may be used to study the effects of excess neurotrophin activity. In such a system, the response to neurotrophin may be increased by engineering an increased number of trkB molecules on cells of the model system relative to cells which have not been so engineered.

It may be preferable to provide an increased number of neurotrophins selectively on cells which normally express neurotrophins.

Cells may be engineered to produce increased amounts of trkB protein by infection with a virus which carries a trkB gene of the invention. Alternatively, the trkB gene may be provided to the cells by transfection.

If the model system is an animal, a recombinant trkB gene may be introduced into the cells of the animal by infection with a virus which carries the trkB gene. Alternatively, a transgenic animal may be created which carries the trkB gene as a transgene.

In order to ensure expression of trkB, the trkB gene should be placed under the control of a suitable promoter sequence. It may be desirable to put the trkB gene under the control of a constitutive and/or tissue specific promoter, including but not limited to the CNS neuron specific enolase, neurofilament, and tyrosine hydroxylase promoter, an inducible promoter, such as the metallothionein promoter, the UV activated promoter in the human immunodeficiency virus long terminal repeat (Valeri, et al., 1988, Nature 333:78–81), or the CMV promoter (as contained in pCMX, infra) or a developmentally regulated promoter.

By increasing the number of cellular trkB molecules, the response to endogenous neurotrophin may be increased. If the model system contains little or no neurotrophin, neurotrophin may be added to the system. It may also be desirable to add additional neurotrophin to the model system in order to evaluate the effects of excess neurotrophin activity. Over expressing neurotrophin (or secreted neurotrophin) may be the preferable method for studying the effects of elevated levels of neurotrophin on cells already expressing trkB. More preferably would be to express trkB in all cells (general expression) and determine which cells are then endowed with functional responsiveness to neurotrophin, thus allowing the potential identification of a second receptor component, if one exists.

2. Models for Decreased Neurotrophin Activity

Alternatively, as an example, and not by way of limitation, an experimental model system may be created which may be used to study the effects of diminished neurotrophin activity. This system may permit identification of processes or neurons which require neurotrophin, and which may represent potential therapeutic targets. In such a system, the response to neurotrophin may be decreased by providing recombinant trkB proteins which are not associated with a cell surface or which are engineered so as to be ineffective in transducing a response to neurotrophin.

For example, trkB protein, peptide, or derivative may be supplied to the system such that the supplied receptor may compete with endogenous trkB for neurotrophin binding, thereby diminishing the response to neurotrophin. The trkB may be a cell free receptor which is either added to the system or produced by the system. For example, a trkB protein which lacks the transmembrane domain may be produced by cells within the system, such as an anchorless trkB that may be secreted from the producing cell. Alternatively, trkB protein, peptide or derivative may be added to an extracellular space within the system.

In additional embodiments of the invention, a recombinant trkB gene may be used to inactivate or "knock out" the endogenous gene by homologous recombination, and thereby create a trkB deficient cell, tissue, or animal. For example, and not by way of limitation, a recombinant trkB gene may be engineered to contain an insertional mutation, for example the neo gene, which inactivates trkB. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact trkB gene may then be identified, e.g. by Southern blotting or Northern blotting or assay of expression. Cells lacking an intact trkB gene may then be fused to early embryo cells to generate transgenic animals deficient in trkB. A comparison of such an animal with an animal not expressing endogenous neurotrophin would reveal that either the two phenotypes match completely or that they do not, implying the presence of additional neurotrophin-like factors or receptors.

Such an animal may be used to define specific neuronal populations, or any other in vivo processes, normally dependent upon neurotrophin. Thus, these populations or processes may be expected to be affected if the animal did not express trkB and therefore could not respond to neurotrophin.

Alternatively, a recombinant trkB protein, peptide, or derivative which competes with endogenous receptor for neurotrophin may be expressed on the surface of cells within the system, but may be engineered so as to fail to transduce a response to neurotrophin binding.

The recombinant trkB proteins, peptides or derivatives described above may bind to neurotrophin with an affinity that is similar to or different from the affinity of endogenous trkB to neurotrophin. To more effectively diminish the response to neurotrophin, the trkB protein, peptide, or derivative may desirably bind to neurotrophin with a greater affinity than that exhibited by the native receptor.

If the trkB protein, peptide, or derivative is produced within the model system, nucleic acid encoding the trkB protein, peptide, or derivative may be supplied to the system by infection, transduction, transfection, etc. or as a transgene. As discussed supra, the trkB gene may be placed under the control of a suitable promoter, which may be, for example, a tissue-specific promoter or an inducible promoter or developmentally regulated promoter.

In a specific embodiment of the invention, the endogenous trkB gene of a cell may be replaced by a mutant trkB gene by homologous recombination. In another embodiment of the invention, a test animal may be immunized against trkB.

In a further embodiment of the invention, trkB expression may be reduced by providing trkB expressing cells with an amount of trkB anti-sense RNA or DNA effective to reduce expression of trkB protein.

3. Diagnostic Applications

According to the present invention, trkB probes may be used to identify cells and tissues which are responsive to neurotrophin in normal or diseased states. The present invention provides for a method of diagnosing a neurological disorder in a patient comprising comparing the levels of expression of trkB in a patient sample with the levels of expression of trkB in a comparable sample from a healthy person, in which a difference in the levels of expression of trkB in the patient compared to the healthy person indicates that a disorder in the patient may be primarily or secondarily related to trkB metabolism. A patient sample may be any cell, tissue, or body fluid but is preferably nervous system tissue or cerebral spinal fluid. The present invention provides for methods for identifying cells which are responsive to neurotrophin comprising detecting trkB expression in such cells. TrkB expression may be evidenced by transcription of trkB mRNA or production of trkB protein. TrkB expression may be detected using probes which identify trkB nucleic acid or protein.

Yet another variety of probe which may be used is anti-trkB antibody or fragments thereof containing the binding domain.

According to the invention, trkB protein, or fragments or derivatives thereof, may be used as an immunogen to generate anti-trkB antibodies. By providing for the production of relatively abundant amounts of trkB protein using recombinant techniques for protein synthesis (based upon the trkB nucleic acid sequences of the invention), the problem of limited quantities of trkB has been obviated.

To further improve the likelihood of producing an anti-trkB immune response, the amino acid sequence of trkB may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphophilic helix, amphophilic sheet, and secondary structure of trkB. Alternatively, the deduced amino acid sequences of trkB from different species could be compared, and relatively non-homologous regions identified; these non-homologous regions would be more likely to be immunogenic across various species.

For preparation of monoclonal antibodies directed toward trkB, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor, et al., 1983, Immunology Today 4:72), and the EBV-hybridoma To technique to produce human monoclonal antibodies (Cole, et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng, et al., 1983, Proc. Natl. Acad. Sci. U.S.A. 80:7308–7312; Kozbor, et al., 1983, Immunology Today 4:72–79; Olsson, et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda, et al., 1985, Nature 314:452).

Various procedures known in the art may be used for the production of polyclonal antibodies to epitopes of trkB. For the production of antibody, various host animals can be immunized by injection with trkB protein, or a fragment or derivative thereof, including but not limited to rabbits, mice, rats., etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

A molecular clone of an antibody to a trkB epitope can be prepared by known techniques. Recombinant DNA methodology (see e.g., Maniatis, et al., 1982, Molecular Cloning, A Laboratory Manual, Cold Spring Harbor Laboratory, Cold Spring Harbor, New York) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

The above-mentioned probes may be used experimentally to identify cells or tissues which hitherto had not been shown to express trkB. Furthermore, these methods may be used to identify the expression of trkB by aberrant tissues, such as malignancies. In additional embodiments, these methods may be used diagnostically to compare the expression of trkB in cells, fluids, or tissue from a patient suffering from a disorder with comparable cells, fluid, or tissue from a healthy person. Fluid is construed to refer to any body fluid, but particularly blood or cerebrospinal fluid. A difference in the levels of expression of trkB in the patient compared to a healthy person may indicate that the patient's disorder may be primarily or secondarily related to trkB metabolism. An increase in levels of trkB, for example, could either indicate that the patient's disorder is associated with an increased sensitivity to normal levels of neurotrophin or, alternatively, may suggest that the patient's neurotrophin levels are low such that the number of receptors is increased by way of compensation. These etiologies may be distinguished from one another by administering neurotrophin to the patient. If his condition worsens, he may suffer from neurotrophin hypersensitivity; if it improves, he may be suffering from a neurotrophin deficiency. Neurotrophin or neurotrophin antagonist-based therapeutic regimens may be chosen accordingly. Differences in expression can be detected at the protein and/or RNA level; i.e. by measuring amounts of trkB protein or trkB RNA in a patient relative to those amounts in healthy persons.

The above-mentioned probes may also be used to select neurotrophin-responsive cells for use in assay systems, as described above, or in U.S. application Ser. No. 07/532,285 filed Jun. 1, 1990 (incorporated by reference herein, or according to standard methods of cell selection or cell sorting.

5.4. Therapeutic Applications

The present invention also provides for methods of treating a patient suffering from a neurological disorder comprising treating the patient with an effective amount of trkB protein, peptide fragment, or derivative thereof capable of binding to a neurotrophin. Therapeutic methods comprising administering trkB, trkB agonists, trkB antagonists (which compete with endogenous neurotrophin), or anti-trkB antibodies are within the scope of the present invention.

The present invention also provides for pharmaceutical compositions comprising trkB protein, peptide fragment, or derivative in a suitable pharmacologic carrier.

The trkB protein, peptide fragment, or derivative may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

As our understanding of neurodegenerative disease/ neurotrauma becomes clearer, it may become apparent that it would be beneficial to decrease the trophic effect of endogenous neurotrophin. Therefore, in areas of nervous system trauma, it may be desirable to provide neurotrophin antagonists, including, but not limited to, soluble forms of trkB which may compete with endogenous cellular receptor for neurotrophin binding. Under such circumstances, it may be desirable to provide neurotrophin antagonist locally at the injury site rather than systemically. Use of a trkB providing implant may be desirable.

Alternatively, certain conditions may benefit from an increase in neurotrophin responsiveness. It may therefore be beneficial to increase the number or binding affinity of trkBs in patients suffering from such conditions. This could be achieved through gene therapy. Selective expression of recombinant trkB in appropriate cells could be achieved using trkB genes controlled by tissue specific or inducible promoters or by producing localized infection with replication defective viruses carrying a recombinant trkB gene. Conditions which may benefit from increased sensitivity to neurotrophin include particularly but are not limited to motorneuron disorders including amyotrophic lateral sclerosis, Werdnig-Hoffmann disease, chronic proximal spinal muscular atrophy, and Guillain-Barre syndrome. Such treatment may also be used for treatment of neurological disorders associated with diabetes, Parkinson's disease, Alzheimer's disease, and Huntington's chorea.

The present invention also has diagnostic and therapeutic utilities. In particular embodiments of the invention, methods of detecting aberrancies in the function or expression of the receptors described herein may be used in the diagnosis of neurological, muscular or other disorders. In other embodiments, manipulation of a receptor or agonists which bind a receptor may be used in the treatment of neurological disorders, including Alzheimer's disease, Parkinson's disease, and amyotrophic lateral sclerosis (Lou Gehrig's disease) or diseases of the muscle or neuromuscular unit. In further embodiments, the extracellular domain of the receptor is utilized as a blocking agent which blocks the binding of receptor to target cells.

In a further embodiment of the invention, patients that suffer from an excess of a particular receptor may be treated by administering an effective amount of anti-sense RNA or anti-sense oligodeoxyribonucleotides corresponding to the receptor gene coding region thereby decreasing expression of the receptor protein.

The present invention also provides for methods of treating a patient suffering from a disease or disorder related to death or degeneration of neuronal cells, epithelial cells or muscle cells comprising treating the patient with an effective amount of the cognate ligand which binds to any of the protein described herein. For example, the cognate ligand to Tie-2, which may be identified using the assay systems described herein, would be useful for identifying antagonists of the Tie-2 receptor found on endothelial cells. Such an antagonists would be useful to inhibit the proliferation of endothelial cells, thus inhibiting tumor growth by inhibiting vascularization. Alternatively, Tie-2 agonists capable of promoting the growth of endothelial cells, would prove useful for promoting the growth of vascular cells, thus promoting wound healing or repair to arteries following surgery.

5.5 Systems for the Assay and Discovery of Agents That Act on Receptor Tyrosine Kinases and of Novel Tyrosine Kinase Receptors The present invention also provides for systems that may be generally used in both the assay of pre-defined agents, as well as the discovery of novel agents, that act on receptor tyrosine kinases. In a related aspect of this invention, the same system can be used to discover unknown receptors that mediate responses to known factors. Once a particular receptor/ligand system is defined (as is done here with trkB and BDNF/NT-3), a variety of additional specific assay systems can be utilized, as detailed in other sections supra.

The present invention reveals that a receptor tyrosine kinase, when introduced into cells that do not normally express this receptor, allows these cells to exhibit profound and easily distinguishable responses to a ligand which binds this receptor. The present invention reveals that the type of response elicited depends on the cell utilized, and not the specific receptor introduced into the cell. Thus, the trkB receptor in PC12 pheochromocytoma cells results in BDNF/NT-3 dependent differentiation, whereas the same receptor in fibroblasts mediates both survival and proliferation in response to either BDNF or NT-3. Appropriate cell lines can be chosen to yield a response of the greatest utility for the assay, as well as discovery of, agents that can act on tyrosine kinase receptors. "Agents" refers to any molecule(s), including but not limited to peptide and non-peptide molecules, that will act in systems to be described in a receptor specific manner. One of the more useful systems to be exploited involves the introduction of the desired receptor (e.g. trkB) into a fibroblast cell line (e.g., the particular clone of NIH3T3 cells to be described below, section 7); thus such a receptor which does not normally mediate proliferative responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol.2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor.

Such systems are not limited to the assay of known ligands for known receptors, but can also be utilized to identify novel agents that might act on these or (or any other) receptors. For example, both the cell line bearing the introduced receptor as well as the parental cell line without the receptor can be exposed to any potential source of an agent that might work through the receptor; any specific effects (e.g. on cell survival or proliferation) on the cell line bearing the receptor can be used to identify sources of agents acting on that receptor, and to eventually purify such an agent.

Receptors also need not be limited to those for which a known ligand exists. In fact, this system may allow for the identification of ligands for "orphan" receptors so named because they have no known ligand. Thus, fibroblasts expressing trkB could have been used in such systems in order to identify and eventually purify the ligands (e.g. BDNF and NT-3) that normally activate trkB; they can now be used to identify additional peptide ligands or other agents (e.g. non-peptide molecules) that could act on these receptors.

Similarly, cell lines, such as fibroblasts, expressing Ehk-1, Ehk-2 can be used to in assay systems useful for identifying their cognate ligands. Because the ehks appear to be expressed in distinctive neuronal populations, including some of the principal ascending central cholinergic nuclei, ligands which bind these receptors are expected to play a role in promoting the growth or survival of these neuronal cells. Because the expression of ehk-1 begins early in development, its cognate ligands may play a role in embryogenesis.

The Ties are broadly expressed in embryonic, neonatal and adult tissues, where they are expressed in endothelial cells. [Maisonpierre, et al. Oncogene 8: 1631–1637 (1993). Tie-2 RNA levels are also significantly elevated in lung and, to a lesser extent, in the adrenal glands. Tie-2 is also expressed in the vasculature surrounding the lens and behind the pigmented epithelium, and it is uniquely expressed in lens epithelium (id). Cells expressing tie-2 RNA are also present in both vascular and epithelial regions of the tongue, heart and intestine. Accordingly, assay systems utilizing the Ties can be used to identify cognate ligands that promote the survival and/or growth of these tissues.

Sources for "agents" could include extracts from a variety of tissues and organisms, or supernatants from cells transfected with genomic DNA or cDNA expression libraries or natural products. In a particular embodiment of this invention, fibroblasts expressing an introduced receptor for which a ligand is desired could be transfected with cDNA expression libraries derived from a potential source of such a ligand; cells which survive and form colonies in defined media lacking fibroblast growth factors (Zhan and Goldfarb, 1986, Mol. Cell. Biol., Vol. 6, pp. 3541–3544) would presumably now be making a growth factor that overcomes their normal requirements via an autocrine loop. To prove that this growth factor is working on the receptor of interest, supernatants harvested from these cells could now be assayed on the parental cell lines to prove that it only has actions on the parental cell line expressing this receptor; the transfected piece of DNA encoding the novel activity desired could then be isolated using traditional means.

The present invention provides for methods for cloning at least a portion of tyrosine kinase receptor gene which may then be used in the identification of ligand/receptor pairs, as set forth supra. Such methods comprise (i) amplifying tyrosine kinase encoding nucleic acid sequences by polymerase chain reaction using a collection of cDNA molecules (such as a cDNA library) as template and using oligonucleotide primers that correspond to regions of known tyrosine kinase molecules, said regions being associated with tyrosine kinase activity; and (ii) cloning the amplified nucleic acid into an appropriate vector molecule, such as a plasmid, bacteriophage, etc. The present invention also provides for tyrosine kinase genes, and portions thereof, cloned by this method. In particular, non-limiting specific embodiments, set forth in Sections 9 and 10, infra, the oligonucleotide primers (SEQ ID NOS:1–5) utilized may be as set forth in FIG. 12A or, alternatively, Table II, infra.

DNA amplified and cloned by this method may then be sequenced using standard techniques. The resulting sequences may then be compared to the sequences of known tyrosine kinase molecules in order to identify clones of particular interest. The present invention further provides for the cloned nucleic acid sequences identified using this method, as set forth in Sections 9 and 10, infra, and for peptides and proteins encoded by cDNAs comprising these sequences. Accordingly, the present invention provides for substantially purified recombinant nucleic acid molecules comprising the nucleic acid sequences (i) substantially as set forth in FIG. 12C for Rtk-1 (SEQ ID NO:11), Rtk-6 (SEQ ID NO:19), Rtk-7 (SEQ ID NO:25), Rtk-8 (SEQ ID NO:32) and Rtk-9 (SEQ ID NO:30); (ii) substantially as set forth in FIG. 13B for Rtk-4 (SEQ ID NO:63) and Rtk-5 (SEQ ID NO:65); (iii) substantially as set forth in FIG. 14 for Rtk-2 (SEQ ID NO:77); (iv) substantially as set forth in FIG. 15 for Rtk-3 (SEQ ID NO:79); (v) substantially encoding the amino acid sequence set forth in FIG. 20 for Rtk-7 (now known as Tie-2; SEQ ID NO:96); (vi) substantially as set forth in FIG. 21 for Rtk-8 (now known as Ehk-2; SEQ ID NO:100); and (vii) substantially as set forth in FIG. 22 for Rtk-9 (now known as Ehk-1; SEQ ID NO:102); or portions thereof comprising at least about ten nucleic acid residues. The present invention also provides for nucleic acids as contained in pBluescript SK-containing Rtk-2 and pBluescript SK-containing Rtk-3 deposited with the American Type Culture Collection and granted accession numbers 75052 and 75053. The present invention further provides for substantially purified protein molecules comprising the amino acid sequences (i) substantially as set forth in FIG. 12C for Rtk-1 (SEQ ID NO:12), Rtk-6 (SEQ ID NO:20), Rtk-7 (SEQ ID NO:26), Rtk-8 (SEQ ID NO:33) and Rtk-9 (SEQ ID NO:31); (ii) substantially as set forth in FIG. 13B for Rtk-4 (SEQ ID NO:64) and Rtk-5 (SEQ ID NO:66); (iii) substantially as set forth in FIG. 14 for Rtk-2 (SEQ ID NO:78); (iv) substantially as set forth in FIG. 15 for Rtk-3 (SEQ ID NO:80); (v) substantially as set forth in FIG. 20 for Rtk-7 (now known as Tie-2; SEQ ID NO:96); (vi) substantially as set forth in FIG. 21 for Rtk-8 (now known as Ehk-2; SEQ ID NO:101); and (vii) substantially as set forth in FIG. 22 for Rtk-9 (now known as Ehk-1; SEQ ID NO:103) or portions thereof comprising at least about six amino acid molecules, or functionally equivalent molecules. Functionally equivalent molecules include those in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which are differentially modified during or after translation, e.g., by glycosylation, proteolytic cleavage, linkage to an antibody molecule or other cellular ligand, etc.

The present invention further provides for cells and microorganisms that carry the recombinant nucleic acid molecules described above, including, but not limited to, Rtk-1, Rtk-6, Rtk-7 (Tie-2), Rtk-8 (Ehk-1), Rtk-9 (Ehk-1), Rtk-2, Rtk-3, Rtk-4 and Rtk-5. In particular embodiments, the cell carrying the recombinant nucleic acid is a fibroblast. In other embodiments, the cell is a bacterium.

Amplified nucleic acid fragments may then be used to identify full-length cDNA clones. In preferred embodiments of the invention, an amplified DNA fragment of interest is used to identify a tissue or cell line that expresses relatively abundant levels of a corresponding mRNA, for example, using Northern blot or dot-blot analysis. Such a tissue or cell line may then be used to generate a cDNA library which may serve as a superior source of a full-length cDNA which comprises the sequence and the amplified fragment.

A reciprocal approach could be used to molecularly clone a receptor for an "orphan" factor (for example, a neurotrophic protein for which no receptor has been isolated). Fibroblasts exposed to this factor normally would not respond, but if transfected with a cDNA expression library prepared from cells thought to be expressing this receptor, occasional transfectants would arise which now express this receptor and should now respond to this factor in an autocrine fashion. Powerful selection mechanisms, such as the ability to form colonies in defined media in the presence of the "orphan" factor, should identify transfectants that express the receptor of interest; the gene encoding this receptor could then be isolated by traditional means.

6. EXAMPLE: trkB ENCODES A FUNCTIONAL RECEPTOR FOR BDNF AND NT-3 BUT NOT NGF

1. Materials and Methods

1. Cell Culture, Neurotrophins, and Iodination of Neurotrophins

COS-M5 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. PC12 cells were cultured in DMEM with 6% FBS and 6% horse serum, (P/S) and 2mM glutamine on Costar tissue culture plates in an atmosphere of 7.5% $CO_2$. PC12 cells obtained from Dr. L. A. Greene's laboratory were utilized in experiments depicted in FIG. 2, and PC12 cells obtained from Dr. E. M. Shooter's laboratory were utilized in experiments depicted in FIG. 5. The human neuroblastoma cell line, SH-SY5Y (obtained from June Biedler, Sloan-Kettering) was cultured in Eagle's minimal essential medium (EMEM) with 10% FBS, (P/S) and 2 mM glutamine.

Murine 2.5S NGF was obtained from Bioproducts for Science (Indianapolis, Ind.). Both human BDNF and NT-3 were produced in CHO cells and purified from CHO cell conditioned media to homogeneity as assessed by silver-stained polyacrylamide gels and amino acid sequence analysis. Purified neurotrophins (NGF, BDNF, and NT-3) were all iodinated using the lactoperoxidase method as described in Hempstead et al., 1989, Science, 243: 373–375. Iodinated neurotrophins were separated from unincorporated $^{125}$I by using a Centriflo CF50A filters (Amicon, Beverly, Mass.). Aggregates were removed using gel filtration (S200) column chromatography.

2. Cloning Rat trkB: Mammalian Expression, Constructs, and Transient Transfections A full-length rat trkB cDNA clone was obtained by screening a rat brain cDNA library in the lambda ZAP2 vector (Stratagene) with rat trkB-specific oligonucleotides corresponding to the most 5' and 3' coding regions of trkB. Both the human LNGFR (Johnson et al., 1986, Cell 47: 545–554) and rat trkB cDNAs were subcloned into the mammalian expression vector, pCMX, to generate pCMX-LNGFR or pCMX-trkB respectively. pCMX-trkB(del) was generated by digesting the pCMX-trkB plasmid with ApaI (which cuts just after the trkB transmembrane domain) and NotI (which cuts just after the trkB coding region in vector sequences), blunting these ends, and religating the plasmid; the trkB coding region generated includes all of the extracellular and transmembrane domains of trkB, but is lacking the C-terminal 320 amino acids.

COS-M5 cells were transiently transfected with either the pCMX-LNGFR, pCMX-trkB, or control vector (pCMX) by the DEAE-dextran transfection protocol. Briefly, COS-M5 cells were plated at a density of $1.5 \times 10^6$ cells per 100 mm plate 24 hours prior to transfection. For transfection, the cells were cultured in serum-free DMEM containing 400 μg/ml of DEAE-dextran, 1 μM chloroquine, 2 mM glutamine, 20 μg/ml insulin, 5 μg/ml transferrin, 33 nM sodium selenite, and 5 μg of the appropriate DNA for 3 hours and 15 minutes at 37° C. in an atmosphere of 5% CO2. The transfection media was aspirated and replaced with phosphate-buffered saline with 10% DMSO for 2 min. Following this DMSO "shock", the COS-M5 cells were placed into DMEM with 10% FBS, 1% each of penicillin and streptomycin, and 2 mM glutamine for 48 hours.

PC12 cells were transiently transfected by electroporation. Briefly, the cells were rinsed prior to transfection in ice-cold Dulbecco's phosphate-buffered saline (calcium and magnesium-free) containing 2 mg/ml glucose and then resuspended in the same buffer at a density of $1.5 \times 10^7$ cells per ml containing 40 μg of the appropriate DNA. PC12 cells were transfected with either pCMX, pCMX-trkB or the pT24-ras plasmid (Yancopoulos et al., 1985, Proc. Natl. Acad. Sci. USA., 82: 5455–5459). The cell mixture was incubated on ice for 10 min. and then quickly brought to room temperature and electroporated in a total volume of 1 ml at 1150 V/cm and 500 uF. Electroporated cells were incubated on ice for 30 minutes prior to plating in DMEM with 6% FBS and 6% horse serum with 1% each of penicillin and streptomycin and 2 mM glutamine; cells were plated on Costar plastic in the absence of any pre-coating. 48 hours after transfection, the cells were treated with 100 ng/ml of neurotrophin or BSA (see Legend of FIG. 5) and neurite outgrowth was scored 48 hours later.

3. Chemical Cross-linking

Cells were harvested in phosphate-buffered saline containing 1 mM EDTA, 1 mg/ml glucose and 25 mM HEPES (PBS-versene) and resuspended at an appropriate density (generally $1 \times 10^6$ cells per ml) in ice-cold binding buffer A (PBS containing 1 mg/ml each of BSA and glucose). pCMX-trkB or pCMX vector transfected COS-M5 cells ($4 \times 10^5$ cells) were incubated on ice with $^{125}$I-labeled neurotrophins (final concentration estimated to be between 0.1 and 0.25 nM) for 90 minutes in the absence or presence of unlabeled NGF, BDNF or NT-3 (see FIGS. 1 and 3). The chemical cross-linker DSS (Pierce, Rockford, Ill.) was used following conditions described in Meakin and Shooter, 1991, Neuron 6: 153–163. The cross-linking reaction was terminated after 90 minutes and quenched with 12 ml of 50 mM Tris buffer containing 160 mM NaCl. Cells were centrifuged at 300×g for 5 minutes and then washed twice with 12 ml of buffer A. Pelleted cells were solubilized in SDS containing 2% of 2-mercaptoethanol, boiled for 5 minutes; radiolabeled cross-linked proteins were resolved on 7% polyacrylamide gels and visualized by autoradiography after exposure of the dried gel to Kodak X-Omat film at −70° C.

4. $^{125}$I -NT-3 Competition Binding Assays

Binding of $^{125}$I-NT-3 to COS-M5 cells transfected with either pCMX-LNGFR, pCMX-trkB or control vector (pCMX) was assessed on cells in suspension. Cells were harvested in PBS-versene and then resuspended in binding buffer A as described above for chemical cross-linking. Cells were incubated with $^{125}$I-NT-3 (estimated between 0.1 and 0.25 nM) in the absence or presence of increasing concentrations of unlabeled NT-3, BDNF, or NGF ranging from 0.3 to 30 nM for NGF and between 1 and 100 nM for BDNF and NT-3 (see FIG. 4C and D). The binding reactions were carried out for 90 minutes on ice. Free $^{125}$I was separated from bound $^{125}$I by quickly centrifuging (30 second spin) the reaction mixture through a sucrose gradient formed in a long-tip microcentrifuge tube. The tubes were immediately frozen in a dry-ice/ethanol bath. The bottom of the reaction tube was cut and then counted in a gamma counter.

5. RNA Isolation and Northern Blotting Analysis

Total cellular RNA isolated from SH-SY5Y and treated or untreated PC12 cells was fractionated on 1% formaldehyde agarose gels, transferred to nylon membranes and hybridized to a $^{32}$P-labeled v-fos probe or a $^{32}$P-labeled c-jun probe as previously described (Squinto et al., 1990, Neuron 5, 757–766); probings for trkB expression were performed using a $^{32}$P-labeled rat trkB probe spanning a region encoding the intra-cytoplasmic tyrosine kinase domain.

2. Results

Figure 1B:
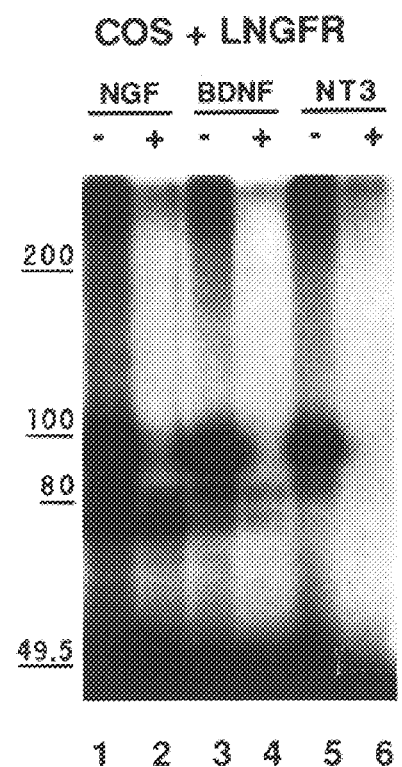
Figure 1C:
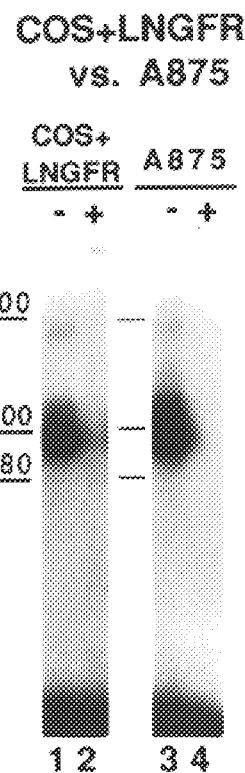

1. All Three Neurotrophins Bind to the LNGFR but BDNF and NT-3 Do Not Act Via the LNGFR To determine whether NT-3, like NGF and BDNF (Rodriguez-Tebar, 1990, Neuron, 4: 487–492), could also bind to the LNGFR, we examined all three neurotrophins for their ability to be chemically cross-linked to the LNGFR protein expressed transiently in COS cells. Each of the three radiolabeled neurotrophins could be specifically cross-linked to a species of the molecular weight expected for the LNGFR (FIG. 1B cross-linked complex reported to be approximately 100 kb by Hosang and Shooter, J.Biol. Chem. 260: 655–662). The cross-linked product was not observed on COS cells that were not expressing the LNGFR protein (FIG. 1A). Furthermore, as expected for specific binding the appearance of the cross-linked products could be competed effectively by an excess of the corresponding unlabeled neurotrophin (FIG. 1B). Computable cross-linking to a polypeptide of the correct size was also observed in a cell line, A875 melanoma, known to stably express large amounts of the LNGFR (FIG. 1C).

Having established that all three neurotrophins bind to the LNGFR protein, we assessed the ability of BDNF and NT-3 to function via low or high affinity NGF receptors. The PC12 cell line, which expresses both classes of NGF receptor, displays prominent responses including both neurite outgrowth and the transcriptional induction of a set of so-called "immediate early genes" in response to NGF (Greene and Tischler, 1976, Proc. Natl. Acad. Sci. U.S.A., 73: 2424–2428; Greenberg, et al., 1985, J.Biol. Chem. 260: 14101–14110, see FIG. 2A, B). However, when PC12 cells were incubated with BDNF or NT-3 at concentrations either below or exceeding that known to be saturating for responses to NGF, we observed neither morphological changes (under conditions optimal for neurite outgrowth, see below) nor the induction of immediate early gene expression FIG. 2A, 2B. This implies that neither low nor high affinity NGF receptors suffice for functional responses to BDNF and NT-3 and that such responses require at least one receptor component not normally found on PC12 cells.

2. BDNF and NT-3, But Not NGF, Bind to Full-length and Truncated Forms of trkB

Figure 3A:
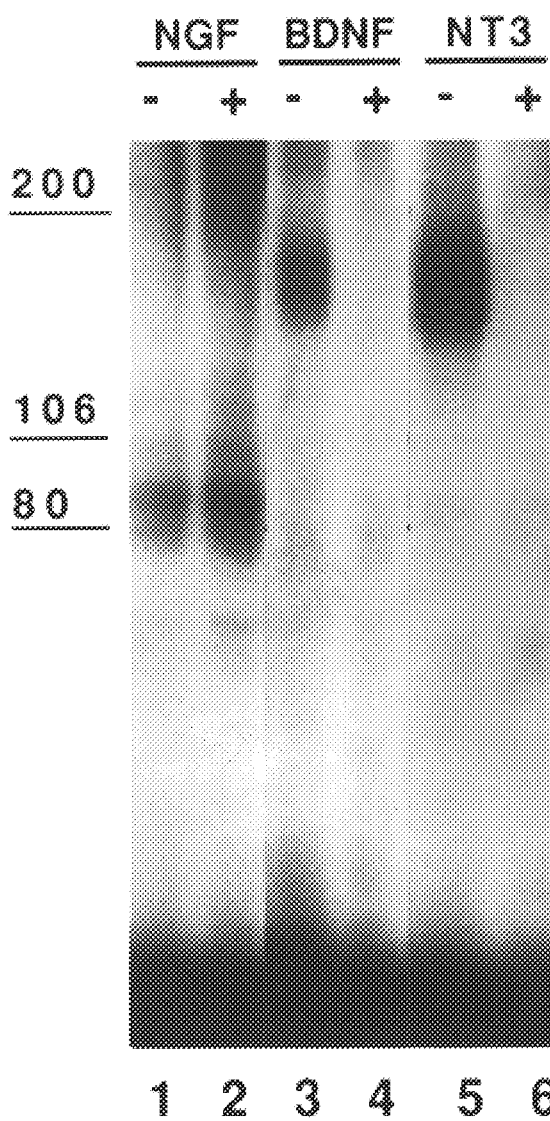
Figure 3B:
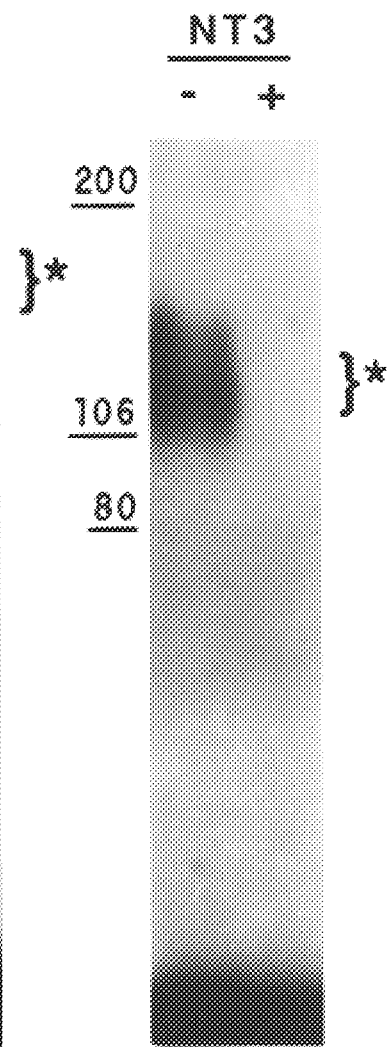

TrkB is not expressed in PC12 cells (Kaplan et al., 1991, Nature 350: 158–160); cell lines expressing trkB have not been described. A full-length trkB cDNA was isolated and transiently expressed in COS cells, on which cross-linking experiments were carried out with radioiodinated neurotrophins. As shown in FIG. 3A both BDNF and NT-3, but not NGF, could be cross-linked to a polypeptide of approximately the expected size for the trkB gene product; some heterogeneity in the size of this cross-linked species was observed, as has been previously reported for the HNGFR cross-linked to NGF (Meakin and Shooter, 1991, Neuron 6: 153–163). Cross-linking of labeled BDNF or NT-3 to the presumptive trkB gene product was not observed in the presence of excess unlabeled homologous ligand (FIG. 3A, lanes labeled "+"). To verify that the protein cross-linked to BDNF or NT-3 actually corresponds to the trkB gene product, and to determine whether certain truncated forms of the protein are capable of binding ligands, a trkB deletion mutant lacking the intracytoplasmic protein-tyrosine kinase domain was constructed and expressed in COS cells. As illustrated in FIG. 3B, radiolabeled ligand (in this case NT-3) was cross-linked efficiently to a surface component of cells expressing the truncated trkB product; furthermore, the marked shift in mobility (corresponding to about 35 kD) observed between the cross-linked species obtained with full-length or truncated trkB proteins agreed well with the known size of the deletion.

Figure 4A:
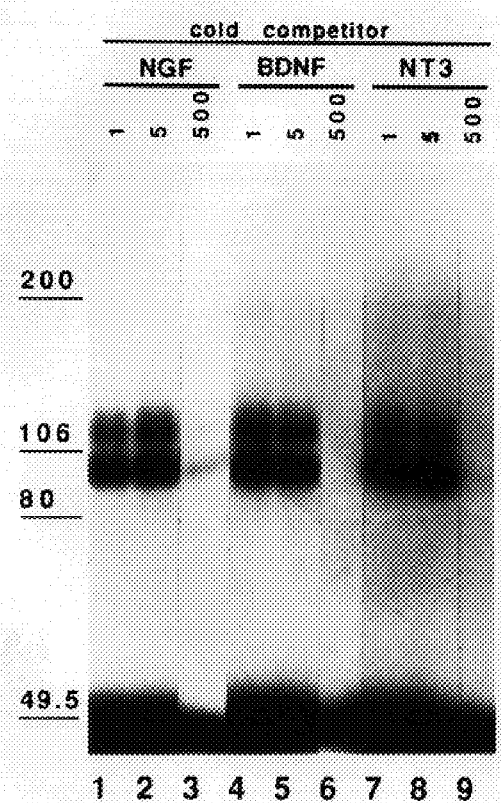

3. BDNF and NT-3, But Not NGF, Compete for Binding to trkB and Display Higher Affinity Binding to trkB Than They do to LNGFR The specificity and relative affinity of binding of the neurotrophins to the LNGFR and to trkB was compared in competition assays. Each of the three unlabeled neurotrophins were effectively able to specifically block the cross-linking of radiolabeled NT-3 to the LNGFR expressed in COS cells when present at 500 nM levels but not at 1–5 nM levels (FIG. 4A). Consistent with these results, the binding of radiolabeled NT-3 to the LNGFR expressed on COS cells was completed similarly by each of the three unlabeled neurotrophins (FIG. 4C); the competition curves suggest dissociation constants in the nanomolar range for all three neurotrophins, extending previous observations for NGF and BDNF (Rodriguez-Tebar et al., 1990, Neuron 4: 487–492).

Figure 4B:
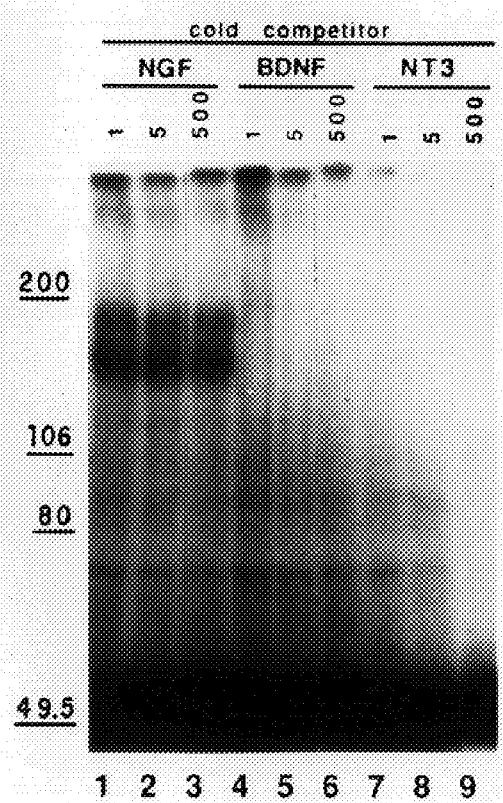
Figure 4D:
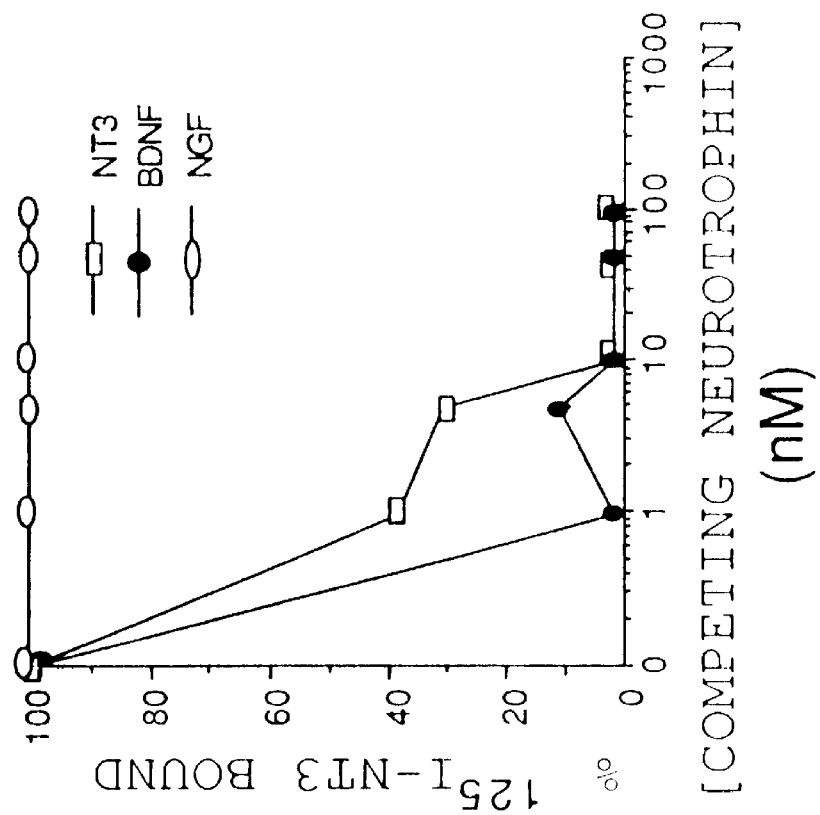
Figure 4C:
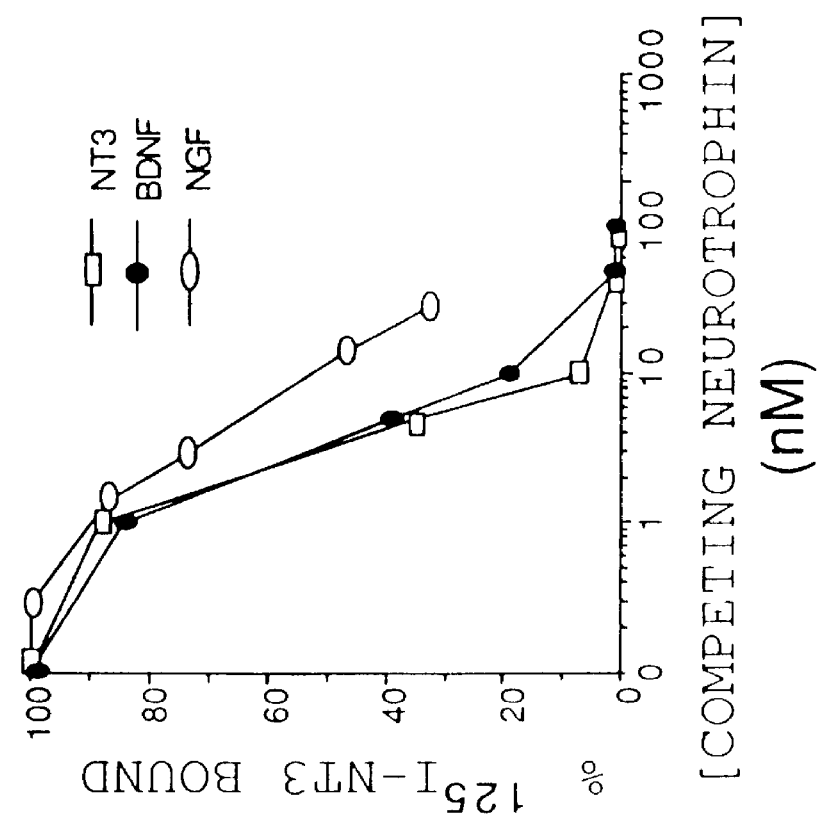

In contrast to the rather high levels of unlabeled ligands required to specifically block binding to the LNGFR, much lower levels of unlabeled BDNF and NT-3 effectively prevented binding of radiolabeled NT-3 to trkB as assayed either by cross-linking (FIG. 4B) or direct binding analysis (FIG. 4D). NGF, even at 500–1000 fold molar excess, did not compete for binding of radiolabeled NT-3 to trkB in either assay (FIG. 4B, 4D). Because the amounts of unlabeled BDNF and NT-3 required to completely inhibit the binding of radiolabeled NT-3 to trkB were 10 to 100-fold lower than those necessary to block binding of NT-3 to the LNGFR, our data suggest that trkB displays considerably higher affinity for both BDNF and NT-3 than does the LNGFR.

4. trkB Mediates Neurite Outgrowth in Response to Both BDNF and NT-3 in PC12 Cells PC12 cells display a characteristic morphological response, neurite extension, indicative of differentiation to a more mature neuronal phenotype when exposed to NGF. As demonstrated above, these cells do not respond to either BDNF or NT-3. To test whether trkB could mediate a biologically relevant response to BDNF or NT-3, PC12 cells were transiently transfected with a trkB expression vector (pCMX-trkB) and incubated with each of the neurotrophins. In order to minimize background, the transfected cells were cultured on standard tissue culture plastic rather than either collagen-coated or Primaria surfaces; under these conditions which are suboptimal for neurite extension (Greene et al., 1987, Meth. Enzymol., 147: 207–216; Chen, et al., 1990, Cell Growth Diff. 1:79–85), NGF induced rather short neurites from control PC12 cells as well as from the trk-B-transfected cells (FIG. 5B). No cells with neurites were seen in the trkB-transfected cultures in the absence of added neurotrophic factor (FIG. 5C). However, many cells in the trkB-transfected PC12 cultures displayed robust neuritic outgrowth in response to either NT-3 or BDNF (FIG. 5D, E); no cells with neurites were seen in PC12 cells transiently transfected with control vectors and treated with BDNF or NT-3. As a positive control to assess transfection efficiency, the PC12 cells were transfected with an activated H-ras gene, which has been shown to induce ligand-independent differentiation of PC12 cells. The number of differentiated cells seen in the ras-transfected cultures indicates the number of transiently transfected PC12 cells in the cultures. Since the number of differentiated cells observed following BDNF treatment of pCMX-trkB transfected PC12 cells is comparable with the number of differentiated cells found in the ras-transfected populations (FIG. 5A, E), our data suggests that every PC12 cell expressing trkB can respond to BDNF while, however, a smaller subset of trkB expressing PC12 cells responded to NT-3 as measured by neurite outgrowth (FIG. 5D); more careful dose-response studies will be required to evaluate the apparent difference between BDNF and NT-3 in this assay. As depicted in FIG. 5, it was striking that the extensive neuritic outgrowth seen in ras-transfected PC12 cells or in pCMX-trkB-transfected PC12 cells subjected to BDNF or NT-3 was qualitatively different than the blunted neuritic outgrowth normally seen in response to NGF under these culture conditions.

Figure 6A:
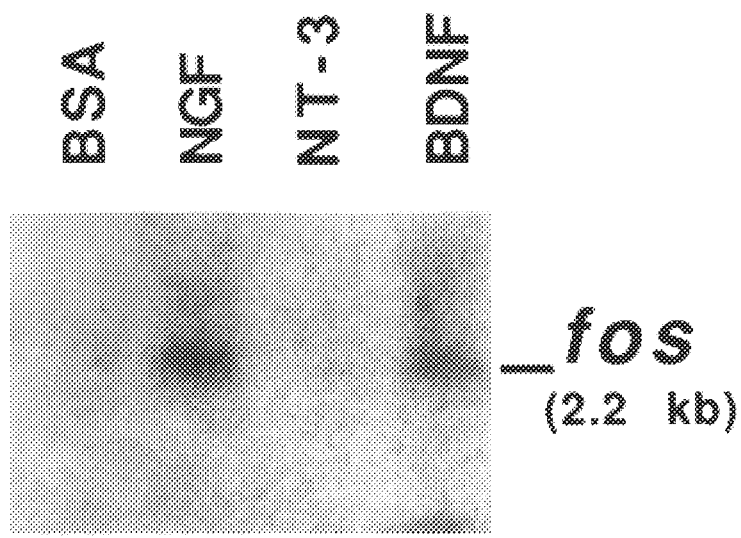
Figure 6B:
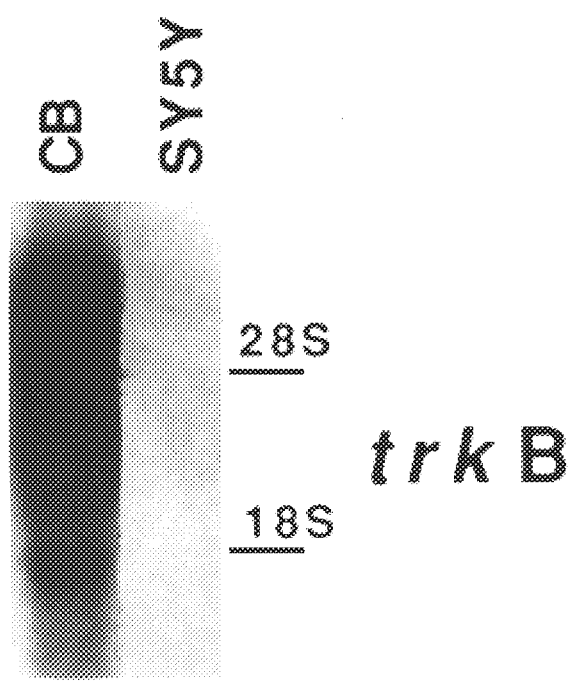

5. SH-SH5Y Human Neuroblastoma Cells Respond to BDNF, But Not NT-3, and do not Express trkB: Evidence for Another Neurotrophin Receptor We have used the induction of immediate early gene expression as an assay (Squinto et al., 1990, Neuron 5:757–766) to search for neuronal tumor cell lines responsive to BDNF, NT-3 and NGF. One such line (SH-SY5Y) was found to express c-fos mRNA in response to both NGF (as previously described) and BDNF, but not NT-3 (FIG. 6A). Further studies have verified that BDNF, but not NT-3, has additional functional effects on SH-HY5Y; for example, BDNF protects these cells from oxidative insults. Although this cell line has been shown to express low levels of both high and low affinity NGF receptors (Chen, et al., 1990, Cell Growth Diff., 1:79–85) and detectable levels of trkAmRNA, it did not express detectable levels of trkBmRNA (FIG. 6B). The apparent lack of trkB expression in a BDNF-responsive cell line, together with its failure to respond to NT-3, leads us to predict that either there are additional modulators of the LNGFR or trkA which confer BDNF responsiveness, or that yet another functional neurotrophin receptor exists which has discrete specificity for BDNF.

3. Discussion

We conclude that trkB encodes an essential component of a functional receptor for BDNF and NT-3, but not for the third neurotrophin family member, NGF. Recent reports indicate that the trkA proto-oncogene, the closest known relative of trkB, similarly encodes an essential component for a high affinity receptor which binds NGF (Kaplan et al., 1991, Nature, 350: 158–160; Klein et al., 1991, EMBO J. 8: 3701–3709). Our observations that normal PC12 cells do not respond to BDNF or NT-3 imply that trkA, which is expressed in PC12 cells, is uniquely activated by only one known member of the neurotrophin family, NGF.

We find that BDNF and NT-3 bind to trkB in the absence of the LNGFR, and that this binding is of higher affinity than their binding to the LNGFR. Similarly, Klein et al. (1991, Cell 65:189–197) report that NGF can bind to trkA with high affinity in cells that do not express the LNGFR. The function of the LNGFR remains unclear. We extend previous findings (Rodriguez-Tebar et al., 1990, Neuron 4: 487–492) by demonstrating that all three neurotrophins bind to the LNGFR with approximately equal, albeit relatively low, affinity; the conservation of this property suggests a significant biological role. It remains possible that the LNGFR modulates the binding of each of the neurotrophins to its appropriate trk receptor. Alternatively, the LNGFR may mediate signal transduction via an independent pathway, or it may not be directly involved in initiating signal transduction. For example it may act to localize, concentrate or trap the neurotrophins on the surface of LNGFR-expressing cells. In this regard it is of interest that neuronal supporting cells (such as Schwann cells) that do not respond to NGF express the LNGFR and up-regulate it in response to injury (Johnson et al., 1988, TINS 11: 299–304), perhaps providing a fixed matrix or path for the concentration and presentation of neurotrophins to regenerating neurons. Alternatively, the LNGFR may act as a "clearance" receptor that reduces free or circulating levels of the neurotrophins; the LNGFR is widely distributed both in the CNS and in the periphery (Maisonpierre et al., 1990, Neuron 5: 501–509), and secreted forms of the LNGFR (DiStefano and Johnson, 1988, Proc. Natl. Acad., Sci. USA, 85: 270–274) may aid in such clearance mechanisms. In regard to non-signalling roles for the LNGFR, related mechanisms specific for BDNF and NT-3 can be proposed based on the presence of truncated forms of trkB. The co-localization of BDNF and truncated trkB transcripts outside of the nervous system (most prominently in lung and skeletal muscle) raises intriguing questions concerning the role of BDNF, trkB and other potential BDNF receptors in non-neural tissues.

The fact that BDNF and NT-3 share a functional receptor, trkB, is consistent with our previous suggestions that the distributions and overlapping neuronal specificities of BDNF and NT-3 particularly link the roles of these two neurotrophins, at least in the central nervous system. During the maturation of different brain regions marked by decreasing NT-3 levels and increasing BDNF levels, the expression of trkB remains relatively constant. However, the identification of a cell line which responds to BDNF but not NT-3 and does not detectably express trkB strongly suggests that these two neurotrophins are not entirely interchangeable, and that there may exist additional receptors or modulatory components, which allow for distinct responses to either BDNF or NT-3. Such modulation may explain, for example, the differing effects of NT-3 and BDNF on PC12 cells transfected with trkB (see above) or on sympathetic neurons (Maisonpierre et al., 1990, Science, 247: 1446–1451). Sympathetic neurons are known to express trkB, although the available in situ hybridization data do not distinguish between the presence of functional or non-functional trkB transcripts in these neurons (Klein et al., 1989, EMBO J. 8: 3701–3709). An evolutionary comparison of BDNF and NT-3 lead us to predict that these two neurotrophins were strictly conserved to maintain their specific interactions with multiple receptors. Although NGF is well conserved evolutionarily compared to most secreted factors, it does not display the striking conservation that BDNF and NT-3 do, perhaps suggesting that it does not interact with as many receptors as the other two known neurotrophins. Our findings place the neurotrophins in the growing class of receptor/ligand systems in which multiple receptors each bind to several different related ligands (reviewed in Cross and Dexter, 1991, Cell, 64: 271–280).

The binding and activation of receptor tyrosine kinases by the neurotrophins reveals that these factors utilize signalling pathways very similar to those activated by mitogenic growth factors. This finding is consistent with recent data that neurotrophic factors can act as mitogens in certain contexts (e.g. Cattaneo and McKay, 1990, Nature, 347: 762–765), but also indicates that signals which initiate the activation of receptor tyrosine kinases normally integrate into non-mitogenic transduction pathways in neurons. Despite differences in ultimate sequelae (i.e. mitogenesis vs.

survival or differentiation), at least some of the early intermediates in tyrosine kinase signalling cascades, such as the ERK family of protein kinases, are similarly activated in both neuronal and non-neuronal cells. Other examples in which activation of receptor-like tryosine kinases in neuronal cells leads to non-mitogenic sequelae include the *Drosophila sevenless* protein, where activation via a non-diffusible ligand is required for the differentiation of photoreceptor cells (Basler, et al., 1991, Cell, 64: 1069–1081).

7. EXAMPLE: TrK MEDIATES BDNF/NT-3-DEPENDENT SURVIVAL AND PROLIFERATION IN FIBROBLASTS LACKING THE LOW-AFFINITY NGF RECEPTOR

1. Materials and Methods

1. Cells, Cell Culture and DNA Transfections

NIH3T3 cells were cultured in Dulbecco's modified Eagle's medium (DMEM) containing 10% bovine calf serum, 1% each of penicillin and streptomycin (P/S) and 2 mM glutamine in an atmosphere of 5% $CO_2$. For defined media assays, defined media was prepared as described in Zhan et al., (1987, Oncogene 1:369–376). While we have demonstrated that our NIH3T3 cells lose viability in growth factor-deficient media (Zhan et al., Oncogen 1:369–376; Zhan and Goldfarb, 1986, Mol. Cell. Biol. 6:3541–3544), it should be noted that some other variants of NIH3T3 cells do not lose viability, but rather quiesce, in growth factor deficient media. DNA transfections (using pLTR-trkB and pLTR-hyg constructs described by Squinto et al., 1991, Cell 65:1–20) into these cells were performed as reported in Wigler, et al. (1979, Cell 16:777–785). COS cell culture and transfection with pCMX-LNGFR were performed as described in Squinto et al. (1991, Cell 65:1–20). Neuronal survival assays using chick dorsal root ganglion neurons were performed described in Rodriguez-Teber and Barde (1988, The Journal of Neuroscience 8:3337–3342).

2. Factors

Preparation, purification and radiolabelling of recombinant human BDNF and NT-3, produced in CHO cells, was as described in Squinto et al. (1991, Cell 65:1–20). Murine 2.5S NGF was obtained from Bioproducts, Indianapolis, Ind. bFGF was purchased from R&D Systems, Inc., Minneapolis, Minn.

3. Survival, Proliferation and Thymidine Incorporation Assays

Survival and proliferation assays were essentially performed as described in Zhan et al. (1987, Oncogene 1:369–376; Zhan and Goldfarb, 1986, Mol. Cell. Biol. 6:3541–3544). In brief, survival assays were performed by plating cells at 20% confluency on poly-D-lysine/fibronectin coated dishes and culturing in defined media (+/– factors) for 5 days; the degree of survival was scored microscopically and ranked from "–", for almost no survival, to "+++", for confluent survival. For proliferation assays, cells were plated at approximately 0.5% confluency on poly-D-lysine/fibronectin coated dishes, cultured for 8 days with or without added factors, and counted in a Coulter counter after trypsinization. For DNA synthesis assays cells were plated in medium containing 3% calf serum, and after achieving quiescence were challenged with indicated factors for 14 hours; the media was then supplemented with $^3$H-thymidine, at 1 microCurie per milliliter, for two hours. Radiolabel incorporation into TCA-insoluble material was subsequently determined as described in Cavalieri and Goldfarb (1987, Mol. Cell. Biol. 7:3544–3560).

4. RNA Isolation and Northern Blotting Analysis

RNA isolation and Northern blotting analysis was conducted as described in Maisonpierre et al. (1990, Neuron 5:501–509).

5. Protein Isolation and western Blotting Analysis

For detection of changes in tyrosine phosphorylation in response to factor addition, cells were starved for one hour in serum-free, defined media and then treated for 5 minutes with the factors as indicated. Cells were then washed in phosphate-buffered saline (PBS) with 1 mM orthovanadate, and lysed in RIPA lysis buffer (PBS containing 1% NP40, 0.1% SDS, 0.5% deoxycholate, 1 mM PMSF, 1 mM orthovanadate and 0.14 U/ml of aprotinin). For the experiments depicted in FIG. 11A, the lysates were precipitated with agarose-conjugated anti-phosphotyrosine monoclonal antibody, designation 4G10 (FOXNY Sp2 derivative myeloma×BALB/c spleen cells), obtained from Upstate Biotechnologies, Inc.; the immunoprecipitates were washed in lysis buffer, suspended by boiling in SDS-containing loading buffer, and run on 6% SDS-acrylamide gels and immunoblotted using the 4G10 anti-phosphotyrosine antibody. For the experiments depicted in FIG. 11B, the total cell lysates were directly electrophoresed on 8% SDS-acrylamide gels prior to immunoblotting using the 4G10 anti-phosphotyrosine antibody. Immunoblots were performed using Immobilon-P membranes; following application of the primary antiphosphotyrosine antibody 4G10, an $^{125}$I-labelled goat anti-mouse polyclonal antibody was used for detection.

2. Results

Figure 7B:
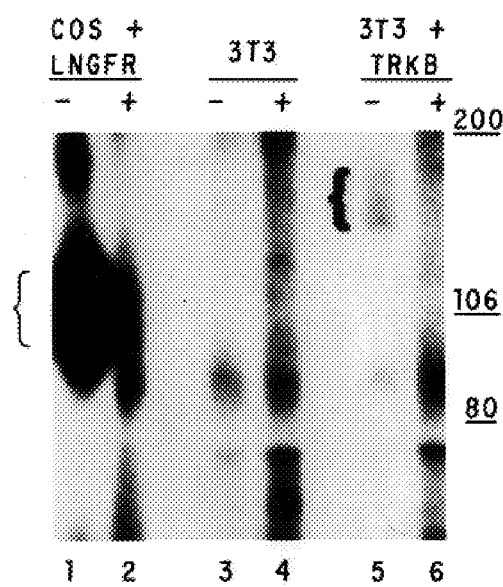

1. BDNF and NT-3 Act as Survival Factors for NIH3T3 Cells Expressing trkB in the Absence of the LNGFR In order to examine the functional capabilities of a trk receptor when expressed in non-neuronal cells, we co-transfected a trkB expression construct (pLTR-trkB, Squinto et al., 1991, Cell 65:1–20) and a hygromycin selectable marker gene (pLTR-hyg) (Murphy and Efstratiadis, 1987, Proc. Natl. Acad. Sci. U.S.A. 84:8277–8281) into the variant NIH3T3 cells described above. These NIH3T3 cells did not express detectable LNGFR as assayed by direct cross-linking to radiolabelled NT-3 (FIG. 7A; compare LNGFR-expressing cells in lanes 1, 2 with NIH3T3 cells in lanes 3, 4) or by $^{125}$I NGF binding studies performed on whole cells. Northern blot analysis also failed to detect LNGFR mRNA in NIH3T3 cells, although this mRNA was readily detectable in PC12 cells (estimated to have 100,000 LNGFRs/cell) or SH-SY5Y cells (which express barely detectable levels of the LNGFR; Chao et al., 1986, Science 232:518–521; Sonnenfeld and Ishii, 1982, J. Neurosci. Res. 8:375–391; FIG. 7B, upper panel). Following co-transfection with pLTR-trkB and pLTR-hyg, the NIH3T3 cells were replated at 20% confluency and then either selected in defined medium alone or in defined media supplemented with 5 nM of either bFGF, NGF, BDNF or NT-3, as well as in complete medium containing hygromycin and calf serum (FIG. 8). Direct selection in defined media revealed that all plated cells survived when the medium was supplemented with bFGF, as expected. Furthermore, no colonies were found when the defined media was not supplemented or supplemented only with NGF, indicating that trkB is incapable of providing a growth signal without stimulation by its cognate ligands. In contrast, several colonies were detected when the pLTR-trkB transfected cells were grown in defined media supplemented with either BDNF or NT-3; somewhat more colonies were found in the BDNF-containing media than in the NT-3 containing media (FIG. 8, left side). No colonies were seen in similar platings performed using the untransfected NIH3T3 cells, cells transfected with pLTR-hyg alone, or cells containing an expression construct for the LNGFR. Thus, transfection of NIH3T3 cells with pLTR-trkB resulted in cells which could form growing colonies in response to either BDNF or NT-3.

Figure 7A:
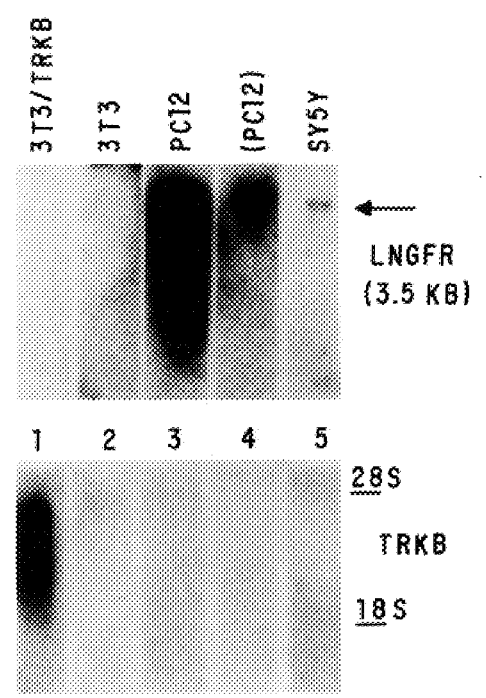
Figure 9A:
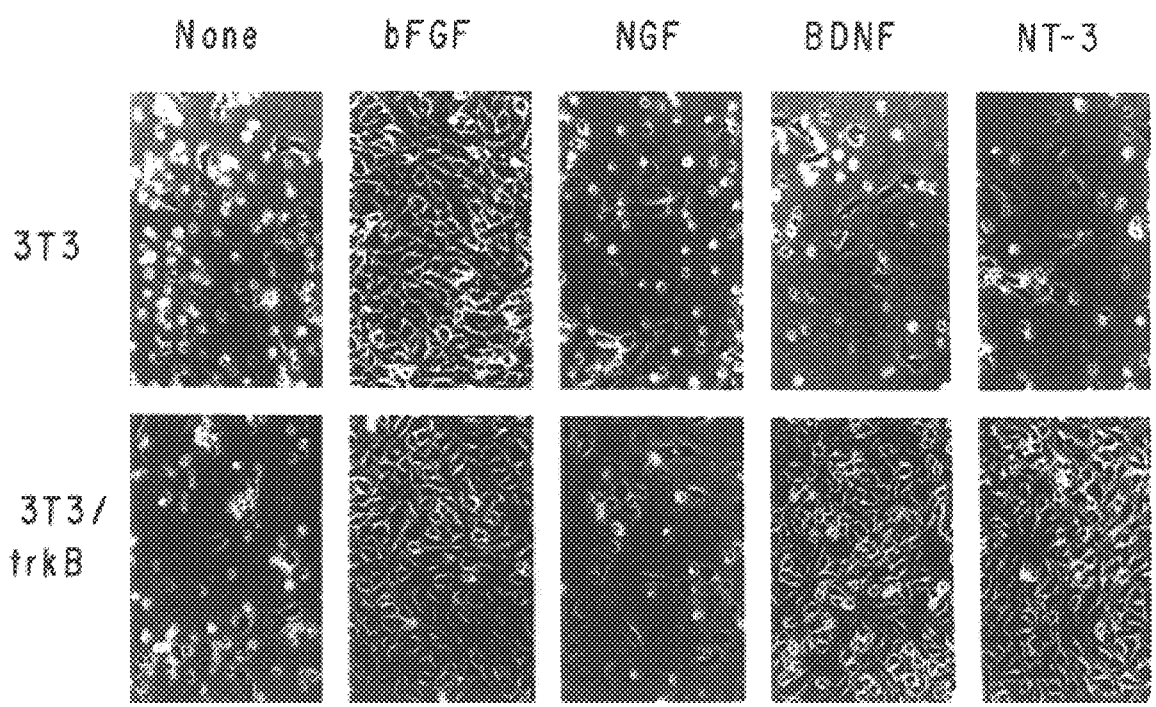

In order to determine whether the majority of trkB-transfected cells could respond to BDNF or NT-3, or whether the colonies described above reflected rare clones in the transfected population, the trkB-transfected cells were first selected in media containing 10% calf serum and hygromycin. These hygromycin-selected cells expressed substantial amounts of trkB transcripts (FIG. 9B, lower panel) and detectable trkB protein as judged by chemical cross-linking to radiolabelled NT-3 (FIG. 7A, lanes 5, 6); the number of trkB receptors in these cells is low in comparison to the number of LNGFR molecules expressed in COS cells transiently transfected with a LNGFR expression construct (FIG. 7A, compare lanes 1, 2 and 5, 6). The trkB-expressing cells were then tested in "survival assays" in which the cells were plated at relatively high density (20% confluency) in defined media alone or in defined media supplemented with 5 nM of bFGF or each of the neurotrophins. Within a few days, almost complete cell death had occurred in unsupplemented defined media or in defined media supplemented with NGF (FIG. 9A). Strikingly, confluent monolayers indicative of relatively uniform survival were seen in cultures of trkB-expressing cells supplemented with either bFGF, BDNF or NT-3 (FIG. 9A, bottom row). Survival was supported by bFGF, but not by any of the three neurotrophins, in cultures of the parental NIH3T3 cells (FIG. 9A, top row), of cells transfected with pLTR-hyg alone, or of cells containing an LNGFR expression vector.

Figure 9B:
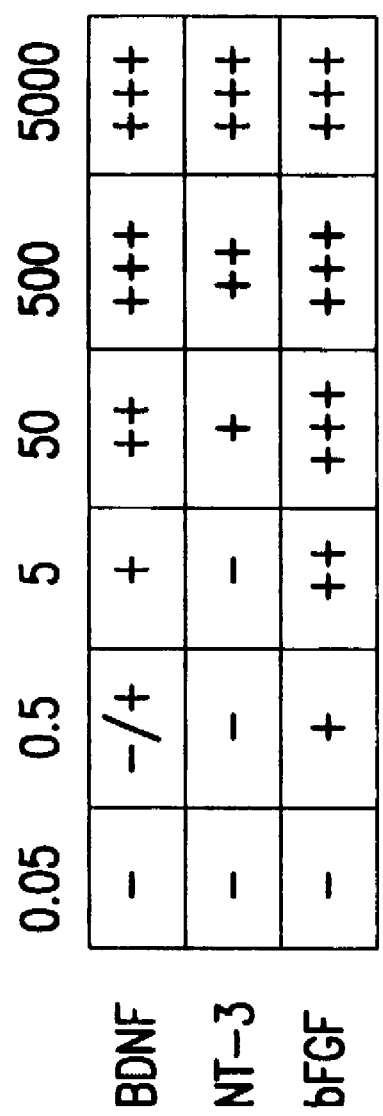

Dose-response survival assays revealed that picomolar concentrations of bFGF, BDNF and NT-3 were effective, with bFGF and BDNF activity obvious at 0.5–5 pM, and NT-3 effects discernible at 50 pM (FIG. 9B). However, NGF was not effective even at 100–1000 fold higher concentrations (FIG. 9A). Thus BDNF was almost as potent as bFGF in promoting survival of trkB-transfected NIH3T3 cells, while NT-3 was at least 10-fold less effective than BDNF in this assay.

2. BDNF and NT-3 Act as Proliferative Factors for TrkB-expressing NIH3T3 Cells

Figure 10A:
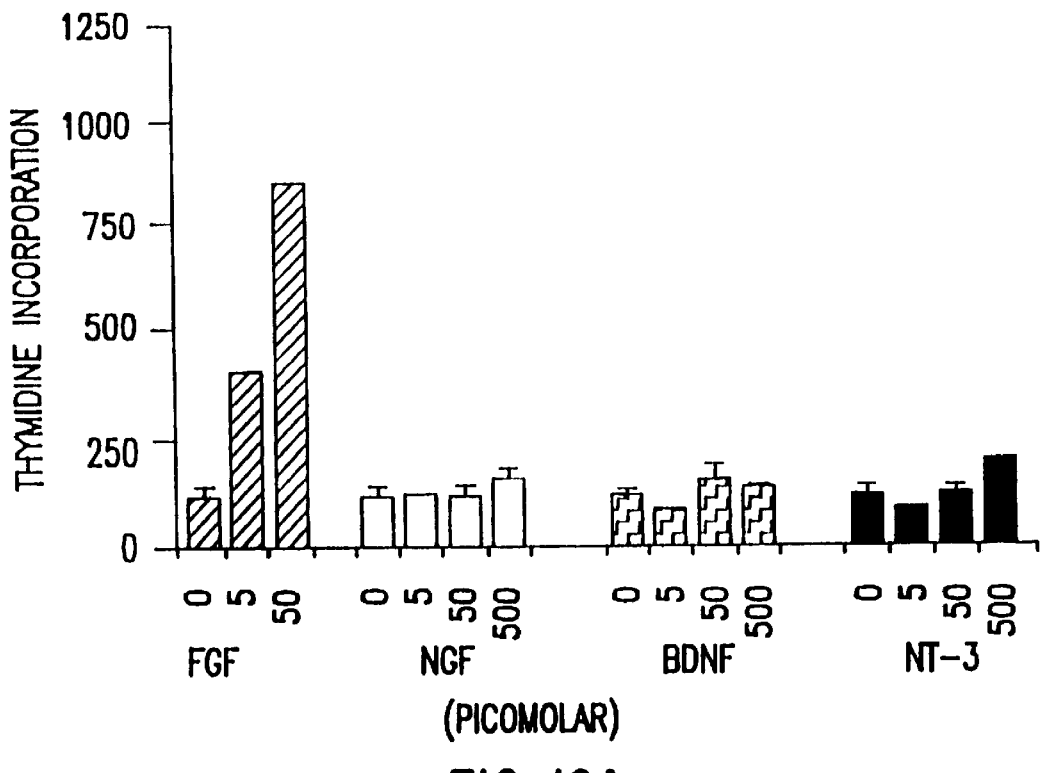
Figure 10B:
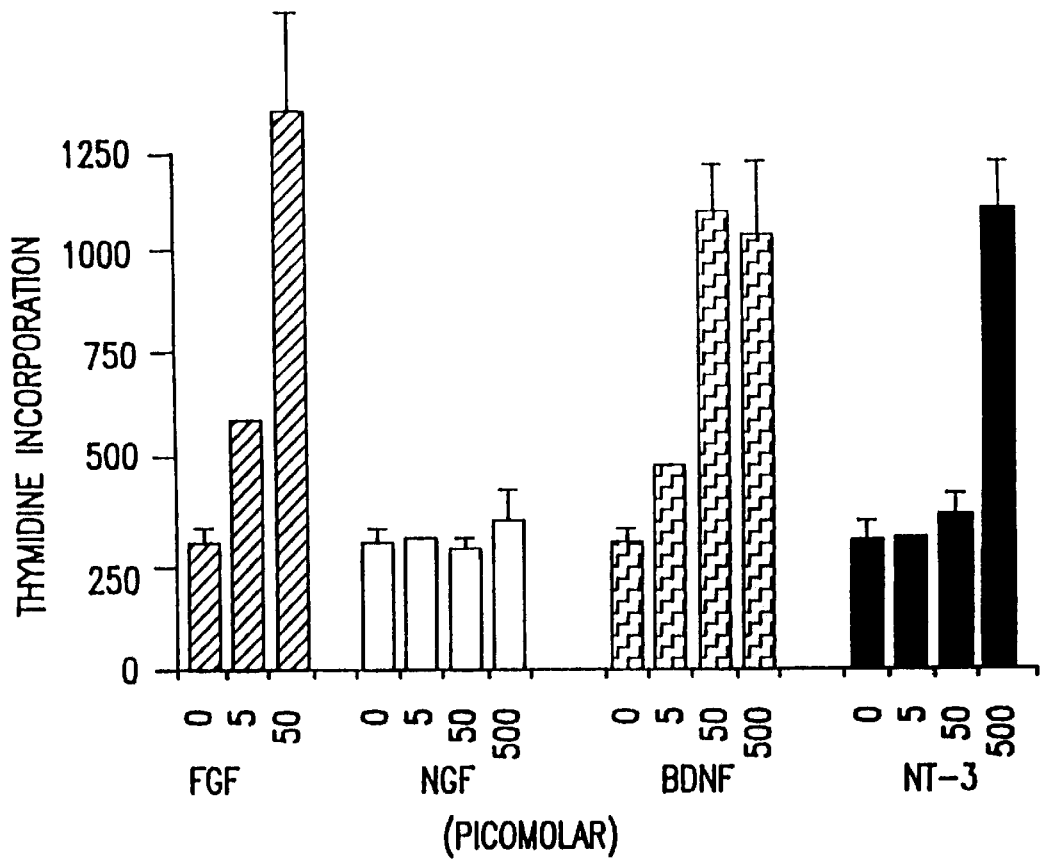
Figure 10C:
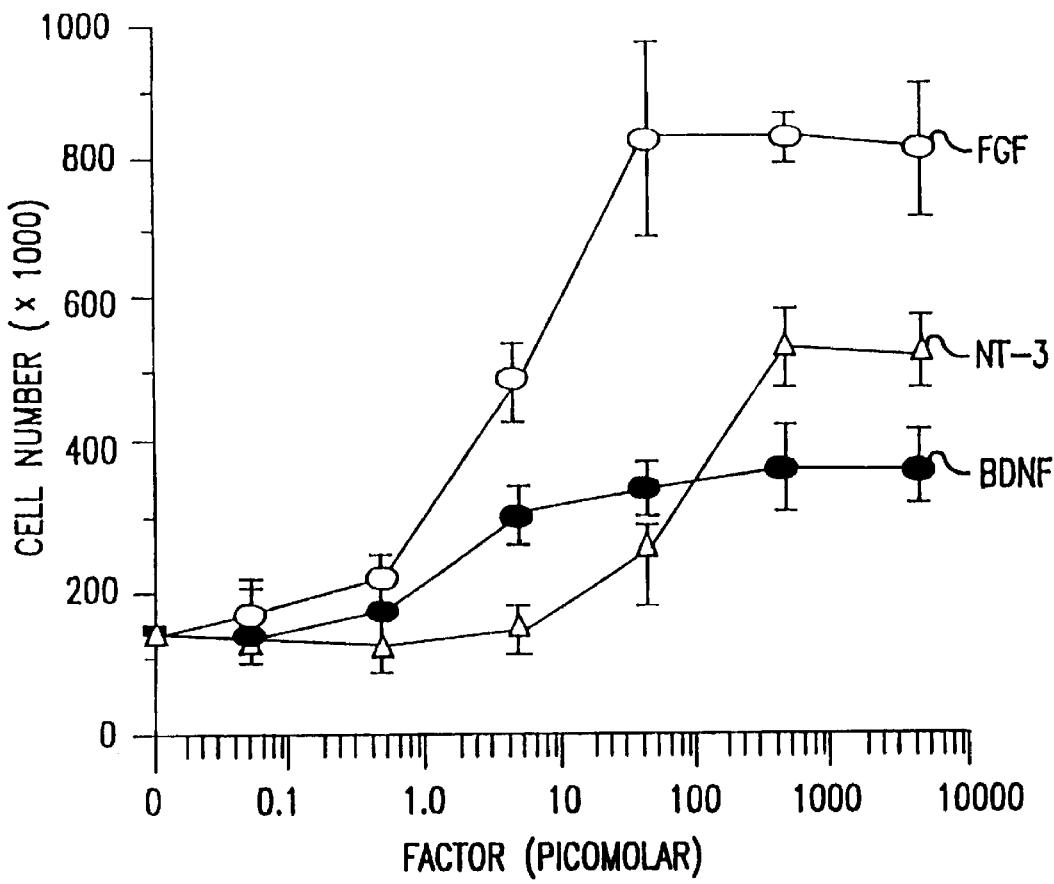
Figure 10D:
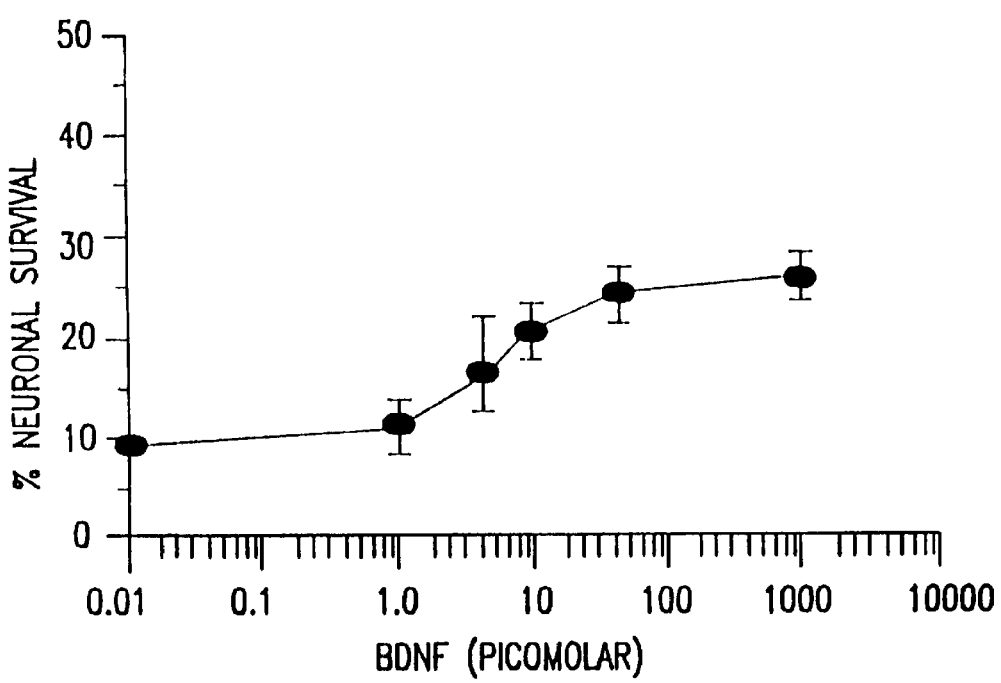

To determine whether BDNF and/or NT-3 activation of trkB provides mitogenic as well as survival signals to NIH 3T3 cells, we tested BDNF and NT-3 for their ability to promote DNA synthesis in trkB-expressing cells by utilizing a thymidine incorporation assay. Cells were grown to confluency in 3% serum, at which point they appeared quiescent based on the absence of mitotic cells; no cell death was apparent under these conditions. The various factors were then directly added to this media, and $^3$H-labeled thymidine incorporation was monitored 12 hours after factor addition. As shown in FIG. 10A, only bFGF was able to induce DNA synthesis in the parental NIH 3T3 cells, while efficient DNA synthesis was also induced by picomolar concentrations of BDNF and NT-3 in the trkB-expressing NIH 3T3 cells (FIG. 10B); the BDNF/NT-3 dose dependencies observed in this assay roughly paralleled those seen in the survival assay (compare FIG. 9B and FIG. 10B). NGF was not capable of inducing DNA synthesis in either the parental or the trkB-expressing cells (FIGS. 10A and 10B).

BDNF and NT-3 were also tested for their ability to promote long-term proliferation of trkB-expressing NIH 3T3 cells. In these assays factors were tested for their ability to enhance the growth rate of sparsely plated parental or trkB-expressing cells; in contrast to the cell death that follows the dense plating of these cells in mitogen-free defined medium, continued proliferation in the absence of notable cell death is seen in cells plated sparsely (at 0.5% confluency) in such medium. In addition to the expected response to bFGF, an enhanced growth rate of trkB-expressing NIH-3T3 cells was seen in response to both BDNF and NT-3 (FIG. 10C); the parental NIH 3T3 cells only responded to bFGF. Again, the dose dependencies of BDNF and NT-3 for proliferation paralleled those seen for the survival and thymidine incorporation assays (compare FIGS. 9B, 10B and 10C).

3. TrkB-expressing Fibroblasts and BDNF-dependent Primary Neurons Display Similar Dose-response Curves for BDNF To determine whether the survival and proliferative effects of BDNF upon trkB-expressing fibroblasts occur at physiologically appropriate neurotrophin levels, we compared the BDNF concentrations required for these effects with the concentrations required in a classical neuronal survival assay using BDNF-dependent neurons isolated from dorsal root ganglia (DRG). Recombinant human BDNF displayed an almost indistinguishable dose-response curve (FIG. 10D) for neuronal survival as was reported for BDNF purified from pig brain (Rodriguez-Tebar and Barde, 1988, The Journal of Neuroscience 8:3337–3342). This dose-response curve on primary neurons is very similar to those described above for survival and proliferation in fibroblasts (compare FIG. 10D to FIGS. 9B, 10B, and 10C). Thus fibroblasts that express trkB in the absence of the LNGFR display a sensitivity to BDNF which is similar to that displayed by BDNF-dependent primary neurons.

Figure 11A:
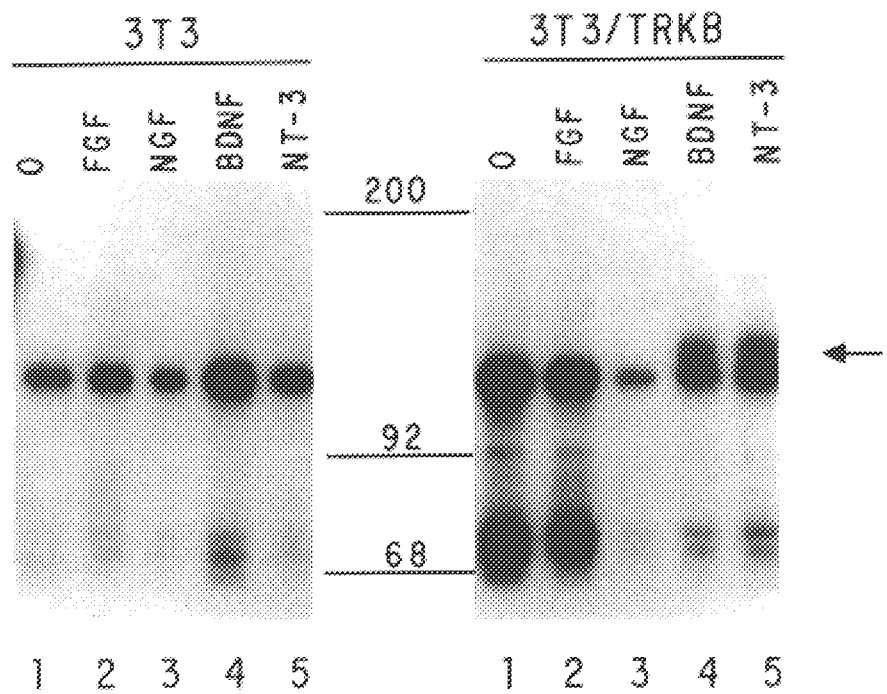

4. BDNF and NT-3 Activate Tyrosine Phosphorylation in TrkB-expressing NIH3T3 Cells In order to examine the signalling pathways triggered by the binding of neurotrophins to TrkB, we have assayed for tyrosine phosphorylation in trkB-expressing NIH3T3 cells following treatment with bFGF or the neurotrophins. Parental or trkB-expressing NIH3T3 cells were treated with factors for five minutes, lysates were prepared, and then immunoprecipitated using an anti-phosphotyrosine antibody. The precipitated proteins were separated by gel electrophoresis, and detected by immunoblotting with the anti-phosphotyrosine antibody. The trkB-expressing NIH3T3 cells treated with BDNF or NT-3 displayed a major tyrosine phosphorylation product of approximately 145 kD, corresponding to the known size of TrkB (FIG. 11B); this product was not seen in parental cells exposed to any of the factors, nor was it seen in trkB-expressing cells exposed to either bFGF or NGF (FIG. 11A). These data suggest that the major 145 kD phosphorylation product induced by BDNF and NT-3 is trkB.

Figure 11B:
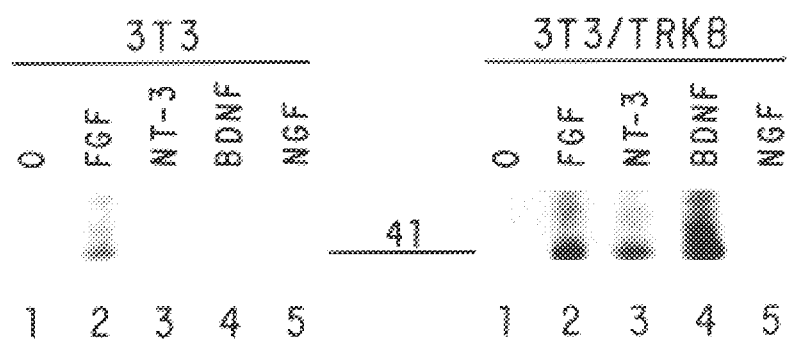

BDNF and NT-3 treatment of trkB-expressing NIH3T3 cells also induced tyrosine-phosphorylation of a 41 kD protein (FIG. 11B). bFGF also induced phosphorylation of a 41 kD protein in both parental and trkB-expressing NIH3T3 cells (FIG. 11B). Based on studies by Boulton, et al. (1991, Cell 65:663–677), this phosphoprotein may correspond to ERK2, a serine/threonine kinase which is activated and tyrosine phosphorylated in PC12 cells in response to NGF. These data are consistent with the notion that neurotrophin and growth factor receptors phosphorylate some of the same targets in both neuronal and non-neuronal cells.

3. Discussion

We have demonstrated that trkB, when expressed in LNGFR-positive PC12 cells, can mediate neurite outgrowth in response to both BDNF and NT-3 (Squinto et al., 1991, Cell 65:1–20). We now provide evidence that a member of the trk family can mediate biologically relevant responses to the neurotrophins without collaborating with the LNGFR; BDNF and NT-3 act as survival and proliferative factors for NIH3T3 cells expressing trkB but no detectable LNGFR. These survival and proliferative effects occurred with a dose-dependence very similar to that required to support survival of primary neurons in culture. Furthermore, the actions of BDNF and NT-3 on trkB-expressing fibroblasts, both biologically and biochemically, are analogous to those of a traditional growth factor, bFGF.

Our findings reveal that the neurotrophin receptors do not appear to be unusual among receptor tyrosine kinases in either their requirement for interactions with other receptor components, or in the types of signals they transduce. Therefore the apparently unique actions of the neurotrophins, in terms of promoting neuronal survival and differentiation as opposed to cell growth, can most probably be attributed to the relatively restricted distribution of the trk receptors in post-mitotic neurons rather than any unique features of the receptor system. Conversely, our data would also suggest that the apparent neurotrophic actions of traditional growth factors, including members of the FGF family, are mediated by signal transduction pathways which overlap those utilized by the neurotrophins.

The identification of the receptors utilized by the neurotrophins, as well as the establishment of non-neuronal cell lines which display survival and proliferative responses to these factors, should prove useful in understanding how the same signals can ultimately be interpreted differently in neurons and non-neuronal cells. We note that the trkB-expressing NIH3T3 cells provide the first example of an immortalized cell line which displays responses to the neurotrophins at physiologically appropriate levels; responses in PC12 cells require approximately 100-fold higher NGF levels than responses in primary neurons. Our studies indicate that survival and proliferation assays utilizing NIH3T3 cells expressing novel receptor tyrosine kinases may be used as a powerful system for the molecular cloning of the ligands for these orphan receptors. Finally, the NIH3T3 system may also be used to provide insight into how neurotrophic factors prevent neuronal cell death; it can now be determined whether the neurotrophins utilize the same or distinct pathways to prevent neuronal versus non-neuronal cell death.

An important issue raised by our data concerns the role of the LNGFR, a low-affinity binding site for all the known neurotrophins. A variety of studies indicate that introduction of the LNGFR into non-neuronal cells does not confer neurotrophin responsiveness upon the recipient cells (Hempstead et al., 1989, Science 243:373–375; Sehgal, et al., 1988, Mol. Cell. Biol. 8:2242–2246). The most direct evidence supporting a functional role for the LNGFR in mediating signal transduction involved an experiment in which the LNGFR was reintroduced into a PC12 cell mutant which had apparently lost all detectable NGF binding and responsiveness (Hempstead et al., 1989, Science 243:373–375; Sehgal, et al., 1988, Mol. Cell. Biol. 8:2242–2246). The resulting transfectant displayed both high and low-affinity NGF binding sites and exhibited limited responsiveness to NGF. It was assumed that this experiment demonstrated that the LNGFR was the only NGF-binding molecule expressed by PC12 cells, and that it collaborated with a second moiety that had no NGF binding ability on its own but which could convert the LNGFR to a signal-transducing high affinity receptor. The observations that the trk proteins bind the neurotrophins, and that PC12 cells normally express trkA, call for a re-interpretation of this critical experiment. While recent publications have differed as to whether trkA requires the LNGFR to generate high affinity NGF binding sites, it should be pointed out that only a single protein, now known to correspond to trkA, can be cross-linked to NGF under high-affinity binding conditions (Hosang and Shooter, 1985, J. Biol. Chem. 260:655–662). Furthermore, an antibody which efficiently prevents NGF binding to the LNGFR blocks all low-affinity but not all high-affinity NGF binding, and does not prevent NGF-induced responses in PC12 cells (Weskamp and Reichardt, 1991, Neuron 6:649–663). In any case, our functional data convincingly demonstrate that the LNGFR appeared not to be required for trkB mediated responses to physiologically appropriate doses of BDNF and NT-3. It still remains possible that the LNGFR somehow modulates trkA or trkB-mediated responses. Alternatively, the LNGFR could play a signalling role in a pathway not involving the trks, although the apparent inability of BDNF or NT-3 to elicit responses from PC12 cells seems to make this a less likely possibility (Squinto et al., 1991, Cell 65:1–20). The finding that the LNGFR is much more widely distributed than the trks (Bothwell, 1991, Curr. Top. Microbiol. Immunol. 165:63–70), particularly within apparent targets of innervation that produce neurotrophins but which are not known to respond to them, seems to support more of an "immunobilization" or "clearance" role rather than a signalling role for the LNGFR.

Our findings add the neurotrophins and the trk proteins to the growing list of factor/receptor systems in which multiple related ligands can act on the same receptor (Cross and Dexter, 1991, Cell 64:271–281). NT-3 and BDNF display dramatically reciprocal expression patterns during development (Maisonpierre et al., 1990a, Neuron 5:501–509). The NT-3 gene is expressed at much higher levels during early development than is the BDNF gene; NT-3 expression then decreases while BDNF levels increase. This reciprocal relationship between NT-3 and BDNF expression is particularly noteworthy in light of our findings that trkB can act as a BDNF receptor, and somewhat less well as an NT-3 receptor. The apparently high levels of NT-3 early in development may allow it to act more generally on receptors such as trkB; when NT-3 expression decreases to low levels unidentified, NT-3 receptors.

8. EXAMPLE: CLONING OF ORPHAN TYROSINE KINASE RECEPTOR MOLECULES

1. Materials and Methods

In FIG. 12E (SEQ ID NOS: 38–50) Roman numerals indicate tyrosine kinase homology domains as identified by Hanks et al. (1988) Science 241, 42–52. Highlighted regions of sequence homology in FIG. 12E (SEQ ID NOS:38–50) (underlined and in bold; lying within the catalytic domain of these proteins) were used in designing degenerate oligonucleotide primers with which to prime PCR reactions using either adult or embryonic (E13) rat brain cDNAs. Resulting amplified DNA fragments were cloned by insertion into plasmids, sequenced and the DNA sequences were compared with those of all known tyrosine kinases.

cDNA templates were generated by reverse transcription of adult and E13 total rat brain RNAs using oligo d(T) primers. Combinatorial PCR reactions with either of the two cDNA groups were done comparing the six combinations of downstream and upstream primers (see Table I below and FIG. 12A)(SEQ ID NOS:1–5) at primer annealing temperatures of 40° C. versus 45° C. Aliquots of the PCR reactions were subjected to electrophoresis on an agarose gel, blotted to nylon and probed with "internal" radiolabeled degenerate oligonucleotides complimentary to the domain VII homology box (see above). Based on the relative intensities of the hybridization signals obtained, five PCR reactions (distinguished by the indicated properties) were selected for further analysis:

TABLE I

| PCR # | t anneal | cDNA source | Primers |
|---|---|---|---|
| 1 | 40° C. | E13 | DLATRN-DVWSLG (SEQ ID NO: 91 and SEQ ID NO: 93) |
| 2 | 40° C. | adult | DLATRN-DVWSYG (SEQ ID NO: 91 and SEQ ID NO: 95) |
| 3 | 40° C. | E13 | DLATRN-DVWSYG (SEQ ID NO: 91 and SEQ ID NO: 95) |
| 4 | 40° C. | adult | DLAARN-DVWSLG (SEQ ID NO: 92 and SEQ ID NO: 93) |
| 5 | 40° C. | E13 | DLAARN-DVWSLG (SEQ ID NO: 92 and SEQ ID NO: 93) |

Size-selected amplified DNA fragments from these PCR reactions were cloned into plasmids as follows: Each of the five PCR pools was digested with XhoI and SstI to cleave sites in the termini of the primers (see below) and then subjected to electrophoresis through a 6% polyacrylamide gel. Ethidium bromide-stained (XhoI/SstI-cut) DNAs of 225 bp, +/−25 bp, were purified by elution from appropriate excised polyacrylamide gel fragments. The eluted DNAs were cloned into compatible XhoI/SstI sites in the Bluescript II KS(−) plasmid, introduced into DH5α $E.$ $coli$ by electroporation, followed plating of transformants on selective agar. Approximately 200 ampicillin-resistant bacterial colonies from each PCR transformation were inoculated into 96-well microtiter plates and have been stored as glycerol stocks at −80° C. Individual colonies from these five pools of PCR clones have been analyzed by sequencing of plasmid DNAs that have been purified by standard plasmid miniprep procedures.

2. Results and Discussion

Oligonucleotide primers corresponding to conserved regions of known tyrosine kinase molecules were used to amplify and clone DNA sequences encoding novel orphan tyrosine kinase receptor molecules. The amino acid sequences of representatives from branches of the tyrosine were aligned (FIG. 12E)(SEQ ID NOS:38–50) and regions of homology within the catalytic domain of these proteins were identified and used to design degenerate oligonucleotide primers, depicted in Table I (supra) and FIG. 12A (SEQ ID NOS:1–5). These primers were then used to prime PCR reactions with, as template, adult or embryonic (E13) rat brain cDNAs. Resulting amplified DNA fragments were then cloned into Bluescript II KS(−) plasmid, sequenced, and the DNA sequences compared with those of known tyrosine kinases.

FIG. 12B (SEQ ID NOS:6–10)presents the amino acid sequences encoded by a number of these clones which are homologous to a number of known tyrosine kinase molecules. The five particular cloned molecules of FIG. 12B (SEQ ID NOS:6–10) bear homology to trk, CSF1R/PDGFT/kit, ret, eck (alpha), and eck (beta) and are termed respectively, Rtk-1(SEQ ID NO:6), Rtk-6 (SEQ ID NO:7), Rtk-7 (SEQ ID NO:8), Rtk-8 (SEQ ID NO:9), and Rtk-9 (SEQ ID NO:10). FIG. 12C presents DNA sequences (SEQ ID NOS:11, 19, 25, 30, and 35) for each of these five tyrosine kinase clones, as well as information about the cDNA source and primers used to amplify each clone. Also shown are alignments of these DNA sequences (SEQ ID NOS:12, 20, 26, 31 and 33)(or their cognate amino acid sequence) with near relatives from the tyrosine kinase superfamily.

FIG. 12D (SEQ ID NO:34) shows the amino acid sequence of a rat brain cDNA that was obtained by probing with the Rtk-1 cDNA sequence shown in FIG. 12C (SEQ ID NO:11). The cDNA clone contains sequences identical to Rtk-1 and an additional 1440 amino acid segment of the gene, and based on alignment with trkA and trkB, may correspond to the carboxy terminus of the Rtk-1 gene product.

FIG. 20 sets forth the entire nucleotide and amino acid sequence for Rtk-7, which is now known as Tie-2 [Maisonpierre, et al. Oncogene 8:1631–1637 (1993)]. FIG. 21 sets forth the entire nucleotide and amino acid sequence for Rtk-8, which is now known as Ehk-2 (SEQ ID NOS: 100 and 101). FIG. 22 sets forth the entire nucleotide and amino acid sequence for Rtk-9, which is now known as Ehk-1 (SEQ ID NOS:102 and 103).

9. EXAMPLE: CLONING OF ORPHAN TRK-LIKE RECEPTOR MOLECULES

1. Materials and Methods

PCR-mediated cloning was performed essentially as described in Section 9, supra, but using cDNA from the human neuroblastoma cell line SY5Y as template, and oligonucleotide primers shown in Table II, infra.

9.2. Results and Discussion

The goal of this work was to identify, by PCR, DNA sequences closely related to trk and trkB genes. Thus, oligodeoxynucleotide primers were designed which correspond to protein regions strongly conserved in all protein kinases, but which at the same time would strongly bias the amplification reaction towards rk-related sequences. For example, trk-10r primer in FIG. 13A corresponds to the -PIRWMPPE- (SEQ ID NO:51) in which trk and trkB are identical, but even their closest known relatives, insulin and insulin-like growth factor receptors have two amino acid substitutions. FIG. 13A (SEQ ID NOS:51–58) shows alignment of tyrosine kinase domains of the members of insulin receptor subfamily with regions of sequence conservation identified earlier by others, and the location of all primers used in this work.

Using cDNA from human neuroblastoma cell line SY5Y as a template, polymerase chain reactions (PCRs) with various combinations of primers were performed. The DNA products were digested with restriction enzymes which cut trk and trkB sequences, and the resistant material was re-amplified and cloned. Individual clones were then sequenced. Amino acid sequences deduced from these DNA sequences revealed the presence of fragments of four novel potential receptors in the pool. These fragments, referred to as Rtk-2 (SEQ ID NO:60), Rtk-3 (SEQ ID NO:62), Rtk-4 (SEQ ID NO:64) and Rtk-5 (SEQ ID NO:66), are depicted in FIG. 13B (Rtk-4 (SEQ ID NO:64) and Rtk-5 (SEQ ID NO:66), FIG. 14 (Rtk-2 (SEQ ID NO:78)), and FIG. 15 (Rtk-3 (SEQ ID NO:80)) and compared with the corresponding region of human trk in FIG. 13C (SEQ ID NO:67). Rtk-2 (SEQ ID NO:72) is shown aligned with human trk (SEQ ID NO:74), rat trkB (SEQ ID NO:73), insulin-related growth faction receptor (SEQ ID NO:75), and insulin receptor (SEQ ID NO:76) in FIG. 13D.

The following oligodeoxynucleotide primers [TRK-9 (SEQ ID NO:87), TRK-10r (SEQ ID NO:88), TRK-5 (SEQ ID NO:89) and TRK-6R (SEQ ID NO:90)] were used in preparation of the PCR fragments (the restriction site "tail" used for cloning is shown in italics, and the degeneracy at particular position is indicated by the letters in parentheses):

TABLE II

Rtk-2 and Rtk-3

| | |
|---|---|
| TRK-9 | ACGTCTCGAG-GC(TCAG) -GG(TCAG) -ATG-GT(TCAG) - TA(TC) - (TC)T (SEQ ID NO: 87) |
| TRK-10r | CATGTCTAGA-GGC-ATC-CA(TCAG) -C(GT) (AGT) - AT (TCAG) - GG (SEQ ID NO: 88) |

Rtk-4

| | |
|---|---|
| TRK-5 | ACGTCTCGAG-AA(AG)-AT(TCA)-GG(TCAG) -GA(TC) - TT(TC) -GG (SEQ ID NO: 84) |
| TRK-10r | CATGTCTAGA-GGC-ATC-CA(TCAG) -C(GT) (AGT) - AT (TCAG) - GG (SEQ ID NO: 88) |

Rtk-5

| | |
|---|---|
| TRK-9 | ACGTCTCGAG-GC(TCAG) -GG(TCAG) -ATG-GT(TCAG) - TA(TC) - (TC) T (SEQ ID NO: 87) |
| TRK-6r | CATGTCTAGA-CC- (GA)AA- (GA)TC- (CTGA)CC- (TGA)AT- (CT)TT (SEQ ID NO: 90) |

Rtk-2 and Rtk-3 sequences are of particular interest. When the deduced amino acid sequences were used to search GenBank, Release 67.0 (03/91) and EMBL (Modified) Release 26.0 (02/91) Databases with TFASTA, the highest homology scores were obtained for trkB and trk sequences. Rtk-2 and Rtk-3 contain the YxxDYY sequence characteristic for trk/insulin-F substitution in the DFG motif which is very strongly conserved in all kinases.

When the Rtk-2 and Rtk-3 probes were hybridized to Northern blots, no signal was obtained with SY5Y RNA. Rtk-2 hybridized to a 6–7 kb band in RNAs from other lines, in particular from CHP100, SKES, and LAN5 cells. Rtk-3 hybridized to a 5 kb band in RNAs from SKN-SH and LAN5 cells. Screening of $1.5 \times 10^6$ clones from SY5Y cDNA library in lambda ZPA II with Rtk-2 probe yielded 5 positive clones, with inserts in the range 1.4–3 kb.

Sequence data for Rtk-2, shown in FIG. 14 (SEQ ID NOS:77–78), indicates that nucleotides 801–875 appear to code for a transmembrane domain, nucleotides 1002–1850 appear to contain a tyrosine kinase domain; and 1–800 code for a continuous open reading frame comprising a ligand binding domain. A 180 amino acid stretch follows the tyrosine kinase domain, in contrast to trks, which terminate shortly following the tyrosine kinase domain.

The partial amino acid sequence of Rtk-3 shown in FIG. 15 (SEQ ID NO:80), which also shows the presence of this stretch beyond the tyrosine kinase domain and shows strong homology to Rtk-2.

Alignment of the Rtk-3 (SEQ ID NO:81)sequence to the sequences for Rtk-2 (SEQ ID NO:82), trks (SEQ ID NOS:83–84), IGFR (SEQ ID NO:85), and Insulin receptor (SEQ ID NO:86), shown in FIG. 16, indicates that Rtk-2 and Rtk-3 share the greatest homology, suggesting they are members of a novel subfamily of tyrosine kinase receptors. Rtk-2 has subsequently been given the designation Ror1; its full sequence, as encoded by pBluescript SK-containing Rtk-2 as deposited with the American Type Culture Collection on Jul. 24, 1991 and designated as 75052 is set forth in FIGS. 26A–G (SEQ ID NOS:104 and 105). The receptor tyrosine kinase comprising the sequence Rtk-3 as encoded by pBluescript SK-containing Rtk-3 as deposited with the American Type Culture Collection on Jul. 24, 1991 and designated as 75053 is set forth in FIGS. 27A–G (SEQ ID NOS:106 and 107).

10. FUNCTIONAL ASSOCIATION OF TRKS WITH NEUROTROPHINS IN RAT EMBRYONIC DORSAL ROOT GANGLIA

1. Materials

Dorsal root ganglion (DRG) from embryonic rat (E14) were dissected and collected in serum-containing medium (F14 medium supplemented with 5% horse serum), as described in Lindsay, et al. (1985, Dev. Biol. 112: 319). For explant assays, ganglia were put onto 35 mm dishes pre-coated with polyornithine (1 mg/ml) and laminin (50 ug/ml). Ganglia were cultured for 24 hours in the presence or absence of neurotrophins at 37° C. in a humidified 3% CO2 atmosphere. The extent of neurite outgrowth was scored with a scale of 0–5. At the end of the culture period, ganglia were rinsed with PBS, following which RNA was prepared using guanidinium thiocyanate, as described in Chomczynski and Sacchi (1987, Analytical Biochem. 162: 156). For dissociated cell assays, ganglia were incubated with 0.1% trypsin at 37° C. for 30 minutes, after which they were triturated and preplated for 2.5 hours. Neurons were then collected and seeded onto 16 mm wells precoated with 100 ug/ml polyornithine and 50 ug/ml laminin. Neurons were cultured for 24 hours in the presence or absence of neurotrophins, and cell counts were scored. RNA from tissues were prepared using standard techniques.

2. Results

Figure 18A:
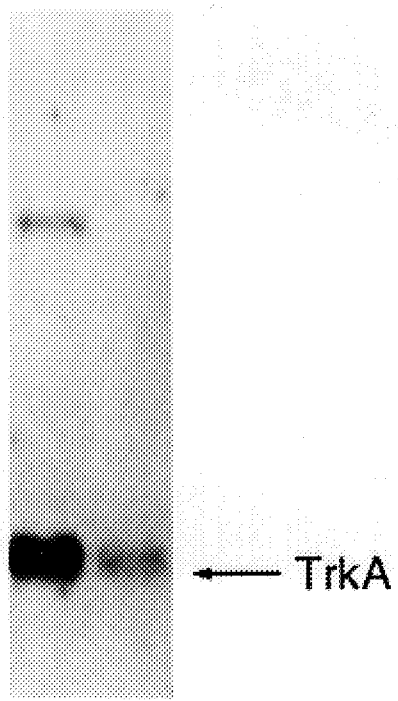
Figure 18B:
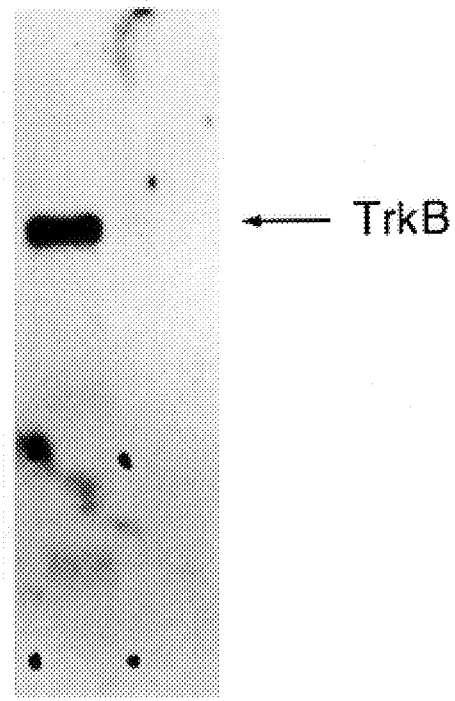
Figure 19A:
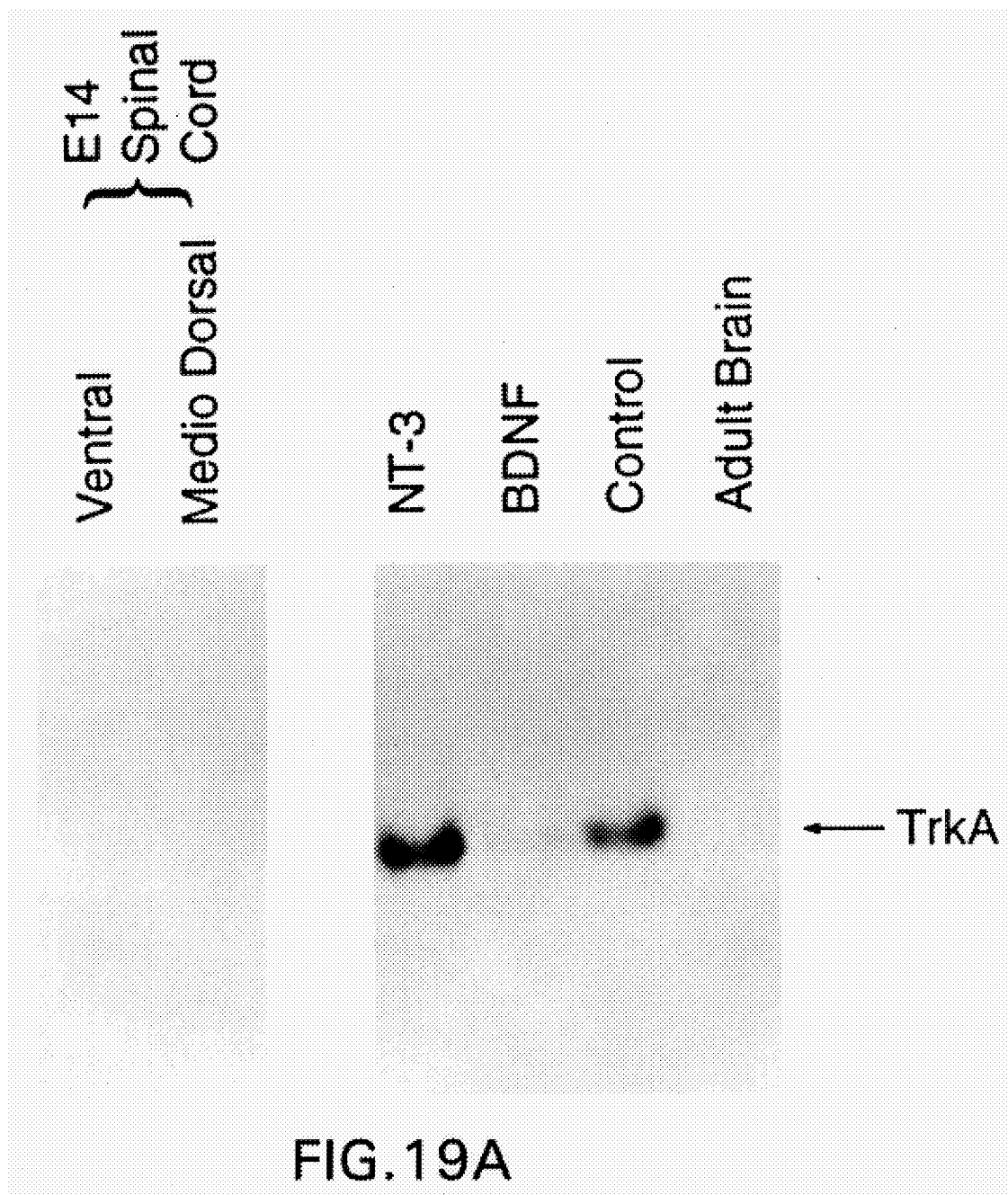
Figure 19B:
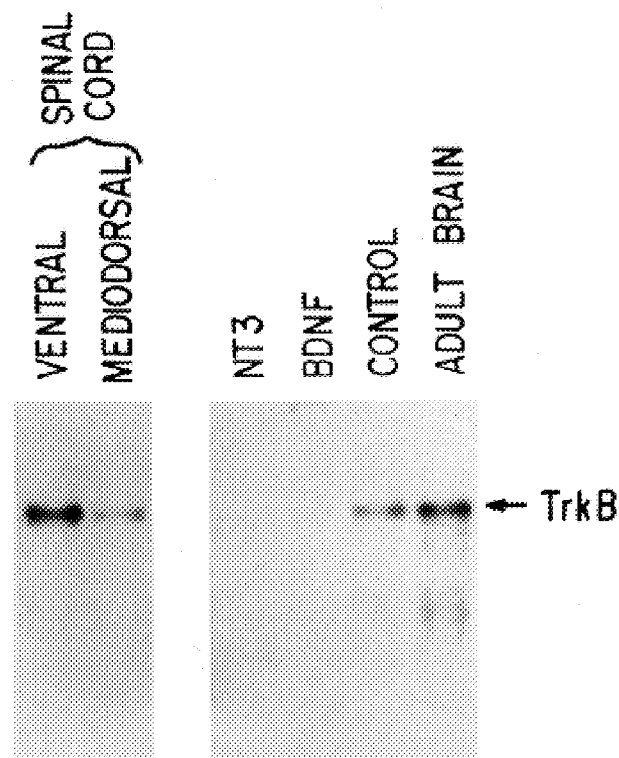
Figure 19C:
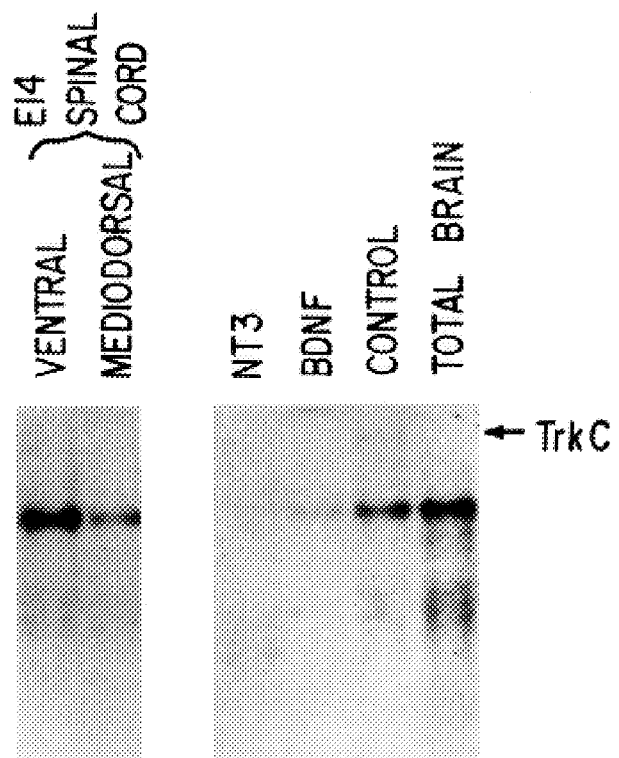

Incubation of DRG with NGF with various concentrations of NGF resulted in massive neurite outgrowth from the explant in a dose-dependent manner (FIG. 17). Similar results were obtained with NT-3. The response saturates at approximately 5 ng/ml of NGF or NT-3. BDNF, on the other hand, produced a weaker, but also consistent, response with DRG explants (FIG. 17).

mRNA levels for trkA, B, and C were examined in the ganglia cultured in the presence or absence of various neurotrophins. In control DRG taken from E14 embryonic rat, mRNA for trkA, B and C can be detected (FIG. 18 and 19). As shown in FIG. 18A, ganglia incubated in the presence of NGF (50 ng/ml) had a significant trkA mRNA level, but undetectable trkB message (FIG. 18B). On the other hand, ganglia incubated in the presence of BDNF (50 ng/ml) revealed significant trkB message (FIG. 19B), but very low levels of trkA (FIG. 19A) and no trkC (FIG. 19C). Finally following treatment with NT-3 (50 ng/ml), ganglia had significant trkC and trkA mRNA, but very low levels of trkB message. These results demonstrate that the neuronal populations surviving in the presence of these neurotrophins possess specific receptors for the respective neurotrophins. That is, following incubation with BDNF, only trkB-containing neurons appear to survive, whereas treatment with NGF resulted in survival of only trkA-containing neurons. Treatment of NT-3 appeared to result in survival of both trk-C and trk-A containing neurons. The fact that specific receptors for the respective neurotrophins are present on distinct cell types suggest that neurotrophins may be used to rescue distinct cell populations in the peripheral nervous system.

11. EXAMPLE: EXPRESSION CLONING OF NOVEL RECEPTORS AND LIGANDS BY SELECTION FOR FIBROBLAST SURVIVAL

1. Materials and Methods

Cells, Cell Culture and DNA Transfections

As described in Section 7.1.1 supra

Factors

As described in Section 7.1.2 supra

Survival Assay

As described in Section 7.1.2 supra

Delayed Survival Assay and Delayed Focus Assay

An isolate of NIH 3T3 cells (referred to here as MG87 cells) which is dependent on growth factor for survival in serum-free, defined media, was transfected as previously described with a mixture of three CMX plasmid-based cDNA libraries: one derived from the brain of rat embryos sacrificed at Day 13 of embryogenesis; the second derived from whole Day 12 embryos; the third from the SY5Y human neuroblastoma cell line. 5 μg of cDNA was transfected per tissue culture plate. 20 μg of rat liver genomic DNA was used as carrier for each plate. The cells were co-transfected with one μg/plate of a neomycin-resistance gene. The cells were allowed to recover in DMEM+10% Calf serum for 24 hours.

For the Delayed Survival Assay, the cells were then split onto poly-D-lysine, fibronectin coated plates in the presence of DMEM, 10% Calf Serum, and 500 μg/ml G418. The cells were fed every three days. When the G418-surviving transfectants approached 30% confluence, (seven to eight days after drug selection), the media was changed to serum free, complete defined media (as previously described), supplemented with a mixture consisting of 5 nM BDNF, 5 nM NGF, 5 nM EGF. Media was changed every day.

For the Delayed Assay, the cells were split onto regular, un-coated tissue culture plates in the presence of DMEM, 10% Calf serum and 500 μg/ml G418. The cells were fed every three days. When the G418-surviving transfectants approached 30% confluence, (seven to eight days after drug selection), the media was changed to 3 Calf Serum DMEM (as previously described), supplemented with a mixture consisting of 5 nM BDNF, 5 nM BDNF, 5 nM NGF, 5 nM NT-3, 5 nM EGF. Media was changed every day.

2. Results

Expression Cloning of BDNF and NGF Receptors by Selection for Factor-dependent Survival of NIH 3T3 Fibroblasts In order to determine if we could use expression cloning to isolate receptors for growth factors, we co-transfected MG 87 cells, which are normally dependent on FGF (Fibroblast Growth Factor) for survival in serum-free defined media, with a mixture of CMX plasmid cDNA libraries derived from rat brain E13, total rat E12 and the SY5Y cell line along with a neomycin selectable marker gene (pGCneo) to see if we could induce survival with one of the following growth factors: BDNF, NGF, NT-3 or EGF.

MG 87 cells normally do not survive in serum-free, defined media with any of these factors. Further, MG 87 cells usually become contact inhibited at confluence in the presence of 3% Calf Serum DMEM, even in the presence of these factors.

Each plate of cells was split into a delayed focus and a delayed survival assay (described above). After one week in defined media+growth factors, or in 3% Calf serum DMEM+growth factors, the plates were examined for surviving colonies (in the delayed survival assay) or for foci (in the delayed focus assay). Four colonies (referred to hereon as cell lines 1, 2, 3 and 4) were observed and harvested, (colonies one and two and four from the delayed survival assay; colony three from the delayed focus assay.

In order to establish which growth factor was mediating survival and proliferation, each cell line was assayed for survival in each of the growth factors individually.

Cell line 1 grew in BDNF and NT-3, but died when grown in NGF or EGF alone. bFGF, which is the normal factor for these cells, supported survival. The cells died, as expected, when no growth factor was added.

Cell line 3 grew in NGF, but died when grown in BDNF, NT-3 or EGF. bFGF, the positive control, again supported survival. These cells also died when no growth factor was added.

Cell lines 2 and 4 grew in all conditions, including the absence of growth factor, indicating that these lines were no longer factor dependent. This confirms that our assay can also be used to isolate genes which mediate factor-independence (putative oncogenes).

DNA from the surviving cell lines was obtained, and subjected to Southern analysis with a rat trkA probe (BgII-BamHI, 500 bp). A hybridizing band was observed in the DNA obtained from Cell Line 3, indicating that this NGF-responsive line had in fact been transfected with the trkA gene. This provides formal evidence for our ability to clone growth factor receptors (and, reciprocally, ligands) using this method.

3. Summary

For the first time, receptors have been functionally isolated by conferring the ability to either survive or proliferate on fibroblasts which normally do not respond to exogenously added growth factors. This system could therefore be used to discover novel receptors to known growth factors. Reciprocally, it should also be possible to isolate novel factors for known receptors using these methods. The subsequent techniques necessary to actually clone the introduced genes are conventional and well-established.

13 TISSUE DISTRIBUTION OF EHK-1 AND EHK-2

Materials and Methods

RNA Northern Blot Analysis. RNA isolation, electrophoresis, blotting and subsequent hybridization with PCR-generated rediolabeled probes was performed as described in Maisonpierre, et al. Science 247:1446–1451 (1990). Hybridization probes were the approximately 220 base pair PCR products that spanned between the DLAARN (SEQ ID NO:92) to DVWSYG (SEQ ID NO:95) motifs of the Ehk-1 and Ehk-2 tyrosine kinase domains. Blots were given final washes at 70° C. in 2×SSC and exposed to X-ray film with an intensifying screen at −80° C. for 5 days.

RNA in situ hybridization. In situ detection of ehk-1 and ehk-2 RNAs in 10 μm fresh frozen sections of rat brain were performed according to previously described methods. [Haub, et al. Proc. Natl. Acad. Sci. USA, 87: 8022–8026 (1990). $^{35}$S-labeled antisense and sense cRNA probes corresponded to regions of the ehk-1 and ehk-2 cDNAs that extended about 550 nucleotides from BstEII sites just upstream of the respective ehk-1 and ehk-2 termination codons, into their 3'-untranslated sequences. Based on sequencing and restriction enzyme analyses of ehk-1 cDNAs, the ehk-1 probe would detect all five different splice variants. Following hybridization, tissue sections were dipped in NTB 2 emulsion (Kodak), developed after 5 weeks and counterstained with cresyl violet. Indicating of anatomical structures (FIGS. 24 and 25) were done according to Paxinos and Watson [The Rat Brain in Stereotaxic Coordinates, 2nd ed. Academic Press; San Diego, Calif. (1986)]. The hybridization signals presented were only detected with antisense cRNA probes and are representative of signals detected in immediately adjacent sections using the same probe.

Results

Cloned, kinase specific PCR products used to identify ehk-1 and ehk-2 were used to probe duplicated Northern blots of rat tissue RNAs. As shown in FIG. 23, the ehk-1 probe detects two major bands of approximately 9.5 kb and 6.6 kb that are almost exclusively limited to RNAs of neural tissues: longer exposures revealed that both bands are evident in cultured hippocampal astrocytes and also faintly evident in ovary and in skin.

The kinase specific ehk-2 probe detects a major band of roughly 14.0 kb that is present only in neural tissues, as well as several minor bands that include a band of 6.4 kb, present in various neural and non-neural RNAs, and a faint band of about 7.0 kb that is predominantly seen in E13 body and head RNAs.

There are several clear differences in the relative distribution and abundance of ehk-1 and ehk-2 transcripts. In E13 embryos, the two major ehk-1 transcripts are noticeably more abundant in head than in body. By post-natal day 1 (P1) these two bands reach their highest level in brain, declining slightly in adult brain. By contrast, the 14.0 kb neural-specific ehk-2 band, which is undetectable in both embryonic head and body RNAs, achieves its greatest abundance in adult brain. Interestingly, the principal ehk-1 and ehk-2 bands are similar in that they decline in cerebellar samples during the transition from P1 to adults, suggesting that the major sites of expression in adult whole brain are predominantly outside the cerebellum.

Longer exposures demonstrate that the ehk-1 and ehk-2 neural-specific bands are also detectable in RNAs from primary cultures of hippocampal astrocytes. This is unexpected because RNA in situ hybridization studies indicate that the two ehk genes are predominantly expression in neurons, not glia. Examination in various established cell lines has indicated that both genes are predominantly expressed in neuronally derived cells, including various neuroepitheliomal and neuroblastomal lines.

Figure 24A:
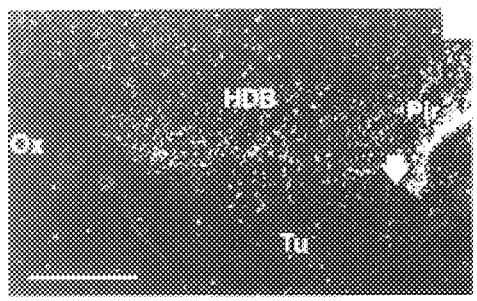
Figure 24B:
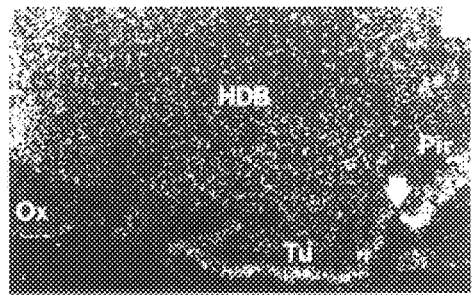
Figure 24C:
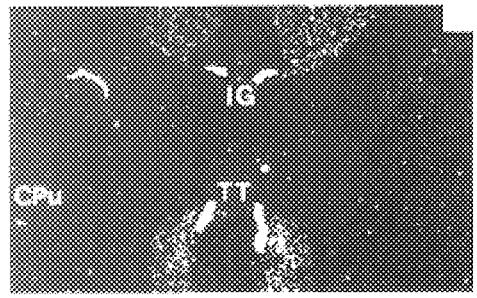
Figure 24D:
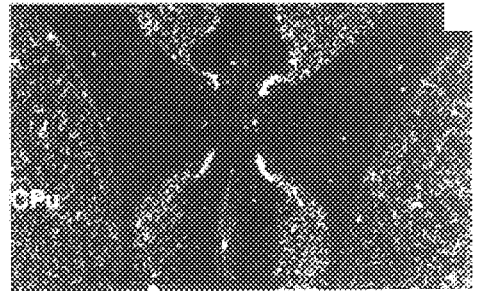
Figure 24E:
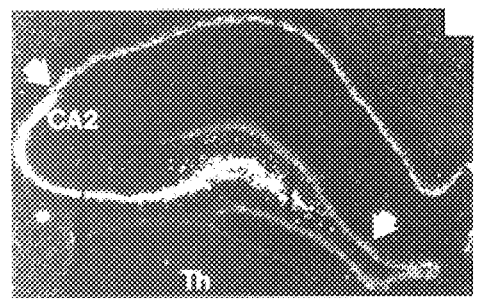
Figure 24F:
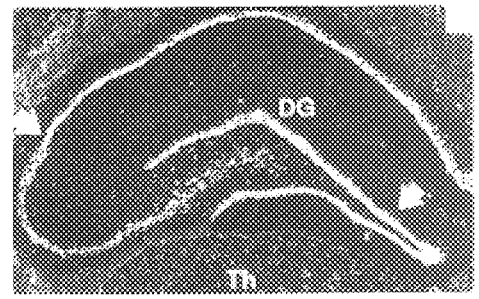
Figure 24G:
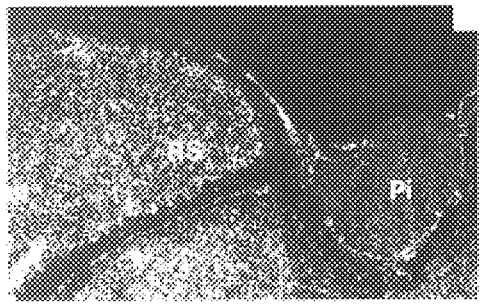
Figure 24H:
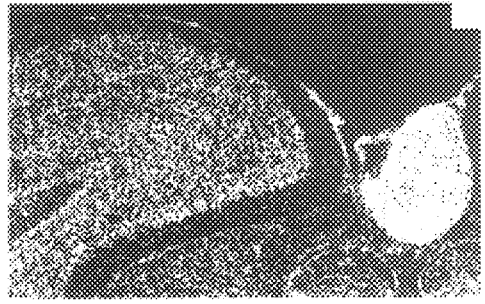
Figure 24I:
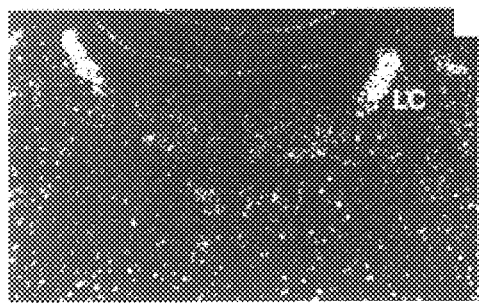
Figure 24J:
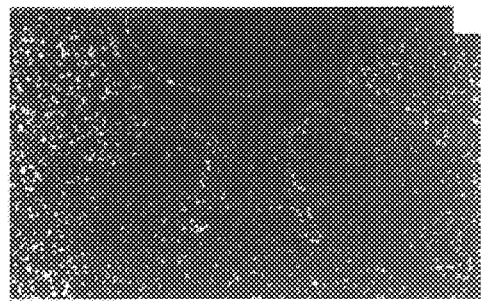
Figure 25A:
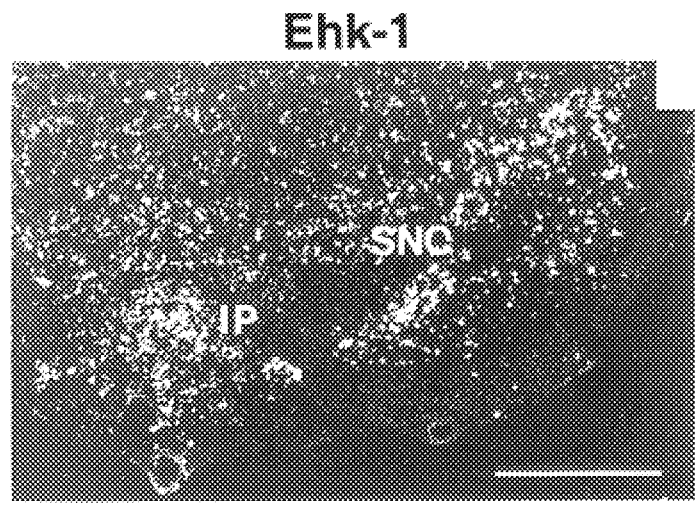
Figure 25B:
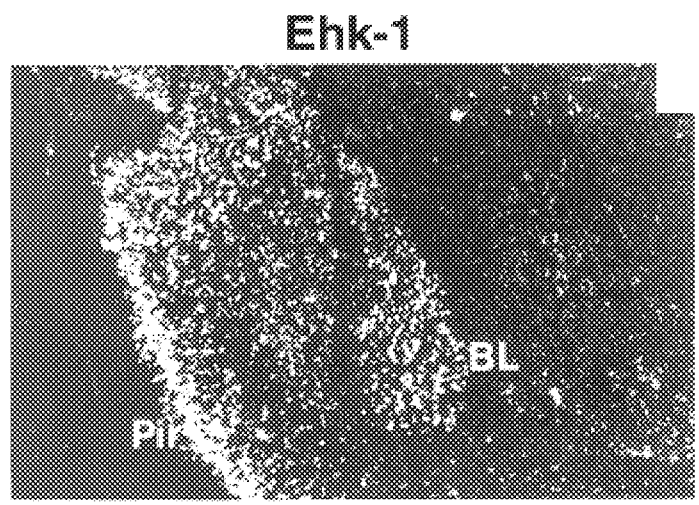
Figure 25C:
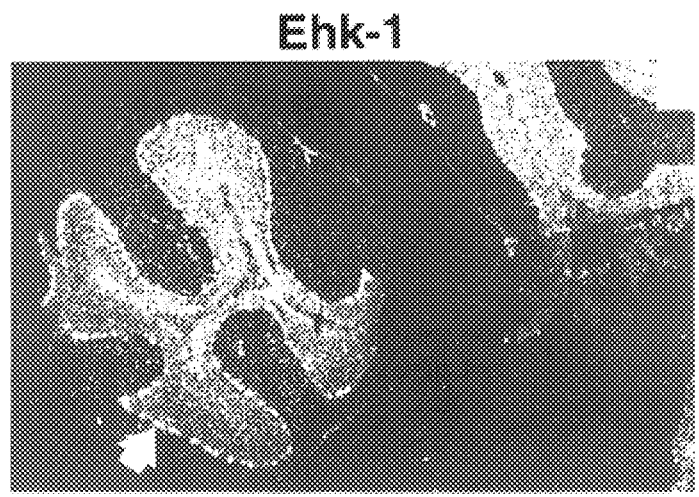
Figure 25D:
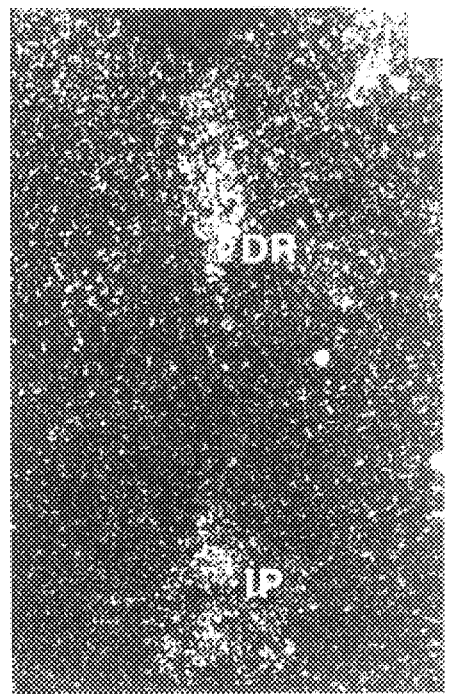
Figure 25E:

In situ RNA hybridization revealed more specifics regarding the major sites of ehk gene expression in the adult central nervous system. FIG. 24 specifically contrasts ehk-1 (a,c,e, g,i) and ehk-2 (b,d,f,h,j) hybridization signals on pairs of nearly adjacent coronal brain sections. Both probes strongly highlight the piriform cortex in the ventrolateral region of the forebrain (FIG. 24a and b), but neurons of the olfactory tubercle are only detected by the ehk-2 probe (FIG. 24b). Where both probes detect cells within the horizontal limb of the diagonal band (FIG. 24a and b), ehk-2 also displays a more general staining pattern over other regions of the section (FIG. 24b). Ehk-1 and ehk-2 signals are clearly evident over elements of the rostral septum (FIG. 24c and d), but the ehk-1 signal is noticeably more intense over neurons associated with the indusium griseum and tenia tecta (FIG. 24c). By contrast, ehk-2 shows a comparatively higher level of expression over caudate-putamen (FIG. 24d), as it also does over other striatal regions (not shown). Within the hippocampal formation (FIG. 24e and f), the ehk-1 signal is particularly intense over pyramidal neurons in CA3 and CA2, but weakens significantly in CA1 (FIG. 24e). The ehk-2 signal is distinguished in that it is comparatively stronger over dentate gyrus (FIG. 24f), as well as over thalamus. Ehk-1 and ehk-2 transcripts show a high degree of similarity in their distributions in the superior colliculus and in retrosplenial cortex (FIG. 24g and h). In pineal gland, however, ehk-1 signals are essentially absent, whereas ehk-2 transcripts are strikingly abundant (FIG. 24h). Ehk-2 but not ehk-1, also showed abundant expression in the pituitary (not shown). By contrast, ehk-1 transcripts are far more abundantly expressed in neurons of the locus coeruleus (FIG. 24i and j).

FIG. 25 shows either ehk-1 or ehk-2 hybridization signals over specific adult brain structures that serve to further distinguish the expression patterns of the two RTKs. Ehk-1 can be seen to strongly highlight neuronal rich densities associated with the interpeduncular nuclei and substantia nigra (FIG. 25a), the basolateral and lateral amygdala (FIG. 25b) and dorsal raphe (FIG. 25d)). By contrast ehk-2 signals were more diffuse over all of these structures, and over sections of amygdala, were indistinguishable from surrounding signal levels (not shown). Comparison of ehk hybridization patterns over adult cerebellum (FIG. 25c) and olfactory bulb (FIG. 25e) revealed interesting differences and similarities in ehk-1 and ehk-2 expression. The ehk-2 probe yielded a particularly strong signal over the glomerular layer of the olfactory bulb (FIG. 25e) whereas ehk-1 hybridization was totally absent from this structure (not shown), and although the ehk-1 probe shows significant hybridization to the granular layer of the cerebellum (FIG. 25c), the ehk-2 signal was comparatively much stronger (not shown). By contrast, both probes showed strong signals over Purkinje cells in the cerebellum (arrow in FIG. 25c; ehk-2 hybridization now shown) and over mitral cells in the olfactory bulb (arrow in FIG. 25e; ehk-1 hybridization not shown), providing examples in which both genes are likely to be coexpressed within the same cell.

Discussion

In adult rat brain, cellular localizations of ehk-1 and ehk-2 transcripts indicate that both genes are primarily expressed in neurons, and reach their highest levels of expression in distinctive neuronal populations that include some of the principal ascending central cholinergic nuclei (interpeduncular region, olfactory tubercle and lateral amygdala) and monoaminergic nuclei (locus coeruleus, dorsal raphe and substantia nigra. The identification of the cognate ligands for these receptors, using the assay systems described herein, will provide molecules that inevitably play a role in the development and maintenance of various neuronal cells populations.

Accordingly, the present invention provides for the novel receptor tyrosine kinases known as Ror1, Ror2, Ehk-1 and Ehk-2 as well as DNA sequences that are degenerate as a result of the genetic code and which encode receptor tyrosine kinases having the activities of the receptors described herein. When used herein, Ror-1, Ror-2, Ehk-1 and Ehk-2 include functionally equivalent molecules in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc. The receptors claimed are useful for developing probes that may be used to analyze neuronal populations. Further they may be utilized for the identification of ligands that promote the growth and/or proliferation of such receptor bearing cells. The invention also provides for tyrosine kinase receptor chimeras, comprising the intracellular or extracellular portion of these receptors and the intracellular or extracellular domain of other known tyrosine kinase receptors.

The invention further provides for both prokaryotic and eukaryotic expression systems for producing such proteins. The invention also provides for Ehk and Ror specific antibodies.

The receptors described herein also have diagnostic utilities. In particular embodiments of the invention, methods of detecting aberrancies in their function or expression may be used in the diagnosis of neurological disorders.

DEPOSIT OF MICROORGANISMS

The following microorganisms were deposited on Jul. 24, 1991 with the American Type Culture Collection, 12301 Parklawn Drive, Rockville, Md. 20852.

|  | ACCESSION NUMBER |
| --- | --- |
| pBluescript SK-containing Rtk-2 | 75052 |
| pBluescript SK-containing Rtk-3 | 75053 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. An isolated and purified nucleic acid molecule comprising ror1, wherein the sequence of said nucleic acid is selected from the group consisting of:
   (a) the sequence of the DNA comprising the coding region of the ror1 DNA sequence contained in the plasmid pBluescript SK-containing Rtk-2 as deposited with the American Type Culture Collection on Jul. 24, 1991 and designated as 75052; and (b) DNA sequences that are degenerate as a result of the genetic code to a DNA sequence of (a).

2. Substantially purified Ror1 comprising a protein encoded by the nucleic acid molecule according to claim 1.

3. An isolated and purified nucleic acid molecule comprising ror2 wherein the sequence of said nucleic acid is selected from the group consisting of:
   (a) the sequence of the DNA comprising the coding region of the ror2 DNA sequence contained in the plasmid pBluescript SK-containing Rtk-3 as deposited with the American Type Culture Collection on Jul. 24, 1991 and designated as 75053; and (b) DNA sequences that are degenerate as a result of the genetic code to a DNA sequence of (a).

4. Substantially purified Ror2 comprising a protein encoded by the nucleic acid molecule according to claim 3.

5. An isolated and purified nucleic acid molecule comprising ehk 1, wherein the sequence of said nucleic acid is selected from the group consisting of:
   (a) the sequence of the DNA comprising the coding region of the ehk 1 DNA sequence set forth in FIG. 22A (SEQ ID NO: 102); and (b) DNA sequence that are degenerate as a result of the genetic code to a DNA sequence of (a).

6. Substantially purified Ehk-1 comprising a protein encoded by the nucleic acid molecule according to claim 5.

7. An isolated and purified nucleic acid molecule comprising ehk 2 wherein the sequence of said nucleic acid is selected from the group consisting of:
   (a) the sequence of the DNA comprising the coding region of the ehk 2 DNA sequence set forth in FIG. 21 (SEQ ID NO: 100); and
   (b) DNA sequences that are degenerate as a result of the genetic code to a DNA sequence of (a).

8. Substantially purified Ehk-2 comprising a protein encoded by the nucleic acid molecule according to claim 7.

* * * * *